(12) United States Patent
Guzzo et al.

(10) Patent No.: US 9,045,468 B2
(45) Date of Patent: Jun. 2, 2015

(54) 2,5-METHANO- AND 2,5-ETHANO-TETRAHYDROBENZAZEPINE DERIVATIVES AND USE THEREOF TO BLOCK REUPTAKE OF NOREPINEPHRINE, DOPAMINE, AND SEROTONIN

(75) Inventors: Peter R. Guzzo, Niskayuna, NY (US); Shuang Liu, Schenectady, NY (US); Kristen N. Ryan, Halfmoon, NY (US); Bruce F. Molino, Slingerlands, NY (US); Russell DeOrazio, Schenectady, NY (US); Richard E. Olson, Orange, CT (US); John E. Macor, Guilford, CT (US)

(73) Assignees: Albany Molecular Research, Inc., Albany, NY (US); Bristol-Myers Squibb Company, Princeton, NJ (US)

( * ) Notice: Subject to any disclaimer, the term of this patent is extended or adjusted under 35 U.S.C. 154(b) by 829 days.

(21) Appl. No.: 13/211,678

(22) Filed: Aug. 17, 2011

(65) Prior Publication Data

US 2012/0046271 A1 Feb. 23, 2012

Related U.S. Application Data

(60) Provisional application No. 61/374,470, filed on Aug. 17, 2010.

(51) Int. Cl.
  *A61K 31/55* (2006.01)
  *C07D 453/00* (2006.01)
  *C07D 519/00* (2006.01)

(52) U.S. Cl.
  CPC ............ *C07D 453/00* (2013.01); *C07D 519/00* (2013.01)

(58) Field of Classification Search
  USPC ...................................... 514/214.03; 540/581
  See application file for complete search history.

(56) References Cited

U.S. PATENT DOCUMENTS

| | | | |
|---|---|---|---|
| 6,150,376 A | 11/2000 | Kozikowski et al. | |
| 6,340,678 B1 | 1/2002 | Matsuhisa et al. | |
| 6,579,885 B2 | 6/2003 | Beck et al. | |
| 7,084,152 B2 | 8/2006 | Beck et al. | |
| 7,163,949 B1 | 1/2007 | Beck et al. | |
| 7,541,357 B2 | 6/2009 | Molino et al. | |
| 7,956,050 B2 | 6/2011 | Molino et al. | |
| 8,153,622 B2 | 4/2012 | Doherty et al. | |
| 8,420,811 B2 | 4/2013 | Lobben et al. | |
| 8,445,494 B2 | 5/2013 | Qiu et al. | |
| 2006/0111393 A1 | 5/2006 | Molino et al. | |
| 2006/0111394 A1 | 5/2006 | Molino et al. | |
| 2008/0234251 A1 | 9/2008 | Doherty et al. | |
| 2010/0137287 A1 | 6/2010 | Guzzo et al. | |
| 2010/0210624 A1 | 8/2010 | Liu et al. | |
| 2010/0292242 A1 | 11/2010 | Liu et al. | |
| 2010/0292243 A1 | 11/2010 | Liu et al. | |
| 2010/0292250 A1 | 11/2010 | Wei et al. | |

FOREIGN PATENT DOCUMENTS

WO 03/049736 A1 6/2003
WO 03/101453 A1 12/2003

OTHER PUBLICATIONS

Klumpp et al., "Reactions of Amino Alcohols in Superacid: The Direct Observation of Dicationic Intermediates and Their Application in Synthesis," Org. Lett. 3(17):2781-2784 (2001).
International Search Report and Written Opinion for Patent Application No. PCT/US2011/048079 (Mar. 26, 2012).
European Search Report for EP11818722.8 dated Dec. 9, 2013.

*Primary Examiner* — Brenda Coleman
(74) *Attorney, Agent, or Firm* — LeClairRyan, a Professional Corporation

(57) ABSTRACT

The compounds of the present invention are represented by the following 2,5-methano- and 2,5-ethano-tetrahydrobenzazepine derivatives having formula (I):

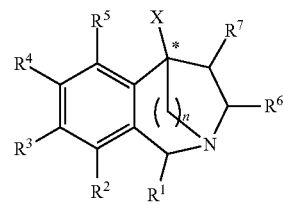

where the carbon atom designated * is in the R or S configuration when n is 1 and the substituents X and $R^1$-$R^7$ are as defined herein.

10 Claims, No Drawings

2,5-METHANO- AND 2,5-ETHANO-TETRAHYDROBENZAZEPINE DERIVATIVES AND USE THEREOF TO BLOCK REUPTAKE OF NOREPINEPHRINE, DOPAMINE, AND SEROTONIN

This application claims the benefit of U.S. Provisional Patent Application Ser. No. 61/374,470, filed Aug. 17, 2011, which is hereby incorporated by reference in its entirety.

FIELD OF THE INVENTION

The present invention relates to compounds, compositions, and methods for the treatment of various neurological and psychological disorders, and the use of the compounds in combination therapy. In particular, the present invention relates to such compounds, compositions, and methods, where the compounds are novel 2,5-methano- and 2,5-ethano-tetrahydrobenzazepine derivatives.

BACKGROUND OF THE INVENTION

Monoamine reuptake inhibitors elevate extracellular levels of serotonin (5-HT), norepinephrine (NE) and/or dopamine (DA) in the brain by binding to one or more of the transporters responsible for reuptake, namely the serotonin transporter (SERT), the norepinephrine transporter (NET) and the dopamine transporter (DAT), thereby blocking reuptake of the neurotransmitter(s) from the synaptic cleft. Monoamine reuptake inhibitors are an established drug class that has proven utility for the treatment of a number of CNS disorders especially major depressive disorder (MDD).

Since the introduction of tricylic antidepressants (TCAs) almost 50 years ago, monoamine reuptake inhibitors with greatly improved safety profiles have significantly enhanced the treatment of depression. Although TCAs are very effective antidepressants, cardiovascular, anticholinergic and sedative side effects are common due to the interaction of TCAs with muscarinic, histaminic and adrenergic receptors. The revolutionary introduction of selective serotonin reuptake inhibitors (SSRIs) in the 1980s allowed a much larger patient population to be treated because of the highly improved safety profile. Over the past decades, inhibitors that selectively block the reuptake of NE or DA, or two of the three neurotransmitters simultaneously, have become available for the treatment of CNS disorders including depression, anxiety, obsessive compulsive disorder (OCD), attention deficit hyperactivity disorder (ADHD), pain and urinary incontinence. Two representative recent reviews (Liu and Molino, *Annual Reports in Medicinal Chemistry*, 42:13 (2007); Walter, *Drug Dev. Res.*, 65:97 (2005)) on monoamine reuptake inhibitors summarize the history and recent development in the monoamine reuptake inhibitor area.

Currently, the major effort in the field of monoamine reuptake inhibitors is focused on improving antidepressant efficacy since 30-40% of patients do not respond to treatment with currently available antidepressants. An additional major objective is to enhance the onset of action. Current antidepressants typically require 2-6 weeks of treatment before clinical efficacy is seen. Clinical trials exploring augmentation strategies, in which a DA reuptake inhibitor or a dual NE/DA reuptake inhibitor is combined with an SSRI, have resulted in improved efficacy in depressed patients refractory to SSRI treatment alone (Patkar et. al, *J. Clin. Psychopharmacol.*, 26:653 (2006); Zisook et al, *Biol. Psychiat.*, 59:203 (2006)). The improved results from clinical trials such as these serve to justify the considerable focus on the development of inhibitors that simultaneously block the reuptake of 5-HT, NE and DA. Because of the continued need for better drugs to treat depression and the opportunities for new clinical indications, efforts to discover novel monoamine reuptake inhibitors continue unabated.

Methylphenidate, currently used for the treatment of attention deficit-hyperactivity disorder, is known to be selective for inhibition of the DAT. Also, U.S. Pat. No. 5,444,070 discloses selective inhibitors of dopamine reuptake as treatments for Parkinson's disease, drug addiction or abuse including cocaine and amphetamines.

Selective norepinephrine reuptake inhibitors (NARI) have also been disclosed. U.S. Pat. No. 6,352,986 describes methods of treating attention deficit-hyperactivity disorder (ADHD), addictive disorders, and psychoactive substance use disorders with Reboxetine. Also, Atomoxetine (STRATTERA®) is currently marketed as a selective NET reuptake inhibitor for ADHD.

The use of selective serotonin reuptake inhibitors (SSRI) has been shown to be effective in treating depressive disorders. Sertraline, citalopram, escitalopram, paroxetine, fluoxetine and fluvoxamine are well known examples of SSRIs used to treat disorders such as depression, obsessive compulsive disorder, and panic attacks. There are several known difficulties with the SSRI class of therapeutics, including the slow onset of action, unwanted side effects, and the existence of a significant subset of the population that is not responsive to SSRI therapy. Recent effort in the clinical development of new SSRIs has focused on the treatment of premature ejaculation (PE) by taking advantage of the ejaculation-delaying side effects of SSRIs. Although SSRIs have been prescribed off-label to treat this condition, an SSRI with rapid onset of action and rapid clearance could be preferred for on-demand treatment of PE. Dapoxetine (LY210448), an SSRI structurally related to fluoxetine with a shorter half-life, was reported to be an effective and generally well tolerated treatment for men with moderate-to-severe PE in clinical trials (Feret, *Formulary*, 40:227 (2005); Pryor et al, *Lancet*, 368:929 (2006)).

Selective inhibitors of DAT, NET, and SERT reuptake may also be co-administered with each other or with other drugs. U.S. Pat. No. 5,532,244 discloses the use of serotonin reuptake inhibitors in combination with a serotonin 1A antagonist for the treatment of obsessive-compulsive disorder, depression, and obesity. The use of a serotonin or norepinephrine reuptake inhibitor in combination with a neurokinin-1 receptor antagonist has been disclosed in U.S. Pat. No. 6,121,261 for the treatment of ADHD. U.S. Pat. No. 4,843,071 discloses the use of a norepinephrine reuptake inhibitor in combination with a norepinephrine precursor in the treatment of obesity, drug abuse, or narcolepsy. U.S. Pat. No. 6,596,741 discloses the use of a NE, DA, or 5-HT inhibitor with either a neurokinin-1 receptor antagonist or a serotonin-1A antagonist for the treatment of a wide variety of conditions.

Also advantageous is the use of compounds that inhibit one or more of the neurotransmitters at the same time. The antidepressant qualities of the dual NET and SERT reuptake inhibitor duloxetine is disclosed in European Patent No. EP 273658. Venlafaxine is disclosed in U.S. Pat. No. 4,535,186 as a reuptake inhibitor of both NE and 5-HT for the treatment of depressive disorders. U.S. Pat. No. 6,635,675 discloses the use of the dual NE and 5-HT reuptake inhibitor milnacipran for the treatment of chronic fatigue syndrome and fibromyalgia syndrome. In addition, dual NE and 5-HT reuptake inhibitors are also disclosed in U.S. Pat. No. 6,136,083 for the treatment of depression. It is also recognized that compounds which inhibit the reuptake of NE, DA, and 5-HT in varying ratios not specifically mentioned here would also be advantageous.

As the first SNRI drug approved, venlafaxine has become one of the first-line choices for depression and anxiety disorder. An active metabolite, desvenlafaxine, is also under clinical development for the treatment of major depressive disorders. Preclinical studies also indicate that desvenlafaxine may be effective in relieving vasomotor symptoms associated with menopause (e.g., hot flashes and night sweats) (Sorbera, et al, *Drugs of Future.*, 31:304 (2006); Albertazzi, *J. Br. Menopause Soc.*, 12:7 (2006)). Desvenlafaxine is reported to be in clinical development for the treatment of fibromyalgia and neuropathic pain, as well as vasomotor symptoms associated with menopause.

In addition to treating major depressive disorder, duloxetine was approved as the first agent for the treatment of painful diabetic neuropathy in the U.S. It also has been used for stress urinary incontinence in women in Europe. In 2007, duloxetine was approved for the treatment of generalized anxiety disorder in the U.S. Most recently, it was approved by the FDA for the management of fibromyalgia.

Milnacipran is currently available for use as an antidepressant in several countries outside the U.S. It is also under clinical development to assess its potential role in the treatment of fibromyalgia syndrome.

After more than a decade of use, bupropion, is considered a safe and effective antidepressant, suitable for use as first-line treatment. In addition, it is approved for smoking cessation and seasonal affective disorder. It is also prescribed off-label to treat the sexual dysfunction induced by SSRIs. Bupropion is often referred to as an atypical antidepressant. It has much lower affinity for the monoamine transporters compared with other monoamine reuptake inhibitors. The mechanism of action of bupropion is still uncertain but may be related to inhibition of dopamine and norepinephrine reuptake transporters as a result of active metabolites. In a recently reported clinical trial, bupropion extended release (XL) had a sexual tolerability profile significantly better than that of escitalopram with similar remission rates and Hospital Anxiety and Depression (HAD) total scores in patients with major despressive disorder (Clayton et al. *J. Clin. Psychiatry*, 67:736 (2006)).

Treating illnesses by inhibiting the reuptake of all three of the monoamines either through combination therapy or "triple inhibitors" may have clinical benefit as well. Triple inhibitors are considered to be the next generation antidepressant (Liang and Richelson, *Primary Psychiatry*, 15(4):50 (2008)). Rationale for inclusion of a dopamine enhancing component in anti-depressant therapy includes observed deficits in dopaminergic function, the success of combination therapy with dopamine agonists and traditional anti-depressants, and an increased sensitivity in dopamine receptors due to chronic anti-depressant administration (Skolnick et al., *Life Sciences*, 73:3175-3179 (2003)). Combination therapy with an SSRI and a noradrenaline and dopamine reuptake inhibitor was shown to be more efficacious in patients with treatment-resistant depression (Lam et al, *J. Clin. Psychiatry*, 65(3):337-340 (2004)). Clinical studies using the combination of bupropion and an SSRI or SNRI have showed improved efficacy for the treatment of MDD in patients refractory to the treatment with SSRIs, SNRIs, or bupropion alone (Zisook et al, *Biol. Psychiat.*, 59:203 (2006); Papkostas, *Depression and Anxiety*, 23:178-181 (2006); Trivedi et al, *New Engl. J. Med.*, 354:1243 (2006)). Other studies using methylphenidate, both immediate release and extended release formula, have shown it to be effective as an augmenting agent in treatment-resistant depression (Patkar et al, *J. Clin. Psychopharmacol.*, 26:653 (2006); Masand et al, *Depression and Anxiety*, 7:89 (1998)). In addition, the combination of bupropion-SR with either SSRIs or norepinephrine and dopamine reuptake inhibitors was found to induce less sexual dysfunction than monotherapy (Kennedy et al, *J. Clin. Psychiatry*, 63 (3):181-186 (2002)). As such, inhibitory activity against DA reuptake, in addition to NE and 5-HT reuptake, is expected to provide a more rapid onset of antidepressant effect than other mixed inhibitors which are selective for NET and SERT over DAT. PCT International Publication Nos. WO 03/101453 and WO 97/30997 disclose a class of compounds which are active against all three monoamine transporters. Also, PCT International Patent Publication No. WO 03/049736 discloses a series of 4-substituted piperidines, each of which displays similar activity against DA, NE, and 5-HT transporters. Bicyclo[2.2.1]heptanes (Axford et al., *Bioorg. Med. Chem. Lett.*, 13:3277-3280 (2003)) and azabicyclo[3.1.0]hexanes (Skolnick et al., *Eur. J. Pharm.*, 461:99-104 (2003)) are also described as triple inhibitors of the three monoamine transporters. 1-(3,4-Dichlorophenyl)-3-azabicyclo[3.1.0]hexane has been shown to be efficacious in treating depression in clinical trials (Beer et al, *J. Clin. Pharmacol.*, 44:1360-1367 (2004)). Current widely used anti-obesity drug sibutramine is believed to work through the inhibition of all three transporters DAT, SERT, and NET (Ryan, *Pharmacotherapy of Obesity*, 245-266 (2004)).

Recent drug approvals with SNRIs for treatment of fibromyalgia and diabetic neuropathy reinforce the utility of this drug class in the treatment of neuropathic pain. Other largely untapped areas which remain to be exploited with this drug class include sexual dysfunction, such as premature ejaculation, irritable bowel syndrome, obesity, neurodegenerative diseases such as Parkinson's disease, restless leg syndrome, and substance abuse and addiction.

Klumpp et al., *Organic Letters* 3:2781-2784 (2001) describes the synthesis of compound of formula I via acid catalyzed intramolecular cyclization. No biological activity of this compound is reported in the above-mentioned reference.

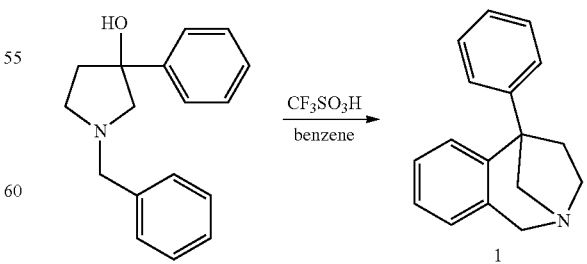

There is still a large need for compounds that block the reuptake of norepinephrine, dopamine, and serotonin and treat various neurological and psychological disorders.

The present invention is directed to achieving this objective.

SUMMARY OF THE INVENTION

The present invention relates to compounds represented by the formula (I) having the following structure:

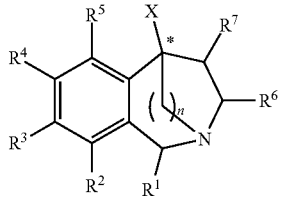

wherein:
n is 1 or 2;
when n is 1, the carbon atom designated * is in the R or S configuration (carbon atom designated * is achiral when n is 2);
X is phenyl, naphthyl, benzofuranyl, benzothiophenyl, indolyl, or indazolyl, each optionally substituted from 1-4 times with substituents as defined below in $R^{13}$;
$R^1$ is H;
$R^2$, $R^4$, and $R^5$ are each independently H, halogen, methyl, ethyl, isopropyl, hydroxy, methoxy, trifluoromethoxy, difluoromethoxy, —CN, —$NH_2$, —NHMe, or —$NMe_2$;
$R^3$ is H, halogen, —$NR^8R^9$, —$OR^{10}$, —$S(O)_pR^{11}$, —CN, —$C(O)R^{11}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, where each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{12}$; or
$R^3$ is a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substituents selected from the group consisting of $C_1$-$C_3$ alkyl, —$C(O)R^{11}$, and —$S(O)_pR^{11}$; or
$R^3$ is a monocyclic or bicyclic aryl or heteroaryl selected from the group consisting of phenyl, pyridyl, 2-oxo-pyridin-1 (2H)-yl, pyrimidinyl, pyridazinyl, 6-oxopyridazin-1(6H)-yl, pyrazinyl, triazinyl, pyranyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indanyl, indenyl, indolyl, isoindolyl, benzofuranyl, benzothiophenyl, indolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, naphthyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, 3-thio-[1,2,4]triazolo[4,3-a]pyridin-2 (3H)-yl, and other 5- or 6-membered aromatic or non-aromatic monocyclic carbocycles or heterocycles, or [5,5]-, [6,5]-, [6,6]-, or [6,7]-fused bicyclic carbocycles or heterocycles containing 1-5 heteroatoms selected from the group consisting of oxygen, nitrogen, and sulfur, each optionally substituted from 1 to 4 times with substituents as defined below in $R^{13}$; or
$R^3$ is —$OR^{14}$;
$R^6$ and $R^7$ are each independently H, methyl, ethyl, gem-dimethyl, or gem-diethyl;
$R^8$ and $R^9$ are each independently selected from the group consisting of H, —$C(O)R^{11}$, $C_1$-$C_4$ alkyl, $C_3$-$C_6$ cycloalkyl, and $C_4$-$C_7$ cycloalkylalkyl, where each of $C_1$-$C_4$ alkyl, $C_3$-$C_6$ cycloalkyl, and $C_4$-$C_7$ cycloalkylalkyl is optionally substituted from 1 to 3 times with substituents as defined below in $R^{10}$; or
$R^8$ and $R^9$ are each independently selected from the group consisting of phenyl, benzyl, and other 5- or 6-membered monocyclic heterocycles, where each of the phenyl, benzyl, and 5- or 6-membered monocyclic heterocycle is optionally substituted from 1 to 3 times with substituents as defined below in $R^{13}$; or
$R^8$ and $R^9$ are taken together with the nitrogen to which they are attached to form a saturated or partially saturated monocyclic or fused bicyclic heterocycle selected from the group consisting of piperidine, pyrrolidine, morpholine, thiomorpholine, [1,2]oxazinane, isoxazolidine, 2-oxopiperidinyl, 2-oxopyrrolidinyl, 3-oxomorpholino, 3-oxothiomorpholino, 5,6,7,8-tetrahydroimidazo[1,2-a]pyrazine, 5,6,7,8-tetrahydro-[1,2,4]triazolo[4,3-a]pyrazine, and other monocyclic or fused bicyclic heterocycles containing 1-4 heteroatoms selected from oxygen, nitrogen and sulfur, wherein the heterocycle is attached to the benzazepine core via the nitrogen atom, and is optionally substituted from 1 to 3 times with a substituent selected independently at each occurrence thereof from the group consisting of halogen, cyano, —$OR^{10}$, —$NR^{10}R^{11}$, —$S(O)_pR^{11}$, —$C(O)R^{11}$, oxo, and $C_1$-$C_4$ alkyl, where each $C_1$-$C_4$ alkyl is optionally substituted from 1 to 3 times with substituents as defined below in $R^{12}$; or
$R^8$ and $R^9$ are taken together with the nitrogen to which they are attached to form a heterocycle selected from the group consisting of piperazine, 2-oxopiperazinyl, 2-oxo-1,4-diazepanyl, 5-oxo-1,4-diazepanyl, 1,4-diazepane, and other heterocycles containing at least two nitrogens in the ring, where the heterocycle is optionally substituted on a ring carbon from 1 to 3 times with a substituent selected independently at each occurrence thereof from the group consisting of halogen, cyano, —$OR^{10}$, —$NR^{10}R^{11}$, —$S(O)_pR^{11}$, —$C(O)R^{11}$, oxo, and $C_1$-$C_4$ alkyl, or on one or more of the at least two nitrogens in the ring from 1 to 3 times with a substituent selected independently at each occurrence thereof from the group consisting of $S(O)_pR^{11}$, —$C(O)R^{11}$, $C_1$-$C_4$ alkyl, aryl, and heteroaryl, wherein each $C_1$-$C_4$ alkyl is optionally substituted from 1 to 3 times with substituents as defined below in $R^{12}$ and wherein each of the aryl or heteroaryl groups is optionally substituted from 1 to 4 times with substituents as defined below in $R^{13}$; or
$R^8$ and $R^9$ are taken together with the nitrogen to which they are attached to form a heterocycle selected from the group consisting of piperazine, 2-oxopiperazinyl, 2-oxo-1,4-diazepanyl, 5-oxo-1,4-diazepanyl, 1,4-diazepane, and other heterocycles containing one additional nitrogen atom in the ring, where the heterocycle is optionally substituted on the additional nitrogen atom with a substituent selected independently at each occurrence thereof from the group consisting of phenyl, benzyl, and 5- or 6-membered aromatic heterocycles containing 1-3 heteroatoms selected from the group consisting of oxygen, nitrogen, and sulfur, where each of the phenyl, benzyl, and 5- and 6-membered heterocycle is optionally substituted from 1 to 3 times with substituents as defined below in $R^{13}$; or when $R^3$ is —$NR^8R^9$ or —$C(O)NR^8R^9$, either $R^8$ or $R^9$ is a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substituents selected from the group consisting of $C_1$-$C_3$ alkyl, —$C(O)R^{11}$, and —$S(O)_pR^{11}$, or either $R^8$ or $R^9$ is a $C_1$-$C_3$ alkyl substituted with a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substitutents selected from the group consisting of $C_1$-$C_3$ alkyl, —$C(O)R^{11}$, and —$S(O)_pR^{11}$;

$R^{10}$ is selected from the group consisting of H, OH, alkoxy, $C_1$-$C_4$ alkyl, $C_3$-$C_6$ cycloalkyl, $C_4$-$C_7$ cycloalkylalkyl, and —$C(O)R^{11}$, where each of $C_1$-$C_4$ alkyl, $C_3$-$C_6$ cycloalkyl, and $C_4$-$C_7$ cycloalkylalkyl is optionally substituted from 1 to 3 times with substituents as defined below in $R^{12}$;

$R^{11}$ is selected from the group consisting of —$NR^8R^9$, $C_1$-$C_4$ alkyl, $C_3$-$C_6$ cycloalkyl, and $C_4$-$C_7$ cycloalkylalkyl, where each of $C_1$-$C_4$ alkyl, $C_3$-$C_6$ cycloalkyl, and $C_4$-$C_7$ cycloalkylalkyl is optionally substituted from 1 to 3 times with substituents as defined below in $R^{12}$; or $R^{10}$ and $R^{11}$ are each independently selected from the group consisting of phenyl, benzyl, pyridazinyl, pyrimidinyl, pyrazinyl, 5- or 6-membered aromatic monocyclic heterocycles, and [5,5]-, [6,5]-, [6,6]-, or [6,7]-fused bicyclic carbocycles or heterocycles, the heterocycles containing 1-5 heteroatoms selected from the group consisting of oxygen, nitrogen, and sulfur, optionally substituted from 1 to 4 times with substituents as defined below in $R^{13}$; or when $R^{10}$ and $R^{11}$ are together attached to a nitrogen, $R^{10}$ and $R^{11}$ are taken together with the nitrogen to which they are attached to form a heterocycle selected from the group consisting of piperidine, pyrrolidine, piperazine, 1,4-diazepane, morpholine, thiomorpholine, and other heterocycles containing 1-4 heteroatoms selected from the group consisting of oxygen, nitrogen, and sulfur, where the heterocycle is optionally substituted from 1 to 3 times with a substituent selected independently at each occurrence thereof from the group consisting of halogen, cyano, —$OR^8$, —$S(O)_pR^8$, —$C(O)R^8$, —$C(O)NR^8R^9$ and $C_1$-$C_4$ alkyl, where each of $C_1$-$C_4$ alkyl is optionally substituted from 1 to 3 times with substituents as defined below in $R^{12}$;

p is 0, 1, or 2;

$R^{12}$ is independently selected at each occurrence from a substituent in the group consisting of —CN, halogen, $C(O)R^{11}$, $C_1$-$C_3$ alkyl, —$OR^{10}$, —$NR^8R^9$, —$S(O)_pR^{11}$, aryl, and heteroaryl, where each of the aryl or heteroaryl groups is optionally substituted from 1 to 4 times with substituents as defined below in $R^{13}$;

$R^{13}$ is independently selected at each occurrence from a substituent in the group consisting of halogen, —$NO_2$, —$OR^{10}$, —$NR^8R^9$, —$NR^{10}C(O)_2R^{11}$, —$NR^{10}C(O)NR^{10}R^{11}$, —$S(O)_pR^{11}$, —CN, —$C(O)R^{11}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined above in $R^{12}$; and $R^{14}$ is a 5- or 6-membered aromatic or non-aromatic monocyclic carbocycle or heterocycle, or [5,5]-, [6,5]-, [6,6]-, or [6,7]-fused bicyclic carbocycle or heterocycle containing 1-5 heteroatoms selected from the group consisting of oxygen, nitrogen, and sulfur, optionally substituted from 1 to 4 times with substituents as defined above in $R^{13}$;

with the proviso that when $R^1$-$R^7$ are all hydrogen, X cannot be phenyl;

or an oxide thereof, a pharmaceutically acceptable salt thereof, a solvate thereof, or prodrug thereof.

Another aspect of the present invention relates to compounds represented by the formula (I) having the following structure:

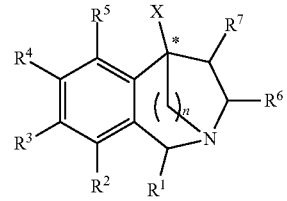

wherein:

n is 1 or 2;

when n is 1, the carbon atom designated * is in the R or S configuration;

X is phenyl, optionally substituted from 1-4 times with substituents as defined below in $R^{13}$;

$R^1$ is H;

$R^2$, $R^4$, and $R^5$ are each independently H, halogen, methyl, ethyl, isopropyl, hydroxy, methoxy, trifluoromethoxy, difluoromethoxy, —CN, —$NH_2$, —NHMe, or —$NMe_2$;

$R^3$ is H, halogen, —$NR^8R^9$, —$OR^{10}$, —$S(O)_pR^{11}$, —CN, —$C(O)R^{11}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, where each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{12}$;

$R^3$ is a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substitutents selected from the group consisting of $C_1$-$C_3$ alkyl, —$C(O)R^{11}$, and —$S(O)_pR^{11}$; or $R^3$ is a monocyclic or bicyclic aryl or heteroaryl selected from the group consisting of phenyl, pyridyl, 2-oxo-pyridin-1 (2H)-yl, pyrimidinyl, pyridazinyl, 6-oxopyridazin-1(6H)-yl, pyrazinyl, triazinyl, pyranyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indanyl, indenyl, indolyl, isoindolyl, benzofuranyl, benzothiophenyl, indolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, naphthyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, 3-thio-[1,2,4]triazolo[4,3-a]pyridin-2(3H)-yl, and other 5- or 6-membered aromatic or non-aromatic monocyclic carbocycles or heterocycles, or [5,5]-, [6,5]-, [6,6]-, or [6,7]-fused bicyclic carbocycles or heterocycles containing 1-5 heteroatoms selected from the group consisting of oxygen, nitrogen, and sulfur, each optionally substituted from 1 to 4 times with substituents as defined below in $R^{13}$; or $R^3$ is $-OR^{14}$;

$R^6$ and $R^7$ are each independently H, methyl, ethyl, gem-dimethyl, or gem-diethyl;

$R^8$ and $R^9$ are each independently selected from the group consisting of H, $-C(O)R^{11}$, $C_1$-$C_4$ alkyl, $C_3$-$C_6$ cycloalkyl, and $C_4$-$C_7$ cycloalkylalkyl, where each of $C_1$-$C_4$ alkyl, $C_3$-$C_6$ cycloalkyl, and $C_4$-$C_7$ cycloalkylalkyl is optionally substituted from 1 to 3 times with substituents as defined below in $R^{10}$; or $R^8$ and $R^9$ are each independently selected from the group consisting of phenyl, benzyl, and other 5- or 6-membered monocyclic heterocycles, where each of the phenyl, benzyl, and 5- or 6-membered monocyclic heterocycle is optionally substituted from 1 to 3 times with substituents as defined below in $R^{13}$; or $R^8$ and $R^9$ are taken together with the nitrogen to which they are attached to form a saturated or partially saturated monocyclic or fused bicyclic heterocycle selected from the group consisting of piperidine, pyrrolidine, morpholine, thiomorpholine, [1,2]oxazinane, isoxazolidine, 2-oxopiperidinyl, 2-oxopyrrolidinyl, 3-oxomorpholino, 3-oxothiomorpholino, 5,6,7,8-tetrahydroimidazo[1,2-a]pyrazine, 5,6,7,8-tetrahydro-[1,2,4]triazolo[4,3-a]pyrazine, and other monocyclic or fused bicyclic heterocycles containing 1-4 heteroatoms selected from oxygen, nitrogen and sulfur, wherein the heterocycle is attached to the benzazepine core via the nitrogen atom, and is optionally substituted from 1 to 3 times with a substituent selected independently at each occurrence thereof from the group consisting of halogen, cyano, $-OR^{10}$, $-NR^{10}R^{11}$, $-S(O)_pR^{11}$, $-C(O)R^{11}$, oxo, and $C_1$-$C_4$ alkyl, where each $C_1$-$C_4$ alkyl is optionally substituted from 1 to 3 times with substituents as defined below in $R^{12}$; or $R^8$ and $R^9$ are taken together with the nitrogen to which they are attached to form a heterocycle selected from the group consisting of piperazine, 2-oxopiperazinyl, 2-oxo-1,4-diazepanyl, 5-oxo-1,4-diazepanyl, 1,4-diazepane, and other heterocycles containing at least two nitrogens in the ring, where the heterocycle is optionally substituted on a ring carbon from 1 to 3 times with a substituent selected independently at each occurrence thereof from the group consisting of halogen, cyano, $-OR^{10}$, $-NR^{10}R^{11}$, $-S(O)_pR^{11}$, $-C(O)R^{11}$, oxo, and $C_1$-$C_4$ alkyl, or on one or more of the at least two nitrogens in the ring from 1 to 3 times with a substituent selected independently at each occurrence thereof from the group consisting of $S(O)_pR^{11}$, $-C(O)R^{11}$, $C_1$-$C_4$ alkyl, aryl, and heteroaryl, wherein each $C_1$-$C_4$ alkyl is optionally substituted from 1 to 3 times with substituents as defined below in $R^{12}$ and wherein each of the aryl or heteroaryl groups is optionally substituted from 1 to 4 times with substituents as defined below in $R^{13}$; or $R^8$ and $R^9$ are taken together with the nitrogen to which they are attached to form a heterocycle selected from the group consisting of piperazine, 2-oxopiperazinyl, 2-oxo-1,4-diazepanyl, 5-oxo-1,4-diazepanyl, 1,4-diazepane, and other heterocycles containing one additional nitrogen atom in the ring, where the heterocycle is optionally substituted on the additional nitrogen atom with a substituent selected independently at each occurrence thereof from the group consisting of phenyl, benzyl, and 5- or 6-membered aromatic heterocycles containing 1-3 heteroatoms selected from the group consisting of oxygen, nitrogen, and sulfur, where each of the phenyl, benzyl, and 5- and 6-membered heterocycle is optionally substituted from 1 to 3 times with substituents as defined below in $R^{13}$; or when $R^3$ is $-NR^8R^9$ or $-C(O)NR^8R^9$, either $R^8$ or $R^9$ is a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substituents selected from the group consisting of $C_1$-$C_3$ alkyl, $-C(O)R^{11}$, and $-S(O)_pR^{11}$, or either $R^8$ or $R^9$ is a $C_1$-$C_3$ alkyl substituted with a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substitutents selected from the group consisting of $C_1$-$C_3$ alkyl, $-C(O)R^{11}$, and $-S(O)_pR^{11}$;

$R^{10}$ is selected from the group consisting of H, OH, alkoxy, $C_1$-$C_4$ alkyl, $C_3$-$C_6$ cycloalkyl, $C_4$-$C_7$ cycloalkylalkyl, and $-C(O)R^{11}$, where each of $C_1$-$C_4$ alkyl, $C_3$-$C_6$ cycloalkyl, and $C_4$-$C_7$ cycloalkylalkyl is optionally substituted from 1 to 3 times with substituents as defined below in $R^{12}$;

$R^{11}$ is selected from the group consisting of $-NR^8R^9$, $C_1$-$C_4$ alkyl, $C_3$-$C_6$ cycloalkyl, and $C_4$-$C_7$ cycloalkylalkyl, where each of $C_1$-$C_4$ alkyl, $C_3$-$C_6$ cycloalkyl, and $C_4$-$C_7$ cycloalkylalkyl is optionally substituted from 1 to 3 times with substituents as defined below in $R^{12}$; or $R^{10}$ and $R^{11}$ are each independently selected from the group consisting of phenyl, benzyl, pyridazinyl, pyrimidinyl, pyrazinyl, 5- or 6-membered aromatic monocyclic heterocycles, and [5,5]-, [6,5]-, [6,6]-, or [6,7]-fused bicyclic carbocycles or heterocycles, the heterocycles containing 1-5 heteroatoms selected from the group consisting of oxygen, nitrogen, and sulfur, optionally substituted from 1 to 4 times with substituents as defined below in $R^{13}$; or when $R^{10}$ and $R^{11}$ are together attached to a nitrogen, $R^{10}$ and $R^{11}$ are taken together with the nitrogen to which they are attached to form a heterocycle selected from the group consisting of piperidine, pyrrolidine, piperazine, 1,4-diazepane, morpholine, thiomorpholine, and other heterocycles containing 1-4 heteroatoms selected from the group consisting of oxygen, nitrogen, and sulfur, where the heterocycle is optionally substituted from 1 to 3 times with a substituent selected independently at each occurrence thereof from the group consisting of halogen, cyano, $-OR^8$, $-S(O)_pR^8$, $-C(O)R^8$, $-C(O)NR^8R^9$ and $C_1$-$C_4$ alkyl, where each of $C_1$-$C_4$ alkyl is optionally substituted from 1 to 3 times with substituents as defined below in $R^{12}$;

p is 0, 1, or 2;

$R^{12}$ is independently selected at each occurrence from a substituent in the group consisting of $-CN$, halogen, $C(O)R^{11}$, $C_1$-$C_3$ alkyl, $-OR^{10}$, $-NR^8R^9$, $-S(O)_pR^{11}$, aryl, and heteroaryl, where each of the aryl or heteroaryl groups is optionally substituted from 1 to 4 times with substituents as defined above in $R^{13}$;

$R^{13}$ is independently selected at each occurrence from a substituent in the group consisting of halogen, —$NO_2$, —$OR^{10}$, —$NR^8R^9$, —$NR^{10}C(O)$ $NR^{10}R^{11}$, —$S(O)_pR^{11}$, —CN, —$C(O)R^{11}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined above in $R^{12}$; and $R^{14}$ is a 5- or 6-membered aromatic or non-aromatic monocyclic carbocycle or heterocycle, or [5,5]-, [6,5]-, [6,6]-, or [6,7]-fused bicyclic carbocycle or heterocycle containing 1-5 heteroatoms selected from the group consisting of oxygen, nitrogen, and sulfur, optionally substituted from 1 to 4 times with substituents as defined below in $R^{13}$;

with the proviso that when $R^1$-$R^7$ are all hydrogen, X cannot be phenyl;

or an oxide thereof, a pharmaceutically acceptable salt thereof, a solvate thereof, or prodrug thereof.

The present invention also relates to pharmaceutical compositions, methods of treatment of various neurological and psychological disorders, and the use of the compounds in combination therapy.

DETAILED DESCRIPTION OF THE INVENTION

The present invention relates to compounds represented by the formula (I) having the following structure:

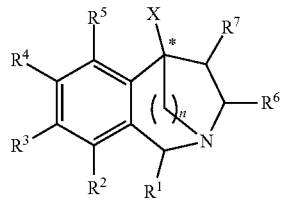

wherein:
n is 1 or 2;
when n is 1, the carbon atom designated * is in the R or S configuration (carbon atom designated * is achiral when n is 2);
X is phenyl, naphthyl, benzofuranyl, benzothiophenyl, indolyl, or indazolyl, each optionally substituted from 1-4 times with substituents as defined below in $R^{13}$;
$R^1$ is H;
$R^2$, $R^4$, and $R^5$ are each independently H, halogen, methyl, ethyl, isopropyl, hydroxy, methoxy, trifluoromethoxy, difluoromethoxy, —CN, —$NH_2$, —NHMe, or —$NMe_2$;
$R^3$ is H, halogen, —$NR^8R^9$, —$OR^{10}$, —$S(O)_pR^{11}$, —CN, —$C(O)R^{11}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, where each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{12}$; or
$R^3$ is a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substitutents selected from the group consisting of $C_1$-$C_3$ alkyl, —$C(O)R^{11}$, and —$S(O)_pR^{11}$; or $R^3$ is a monocyclic or bicyclic aryl or heteroaryl selected from the group consisting of phenyl, pyridyl, 2-oxo-pyridin-1 (2H)-yl, pyrimidinyl, pyridazinyl, 6-oxopyridazin-1(6H)-yl, pyrazinyl, triazinyl, pyranyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indanyl, indenyl, indolyl, isoindolyl, benzofuranyl, benzothiophenyl, indolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, naphthyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-c]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-c]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, 3-thio-[1,2,4]triazolo[4,3-a]pyridin-2(3H)-yl, and other 5- or 6-membered aromatic or non-aromatic monocyclic carbocycles or heterocycles, or [5,5]-, [6,5]-, [6,6]-, or [6,7]-fused bicyclic carbocycles or heterocycles containing 1-5 heteroatoms selected from the group consisting of oxygen, nitrogen, and sulfur, each optionally substituted from 1 to 4 times with substituents as defined below in $R^{13}$; or $R^3$ is —$OR^{14}$;

$R^6$ and $R^7$ are each independently H, methyl, ethyl, gem-dimethyl, or gem-diethyl, $R^8$ and $R^9$ are each independently selected from the group consisting of H, —$C(O)R^{11}$, $C_1$-$C_4$ alkyl, $C_3$-$C_6$ cycloalkyl, and $C_4$-$C_7$ cycloalkylalkyl, where each of $C_1$-$C_4$ alkyl, $C_3$-$C_6$ cycloalkyl, and $C_4$-$C_7$ cycloalkylalkyl is optionally substituted from 1 to 3 times with substituents as defined below in $R^{10}$; or $R^8$ and $R^9$ are each independently selected from the group consisting of phenyl, benzyl, and other 5- or 6-membered monocyclic heterocycles, where each of the phenyl, benzyl, and 5- or 6-membered monocyclic heterocycle is optionally substituted from 1 to 3 times with substituents as defined below in $R^{13}$; or $R^8$ and $R^9$ are taken together with the nitrogen to which they are attached to form a saturated or partially saturated monocyclic or fused bicyclic heterocycle selected from the group consisting of piperidine, pyrrolidine, morpholine, thiomorpholine, [1,2]oxazinane, isoxazolidine, 2-oxopiperidinyl, 2-oxopyrrolidinyl, 3-oxomorpholino, 3-oxothiomorpholino, 5,6,7,8-tetrahydroimidazo[1,2-a]pyrazine, 5,6,7,8-tetrahydro-[1,2,4]triazolo[4,3-a]pyrazine, and other monocyclic or fused bicyclic heterocycles containing 1-4 heteroatoms selected from oxygen, nitrogen and sulfur, wherein the heterocycle is attached to the benzazepine core via the nitrogen atom, and is optionally substituted from 1 to 3 times with a substituent selected independently at each occurrence thereof from the group consisting of halogen, cyano, —$OR^{10}$, —$NR^{10}R^{11}$, —$S(O)_pR^{11}$, —$C(O)R^{11}$, oxo, and $C_1$-$C_4$ alkyl, where each $C_1$-$C_4$ alkyl is optionally substituted from 1 to 3 times with substituents as defined below in $R^{12}$; or $R^8$ and $R^9$ are taken together with the nitrogen to which they are attached to form a heterocycle selected from the group consisting of piperazine, 2-oxopiperazinyl, 2-oxo-1,4-diazepanyl, 5-oxo-1,4-diazepanyl, 1,4-diazepane, and other heterocycles containing at least two nitrogens in the ring, where the heterocycle is optionally substituted on a ring carbon from 1 to 3 times with a substituent selected independently at each occurrence thereof from the group consisting of halogen, cyano, —$OR^{10}$, —$NR^{10}R^{11}$, —$S(O)_pR^{11}$, —$C(O)R^{11}$, oxo, and $C_1$-$C_4$ alkyl, or on one or more of the at least two nitrogens in the ring from 1 to 3 times with a substituent selected independently at each occurrence thereof from the group consisting of $S(O)_pR^{11}$, —$C(O)R^{11}$, $C_1$-$C_4$ alkyl, aryl, and heteroaryl, wherein each $C_1$-$C_4$ alkyl is optionally substituted from 1 to 3 times with substituents as defined below in $R^{12}$ and wherein each of the aryl or heteroaryl groups is optionally substituted from 1 to 4 times with substituents as defined below in $R^{13}$; or $R^8$ and $R^9$ are taken together with the nitrogen to which they are attached to form a heterocycle selected from the group consisting of piperazine, 2-oxopiperazinyl, 2-oxo-1,4-diazepanyl, 5-oxo-1,4-diazepanyl, 1,4-diazepane, and other heterocycles containing one additional nitrogen atom in the ring, where the heterocycle is optionally substituted on the additional nitrogen atom with a substituent selected independently at each occurrence thereof from the group consisting of phenyl, benzyl, and 5- or 6-membered aromatic heterocycles containing 1-3 heteroatoms selected from the group consisting of oxygen, nitrogen, and sulfur, where each of the phenyl, benzyl, and 5- and 6-membered heterocycle is optionally substituted from 1 to 3 times with substituents as defined below in $R^{13}$; or when $R^3$ is —$NR^8R^9$ or —$C(O)NR^8R^9$, either $R^8$ or $R^9$ is a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substituents selected from the group consisting of $C_1$-$C_3$ alkyl, —$C(O)R^{11}$, and —$S(O)_pR^{11}$, or either $R^8$ or $R^9$ is a $C_1$-$C_3$ alkyl substituted with a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substituents selected from the group consisting of $C_1$-$C_3$ alkyl, —$C(O)R^{11}$, and —$S(O)_pR^{11}$;

$R^{10}$ is selected from the group consisting of H, OH, alkoxy, $C_1$-$C_4$ alkyl, $C_3$-$C_6$ cycloalkyl, $C_4$-$C_7$ cycloalkylalkyl, and —$C(O)R^{11}$, where each of $C_1$-$C_4$ alkyl, $C_3$-$C_6$ cycloalkyl, and $C_4$-$C_7$ cycloalkylalkyl is optionally substituted from 1 to 3 times with substituents as defined below in $R^{12}$;

$R^{11}$ is selected from the group consisting of —$NR^8R^9$, $C_1$-$C_4$ alkyl, $C_3$-$C_6$ cycloalkyl, and $C_4$-$C_7$ cycloalkylalkyl, where each of $C_1$-$C_4$ alkyl, $C_3$-$C_6$ cycloalkyl, and $C_4$-$C_7$ cycloalkylalkyl is optionally substituted from 1 to 3 times with substituents as defined below in $R^{12}$; or $R^{10}$ and $R^{11}$ are each independently selected from the group consisting of phenyl, benzyl, pyridazinyl, pyrimidinyl, pyrazinyl, 5- or 6-membered aromatic monocyclic heterocycles, and [5,5]-, [6,5]-, [6,6]-, or [6,7]-fused bicyclic carbocycles or heterocycles, the heterocycles containing 1-5 heteroatoms selected from the group consisting of oxygen, nitrogen, and sulfur, optionally substituted from 1 to 4 times with substituents as defined below in $R^{13}$; or when $R^{10}$ and $R^{11}$ are together attached to a nitrogen, $R^{10}$ and $R^{11}$ are taken together with the nitrogen to which they are attached to form a heterocycle selected from the group consisting of piperidine, pyrrolidine, piperazine, 1,4-diazepane, morpholine, thiomorpholine, and other heterocycles containing 1-4 heteroatoms selected from the group consisting of oxygen, nitrogen, and sulfur, where the heterocycle is optionally substituted from 1 to 3 times with a substituent selected independently at each occurrence thereof from the group consisting of halogen, cyano, —$OR^8$, —$S(O)_pR^8$, —$C(O)R^8$, —$C(O)NR^8R^9$ and $C_1$-$C_4$ alkyl, where each of $C_1$-$C_4$ alkyl is optionally substituted from 1 to 3 times with substituents as defined below in $R^{12}$;

p is 0, 1, or 2;

$R^{12}$ is independently selected at each occurrence from a substituent in the group consisting of —CN, halogen, $C(O)R^{11}$, $C_1$-$C_3$ alkyl, —$OR^{10}$, —$NR^8R^9$, —$S(O)_pR^{11}$, aryl, and heteroaryl, where each of the aryl or heteroaryl groups is optionally substituted from 1 to 4 times with substituents as defined below in $R^{13}$;

$R^{13}$ is independently selected at each occurrence from a substituent in the group consisting of halogen, —$NO_2$, —$OR^{10}$, —$NR^8R^9$, —$NR^{10}C(O)_2R^{11}$, —$NR^{10}C(O)NR^{10}R^{11}$, —$S(O)_pR^{11}$, —CN, —$C(O)R^{11}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined above in $R^{12}$; and $R^{14}$ is a 5- or 6-membered aromatic or non-aromatic monocyclic carbocycle or heterocycle, or [5,5]-, [6,5]-, [6,6]-, or [6,7]-fused bicyclic carbocycle or heterocycle containing 1-5 heteroatoms selected from the group consisting of oxygen, nitrogen, and sulfur, optionally substituted from 1 to 4 times with substituents as defined above in $R^{13}$;

with the proviso that when $R^1$-$R^7$ are all hydrogen, X cannot be phenyl;

or an oxide thereof, a pharmaceutically acceptable salt thereof, a solvate thereof, or prodrug thereof.

The present invention also relates to compounds represented by the formula (I) having the following structure:

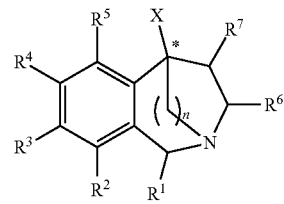

wherein:

n is 1 or 2;

when n is 1, the carbon atom designated * is in the R or S configuration;

X is phenyl, optionally substituted from 1-4 times with substituents as defined below in $R^{13}$;

$R^1$ is H;

$R^2$, $R^4$, and $R^5$ are each independently H, halogen, methyl, ethyl, isopropyl, hydroxy, methoxy, trifluoromethoxy, difluoromethoxy, —CN, —$NH_2$, —NHMe, or —$NMe_2$;

$R^3$ is H, halogen, —$NR^8R^9$, —$OR^{10}$, —$S(O)_pR^{11}$, —CN, —$C(O)R^{11}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, where each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{12}$;

$R^3$ is a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substitutents selected from the group consisting of $C_1$-$C_3$ alkyl, —C(O)$R^{11}$, and —S(O)$_p R^{11}$; or $R^3$ is a monocyclic or bicyclic aryl or heteroaryl selected from the group consisting of phenyl, pyridyl, 2-oxo-pyridin-1 (2H)-yl, pyrimidinyl, pyridazinyl, 6-oxopyridazin-1(6H)-yl, pyrazinyl, triazinyl, pyranyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indanyl, indenyl, indolyl, isoindolyl, benzofuranyl, benzothiophenyl, indolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, naphthyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, 3-thio-[1,2,4]triazolo[4,3-a]pyridin-2(3H)-yl, and other 5- or 6-membered aromatic or non-aromatic monocyclic carbocycles or heterocycles, or [5,5]-, [6,5]-, [6,6]-, or [6,7]-fused bicyclic carbocycles or heterocycles containing 1-5 heteroatoms selected from the group consisting of oxygen, nitrogen, and sulfur, each optionally substituted from 1 to 4 times with substituents as defined below in $R^{13}$; or $R^3$ is —O$R^{14}$;

$R^6$ and $R^7$ are each independently H, methyl, ethyl, gem-dimethyl, or gem-diethyl;

$R^8$ and $R^9$ are each independently selected from the group consisting of H, —C(O)$R^{11}$, $C_1$-$C_4$ alkyl, $C_3$-$C_6$ cycloalkyl, and $C_4$-$C_7$ cycloalkylalkyl, where each of $C_1$-$C_4$ alkyl, $C_3$-$C_6$ cycloalkyl, and $C_4$-$C_7$ cycloalkylalkyl is optionally substituted from 1 to 3 times with substituents as defined below in $R^{10}$; or $R^8$ and $R^9$ are each independently selected from the group consisting of phenyl, benzyl, and other 5- or 6-membered monocyclic heterocycles, where each of the phenyl, benzyl, and 5- or 6-membered monocyclic heterocycle is optionally substituted from 1 to 3 times with substituents as defined below in $R^{13}$; or $R^8$ and $R^9$ are taken together with the nitrogen to which they are attached to form a saturated or partially saturated monocyclic or fused bicyclic heterocycle selected from the group consisting of piperidine, pyrrolidine, morpholine, thiomorpholine, [1,2]oxazinane, isoxazolidine, 2-oxopiperidinyl, 2-oxopyrrolidinyl, 3-oxomorpholino, 3-oxothiomorpholino, 5,6,7,8-tetrahydroimidazo[1,2-a]pyrazine, 5,6,7,8-tetrahydro-[1,2,4]triazolo[4,3-a]pyrazine, and other monocyclic or fused bicyclic heterocycles containing 1-4 heteroatoms selected from oxygen, nitrogen and sulfur, wherein the heterocycle is attached to the benzazepine core via the nitrogen atom, and is optionally substituted from 1 to 3 times with a substituent selected independently at each occurrence thereof from the group consisting of halogen, cyano, —O$R^{10}$, —N$R^{10}R^{11}$, —S(O)$_p R^{11}$, —C(O)$R^{11}$, oxo, and $C_1$-$C_4$ alkyl, where each $C_1$-$C_4$ alkyl is optionally substituted from 1 to 3 times with substituents as defined below in $R^{12}$; or $R^8$ and $R^9$ are taken together with the nitrogen to which they are attached to form a heterocycle selected from the group consisting of piperazine, 2-oxopiperazinyl, 2-oxo-1,4-diazepanyl, 5-oxo-1,4-diazepanyl, 1,4-diazepane, and other heterocycles containing at least two nitrogens in the ring, where the heterocycle is optionally substituted on a ring carbon from 1 to 3 times with a substituent selected independently at each occurrence thereof from the group consisting of halogen, cyano, —O$R^{10}$, —N$R^{10}R^{11}$, —S(O)$_p R^{11}$, —C(O)$R^{11}$, oxo, and $C_1$-$C_4$ alkyl, or on one or more of the at least two nitrogens in the ring from 1 to 3 times with a substituent selected independently at each occurrence thereof from the group consisting of S(O)$_p R^{11}$, —C(O)$R^{11}$, $C_1$-$C_4$ alkyl, aryl, and heteroaryl, wherein each $C_1$-$C_4$ alkyl is optionally substituted from 1 to 3 times with substituents as defined below in $R^{12}$ and wherein each of the aryl or heteroaryl groups is optionally substituted from 1 to 4 times with substituents as defined below in $R^{13}$; or $R^8$ and $R^9$ are taken together with the nitrogen to which they are attached to form a heterocycle selected from the group consisting of piperazine, 2-oxopiperazinyl, 2-oxo-1,4-diazepanyl, 5-oxo-1,4-diazepanyl, 1,4-diazepane, and other heterocycles containing one additional nitrogen atom in the ring, where the heterocycle is optionally substituted on the additional nitrogen atom with a substituent selected independently at each occurrence thereof from the group consisting of phenyl, benzyl, and 5- or 6-membered aromatic heterocycles containing 1-3 heteroatoms selected from the group consisting of oxygen, nitrogen, and sulfur, where each of the phenyl, benzyl, and 5- and 6-membered heterocycle is optionally substituted from 1 to 3 times with substituents as defined below in $R^{13}$; or when $R^3$ is —N$R^8R^9$ or —C(O)N$R^8R^9$, either $R^8$ or $R^9$ is a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substituents selected from the group consisting of $C_1$-$C_3$ alkyl, —C(O)$R^{11}$, and —S(O)$_p R^{11}$, or either $R^8$ or $R^9$ is a $C_1$-$C_3$ alkyl substituted with a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substitutents selected from the group consisting of $C_1$-$C_3$ alkyl, —C(O)$R^{11}$, and —S(O)$_p R^{11}$;

$R^{10}$ is selected from the group consisting of H, OH, alkoxy, $C_1$-$C_4$ alkyl, $C_3$-$C_6$ cycloalkyl, $C_4$-$C_7$ cycloalkylalkyl, and —C(O)$R^{11}$, where each of $C_1$-$C_4$ alkyl, $C_3$-$C_6$ cycloalkyl, and $C_4$-$C_7$ cycloalkylalkyl is optionally substituted from 1 to 3 times with substituents as defined below in $R^{12}$;

$R^{11}$ is selected from the group consisting of —N$R^8R^9$, $C_1$-$C_4$ alkyl, $C_3$-$C_6$ cycloalkyl, and $C_4$-$C_7$ cycloalkylalkyl, where each of $C_1$-$C_4$ alkyl, $C_3$-$C_6$ cycloalkyl, and $C_4$-$C_7$ cycloalkylalkyl is optionally substituted from 1 to 3 times with substituents as defined below in $R^{12}$; or $R^{10}$ and $R^{11}$ are each independently selected from the group consisting of phenyl, benzyl, pyridazinyl, pyrimidinyl, pyrazinyl, 5- or 6-membered aromatic monocyclic heterocycles, and [5,5]-, [6,5]-, [6,6]-, or [6,7]-fused bicyclic carbocycles or heterocycles, the heterocycles containing 1-5 heteroatoms selected from the group consisting of oxygen, nitrogen, and sulfur, optionally substituted from 1 to 4 times with substituents as defined below in $R^{13}$; or when $R^{10}$ and $R^{11}$ are together attached to a nitrogen, $R^{10}$ and $R^{11}$ are taken together with the nitrogen to which they are attached to form a heterocycle selected from the group consisting of piperidine, pyrrolidine, piperazine, 1,4-diazepane, morpholine, thiomorpholine, and other heterocycles containing 1-4 heteroatoms selected from the group consisting of oxygen, nitrogen, and sulfur, where the heterocycle is optionally substituted from 1 to 3 times with a substituent selected independently at each occurrence thereof from the group consisting of halogen, cyano, —$OR^8$, —$S(O)_pR^8$, —$C(O)R^8$, —$C(O)NR^8R^9$ and $C_1$-$C_4$ alkyl, where each of $C_1$-$C_4$ alkyl is optionally substituted from 1 to 3 times with substituents as defined below in $R^{12}$;

p is 0, 1, or 2;

$R^{12}$ is independently selected at each occurrence from a substituent in the group consisting of —CN, halogen, $C(O)R^{11}$, $C_1$-$C_3$ alkyl, —$OR^{10}$, —$NR^8R^9$, —$S(O)_pR^{11}$, aryl, and heteroaryl, where each of the aryl or heteroaryl groups is optionally substituted from 1 to 4 times with substituents as defined above in $R^{13}$;

$R^{13}$ is independently selected at each occurrence from a substituent in the group consisting of halogen, —$NO_2$, —$OR^{10}$, —$NR^8R^9$, —$NR^{10}C(O)_2R^{11}$, —$NR^{10}C(O)NR^{10}R^{11}$, —$S(O)_pR^{11}$, —CN, —$C(O)R^{11}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, where each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined above in $R^{12}$; and $R^{14}$ is a 5- or 6-membered aromatic or non-aromatic monocyclic carbocycle or heterocycle, or [5,5]-, [6,5]-, [6,6]-, or [6,7]-fused bicyclic carbocycle or heterocycle containing 1-5 heteroatoms selected from the group consisting of oxygen, nitrogen, and sulfur, optionally substituted from 1 to 4 times with substituents as defined below in $R^{13}$;

with the proviso that when $R^1$-$R^7$ are all hydrogen, X cannot be phenyl;

or an oxide thereof, a pharmaceutically acceptable salt thereof, a solvate thereof, or prodrug thereof.

As used above, and throughout the description of the invention, the following terms, unless otherwise indicated, shall be understood to have the following meanings:

The term "monocyclic carbocycle" means a monocyclic ring system of to about 8 ring carbon atoms, preferably 5 or 6. The ring is nonaromatic, but may contain one or more carbon-carbon double bonds. Representative monocyclic carbocycles include cyclopentyl, cyclohexyl, cyclopentenyl, cyclohexenyl, and the like.

The term "monocyclic heterocycle" means a monocyclic ring system consisting of about 5 to 8 ring atoms, preferably 5 or 6, in which one or more of the atoms in the ring system is/are element(s) other than carbon, for example, nitrogen, oxygen, or sulfur. The prefix aza, oxa, or thio before heterocycle means that at least a nitrogen, oxygen, or sulfur atom, respectively, is present as a ring atom. A nitrogen atom of a heteroaryl is optionally oxidized to the corresponding N-oxide. The ring is nonaromatic, but may be fused to an aromatic ring. Representative monocyclic heterocycles include pyrrolidine, piperidine, piperazine, morpholine, and the like.

The term "aromatic monocyclic heterocycle" means a monocyclic ring system consisting of about 5 to 8 ring atoms, preferably 5 or 6, in which one or more of the atoms in the ring system is/are element(s) other than carbon, for example, nitrogen, oxygen, or sulfur. The prefix aza, oxa, or thio before heterocycle means that at least a nitrogen, oxygen, or sulfur atom, respectively, is present as a ring atom. A nitrogen atom of a heteroaryl is optionally oxidized to the corresponding N-oxide. The ring is aromatic. Representative aromatic monocyclic heterocycles include pyridyl, 2-oxo-pyridin-1 (2H)-yl, pyrimidinyl, pyridazinyl, 6-oxopyridazin-1(6H)-yl, pyrazinyl, triazinyl, pyranyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, and the like. For lactam analogues of "aromatic monocyclic heterocycles" such as pyridin-2(1H)-one, pyridazin-3(2H)-one, and the like, when these lactam analogues are structurally connected through the nitrogen atom adjacent to the lactam carbonyl, these lactam analogues of aromatic monocyclic heterocycle are considered as "aromatic monocyclic heterocycle" in this invention. In addition, when a nitrogen containing heterocyle is substituted by hydroxyl group on the carbon adjacent to the nitrogen, the substituted heterocycle can be named as either tautomers as exemplified by the following examples:

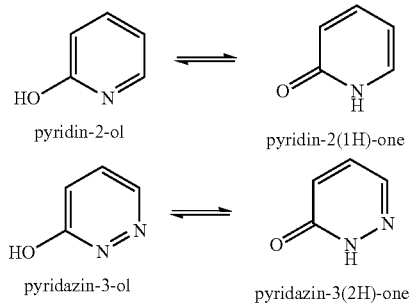

The term "fused bicyclic carbocycle" means a bicyclic ring system consisting of about 8 to 11 ring carbon atoms, preferably 9 or 10. One or both of the rings may be aromatic. Representative fused bicyclic carbocycles include indenyl, indanyl, naphthyl, dihydronaphthyl, tetrahydronaphthyl, benzocycloheptenyl, dihydrobenzocycloheptenyl, tetrahydrobenzocycloheptenyl, and the like.

The term "fused bicyclic heterocycle" means a bicyclic ring system consisting of about 8 to 13 ring atoms, preferably 9 or 10, in which one or more of the atoms in the ring system is/are element(s) other than carbon, for example, nitrogen, oxygen, or sulfur. In the case of multicyclic ring system, only one of the rings needs to be aromatic for the ring system to be defined as "Heteroaryl". The prefix aza, oxa, or thio before heterocycle means that at least a nitrogen, oxygen, or sulfur atom, respectively, is present as a ring atom. A nitrogen atom of a heteroaryl is optionally oxidized to the corresponding N-oxide.

Representative fused bicyclic heterocycles include indolyl, isoindolyl, benzofuranyl, benzothiophenyl, indolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo [5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo [2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, and 3-thio-[1,2,4]triazolo[4,3-a]pyridin-2(3H)-yl.

For lactam analogues of "fused bicyclic heterocycles" such as [1,2,4]triazolo[4,3-a]pyridin-3(2H)-one, and the like, when these lactams analogues are structurally connected through the nitrogen atom adjacent to the lactam carbonyl, these lactam analogues of aromatic monocyclic heterocycle are considered as "fused bicyclic heterocycle" in this invention.

A compound with a hydroxy group drawn next to a nitrogen on a heterocycle can exist as the "keto" form. For example, 3-(2-hydroxy-[1,2,4]triazolo[1,5-a]pyridin-6-yl) propanoic acid can exist as 3-(2-oxo-2,3-dihydro-[1,2,4]triazolo[1,5-a]pyridin-6-yl)propanoic acid.

The term "bridged bicyclic ring" means a bridged bicyclic ring containing 6-12 carbon atoms and optionally containing one or more heteroatoms selected from the group consisting of oxygen, nitrogen, and sulfur. Representative bridged bicyclic rings include quinuclidine, 9-azabicyclo[3.3.1]nonane, 7-azabicyclo[2.2.1]heptane, 2,5-diazabicyclo[2.2.2]octane, and the like.

The term "alkyl" means an aliphatic hydrocarbon group which may be straight or branched having about 1 to about 6 carbon atoms in the chain. Branched means that one or more lower alkyl groups such as methyl, ethyl or propyl are attached to a linear alkyl chain. Representative alkyl groups include methyl, ethyl, n-propyl, i-propyl, n-butyl, t-butyl, n-pentyl, and 3-pentyl.

When an alkyl is substituted from 1 to 3 times with halogen, the substituted groups include $CF_3$, $CF_2H$, $CH_2CF_3$, $CH_2CF_2H$ and the alike.

The term "term-ethyl" means two ethyl groups that substitute the two hydrogen atoms on a methylene group.

The term "term-dimethyl" means two methyl groups that substitute the two hydrogen atoms on a methylene group.

The term "alkenyl" means an aliphatic hydrocarbon group containing a carbon-carbon double bond and which may be straight or branched having 2 to about 6 carbon atoms in the chain. Preferred alkenyl groups have 2 to about 4 carbon atoms in the chain. Branched means that one or more lower alkyl groups such as methyl, ethyl or propyl are attached to a linear alkenyl chain. Representative alkenyl groups include ethenyl, propenyl, n-butenyl, and i-butenyl.

The term "alkynyl" means an aliphatic hydrocarbon group containing a carbon-carbon triple bond and which may be straight or branched having 2 to about 6 carbon atoms in the chain. Preferred alkynyl groups have 2 to about 4 carbon atoms in the chain. Branched means that one or more lower alkyl groups such as methyl, ethyl or propyl are attached to a linear alkynyl chain. Representative alkynyl groups include ethynyl, propynyl, n-butynyl, 2-butynyl, 3-methylbutynyl, and n-pentynyl.

The term "cycloalkyl" means a non-aromatic mono- or multicyclic ring system of about 3 to about 7 carbon atoms, preferably of about 5 to about 7 carbon atoms. Representative monocyclic cycloalkyl include cyclopentyl, cyclohexyl, cycloheptyl, and the like.

The term "cycloalkylalkyl" means a cycloalkyl-alkyl-group in which the cycloalkyl and alkyl are as defined herein. Representative cycloalkylalkyl groups include cyclopropylmethyl and cyclopentylmethyl.

The term "aryl" means an aromatic monocyclic or multicyclic ring system (including fused bicyclic ring systems) of 6 to about 14 carbon atoms, preferably of 6 to about 10 carbon atoms. In the case of a multicyclic ring system, only one of the rings needs to be aromatic for the ring system to be defined as "aryl". Representative aryl groups include phenyl and naphthyl.

The term "heteroaryl" means an aromatic monocyclic or multicyclic ring system (including fused bicyclic ring systems) of 6 to about 14 ring atoms, preferably of 6 to about 10 ring atoms, in which one or more of the atoms in the ring system is/are element(s) other than carbon, for example, nitrogen, oxygen or sulfur. In the case of a multicyclic ring system, only one of the rings needs to be aromatic for the ring system to be defined as "heteroaryl". Representative heteroaryl groups include pyridinyl, pyridyl, 2-oxo-pyridin-1(2H)-yl, pyrimidinyl, pyridazinyl, 6-oxopyridazin-1(6H)-yl, pyrazinyl, triazinyl, pyranyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indolyl, isoindolyl, benzofuranyl, benzothiophenyl, indolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, and 3-thio-[1,2,4]triazolo[4,3-a]pyridin-2(3H)-yl, and the like.

The term "alkoxy" means an alkyl-O-group where the alkyl group is as herein described. Representative alkoxy groups include methoxy, ethoxy, n-propoxy, i-propoxy, n-butoxy and heptoxy.

When the alkyl group of the "alkoxy" is substituted from 1 to 3 times with halogen, the "alkoxy" groups include $OCF_3$, $OCF_2H$, $OCH_2CF_3$, $OCH_2CF_2H$ and the like.

The term "halo" or "halogen" means fluoro, chloro, bromo, or iodo.

The term "substituted" or "substitution" of an atom means that one or more hydrogen on the designated atom is replaced with a selection from the indicated group, provided that the designated atom's normal valency is not exceeded. "Unsubstituted" atoms bear all of the hydrogen atoms dictated by their valency. When a substituent is keto or oxo (i.e., =O), then 2 hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent. As used herein, when an atom or group is optionally substituted multiple times, each such substitution is independently selected.

The term "compounds of the invention", and equivalent expressions, are meant to embrace compounds of general formula (I) as hereinbefore described, which expression includes the prodrugs, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

The term "pharmaceutically acceptable salts" means the relatively non-toxic, inorganic and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed. Representative acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulphamates, malonates, salicylates, propionates, methylene-bis-b-hydroxynaphthoates, gentisates, isethionates, di-p-toluoyltartrates, methane-sulphonates, ethanesulphonates, benzenesulphonates, p-toluenesulphonates, cyclohexylsulphamates and quinateslaurylsulphonate salts, and the like. (See, for example Berge et al., *J Pharm Sci,* 66:1-sup.19 (1977) and *Remington's Pharmaceutical Sciences,* 17th ed, p. 1418, Mack Publishing Company, Easton, Pa. (1985), which are hereby incorporated by reference in their entirety.) Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide. Suitable amine base addition salts are prepared from amines which have sufficient basicity to form a stable salt, and preferably include the following amines which are frequently used in medicinal chemistry because of their low toxicity and acceptability for medical use: ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

The term "pharmaceutically acceptable prodrugs" as used herein means those prodrugs of the compounds useful according to the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" means compounds that are rapidly transformed in vivo to yield the parent compound of the above formula, for example by hydrolysis in blood. Functional groups which may be rapidly transformed, by metabolic cleavage, in vivo form a class of groups reactive with the carboxyl group of the compounds of this invention. They include, but are not limited to such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds useful according to this invention are cleaved in vivo, the compounds bearing such groups act as prodrugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion of prodrugs is provided in the following: Bundgaard, ed., *Design of Prodrugs,* Elsevier (1985); Widder et al., *Methods in Enzymology,* ed., Academic Press, 42:309-396 (1985); "Design and Applications of Prodrugs," Krogsgaard-Larsen, ed., *A Textbook of Drug Design and Development,* Chapter 5:113-191 (1991); Bundgaard, *"Advanced Drug Delivery Reviews,"* 8:1-38 (1992); Bundgaard et al., *Journal of Pharmaceutical Sciences,* 77:285 (1988); Nakeya et al., *Chem Pharm Bull,* 32:692 (1984); Higuchi, "Pro-drugs as Novel Delivery Systems" Roche, ed., A.C.S. Symposium Series, Vol. 14, and "Bioreversible Carriers in Drug Design" American Pharmaceutical Association and Pergamon Press (1987), which are hereby incorporated by reference in their entirety. Examples of prodrugs include, but are not limited to, acetate, formate and benzoate derivatives of alcohol and amine functional groups in the compounds of the invention.

The term "therapeutically effective amounts" is meant to describe an amount of compound of the present invention effective in increasing the levels of serotonin, norepinephrine or dopamine at the synapse and thus producing the desired therapeutic effect. Such amounts generally vary according to a number of factors well within the purview of ordinarily skilled artisans given the description provided herein to determine and account for. These include, without limitation: the particular subject, as well as its age, weight, height, general physical condition and medical history, the particular compound used, as well as the carrier in which it is formulated and the route of administration selected for it; and, the nature and severity of the condition being treated.

The term "pharmaceutical composition" means a composition comprising compounds of formula (I) and at least one component selected from the group comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin. Examples of suitable carriers, diluents, solvents or vehicles include water, ethanol, polyols, suitable mixtures thereof, vegetable oils (such as olive oil) and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

The term "pharmaceutically acceptable" means it is, within the scope of sound medical judgment, suitable for use in contact with the cells of humans and lower animals without undue toxicity, irritation, allergic response and the like, and are commensurate with a reasonable benefit/risk ratio.

The term "pharmaceutically acceptable dosage forms" means dosage forms of the compound of the invention, and includes, for example, tablets, dragees, powders, elixirs, syrups, liquid preparations, including suspensions, sprays, inhalants tablets, lozenges, emulsions, solutions, granules, capsules and suppositories, as well as liquid preparations for injections, including liposome preparations. Techniques and formulations generally may be found in Remington's Pharmaceutical Sciences, 17th ed, Easton, Pa., Mack Publishing Company (1985), which is hereby incorporated by reference in its entirety.

One embodiment of the present invention relates to the compound of formula (I), wherein $R^3$ is —OH, —OCH$_3$, —CH$_3$, —NHCH$_2$CH$_2$OH, 3-(pyridin-4-yl)propoxyl, 3-(pyridin-3-yl)propoxyl, or 3-(pyridin-2-yl)propoxyl.

One embodiment of the present invention relates to the compound of formula (I), wherein $R^3$ is

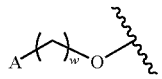

wherein A is 5- or 6-membered aromatic or non-aromatic monocyclic carbocycle or heterocycle, or a [5,5]-, [6,5]-, [6,6]-, or [6,7]-fused bicyclic carbocycle or heterocycle containing 1-5 heteroatoms selected from the group consisting of oxygen, nitrogen, and sulfur, optionally substituted from 1 to 4 times with substituents as defined in $R^{13}$ and W is 1, 2, 3, or 4.

One embodiment of the present invention relates to the compound of formula (I), wherein $R^3$ is

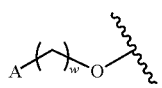

wherein A is $NR^8R^9$ and W is 2, 3, or 4.

One embodiment of the present invention relates to the compound of formula (I), where n is 1 and X is phenyl optionally substituted from 1-4 times with substituents as defined in $R^{13}$.

One embodiment of the present invention relates to the compound of formula (I), where n is 2 and X is phenyl optionally substituted from 1-4 times with substituents as defined in $R^{13}$.

Another embodiment of the present invention relates to the compound of formula (I), where n is 1, X is phenyl optionally substituted from 1-4 times with substituents as defined in $R^{13}$, and $R^3$ is substituted monocyclic or bicyclic aryl or heteroaryl.

Another embodiment of the present invention relates to the compound of formula (I), where n is 2, X is phenyl optionally substituted from 1-4 times with substituents as defined in $R^{13}$, and $R^3$ is substituted monocyclic or bicyclic aryl or heteroaryl.

Another embodiment of the present invention relates to the compound of formula (I), where n is 1, X is phenyl optionally substituted from 1-4 times with substituents as defined in $R^{13}$, and $R^3$ is H, —$NR^8R^9$, —$OR^{14}$, —$S(O)_pR^{11}$, $C(O)R^{11}$, —CN, halogen, or $C_1$-$C_6$ alkyl, where each of the $C_1$-$C_6$ alkyl is optionally substituted from 1 to 3 times with substituents as defined above in $R^{12}$.

Another embodiment of the present invention relates to the compound of formula (I), where n is 2, X is phenyl optionally substituted from 1-4 times with substituents as defined in $R^{13}$, and $R^3$ is H, —$NR^8R^9$, —$OR^{10}$, —$OR^{14}$, —$S(O)_pR^{11}$, $C(O)R^{11}$, —CN, halogen, or $C_1$-$C_6$ alkyl, where each of the $C_1$-$C_6$ alkyl is optionally substituted from 1 to 3 times with substituents as defined above in $R^{12}$.

Another embodiment of the present invention relates to the compound of formula (I) where:
X is phenyl, optionally substituted from 1 to 3 times with chloro or fluoro;
n is 1;
$R^1$, $R^2$, $R^4$, $R^5$, $R^6$, and $R^7$ are all H; and
$R^3$ is substituted monocyclic or bicyclic aryl or heteroaryl.

Another embodiment of the present invention relates to the compound of formula (I) where:
X is phenyl, optionally substituted from 1 to 3 times with chloro or fluoro;
n is 2;
$R^1$, $R^2$, $R^4$, $R^5$, $R^6$, and $R^7$ are all H; and
$R^3$ is substituted monocyclic or bicyclic aryl or heteroaryl.

Another embodiment of the present invention relates to the compound of formula (I) where:
X is phenyl, optionally substituted from 1 to 3 times with chloro or fluoro;
n is 1;
$R^1$, $R^2$, $R^4$, $R^5$, $R^6$, and $R^7$ are all H; and
$R^3$ is H, —$NR^8R^9$, —$OR^{10}$, —$OR^{14}$, —$S(O)_pR^{11}$, $C(O)R^{11}$, —CN, halogen, or $C_1$-$C_6$ alkyl, where each of the $C_1$-$C_6$ alkyl is optionally substituted from 1 to 3 times with substituents as defined above in $R^{12}$.

Another embodiment of the present invention relates to the compound of formula (I) where:
X is phenyl, optionally substituted from 1 to 3 times with chloro or fluoro;
n is 2;
$R^1$, $R^2$, $R^4$, $R^5$, $R^6$, and $R^7$ are all H; and
$R^3$ is H, —$NR^8R^9$, —$OR^{10}$, —$OR^{14}$, —$S(O)_pR^{11}$, —$C(O)R^{11}$, —CN, halogen, or $C_1$-$C_6$ alkyl, where each of the $C_1$-$C_6$ alkyl is optionally substituted from 1 to 3 times with substituents as defined above in $R^{12}$.

Another embodiment of the present invention relates to the compound of formula (I) where:
X is phenyl, optionally substituted from 1 to 3 times with chloro or fluoro;
n is 1;

R¹, R², R⁴, R⁵, R⁶, and R⁷ are all H; and
R³ is hydroxy, methoxy, difluoromethoxy, [1,2,4]triazolo[1,5-a]pyridin-6-yl, 7-methyl-[1,2,4]triazolo[1,5-a]pyridin-6-yl, [1,2,4]triazolo[4,3-a]pyridin-6-yl, 3-methyl-[1,2,4]triazolo[4,3-a]pyridin-6-yl, 3-(trifluoromethyl)-[1,2,4]triazolo[4,3-a]pyridin-6-yl, 3-oxo-[1,2,4]triazolo[4,3-a]pyridin-2(3H)-yl, 2-oxo-pyridin-1-yl, 6-(methoxy)pyridazin-3-yl, 6-(hydroxy)pyridazin-3-yl, 6-(trifluoromethyl)pyridazin-3-yl, 6-(difluoromethoxy)pyridazin-3-yl, 6-(hydroxy)pyridazin-3-yl, 4-cyanophenyl, 3-cyanophenyl, 4-(methylsulfonyl)phenyl, 2-oxo-2,3-dihydrobenzo[d]oxazol-6-yl, pyrimidin-5-yl, pyrazinyl, 5-aminopyrazinyl, quinoxalin-2-yl, 5-methyl-1,3,4-thiadiazol-2-yl, morpholinyl, 4-(ethylsulfonyl)piperazin-1-yl, 6-(trifluoromethyl)pyridazin-3-yloxy, pyrazin-2-yloxy, 5-amino-pyrazin-2-yloxy, 3-(pyridin-4-yl)propoxy, 3-(pyridin-3-yl)propoxy, 5-(methylsulfonyl)pyrimidin-2-yl, 6-(methylcarbamoyl)pyridazin-3-yl, 6-carbamoylpyridazin-3-yl, 5-(methylcarbamoyl)pyrimidin-2-yl, or 5-carbamoylpyrimidin-2-yl.

Another embodiment of the present invention relates to the compound of formula (I) where:
X is phenyl, optionally substituted from 1 to 3 times with chloro or fluoro;
n is 2;
R¹, R², R⁴, R⁵, R⁶, and R⁷ are all H; and
R³ is hydroxy, methoxy, difluoromethoxy, [1,2,4]triazolo[1,5-a]pyridin-6-yl, 7-methyl-[1,2,4]triazolo[1,5-a]pyridin-6-yl, [1,2,4]triazolo[4,3-a]pyridin-6-yl, 3-methyl-[1,2,4]triazolo[4,3-a]pyridin-6-yl, 3-(trifluoromethyl)-[1,2,4]triazolo[4,3-a]pyridin-6-yl, 3-oxo-[1,2,4]triazolo[4,3-a]pyridin-2(3H)-yl, 2-oxo-pyridin-1-yl, 6-(methoxy)pyridazin-3-yl, 6-(hydroxy)pyridazin-3-yl, 6-(trifluoromethyl)pyridazin-3-yl, 6-(difluoromethoxy)pyridazin-3-yl, 6-(hydroxy)pyridazin-3-yl, 4-cyanophenyl, 3-cyanophenyl, 4-(methylsulfonyl)phenyl, 2-oxo-2,3-dihydrobenzo[d]oxazol-6-yl, pyrimidin-5-yl, pyrazinyl, 5-aminopyrazinyl, quinoxalin-2-yl, 5-methyl-1,3,4-thiadiazol-2-yl, morpholinyl, 4-(ethylsulfonyl)piperazin-1-yl, 6-(trifluoromethyl)pyridazin-3-yloxy, pyrazin-2-yloxy, 5-amino-pyrazin-2-yloxy, 3-(pyridin-4-yl)propoxy, 3-(pyridin-3-yl)propoxy, 5-(methylsulfonyl)pyrimidin-2-yl, 6-(methylcarbamoyl)pyridazin-3-yl, 6-carbamoylpyridazin-3-yl, 5-(methylcarbamoyl)pyrimidin-2-yl, or 5-carbamoylpyrimidin-2-yl.

Another embodiment of the present invention relates to the compound of formula (I) where:
X is phenyl, optionally substituted from 1 to 3 times with chloro or fluoro;
n is 2;
R¹, R², R⁴, R⁵, R⁶, and R⁷ are all H; and
R³ is 6-(1-hydroxyethyl)pyridazin-3-yl, 6-(2-hydroxypropan-2-yl)pyridazin-3-yl, 6-(2,2,2-trifluoro-1-hydroxyethyl)pyridazin-3-yl, 6-(2,2-difluoro-1-hydroxyethyl)pyridazin-3-yl, 2-(1-hydroxyethyl)pyrimidin-5-yl, 2-(2-hydroxypropan-2-yl)pyrimidin-5-yl, 2-(2,2,2-trifluoro-1-hydroxyethyl)pyrimidin-5-yl, or 2-(2,2-difluoro-1-hydroxyethyl)pyrimidin-5-yl.

Another embodiment of the present invention relates to the compound of formula (I) where:
X is phenyl, optionally substituted from 1 to 3 times with chloro or fluoro;
n is 1;
R¹, R², R⁴, R⁵, R⁶, and R⁷ are all H; and
R³ is 6-(1-hydroxyethyl)pyridazin-3-yl, 6-(2-hydroxypropan-2-yl)pyridazin-3-yl, 6-(2,2,2-trifluoro-1-hydroxyethyl)pyridazin-3-yl, 6-(2,2-difluoro-1-hydroxyethyl)pyridazin-3-yl, 2-(1-hydroxyethyl)pyrimidin-5-yl, 2-(2-hydroxypropan-2-yl)pyrimidin-5-yl, 2-(2,2,2-trifluoro-1-hydroxyethyl)pyrimidin-5-yl, or 2-(2,2-difluoro-1-hydroxyethyl)pyrimidin-5-yl.

Specific compounds of formula (I) of the present invention include the following tetrahydrobenzazepine compounds:
5-(4-chlorophenyl)-8-methoxy-2,5-methano-2,3,4,5-tetrahydro-1H-benzo[c]azepine;
5-(4-chlorophenyl)-2,5-methano-2,3,4,5-tetrahydro-1H-benzo[c]azepin-8-ol;
8-([1,2,4]triazolo[1,5-a]pyridin-6-yl)-5-(4-chlorophenyl)-2,5-methano-2,3,4,5-tetrahydro-1H-benzo[c]azepine;
5-(4-chlorophenyl)-2,5-methano-8-(3-(trifluoromethyl)-[1,2,4]triazolo[4,3-a]pyridin-6-yl)-2,3,4,5-tetrahydro-1H-benzo[c]azepine;
5-(4-chlorophenyl)-2,5-methano-8-(6-(trifluoromethyl)pyridazin-3-yl)-2,3,4,5-tetrahydro-1H-benzo[c]azepine;
5-(4-chlorophenyl)-8-(6-(difluoromethoxy)pyridazin-3-yl)-2,5-methano-2,3,4,5-tetrahydro-1H-benzo[c]azepine;
6-(5-(4-chlorophenyl)-2,5-methano-2,3,4,5-tetrahydro-1H-benzo[c]azepin-8-yl)pyridazin-3-ol;
4-(5-(4-chlorophenyl)-2,5-methano-2,3,4,5-tetrahydro-1H-benzo[c]azepin-8-yl)benzonitrile;
5-(4-chlorophenyl)-2,5-methano-8-(4-(methylsulfonyl)phenyl)-2,3,4,5-tetrahydro-1H-benzo[c]azepine;
8-([1,2,4]triazolo[1,5-a]pyridin-6-yl)-5-(3,4-dichlorophenyl)-2,5-methano-2,3,4,5-tetrahydro-1H-benzo[c]azepine;
8-(2-oxo-2,3-dihydrobenzo[d]oxazol-6-yl)-5-(3,4-dichlorophenyl)-2,5-methano-2,3,4,5-tetrahydro-1H-benzo[c]azepine;
5-(4-chlorophenyl)-8-methoxy-2,5-ethano-2,3,4,5-tetrahydro-1H-2-benzo[c]azepine;
5-(4-chlorophenyl)-2,5-ethano-2,3,4,5-tetrahydro-1H-2-benzo[c]azepin-8-ol;
5-(4-chlorophenyl)-8-(6-(difluoromethoxy)pyridazin-3-yl)-2,5-ethano-2,3,4,5-tetrahydro-1H-2-benzo[c]azepine;
5-(4-chlorophenyl)-2,5-ethano-8-(pyrimidin-5-yl)-2,3,4,5-tetrahydro-1H-benzo[c]azepine;
5-(4-chlorophenyl)-2,5-ethano-8-(pyrazin-2-yl)-2,3,4,5-tetrahydro-1H-benzo[c]azepine;
5-(5-(4-chlorophenyl)-2,5-ethano-2,3,4,5-tetrahydro-1H-benzo[c]azepin-8-yl)pyrazin-2-amine;
8-([1,2,4]triazolo[1,5-a]pyridin-6-yl)-5-(4-chlorophenyl)-2,5-ethano-2,3,4,5-tetrahydro-1H-benzo[c]azepine;
5-(4-chlorophenyl)-2,5-ethano-8-(3-methyl-[1,2,4]triazolo[4,3-a]pyridin-6-yl)-2,3,4,5-tetrahydro-1H-benzo[c]azepine;
5-(4-chlorophenyl)-2,5-ethano-8-(quinoxalin-2-yl)-2,3,4,5-tetrahydro-1H-benzo[c]azepine;
6-(5-(4-chlorophenyl)-2,5-ethano-2,3,4,5-tetrahydro-1H-benzo[c]azepin-8-yl)-3,3a-dihydrobenzo[d]oxazol-2 (7aH)-one;
2-(5-(4-chlorophenyl)-2,5-ethano-2,3,4,5-tetrahydro-1H-benzo[c]azepin-8-yl)-[1,2,4]triazolo[4,3-a]pyridin-3 (2H)-one;
1-(5-(4-chlorophenyl)-2,5-ethano-2,3,4,5-tetrahydro-1H-benzo[c]azepin-8-yl)pyridin-2(1H)-one;
2-(5-(4-chlorophenyl)-2,5-ethano-2,3,4,5-tetrahydro-1H-benzo[c]azepin-8-yl)-5-methyl-1,3,4-thiadiazole;
5-(4-chlorophenyl)-2,5-ethano-8-(4-(methylsulfonyl)phenyl)-2,3,4,5-tetrahydro-1H-benzo[c]azepine;
3-(5-(4-chlorophenyl)-2,5-ethano-2,3,4,5-tetrahydro-1H-benzo[c]azepin-8-yl)benzonitrile;
4-(5-(4-chlorophenyl)-2,5-ethano-2,3,4,5-tetrahydro-1H-benzo[c]azepin-8-yl)morpholine;
5-(4-chlorophenyl)-8-(4-(ethylsulfonyl)piperazin-1-yl)-2,5-ethano-2,3,4,5-tetrahydro-1H-benzo[c]azepine;

5-(4-chlorophenyl)-2,5-ethano-8-(6-(trifluoromethyl)pyridazin-3-yloxy)-2,3,4,5-tetrahydro-1H-benzo[c]azepine;
5-(4-chlorophenyl)-2,5-ethano-8-(pyrazin-2-yloxy)-2,3,4,5-tetrahydro-1H-benzo[c]azepine;
5-(5-(4-chlorophenyl)-2,5-ethano-2,3,4,5-tetrahydro-1H-benzo[c]azepin-8-yloxy)pyrazin-2-amine;
5-(4-chlorophenyl)-2,5-ethano-8-(3-(pyridin-4-yl)propoxy)-2,3,4,5-tetrahydro-1H-benzo[c]azepine;
5-(4-chlorophenyl)-2,5-ethano-8-(3-(pyridin-3-yl)propoxy)-2,3,4,5-tetrahydro-1H-benzo[c]azepine;
8-([1,2,4]triazolo[1,5-a]pyridin-6-yl)-5-(3,4-dichlorophenyl)-2,5-ethano-2,3,4,5-tetrahydro-1H-benzo[c]azepine;
6-(5-(3,4-dichlorophenyl)-2,5-ethano-2,3,4,5-tetrahydro-1H-benzo[c]azepin-8-yl)-3,3a-dihydrobenzo[d]oxazol-2(7aH)-one;
5-(3,4-dichlorophenyl)-8-(6-(difluoromethoxy)pyridazin-3-yl)-2,5-ethano-2,3,4,5-tetrahydro-1H-benzo[c]azepine;
5-(3,4-dichlorophenyl)-8-(6-methoxypyridazin-3-yl)-2,5-ethano-2,3,4,5-tetrahydro-1H-benzo[c]azepine;
6-(5-(3,4-dichlorophenyl)-2,5-ethano-2,3,4,5-tetrahydro-1H-benzo[c]azepin-8-yl)pyridazin-3-ol;
5-(5-(3,4-dichlorophenyl)-2,5-ethano-2,3,4,5-tetrahydro-1H-benzo[c]azepin-8-yl)pyrazin-2-amine;
5-(3,4-dichlorophenyl)-2,5-ethano-8-(7-methyl-[1,2,4]triazolo[1,5-a]pyridin-6-yl)-2,3,4,5-tetrahydro-1H-benzo[c]azepine;
5-(3,4-dichlorophenyl)-2,5-ethano-8-(pyrazin-2-yloxy)-2,3,4,5-tetrahydro-1H-benzo[c]azepine;
5-(3,4-dichlorophenyl)-2,5-ethano-8-(6-(trifluoromethyl)pyridazin-3-yloxy)-2,3,4,5-tetrahydro-1H-benzo[c]azepine;
5-(3,4-dichlorophenyl)-2,5-ethano-8-(difluoromethoxy)-2,3,4,5-tetrahydro-1H-benzo[c]azepine;
5-(3-chloro-4-fluorophenyl)-2,5-ethano-8-(6-(trifluoromethyl)pyridazin-3-yloxy)-2,3,4,5-tetrahydro-1H-benzo[c]azepine;
5-(4-chloro-3-fluorophenyl)-2,5-ethano-8-(6-(trifluoromethyl)pyridazin-3-yloxy)-2,3,4,5-tetrahydro-1H-benzo[c]azepine;
5-(3-chlorophenyl)-2,5-ethano-8-(6-(trifluoromethyl)pyridazin-3-yloxy)-2,3,4,5-tetrahydro-1H-benzo[c]azepine;
2,5-ethano-5-(4-(trifluoromethyl)phenyl)-8-(6-(trifluoromethyl)pyridazin-3-yloxy)-2,3,4,5-tetrahydro-1H-benzo[c]azepine;
5-(3,4-difluorophenyl)-2,5-ethano-8-(6-(trifluoromethyl)pyridazin-3-yloxy)-2,3,4,5-tetrahydro-1H-benzo[c]azepine;
5-(4-fluorophenyl)-2,5-ethano-8-(6-(trifluoromethyl)pyridazin-3-yloxy)-2,3,4,5-tetrahydro-1H-benzo[c]azepine;
5-(3-chloro-4-fluorophenyl)-2,5-ethano-8-(6-(trifluoromethyl)pyridazin-3-yl)-2,3,4,5-tetrahydro-1H-benzo[c]azepine;
8-([1,2,4]triazolo[1,5-a]pyridin-6-yl)-5-(3-chloro-4-fluorophenyl)-2,5-ethano-2,3,4,5-tetrahydro-1H-benzo[c]azepine;
8-([1,2,4]triazolo[1,5-a]pyridin-6-yl)-5-(3-chloro-4-fluorophenyl)-2,5-methano-2,3,4,5-tetrahydro-1H-benzo[c]azepine;
5-(3-chloro-4-fluorophenyl)-2,5-methano-8-(6-(trifluoromethyl)pyridazin-3-yl)-2,3,4,5-tetrahydro-1H-benzo[c]azepine;
5-(4-chlorophenyl)-2,5-ethano-8-(5-(methylsulfonyl)pyrimidin-2-yl)-1,3,4,5-tetrahydro-1H-benzo[c]azepine;
5-(4-fluorophenyl)-2,5-ethano-8-(5-(methylsulfonyl)pyrimidin-2-yl)-1,3,4,5-tetrahydro-1H-benzo[c]azepine;
5-(3,4-difluorophenyl)-2,5-ethano-8-(5-(methylsulfonyl)pyrimidin-2-yl)-1,3,4,5-tetrahydro-1H-benzo[c]azepine;
5-(3,4-dichlorophenyl)-2,5-ethano-8-(5-(methylsulfonyl)pyrimidin-2-yl)-1,3,4,5-tetrahydro-1H-benzo[c]azepine;
5-(3-chloro-4-fluorophenyl)-2,5-ethano-8-(5-(methylsulfonyl)pyrimidin-2-yl)-1,3,4,5-tetrahydro-1H-benzo[c]azepine;
5-(4-chloro-3-fluorophenyl)-2,5-ethano-8-(5-(methylsulfonyl)pyrimidin-2-yl)-1,3,4,5-tetrahydro-1H-benzo[c]azepine;
6-(5-(4-chlorophenyl)-1,3,4,5-tetrahydro-2,5-ethanobenzo[c]azepin-8-yl)-N-methylpyridazine-3-carboxamide;
6-(5-(4-fluorophenyl)-1,3,4,5-tetrahydro-2,5-ethanobenzo[c]azepin-8-yl)-N-methylpyridazine-3-carboxamide;
6-(5-(3,4-fluorophenyl)-1,3,4,5-tetrahydro-2,5-ethanobenzo[c]azepin-8-yl)-N-methylpyridazine-3-carboxamide;
6-(5-(3,4-dichlorophenyl)-1,3,4,5-tetrahydro-2,5-ethanobenzo[c]azepin-8-yl)-N-methylpyridazine-3-carboxamide;
6-(5-(4-chloro-3-fluorophenyl)-1,3,4,5-tetrahydro-2,5-ethanobenzo[c]azepin-8-yl)-N-methylpyridazine-3-carboxamide;
6-(5-(3-chloro-4-fluorophenyl)-1,3,4,5-tetrahydro-2,5-ethanobenzo[c]azepin-8-yl)-N-methylpyridazine-3-carboxamide;
6-(5-(4-chlorophenyl)-1,3,4,5-tetrahydro-2,5-ethanobenzo[c]azepin-8-yl)-pyridazine-3-carboxamide;
6-(5-(4-fluorophenyl)-1,3,4,5-tetrahydro-2,5-ethanobenzo[c]azepin-8-yl)-pyridazine-3-carboxamide;
6-(5-(3,4-fluorophenyl)-1,3,4,5-tetrahydro-2,5-ethanobenzo[c]azepin-8-yl)-pyridazine-3-carboxamide;
6-(5-(3,4-dichlorophenyl)-1,3,4,5-tetrahydro-2,5-ethanobenzo[c]azepin-8-yl)-pyridazine-3-carboxamide;
6-(5-(4-chloro-3-fluorophenyl)-1,3,4,5-tetrahydro-2,5-ethanobenzo[c]azepin-8-yl)-pyridazine-3-carboxamide;
6-(5-(3-chloro-4-fluorophenyl)-1,3,4,5-tetrahydro-2,5-ethanobenzo[c]azepin-8-yl)-pyridazine-3-carboxamide;
2-(5-(4-chlorophenyl)-1,3,4,5-tetrahydro-2,5-ethanobenzo[c]azepin-8-yl)-N-methylpyrimidine-5-carboxamide;
2-(5-(4-fluorophenyl)-1,3,4,5-tetrahydro-2,5-ethanobenzo[c]azepin-8-yl)-N-methylpyrimidine-5-carboxamide;
2-(5-(3,4-dichlorophenyl)-1,3,4,5-tetrahydro-2,5-ethanobenzo[c]azepin-8-yl)-N-methylpyrimidine-5-carboxamide;
2-(5-(3,4-difluorophenyl)-1,3,4,5-tetrahydro-2,5-ethanobenzo[c]azepin-8-yl)-N-methylpyrimidine-5-carboxamide;
2-(5-(3-chloro-4-fluorophenyl)-1,3,4,5-tetrahydro-2,5-ethanobenzo[c]azepin-8-yl)-N-methylpyrimidine-5-carboxamide;
2-(5-(4-chloro-3-fluorophenyl)-1,3,4,5-tetrahydro-2,5-ethanobenzo[c]azepin-8-yl)-N-methylpyrimidine-5-carboxamide;
2-(5-(4-chlorophenyl)-1,3,4,5-tetrahydro-2,5-ethanobenzo[c]azepin-8-yl)-pyrimidine-5-carboxamide;
2-(5-(4-fluorophenyl)-1,3,4,5-tetrahydro-2,5-ethanobenzo[c]azepin-8-yl)-pyrimidine-5-carboxamide;
2-(5-(3,4-dichlorophenyl)-1,3,4,5-tetrahydro-2,5-ethanobenzo[c]azepin-8-yl)-pyrimidine-5-carboxamide;
2-(5-(3,4-difluorophenyl)-1,3,4,5-tetrahydro-2,5-ethanobenzo[c]azepin-8-yl)-pyrimidine-5-carboxamide;
2-(5-(3-chloro-4-fluorophenyl)-1,3,4,5-tetrahydro-2,5-ethanobenzo[c]azepin-8-yl)-pyrimidine-5-carboxamide; and
2-(5-(4-chloro-3-fluorophenyl)-1,3,4,5-tetrahydro-2,5-ethanobenzo[c]azepin-8-yl)-pyrimidine-5-carboxamide.

Other embodiments of the present invention are compounds of formula (I) where n is 1 and the carbon atom designated * is in the R configuration.

Other embodiments of the present invention are compounds of formula (I) where n is 1 and the carbon atom designated * is in the S configuration.

Another embodiment of the present invention is a mixture of stereoisomeric compounds of formula (I) where n is 1 and the carbon atom designated * is in the R or S configuration.

Other embodiments of the present invention are compounds of formula (I) where n is 1 and the compound is a (+) stereoisomer.

Other embodiments of the present invention are compounds of formula (I) where n is 1 and the compound is a (−) stereoisomer.

Another embodiment of the present invention is a mixture of stereoisomeric compounds of formula (I) where n is 1 and the compound is a mixture of (+) and (−) stereoisomers.

Within these embodiments, the selection of a particular preferred substituent at any one of $R^1$-$R^7$ does not affect the selection of a substituent at any of the others of $R^1$-$R^7$. That is, preferred compounds provided herein have any of the preferred substituents at any of the positions.

Single enantiomers, any mixture of enantiomers, including racemic mixtures, or diastereomers (both separated and as any mixtures) of the compounds of the present invention are also included within the scope of the invention.

The scope of the present invention also encompasses active metabolites of the present compounds.

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Another aspect of the present invention is a pharmaceutical composition containing a therapeutically effective amount of the compound of formula (I) and a pharmaceutically acceptable carrier.

Another aspect of the present invention relates to a method of treating a disorder which is created by or is dependent upon decreased availability of serotonin, norepinephrine, or dopamine. The method involves administering to a patient in need of such treatment a therapeutically effective amount of a compound of formula (I), or a pharmaceutically acceptable salt thereof. The method of the present invention is capable of treating subjects afflicted with various neurological and psychiatric disorders including, without limitation: attention deficit hyperactivity disorder (ADHD), cognition impairment, anxiety disorders, generalized anxiety disorder (GAD), panic disorder, bipolar disorder or manic depression or manic-depressive disorder, obsessive compulsive disorder (OCD), posttraumatic stress disorder (PTSD), acute stress disorder, social phobia, simple phobias, pre-menstrual dysphoric disorder (PMDD), social anxiety disorder (SAD), major depressive disorder (MDD), postnatal depression, dysthymia, depression associated with Alzheimer's disease, Parkinson's disease, or psychosis, supranuclear palsy, eating disorders, obesity, anorexia nervosa, bulimia nervosa, binge eating disorder, diabetes, ischemic diseases, pain, substance abuse disorders, chemical dependencies, nicotine addiction, cocaine addiction, amphetamine addiction, alcohol addiction, Lesch-Nyhan syndrome, neurodegenerative diseases, Parkinson's disease, late luteal phase syndrome or narcolepsy, psychiatric symptoms, anger, rejection sensitivity, movement disorders, extrapyramidal syndrome, Tic disorders, restless leg syndrome (RLS), tardive dyskinesia, supranuclear palsy, sleep related eating disorder (SRED), night eating syndrome (NES), stress urinary incontinence (SUI), migraine, neuropathic pain, diabetic neuropathy, lower back pain, fibromyalgia syndrome (FS), osteoarthritis pain, arthritis pain, chronic fatigue syndrome (CFS), sexual dysfunction, premature ejaculation, male impotence, thermoregulatory disorders (e.g., hot flashes associated with menopause), and irritable bowel syndrome (IBS).

The compounds provided herein are particularly useful in the treatment of these and other disorders due, at least in part, to their ability to selectively bind to the transporter proteins for certain neurochemicals with a greater affinity than to the transporter proteins for other neurochemicals.

Another embodiment of the present invention is a method of inhibiting synaptic norepinephrine uptake in a patient in need thereof. The method involves administering a therapeutically effective inhibitory amount of a compound of formula (I).

Another embodiment of the present invention is a method of inhibiting synaptic serotonin uptake in a patient in need thereof. The method involves administering a therapeutically effective inhibitory amount of a compound of formula (I).

Another embodiment of the present invention is a method of inhibiting synaptic dopamine uptake in a patient in need thereof. The method involves administering a therapeutically effective inhibitory amount of a compound of formula (I).

Another embodiment of the present invention is a therapeutic method described herein, where the (+)-stereoisomer of the compound of formula (I) is employed, when n is equal to 1.

Another embodiment of the present invention is a therapeutic method described herein, where the (−)-stereoisomer of the compound of formula (I) is employed, when n is equal to 1.

Another embodiment of the present invention relates to a method of treating a disorder referred to in the above-mentioned embodiments in a patient in need thereof. The method involves inhibiting synaptic serotonin and norepinephrine uptake by administering a therapeutically effective inhibitory amount of the compound of formula (I), which functions as both a dual acting serotonin and norepinephrine uptake inhibitor.

Another embodiment of the present invention relates to a method of treating a disorder referred to in the above-mentioned embodiments in a patient in need thereof. The method involves inhibiting synaptic serotonin and dopamine uptake by administering a therapeutically effective inhibitory amount of the compound of formula (I), which functions as both a dual acting serotonin and dopamine uptake inhibitor.

Another embodiment of the present invention relates to a method of treating a disorder referred to in the above-mentioned embodiments in a patient in need thereof. The method involves inhibiting synaptic dopamine and norepinephrine uptake by administering a therapeutically effective inhibitory amount of the compound of formula (I), which functions as both a dual acting dopamine and norepinephrine uptake inhibitor.

Another embodiment of the present invention relates to a method of treating a disorder referred to in the above-mentioned embodiments in a patient in need thereof. The method involves inhibiting synaptic norepinephrine, dopamine, and serotonin uptake by administering a therapeutically effective inhibitory amount of the compound of formula (I), which functions as a triple acting norepinephrine, dopamine, and serotonin uptake inhibitor.

Another embodiment of the present invention relates to a method for inhibiting serotonin uptake in mammals. The method involves administering to a mammal requiring increased neurotransmission of serotonin a pharmaceutically effective amount of the compound of formula (I).

Another embodiment of the present invention relates to a method for inhibiting dopamine uptake in mammals. The method involves administering to a mammal requiring increased neurotransmission of dopamine a pharmaceutically effective amount of the compound of formula (I).

Another embodiment of the present invention relates to a method for inhibiting norepinephrine uptake in mammals. The method involves administering to a mammal requiring increased neurotransmission of norepinephrine a pharmaceutically effective amount of the compound of formula (I).

Another embodiment of the present invention relates to a method of suppressing the desire of humans to smoke. The method involves administering to a human in need of such suppression an effective dose, to relieve the desire to smoke, of the compound of formula (I).

Another embodiment of the present invention relates to a method of suppressing the desire of humans to consume alcohol. The method involves administering to a human in need of such suppression an effective dose, to relieve the desire to consume alcohol, of the compound of formula (I).

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

Compounds according to the invention, for example, starting materials, intermediates, or products, are prepared as described herein or by the application or adaptation of known methods, by which is meant methods used heretofore or described in the literature.

Compounds useful according to the invention may be prepared by the application or adaptation of known methods, by which is meant methods used heretofore or described in the literature, for example, those described by Larock, *Comprehensive Organic Transformations*, Wiley-VCH publishers, New York (1989), which is hereby incorporated by reference in its entirety.

A compound of formula (I) including a group containing one or more nitrogen ring atoms, may be converted to the corresponding compound wherein one or more nitrogen ring atom of the group is oxidized to an N-oxide, preferably by reacting with a peracid, for example peracetic acid in acetic acid or m-chloroperoxybenzoic acid in an inert solvent such as dichloromethane, at a temperature from about room temperature to reflux, preferably at elevated temperature.

In the reactions described hereinafter, it may be necessary to protect reactive functional groups, for example hydroxy, amino, imino, thio, or carboxy groups, where these are desired in the final product, to avoid their unwanted participation in the reactions. Conventional protecting groups may be used in accordance with standard practice (e.g., Wuts et al., *Protective Groups in Organic Chemistry* (4$^{th}$ Edition), Wiley (2006), and McOmie, *Protective Groups in Organic Chemistry*, Plenum Press (1973), which are hereby incorporated by reference in their entirety).

In the reaction schemes described hereinafter, the synthesis of tetrahydrobenzazepines of the formula (I) functionalized at $R^3$ with aryl, heteroaryl, or heterocylic groups is described.

The novel methano- and ethano-tetrahydrobenzazepine reuptake inhibitors of formula (I; $R^3$=aryl, heteroaryl, or heterocyclic) of the present invention can be prepared by the general scheme outlined below (Scheme 1). Treatment of intermediates with the formula (II) with an aryl or heteroaryl Grignard or an aryl or heteroaryl lithium reagent X-M generates intermediates with the formula (III), where X is the corresponding aryl or heteroaryl group. Compounds of formula (III) may be cyclized to the tetrahydrobenzazepine compounds of formula (IV) by treatment with a strong acid. Suitable acids include, but are not limited to, concentrated sulfuric acid, polyphosphoric acid, and trifluoromethanesulfonic acid. The reactions are run neat or in the optional presence of a co-solvent such as, for example, methylene chloride or 1,2-dichloroethane. The cyclizations may be conducted at temperatures ranging from 0° C. up to the reflux point of the solvent employed. One skilled in the art of heterocyclic chemistry will readily understand these conditions or may consult the teachings of Euerby et al., *J. Chem. Research* (S), 40-41 (1987), which is hereby incorporated by reference in its entirety. Cyclizations may also be effected by treatment of compounds of formula (III) with strong Lewis acids, such as for example, aluminum trichloride, typically in halogenated solvents, such as methylene chloride.

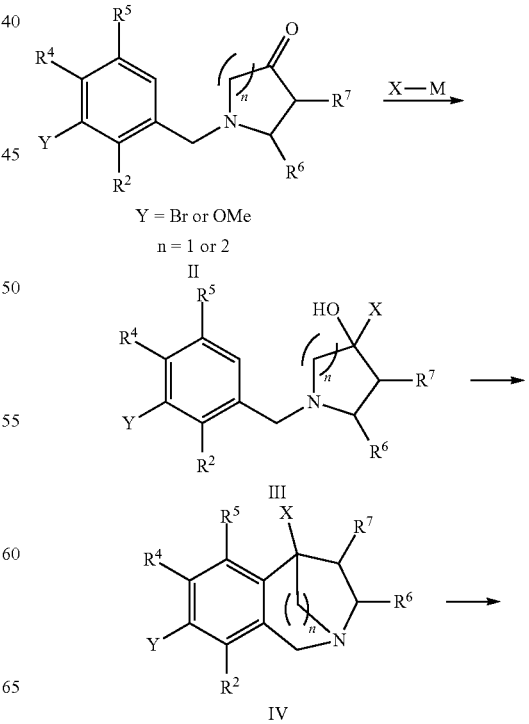

Scheme 1

-continued

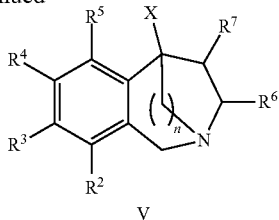

V

Compounds of Formula (IV, Y=OMe) may be converted to compounds of Formula (IV, Y=OH) by a demethylation procedure such as, but not limited to, heating to reflux in aqueous HBr with or without an organic solvent such as acetic acid, or treatment with $BBr_3$ in methylene chloride at low temperature. One skilled in the art will understand the optimal combination of demethylation agents and reaction conditions needed or may seek guidance from the text of Wuts et al., *Protective Groups in Organic Chemistry* ($4^{th}$ Edition), published by Wiley (2006), which is hereby incorporated by reference in its entirety.

Compounds of Formula (IV, Y=OH) may be converted to compounds of formula (IV; $OSO_2CF_3$) by reacting with a triflating reagent such as trifluoromethanesulfonic anhydride in the presence of a base such as pyridine in a halogenated solvent such as methylene chloride. Compounds of formula (V) of this invention may be prepared by treatment of compounds of Formula (IV; Y=Br, $OSO_2CF_3$) with aryl or heteroaryl boronic acids or aryl or heteroaryl boronic acid esters with formula Z—$R^3$ where Z is equivalent to $B(OH)_2$ or $B(OR^a)(OR^b)$ (where $R^a$ and $R^b$ are lower alkyl, i.e., $C_1$-$C_6$ alkyl, or taken together, $R^a$ and $R^b$ are lower alkylene, i.e., $C_2$-$C_{12}$ alkylene) in the presence of a metal catalyst with or without a base in an inert solvent to give tetrahydroisoquinoline compounds of Formula (VII). Metal catalysts include, but are not limited to, salts or phosphine complexes of Cu, Pd, or Ni (e.g., $Cu(OAc)_2$, $PdCl_2 (PPh_3)_2$, and $NiCl_2 (PPh_3)_2$). Bases may include, but are not limited to, alkaline earth metal carbonates, alkaline earth metal bicarbonates, alkaline earth metal hydroxides, alkali metal carbonates, alkali metal bicarbonates, alkali metal hydroxides, alkali metal hydrides (preferably sodium hydride), alkali metal alkoxides (preferably sodium methoxide or sodium ethoxide), alkaline earth metal hydrides, alkali metal dialkylamides (preferably lithium diisopropylamide), alkali metal bis(trialkylsilyl)amides (preferably sodium bis(trimethylsilyl)amide), trialkyl amines (preferably diisopropylethylamine or triethylamine), and aromatic amines (preferably pyridine). Inert solvents may include, but are not limited to acetonitrile, dialkyl ethers (preferably diethyl ether), cyclic ethers (preferably tetrahydrofuran or 1,4-dioxane), N,N-dialkylacetamides (preferably dimethylacetamide), N,N-dialkylformamides (preferably dimethylformamide), dialkylsulfoxides (preferably dimethylsulfoxide), aromatic hydrocarbons (preferably benzene or toluene), and haloalkanes (preferably methylene chloride). Preferred reaction temperatures range from room temperature up to the boiling point of the solvent employed. The reactions may be run in conventional glassware or in one of many commercially available parallel synthesizer units. Non-commercially available boronic acids or boronic acid esters may be obtained from the corresponding optionally substituted aryl halide as described by Gao, *Tetrahedron,* 50:979-988 (1994), which is hereby incorporated by reference in its entirety. It will also be appreciated by one skilled in the art that compounds of Formula (IV, Y=Br, $OSO_2CF_3$) may be converted to the corresponding boronic acids or boronate esters and subsequently treated with the aryl or heteroaryl halides or triflate $R^3$—X (X=Cl, Br, I, $OSO_2CF_3$) in discreet steps or in tandem as taught by Baudoin, *J Org Chem,* 67:1199-1207 (2002), which is hereby incorporated in its entirety.

The pyrrolidinone intermediates (II; n=1) may be prepared according to the reactions outlined in Scheme 2. Reductive amination of the aldehyde intermediate (VI) with the appropriately substituted pyrrolidin-3-ol intermediate (VII) generates the benzylamine intermediate (VIII). Reductive amination may involve the use of various reducing agents including, but not limited to, sodium triacetoxyborohydride and sodium borohydride, and may be catalyzed by various reagents including, but not limited to, magnesium sulfate and titanium isopropoxide. Intermediate (II; n=1) can then be obtained via oxidation of the alcohol to the ketone under a wide variety of conditions familiar to one skilled in the art of organic synthesis (see, e.g., Larock, *Comprehensive Organic Transformations,* Wiley-VCH publishers (1989), which is hereby incorporated by reference in its entirety).

Scheme 2

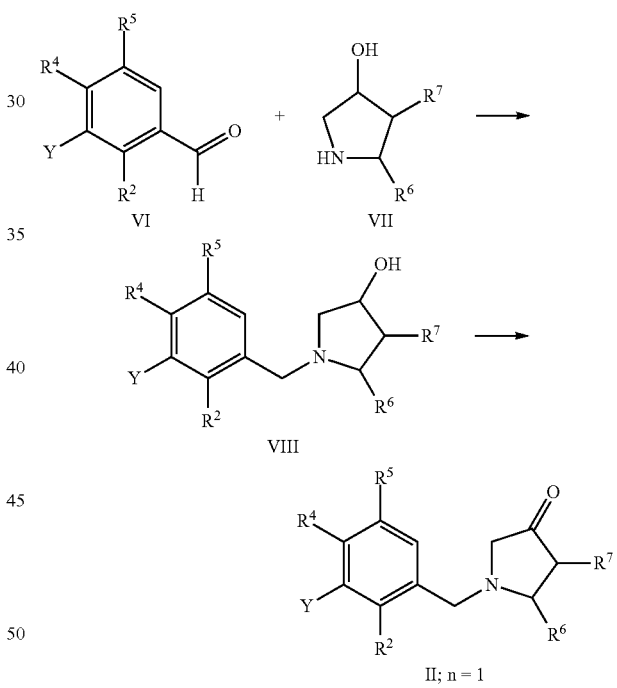

II; n = 1

The piperidinone intermediates (II; n=2) can be prepared in a similar fashion or according to the method outlined in Scheme 3. Under similar reductive amination conditions as above, reaction of benzaldehyde intermediate (VI) with the appropriately substituted piperidin-4-one (ketone protected with acetal or other appropriate protecting group) intermediate (IX) provides benzylamine intermediate (X). The protecting group can then be removed according to methods described in Wuts et al., *Protective Groups in Organic Chemistry* ($4^{th}$ Edition), Wiley (2006), and McOmie, *Protective Groups in Organic Chemistry,* Plenum Press (1973), which are hereby incorporated by reference in their entirety, to reveal the desired piperidinone intermediates (II; n=2).

Scheme 3

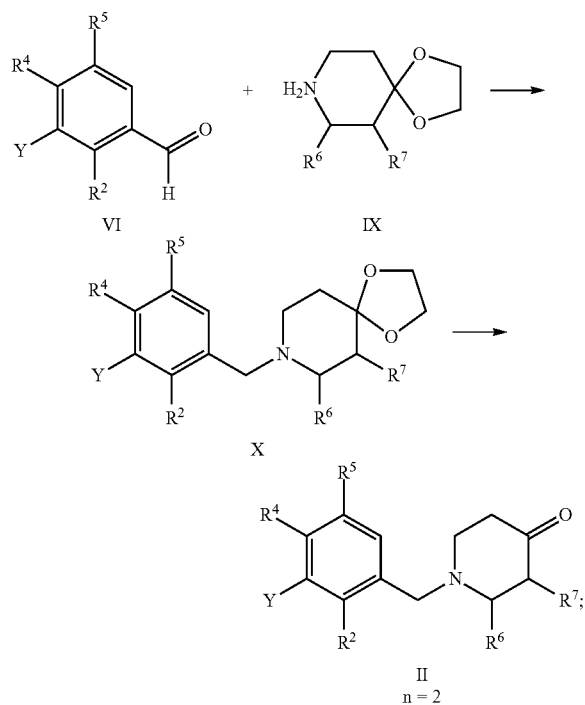

The methano-tetrahydrobenzazepine derivatives (compounds of formula (I) where n is 1) may be obtained in enantiomerically pure (R) and (S) form by crystallization with chiral salts as well known to one skilled in the art, or alternatively, may be isolated through chiral HPLC employing commercially available chiral columns.

It will be appreciated that compounds according to the present invention may contain asymmetric centers. These asymmetric centers may independently be in either the R or S configuration and such compounds are able to rotate a plane of polarized light in a polarimeter. If said plane of polarized light is caused by the compound to rotate in a counterclockwise direction, the compound is said to be the (−) stereoisomer of the compound. If said plane of polarized light is caused by the compound to rotate in a clockwise direction, the compound is said to be the (+) stereoisomer of the compound. It will be apparent to those skilled in the art that certain compounds useful according to the invention may also exhibit geometrical isomerism. It is to be understood that the present invention includes individual geometrical isomers and stereoisomers and mixtures thereof, including racemic mixtures, of compounds of formula (I) herein above. Such isomers can be separated from their mixtures, by the application or adaptation of known methods, for example chromatographic techniques and recrystallization techniques, or they are separately prepared from the appropriate isomers of their intermediates.

Radiolabelled compounds of the invention are synthesized by a number of techniques well known to those of ordinary skill in the art, e.g., by using starting materials incorporating therein one or more radioisotopes. Compounds of the present invention where a stable radioisotope, such as carbon-14, tritium, iodine-121, or another radioisotope, has been introduced synthetically are useful diagnostic agents for identifying areas of the brain or central nervous system that may be affected by disorders where norepinephrine, dopamine, or serotonin transporters and their uptake mechanism are implicated.

The present invention provides compositions containing the compounds described herein, including, in particular, pharmaceutical compositions comprising therapeutically effective amounts of the compounds and pharmaceutically acceptable carriers.

It is a further object of the present invention to provide kits having a plurality of active ingredients (with or without carrier) which, together, may be effectively utilized for carrying out the novel combination therapies of the invention.

It is another object of the invention to provide a novel pharmaceutical composition which is effective, in and of itself, for utilization in a beneficial combination therapy because it includes a plurality of active ingredients which may be utilized in accordance with the invention.

The present invention also provides kits or single packages combining two or more active ingredients useful in treating the disease. A kit may provide (alone or in combination with a pharmaceutically acceptable diluent or carrier) the compounds of formula (I) and the additional active ingredient (alone or in combination with diluent or carrier) selected from a serotonin 1A receptor antagonist, a selective neurokinin-1 receptor antagonist, and a norepinephrine precursor.

In practice, the compounds of the present invention may generally be administered parenterally, intravenously, subcutaneously, intramuscularly, colonically, nasally, intraperitoneally, rectally, or orally.

The products according to the present invention may be presented in forms permitting administration by the most suitable route and the invention also relates to pharmaceutical compositions containing at least one product according to the invention which are suitable for use in human or veterinary medicine. These compositions may be prepared according to the customary methods, using one or more pharmaceutically acceptable adjuvants or excipients. The adjuvants comprise, inter alia, diluents, sterile aqueous media, and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavorings, colorings, or stabilizers in order to obtain pharmaceutically acceptable preparations.

The choice of vehicle and the content of active substance in the vehicle are generally determined in accordance with the solubility and chemical properties of the product, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulfate, and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol, and chloroform or mixtures thereof may also be used.

For parenteral administration, emulsions, suspensions, or solutions of the products according to the invention in vegetable oil, for example sesame oil, groundnut oil, or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride, and that they are sterilized by heating, irradiation, or microfiltration.

Suitable compositions containing the compounds of the present invention may be prepared by conventional means. For example, compounds of the present invention may be dissolved or suspended in a suitable carrier for use in a nebulizer or a suspension or solution aerosol, or may be absorbed or adsorbed onto a suitable solid carrier for use in a dry powder inhaler.

Solid compositions for rectal administration include suppositories formulated in accordance with known methods and containing at least one compound of formula (I).

The percentage of active ingredient in the compositions of the present invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.01 to about 100 mg/kg body weight, preferably about 0.01 to about 10 mg/kg body weight per day by inhalation, from about 0.01 to about 100 mg/kg body weight, preferably 0.1 to 70 mg/kg body weight, more especially 0.5 to 10 mg/kg body weight per day by oral administration, and from about 0.01 to about 50 mg/kg body weight, preferably 0.01 to 10 mg/kg body weight per day by intravenous administration. In each particular case, the doses will be determined in accordance with the factors distinctive to the subject to be treated, such as age, weight, general state of health, and other characteristics which can influence the efficacy of the medicinal product.

The products according to the present invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. It goes without saying that, for other patients, it will be necessary to prescribe not more than one or two doses per day.

The present invention provides compounds which inhibit synaptic norepinephrine, dopamine, and serotonin uptake and are, therefore, believed to be useful in treating a disorder which is created by or is dependent upon decreased availability of serotonin, norepinephrine, or dopamine. Although the compounds of formula (I) inhibit synaptic norepinephrine, dopamine, and serotonin uptake, in any individual compound, these inhibitory effects may be manifested at the same or vastly different concentrations or doses. As a result, some compounds of formula (I) are useful in treating such a disorder at doses at which synaptic norepinephrine uptake may be substantially inhibited but at which synaptic serotonin uptake or dopamine uptake is not substantially inhibited, or vice versa. Also, some compounds of formula (I) are useful in treating such a disorder at doses at which synaptic dopamine uptake may be substantially inhibited but at which synaptic norepinephrine or serotonin uptake is not substantially inhibited, or vice versa. And, conversely, some compounds of formula (I) are useful in treating such a disorder at doses at which synaptic serotonin uptake may be substantially inhibited but at which synaptic norepinephrine or dopamine uptake is not substantially inhibited, or vice versa. Other compounds of formula (I) are useful in treating such a disorder at doses at which synaptic norepinephrine, dopamine, and serotonin uptake are substantially inhibited.

The present invention provides compounds where the inhibitory effects on serotonin and norepinephrine uptake occurs at similar or even the same concentrations of these compounds, while the effects on inhibition of dopamine uptake occurs at vastly different concentrations or doses. As a result, some compounds of formula (I) are useful in treating such a disorder at doses at which synaptic serotonin and norepinephrine uptake may be substantially inhibited but at which synaptic dopamine uptake is not substantially inhibited, or vice versa.

The present invention provides compounds where the inhibitory effects on serotonin and dopamine uptake occurs at similar or even the same concentrations of these compounds while the effects on inhibition of norepinephrine uptake occurs at vastly different concentrations or doses. As a result, some compounds of formula (I) are useful in treating such a disorder at doses at which synaptic serotonin and dopamine uptake may be substantially inhibited but at which synaptic norepinephrine uptake is not substantially inhibited, or vice versa.

The present invention provides compounds where the inhibitory effects on norepinephrine and dopamine uptake occurs at similar or even the same concentrations of these compounds while the effects on inhibition of dopamine uptake occurs at vastly different concentrations or doses. As a result, some compounds of formula (I) are useful in treating such a disorder at doses at which synaptic norepinephrine and dopamine uptake may be substantially inhibited but at which synaptic serotonin uptake is not substantially inhibited, or vice versa.

The present invention provides compounds where the inhibitory effects on norepinephrine, dopamine, and serotonin uptake occur at similar or even the same concentration. As a result, some compounds of formula (I) are useful in treating such a disorder at doses at which synaptic norepinephrine, dopamine, and serotonin uptake may all be substantially inhibited.

The concentrations or doses at which a test compound inhibits synaptic norepinephrine, dopamine, and serotonin uptake is readily determined by the use of standard assay and techniques well known and appreciated by one of ordinary skill in the art. For example, the degree of inhibition at a particular dose in rats can be determined by the method of Dudley, *J Pharmacol Exp Ther*, 217:834-840 (1981), which is hereby incorporated by reference in its entirety.

The therapeutically effective inhibitory dose is one that is effective in substantially inhibiting synaptic norepinephrine uptake, synaptic dopamine uptake, or synaptic serotonin uptake or inhibiting the synaptic uptake of two or more of norepinephrine, dopamine, and serotonin uptake. The therapeutically effective inhibitory dose can be readily determined by those skilled in the art by using conventional range finding techniques and analogous results obtained in the test systems described above.

Compounds of this invention provide a particularly beneficial therapeutic index relative to other compounds available for the treatment of similar disorders. Without intending to be limited by theory, it is believed that this is due, at least in part, to some of the compounds having higher binding affinities for one or two of the neurotransmitter transporters, e.g., selectivity towards the norepinephrine transporter protein ("NET")

over the transporters for other neurochemicals, e.g., the dopamine transporter protein ("DAT") and the serotonin transporter protein ("SERT").

Other compounds of the present invention may demonstrate selectivity towards the SERT over the transporters for other neurochemicals, e.g., the DAT and the NET.

Still other compounds of the present invention may demonstrate selectivity towards the DAT over the transporters for other neurochemicals, e.g., the SERT and the NET.

Yet other compounds of the present invention may demonstrate selectivity towards the NET over the transporters for other neurochemicals, e.g., the SERT and the DAT.

Other compounds of the present invention may demonstrate selectivity towards the SERT and the NET over the transporter for other neurochemical, e.g., the DAT.

Still other compounds of the present invention may demonstrate selectivity towards the SERT and the DAT over the transporter for other neurochemical, e.g., the NET.

Still other compounds of the present invention may demonstrate selectivity towards the NET and the DAT over the transporter for other neurochemical, e.g., the SERT.

Finally other compounds possess nearly identical affinity towards the NET, the DAT, and the SERT.

Binding affinities are demonstrated by a number of means well known to ordinarily skilled artisans, including, without limitation, those described in the Examples section hereinbelow. Briefly, for example, protein-containing extracts from cells, e.g., HEK293E cells, expressing the transporter proteins are incubated with radiolabelled ligands for the proteins. The binding of the radioligands to the proteins is reversible in the presence of other protein ligands, e.g., the compounds of the present invention; said reversibility, as described below, provides a means of measuring the compounds' binding affinities for the proteins ($IC_{50}$ or Ki). A higher $IC_{50}$/Ki value for a compound is indicative that the compound has less binding affinity for a protein than is so for a compound with a lower $IC_{50}$/Ki; conversely, lower $IC_{50}$/Ki values are indicative of greater binding affinities.

The in vivo affinity of the compounds to the three transporter proteins, SERT, DAT, and NET are demonstrated by means well known to those of ordinary skill in the art, including, without limitation, those described in the Examples section below.

To access occupancy in humans, methods such as PET (positron emission tomography) or SPECT (single photon emission computed tomography) are used.

Accordingly, the difference in compound selectivity in vivo for protein is indicated by a higher percent occupancy value (or percent inhibition of the [$^3$H] ligand compound used in the Examples section) at the transporter protein for which the compound is more selective, and a lower percent occupancy (or percent inhibition of the $^3$[H] ligand compound used in the Examples section) for the protein for which the compound is less selective. Compounds provided herein possess a wide range of selectivity profiles for the norepinephrine, dopamine, and serotonin transporters as reflected by experimentally determined percent occupancy values.

Selected compounds of the present invention, when administrated at a pharmaceutically feasible dose via means such as, but not limited to, oral, intravenous, subcutaneous, intraperitoneal and intramuscular, have statistically significant percent occupancy value(s) at one, two or all of the biogenic amine transporters NET, DAT, or SERT.

Selected compounds of the present invention, when administrated at a pharmaceutically feasible dose via means such as, but not limited to, oral, intravenous, subcutaneous, intraperitoneal and intramuscular, have 10%-100% occupancy value(s) at one, two or all of the biogenic amine transporters NET, DAT, or SERT. In one embodiment, compounds of the present invention have 40%-100% occupancy value(s) at one, two, or all of the biogenic amine transporters NET, DAT, or SERT. In another embodiment, compounds of the present invention have 60%-100% occupancy at SERT, 10%-50% occupancy at DAT, and 0%-100% occupancy at NET. In a further embodiment, compounds of the present invention have 70%-100% occupancy at SERT, 20-40% occupancy at DAT, and 0%-100% occupancy at NET. In another embodiment, compounds of the present invention have 80%-100% occupancy at SERT, 15-50% occupancy at DAT, and 0%-80% occupancy at NET. In a further embodiment, compounds of the present invention have 80%-100% occupancy at SERT, 15-50% occupancy at DAT, and 15%-50% occupancy at NET. In another embodiment, compounds of the present invention have 80%-100% occupancy at SERT, 20-40% occupancy at DAT, and 0%-80% occupancy at NET. In a further embodiment, compounds of the present invention have 80%-100% occupancy at SERT, 0-10% occupancy at DAT, and 0%-80% occupancy at NET. In yet another embodiment, compounds of the present invention have 0-20% occupancy at SERT, 20-50% occupancy at DAT, and 0%-100% occupancy at NET.

EXAMPLES

The following examples are provided to illustrate embodiments of the present invention but are by no means intended to limit its scope.

Example 1

Preparation of rac-5-(4-chlorophenyl)-8-methoxy-2,5-methano-2,3,4,5-tetrahydro-1H-benzo[c]azepine, L-tartrate Salt

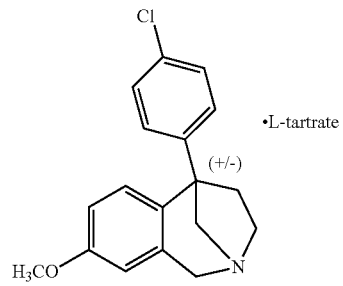 [SMILES: COc1ccc2c(c1)CN1CCC2(c2ccc(Cl)cc2)C1]

Step A: To pyrrolidin-3-ol (3.4 g, 39 mmol) in methanol (150 mL) was added 3-methoxybenzaldehyde (6.4 g, 47 mmol) and iodine (0.40 g, 32 mmol). After stirring for 5 h, the reaction mixture was cooled to 0° C. and sodium borohydride (2.9 g, 78 mmol) was added portionwise. The reaction mixture was warmed to ambient temperature and stirred overnight. Water (10 mL) was added and most of the tetrahydrofuran was removed in vacuo. Additional water (25 mL) was added and the aqueous layer was extracted with methylene chloride (50 mL). The organic layer was dried over sodium sulfate and concentrated in vacuo. The residue was purified by column chromatography (methylene chloride to 90:9:1 methylene chloride/methanol/ammonium hydroxide) to provide 1-(3-methoxybenzyl)pyrrolidin-3-ol (2.0 g, 25%) as a yellow oil: $^1$H NMR (DMSO-$d_6$, 300 MHz) δ 7.21 (dd, J=8.1, 8.1 Hz, 1H), 6.87-6.77 (m, 3H), 4.66 (d, J=4.5 Hz, 1H), 4.21-4.14 (m, 1H), 3.73 (s, 3H), 3.56-3.45 (m, 2H), 2.64 (dd, J=9.6, 6.3 Hz, 1H), 2.58-2.49 (m, 1H), 2.43-2.34 (m, 1H), 2.28 (dd, J=9.6, 7.5 Hz, 1H), 2.04-1.92 (m, 1H), 1.57-1.51 (m, 1H).

Step B: To a −50 to −60° C. cooled solution of oxalyl chloride (5.3 mL of a 2 M solution in methylene chloride, 10.6 mmol) in methylene chloride (5.3 mL) was added methyl sulfoxide (1.5 mL, 21.2 mmol) in methylene chloride (5 mL). After 3 min, a solution of 1-(3-methoxybenzyl)pyrrolidin-3-ol (2.0 g, 9.6 mmol) from Step A above in methylene chloride (10 mL) was added dropwise. After 25 min added triethylamine (6.8 mL, 4.8 mmol) and the reaction mixture was warmed to ambient temperature. Water (30 mL) was added and the aqueous layer was separated and extracted with methylene chloride (20 mL). The combined organic layers were dried over sodium sulfate and concentrated in vacuo. The residue was purified by column chromatography (methylene chloride to 1:1 methylene chloride/ethyl acetate) to provide 1-(3-methoxybenzyl)pyrrolidin-3-one (1.3 g, 66%) as a colorless oil: $^1$H NMR (DMSO-$d_6$, 300 MHz) δ 7.24 (dd, J=8.1, 8.1 Hz, 1H), 6.91-6.81 (m, 3H), 3.74 (s, 3H), 3.65 (s, 2H), 2.87-2.82 (m, 4H), 2.37-2.32 (m, 2H).

Step C: To 1-bromo-4-chlorobenzene (424 mg, 2.21 mmol) in tetrahydrofuran (10 mL), at −78° C., was added n-butyllithium (1.0 mL of a 2.5 M solution in hexanes, 2.4 mmol) dropwise. After 0.5 h, a solution of the ketone (500 mg, 2.43 mmol) from Step B above in tetrahydrofuran (5 mL) was added dropwise. The reaction mixture was stirred at −78° C. for 0.5 h and then warmed to 0° C. After 1.5 h, the reaction mixture was quenched with saturated ammonium chloride (5 mL) and warmed to ambient temperature. The mixture was diluted with ethyl acetate (50 mL) and washed with saturated ammonium chloride (20 mL), water (20 mL), brine (20 mL), dried over sodium sulfate and concentrated in vacuo. Purification by silica gel chromatography (5% ethyl acetate/methylene chloride to 80% ethyl acetate/methylene chloride) gave 3-(4-chlorophenyl)-1-(3-methoxybenzyl)pyrrolidin-3-ol (250 mg, 35%) as a yellow oil: $^1$H NMR (CDCl$_3$, 300 MHz) δ 7.50-7.42 (m, 2H), 7.34-7.29 (m, 2H), 7.27-7.22 (m, 1H), 6.96-6.91 (m, 2H), 6.83-6.80 (m, 1H), 3.82 (s, 3H), 3.57 (br s, 2H), 2.89-2.75 (m, 2H), 2.51-2.41 (m, 2H), 2.21-2.08 (m, 2H), 1.73-1.69 (m, 2H), 1.57 (s, 1H).

Step D: To 3-(4-chlorophenyl)-1-(3-methoxybenzyl)pyrrolidin-3-ol (130 mg, 0.41 mmol) from Step C above in methylene chloride (1.5 mL) was added triflic acid (2 mL). After 3.5 h, the reaction mixture was carefully poured over ice (ca. 10 g), made strongly basic with 6N sodium hydroxide and extracted with methylene chloride. The organic layer was dried over sodium sulfate and concentrated in vacuo. The residue was purified by column chromatography (methylene chloride to 90:9:1 methylene chloride/methanol/ammonium hydroxide) to provide 5-(4-chlorophenyl)-8-methoxy-2,5-methano-2,3,4,5-tetrahydro-1H-benzo[c]azepine (118 mg, 96%).

Step E: To the benzazepine (16 mg, 0.053 mmol) from Step D above in methanol (3 mL) was added L-tartaric acid (8 mg, 0.053 mmol) in water (12 mL). The resultant solution was lyophilized to give rac-5-(4-chlorophenyl)-8-methoxy-2,5-methano-2,3,4,5-tetrahydro-1H-benzo[c]azepine, L-tartrate salt (21 mg, quantitative, AUC HPLC 98.2%) as a white solid: $^1$H NMR (DMSO-$d_6$, 500 MHz) δ 7.47-7.45 (m, 2H), 7.39-7.35 (m, 2H), 6.68 (s, 1H), 6.60-6.68 (m, 1H), 6.27 (d, J=8.5 Hz, 1H), 4.47 (d, J=17.0 Hz, 1H), 4.06 (s, 1.4H), 3.99 (d, J=17.0 Hz, 1H), 3.69-3.67 (m, 4H), 3.41-3.39 (m, 1H), 3.06-3.00 (m, 1H), 2.99-2.96 (m, 1H), 2.38-2.34 (m, 2H); ESI MS m/z 300 [M+H]$^+$.

Example 2

Preparation of rac-5-(4-chlorophenyl)-2,5-methano-2,3,4,5-tetrahydro-1H-benzo[c]azepin-8-ol, L-tartrate Salt

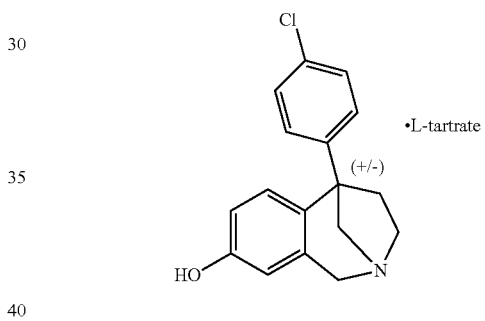

Step A: A mixture of 5-(4-chlorophenyl)-8-methoxy-2,5-methano-2,3,4,5-tetrahydro-1H-benzo[c]azepine (100 mg, 0.33 mmol) from Step D of Example 1 in 48% hydrobromic acid in water (2 mL) and acetic acid (2 mL) was heated to 135° C. After 4 h, the reaction mixture was cooled to ambient temperature, brought to ca. pH 7-8 with 1 N sodium hydroxide and saturated sodium bicarbonate and extracted with ethyl acetate (2×). The combined organics were washed with brine and concentrated in vacuo. The residue was purified by column chromatography (methylene chloride to 90:9:1 methylene chloride/methanol/ammonium hydroxide) to provide 5-(4-chlorophenyl)-2,5-methano-2,3,4,5-tetrahydro-1H-benzo[c]azepin-8-ol (67 mg, 70%) as a white solid.

Step B: To the benzazepinol (25 mg, 0.087 mmol) from Step A above in methanol (1.5 mL) and acetonitrile (4 mL) was added L-tartaric acid (13 mg, 0.087 mmol) in water (20 mL). The resultant solution was lyophilized to give rac-5-(4-chlorophenyl)-2,5-methano-2,3,4,5-tetrahydro-1H-benzo[c]azepin-8-ol, L-tartrate salt (42 mg, quantitative, AUC HPLC 98.8%) as an off-white solid: $^1$H NMR (DMSO-$d_6$, 500 MHz) δ 9.30 (br s, 1H), 7.48-7.46 (m, 2H), 7.38-7.35 (m, 2H), 6.51 (d, J=2.0 Hz, 1H), 6.45 (dd, J=8.5, 2.5 Hz, 1H), 6.19 (d, J=8.5 Hz, 1H), 4.52 (d, J=16.5 Hz, 1H), 4.10-4.05 (m, 3H), 3.79 (d, J=10.5 Hz, 1H), 3.55-3.49 (m, 1H), 3.17-3.00 (m, 2H), 2.42-2.36 (m, 2H); ESI MS m/z 286 [M+H]+.

Example 3

Preparation of (+)- and (−)-8-([1,2,4]triazolo[1,5-a]pyridin-6-yl)-5-(4-chlorophenyl)-2,5-methano-2,3,4,5-tetrahydro-1H-benzo[c]azepine, L-tartrate Salts

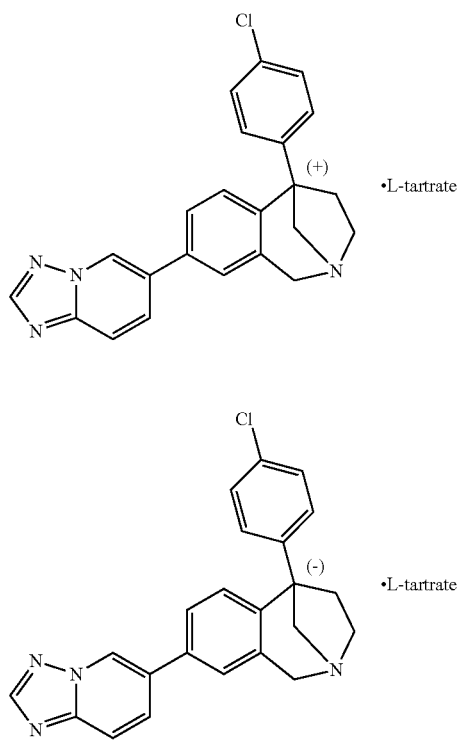

Step A: To a suspension of 5-(4-chlorophenyl)-2,5-methano-2,3,4,5-tetrahydro-1H-benzo[c]azepin-8-ol (270 mg, 0.94 mmol) from Step A of Example 2 in methylene chloride (10 mL), at −20° C., was added pyridine (0.084 mL, 1.0 mmol) and triflic anhydride (0.018 mL, 1.0 mmol). After 1 h, additional pyridine (0.020 mL, 0.25 mmol) and triflic anhydride (0.031 mL, 0.18 mmol) were added. After 0.5 h at 0° C., additional pyridine (0.020 mL, 0.25 mmol) and triflic anhydride (0.031 mL, 0.18 mmol) were added. After 1.25 h, the reaction mixture was diluted with methylene chloride (20 mL) and saturated sodium bicarbonate (10 mL) was added. The organic layer was separated and washed with brine (10 mL), dried over sodium sulfate and concentrated in vacuo to provide 5-(4-chlorophenyl)-2,5-methano-2,3,4,5-tetrahydro-1H-benzo[c]azepin-8-yl trifluoromethanesulfonate which was used directly in the next step: $^1$H NMR (DMSO-$d_6$, 300 MHz) δ 7.50-7.30 (m, 4H), 7.24 (s, 1H), 7.10 (d, J=8.5 Hz, 1H), 6.50 (d, J=9.0 Hz, 1H), 4.42 (d, J=17.5 Hz, 1H), 3.97 (d, J=17.0 Hz, 1H), 3.66 (d, J=11.0 Hz, 1H), 3.39-3.30 (m, 1H), 3.00-2.91 (m, 1H), 2.86 (d, J=11.0 Hz, 1H), 2.40-2.32 (m, 2H).

Step B: A mixture of bis(pinacolato)diboron (286 mg, 1.12 mmol), potassium acetate (276 mg, 2.81 mmol) and the triflate (393 mg, 0.94 mmol) from Step A above, in DMSO (10 mL), was purged with argon for 5 min. Next, 1,1'-bis(diphenylphosphino)ferrocenedichloropalladium (77 mg, 0.94 mmol) was added and the mixture was purged again with argon. The reaction mixture was heated at 80° C. for 2 h. After cooling to ambient temperature, the reaction mixture was diluted with ethyl acetate (70 mL), washed with water (2×20 mL), brine (20 mL), dried over sodium sulfate and concentrated in vacuo to provide 5-(4-chlorophenyl)-2,5-methano-8-(4,4,5,5-tetramethyl-1,3,2-dioxaborolan-2-yl)-2,3,4,5-tetrahydro-1H-benzo[c]azepine (crude) as a brown solid: ESI MS m/z 396 [M+H]+.

Step C: A mixture of the boronate ester (372 mg, 0.94 mmol) from Step B above, 6-bromo-[1,2,4]triazolo[1,5-a]pyridine (223 mg, 1.13 mmol) and cesium carbonate (919 mg, 2.82 mmol), in water (1 mL) and N,N-dimethylformamide (5 mL) was degassed with argon. Next, [1,1'-bis(diphenylphosphino)ferrocene]palladium(II) dichloromethane adduct (38 mg, 0.047 mmol) was added, the mixture was degassed again and heated to 90° C. for 3 h. The reaction mixture was diluted with water (25 mL) and extracted with ethyl acetate (2×25 mL). The combined organics were washed with water (2×20 mL), brine (20 mL), dried over sodium sulfate, filtered and concentrated in vacuo. The residue was purified by column chromatography (methylene chloride to 90:9:1 methylene chloride/methanol/ammonium hydroxide) and preparative TLC (90:9:1 methylene chloride/methanol/ammonium hydroxide) to give 8-([1,2,4]triazolo[1,5-a]pyridin-6-yl)-5-(4-chlorophenyl)-2,5-methano-2,3,4,5-tetrahydro-1H-benzo[c]azepine (77 mg, 21%).

Step D: The benzazepine from Step C above (115 mg) was resolved by preparative chiral HPLC(CHIRALPAK AD column, using 85:15:0.1 heptane/isopropyl alcohol/diethylamine as the eluent) to give the (−)-enantiomer (33 mg) and the (+)-enantiomer (37 mg).

Step E: To the (−)-enantiomer (33 mg, 0.085 mmol) from Step D above in acetonitrile (1.5 mL) was added L-tartaric acid (12.8 mg, 0.085 mmol) in water (4 mL). The resultant solution was lyophilized to give (−)-8-([1,2,4]triazolo-[1,5-a]pyridin-6-yl)-5-(4-chlorophenyl)-2,5-methano-2,3,4,5-tetrahydro-1H-benzo[c]azepine, L-tartrate salt (47 mg, 97%, AUC HPLC >99%) as an off-white solid: $^1$H NMR (CD$_3$OD, 500 MHz) δ 9.05 (s, 1H), 8.43 (s, 1H), 7.98 (d, J=9.5 Hz, 1H), 7.84 (d, J=9.5 Hz, 1H), 7.63 (s, 1H), 7.54-7.40 (m, 5H), 6.74 (d, J=8.0 Hz, 1H), 5.03-4.97 (m, 1H), 4.60-4.56 (m, 1H), 4.43 (s, 2H), 4.20-4.17 (m, 1H), 4.02-3.97 (m, 1H), 3.62-3.50 (m, 2H), 2.83-2.77 (m, 1H), 2.69-2.66 (m, 1H); ESI MS m/z 387 [M+H]+; $[\alpha]^{24}_D$ −25.9° (c 0.14, methanol).

Step F: To the (+)-enantiomer (37 mg, 0.095 mmol) from Step D above in acetonitrile (1.5 mL) was added L-tartaric acid (14.3, 0.095 mmol) in water (4 mL). The resultant solution was lyophilized to give (+)-8-([1,2,4]triazolo[1,5-a]pyridin-6-yl)-5-(4-chlorophenyl)-2,5-methano-2,3,4,5-tetrahydro-1H-benzo[c]azepine, L-tartrate salt (47 mg, 85%, AUC HPLC >99%) as an off-white solid: $^1$H NMR (CD$_3$OD, 500 MHz) δ 9.05 (s, 1H), 8.43 (s, 1H), 7.98 (dd, J=9.0, 1.5 Hz, 1H), 7.84 (d, J=9.5 Hz, 1H), 7.63 (d, J=1.5 Hz, 1H), 7.54-7.40 (m, 5H), 6.74 (d, J=8.0 Hz, 1H), 5.03-4.97 (m, 1H), 4.60-4.56 (m, 1H), 4.43 (s, 2H), 4.20-4.17 (m, 1H), 4.02-3.97 (m, 1H), 3.62-3.50 (m, 2H), 2.83-2.77 (m, 1H), 2.69-2.66 (m, 1H); ESI MS m/z 387 [M+H]$^+$; [α]$^{24}_D$+24.0° (c 0.13, methanol).

Example 4

Preparation of rac-5-(4-chlorophenyl)-2,5-methano-8-(3-(trifluoromethyl)-[1,2,4]triazolo[4,3-a]pyridin-6-yl)-2,3,4,5-tetrahydro-1H-benzo[c]azepine, L-tartrate Salt

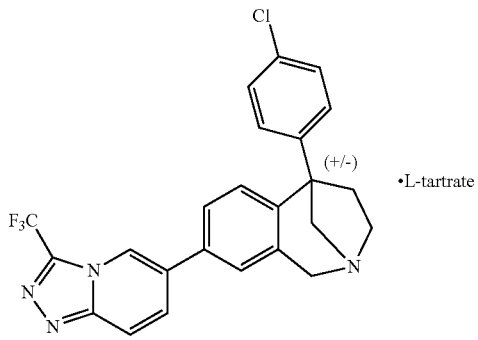 [SMILES: FC(F)(F)c1nnc2ccc(-c3ccc4c(c3)CN3CCC4(c4ccc(Cl)cc4)C3)cn12]

This compound was prepared from 5-(4-chlorophenyl)-2,5-methano-8-(4,4,5,5-tetramethyl-1,3,2-dioxaborolan-2-yl)-2,3,4,5-tetrahydro-1H-benzo[c]azepine from Step B of Example 3 and 6-bromo-3-(trifluoromethyl)-[1,2,4]triazolo[4,3-a]pyridine, following the procedures of Steps C and E of Example 3. Rac-5-(4-chloro-3-fluorophenyl)-2-methyl-8-(6-(trifluoromethyl)pyridazin-3-yl)-2,3,4,5-tetrahydro-1H-benzo[c]azepine, L-tartrate salt (52 mg, AUC HPLC >99%) was obtained as a white solid: $^1$H NMR (CD$_3$OD, 500 MHz) δ 8.57 (s, 1H), 8.02 (d, J=9.5 Hz, 1H), 7.92 (d, J=9.5 Hz, 1H), 7.63 (s, 1H), 7.54-7.44 (m, 5H), 6.77 (d, J=8.5 Hz, 1H), 5.00-4.96 (m, 1H), 4.62-4.59 (m, 1H), 4.19 (br s, 1H), 4.01 (br s, 1H), 3.62 (br s, 1H), 3.56 (br s, 1H), 2.82 (d, J=7.0 Hz, 1H), 2.70-2.66 (m 1H); ESI MS m/z 455 [M+H]$^+$.

Example 5

Preparation of rac-5-(4-chlorophenyl)-2,5-methano-8-(6-(trifluoromethyl)pyridazin-3-yl)-2,3,4,5-tetrahydro-1H-benzo[c]azepine, L-tartrate Salt

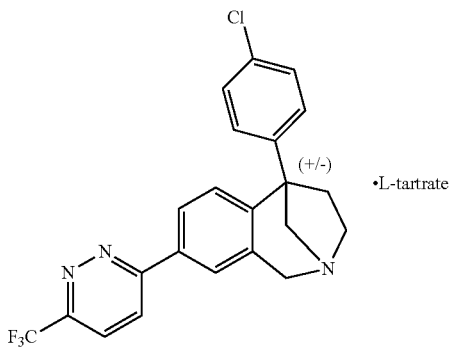 [SMILES: FC(F)(F)c1ccc(-c2ccc3c(c2)CN2CCC3(c3ccc(Cl)cc3)C2)nn1]

This compound was prepared from 5-(4-chlorophenyl)-2,5-methano-8-(4,4,5,5-tetramethyl-1,3,2-dioxaborolan-2-yl)-2,3,4,5-tetrahydro-1H-benzo[c]azepine from Step B of Example 3 and 3-chloro-6-(trifluoromethyl)pyridazine, following the procedures of Steps C and E of Example 3. rac-5-(4-chlorophenyl)-2,5-methano-8-(6-(trifluoromethyl)pyridazin-3-yl)-2,3,4,5-tetrahydro-1H-benzo[c]azepine, L-tartrate salt (27 mg, AUC HPLC >99%) was obtained as a white solid: $^1$H NMR (CD$_3$OD, 500 MHz) δ 8.35 (d, J=9.0 HZ, 1H), 8.17-8.14 (m, 2H), 7.95 (d, J=7.5 Hz, 1H), 7.52-7.46 (m, 4H), 6.82 (d, J=8.5 Hz, 1H), 5.03 (br s, 1H), 4.65 (br s, 1H), 4.45 (s, 2H), 4.23 (br s, 1H), 4.02 (br s, 1H), 3.64-3.59 (m, 2H), 2.83 (br s, 1H), 2.71 (br s, 1H); ESI MS m/z 416 [M+H]$^+$.

Example 6

Preparation of (+)- and (−)-5-(4-chlorophenyl)-8(6-(difluoromethoxy)pyridazin-3-yl)-2,5-methano-2,3,4,5-tetrahydro-1H-benzo[c]azepine, L-tartrate Salts

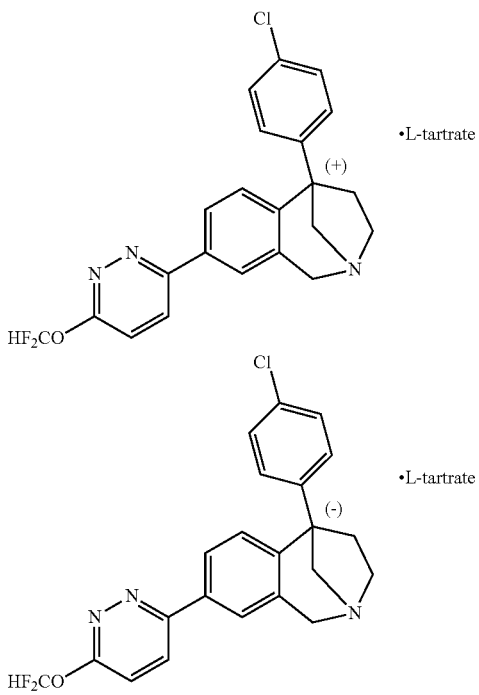

Step A: A procedure similar to Step C of Example 3 was used to couple 5-(4-chlorophenyl)-2,5-methano-8-(4,4,5,5-tetramethyl-1,3,2-dioxaborolan-2-yl)-2,3,4,5-tetrahydro-1H-benzo[c]azepine with 3-chloro-6-(difluoromethoxy)pyridazine. The desired coupling product was obtained in 32% yield as a white solid.

Step B: The benzazepine from Step A above was resolved by preparative chiral HPLC (CHIRALPAK AD column, using 95:5:0.1 acetonitrile/isopropyl alcohol/diethylamine as the eluent) to give the (+)-enantiomer [[α]$^{24}_D$+26.0° (c 0.23, methanol)] and the (−)-enantiomer [[α]$^{24}_D$−19.6° (c 0.15, methanol)].

Step C: Following the procedure of Step E of Example 3, the (+)-enantiomer from Step B above was converted to the corresponding L-tartrate salt to give (+)-5-(4-chlorophenyl)-8(6-(difluoromethoxy)pyridazin-3-yl)-2,5-methano-2,3,4,5-tetrahydro-1H-benzo[c]azepine, L-tartrate salt (254 mg, 99%, AUC HPLC >99%) as a white solid: $^1$H NMR (CD$_3$OD, 500 MHz) δ 8.19 (d, J=9.5 Hz, 1H), 7.95 (s, 1H), 7.80 (d, J=8.5 Hz, 1H), 7.74 (t, J=72.0 Hz, 1H), 7.51-7.44 (m, 5H), 6.77 (d, J=8.5 Hz, 1H), 5.03-5.01 (m, 1H), 4.61 (br s, 1H), 4.40 (s, 2.2H), 4.29 (br s, 1H), 4.01 (br s, 1H), 3.66-3.57 (m, 2H), 2.81 (br s, 1H), 2.70 (br s, 1H); ESI MS m/z 414 [M+H]$^+$. Anal. Calcd. For $C_{22}H_{18}ClF_2N_3O \cdot 1.1C_4H_6O_6 \cdot 0.8H_2O$: C, 53.44; H, 4.45; N, 7.08. Found: C, 53.36; H, 4.21; N, 7.12.

Step D: Following the procedure of Step E of Example 3, the (−)-enantiomer from Step B above was converted to the corresponding L-tartrate salt to give (−)-5-(4-chlorophenyl)-8-(6-(difluoromethoxy)pyridazin-3-yl)-2,5-methano-2,3,4,5-tetrahydro-1H-benzo[c]azepine, L-tartrate salt (254 mg, 99%, AUC HPLC >99%) as a white solid: $^1$H NMR (CD$_3$OD, 500 MHz) δ 8.19 (d, J=9.5 Hz, 1H), 7.95 (s, 1H), 7.80 (d, J=8.5 Hz, 1H), 7.74 (t, J=72.0 Hz, 1H), 7.50-7.44 (m, 5H), 6.76 (d, J=8.0 Hz, 1H), 5.03-5.01 (m, 1H), 4.61 (br s, 1H), 4.40 (s, 1.8H), 4.29 (br s, 1H), 4.01 (br s, 1H), 3.66-3.57 (m, 2H), 2.81 (br s, 1H), 2.70 (br s, 1H); ESI MS m/z 414 [M+H]$^+$. Anal. Calcd. For $C_{22}H_{18}ClF_2N_3O \cdot 0.9C_4H_6O_6 \cdot 1.4H_2O$: C, 53.55; H, 4.60; N, 7.32. Found: C, 53.46; H, 4.52; N, 7.31.

Example 7

Preparation of (+)- and (−)-6-(5-(4-chlorophenyl)-2,5-methano-2,3,4,5-tetrahydro-1H-benzo[c]azepin-8-yl)pyridazin-3-ol, L-tartrate Salts

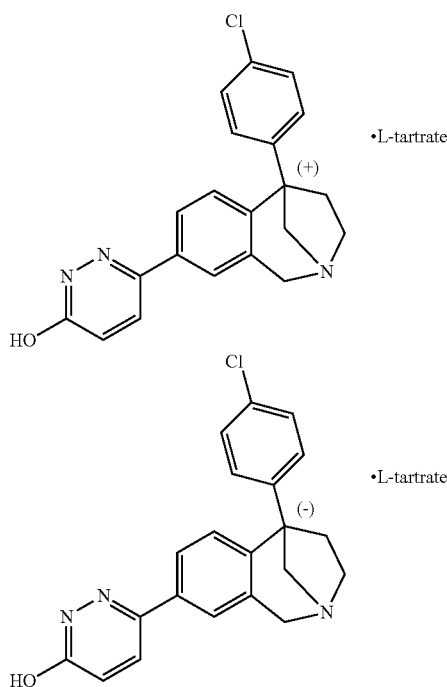

Step A: (+)-5-(4-chlorophenyl)-8-(4-(difluoromethoxy)phenyl)-2,5-methano-2,3,4,5-tetrahydro-1H-benzo[c]azepine L-tartrate salt (63 mg, 0.11 mmol) from Step C of Example 6 was dissolved in aqueous 1N HCl solution and refluxed overnight. The reaction mixture was extracted with methylene chloride (3×), washed with saturated aqueous sodium bicarbonate, dried over sodium sulfate, filtered, and concentrated to give (+)-6-(5-(4-chlorophenyl)-2,5-methano-2,3,4,5-tetrahydro-1H-benzo[c]azepin-8-yl)pyridazin-3-ol (23 mg, 56%).

Step B: Following the procedure of Step E of Example 3, the benzazepine (23 mg, 0.063 mmol) from Step A above was converted to the corresponding L-tartrate salt to give (+)-6-(5-(4-chlorophenyl)-2,5-methano-2,3,4,5-tetrahydro-1H-benzo[c]azepin-8-yl)pyridazin-3-ol, L-tartrate salt (32 mg, 99%, AUC HPLC >99%) as a white solid: $^1$H NMR (CD$_3$OD, 500 MHz) δ 7.99 (d, J=10.0 Hz, 1H), 7.79 (s, 1H), 7.66 (dd, J=8.5, 1.5 Hz, 1H), 7.50-7.43 (m, 4H), 7.04 (d, J=10.0 Hz, 1H), 6.71 (d, J=8.5 Hz, 1H), 4.99 (d, J=16.0 Hz, 1H), 4.59 (d, J=16.0 Hz, 1H), 4.45 (s, 2H), 4.19 (d, J=10.5 Hz, 1H), 4.01 (t, J=11.5 Hz, 1H), 3.62 (d, J=10.5 Hz, 1H), 3.58-2.52 (m, 1H), 2.84-2.77 (m, 1H), 2.69-2.65 (m, 1H); ESI MS m/z 364 [M+H]$^+$.

Step C: (−)-5-(4-chlorophenyl)-8-(4-(difluoromethoxy)phenyl)-2,5-methano-2,3,4,5-tetrahydro-1H-benzo[c]azepine L-tartrate salt (52 mg, 0.092 mmol) from Step D of Example 6 was dissolved in aqueous 1N HCl solution and refluxed overnight. The reaction mixture was extracted with methylene chloride (3×), washed with saturated aqueous sodium bicarbonate, dried over sodium sulfate, filtered, and concentrated to give (−)-6-(5-(4-chlorophenyl)-2,5-methano-2,3,4,5-tetrahydro-1H-benzo[c]azepin-8-yl)pyridazin-3-ol (19 mg, 57%).

Step D: Following the procedure of Step E of Example 3, the benzazepine (19 mg, 0.052 mmol) from Step C above was converted to the corresponding L-tartrate salt to give (−)-6-(5-(4-chlorophenyl)-2,5-methano-2,3,4,5-tetrahydro-1H-benzo[c]azepin-8-yl)pyridazin-3-ol, L-tartrate salt (26 mg, 99%, AUC HPLC >99%) as a white solid: $^1$H NMR (CD$_3$OD, 500 MHz) δ 7.99 (d, J=10.0 Hz, 1H), 7.79 (s, 1H), 7.66 (dd, J=8.5, 1.5 Hz, 1H), 7.50-7.43 (m, 4H), 7.04 (d, J=10.0 Hz, 1H), 6.71 (d, J=8.5 Hz, 1H), 4.99 (d, J=16.0 Hz, 1H), 4.59 (d, J=16.0 Hz, 1H), 4.45 (s, 2H), 4.19 (d, J=10.5 Hz, 1H), 4.01 (t, J=11.5 Hz, 1H), 3.62 (d, J=10.5 Hz, 1H), 3.58-2.52 (m, 1H), 2.84-2.77 (m, 1H), 2.69-2.65 (m, 1H); ESI MS m/z 364 [M+H]$^+$.

Example 8

Preparation of rac-4-(5-(4-chlorophenyl)-2,5-methano-2,3,4,5-tetrahydro-1H-benzo[c]azepin-8-yl)benzonitrile, L-tartrate Salt

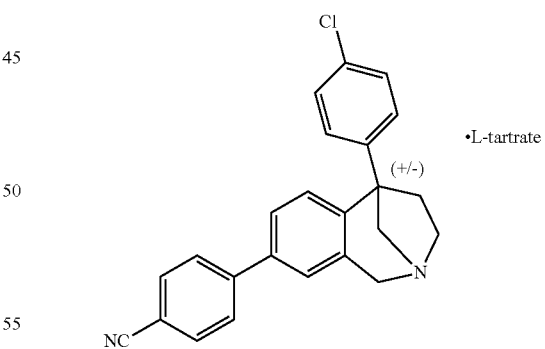

This compound was prepared from 5-(4-chlorophenyl)-2,5-methano-8-(4,4,5,5-tetramethyl-1,3,2-dioxaborolan-2-yl)-2,3,4,5-tetrahydro-1H-benzo[c]azepine from Step B of Example 3 and 4-iodobenzonitrile, following the procedures of Steps C and E of Example 3. rac-4-(5-(4-chlorophenyl)-2,5-methano-2,3,4,5-tetrahydro-1H-benzo[c]azepin-8-yl)benzonitrile, L-tartrate salt (59 mg, AUC HPLC 98.7%) was obtained as an off-white solid: $^1$H NMR (DMSO-d$_6$, 500 MHz) δ 7.90 (d, J=8.0 Hz, 2H), 7.80 (d, J=8.5 Hz, 2H), 7.54-7.43 (m, 6H), 6.51 (d, J=8.0 Hz, 1H), 4.62 (d, J=16.5 Hz, 1H), 4.21-4.19 (m, 3H), 3.86 (d, J=10.0 Hz, 1H), 3.51 (br s, 1H), 3.18-3.12 (m, 2H), 2.51-2.49 (m, 2H); ESI MS m/z 371 [M+H]⁺.

Example 9

Preparation of rac-5-(4-chlorophenyl)-2,5-methano-8-(4-(methylsulfonyl)phenyl)-2,3,4,5-tetrahydro-1H-benzo[c]azepine, L-tartrate Salt

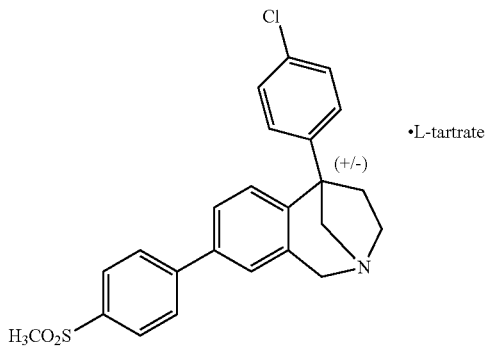

This compound was prepared from 5-(4-chlorophenyl)-2,5-methano-8-(4,4,5,5-tetramethyl-1,3,2-dioxaborolan-2-yl)-2,3,4,5-tetrahydro-1H-benzo[c]azepine from Step B of Example 3 and 1-chloro-4-(methylsulfonyl)benzene, following the procedures of Steps C and E of Example 3. rac-5-(4-chlorophenyl)-2,5-methano-8-(4-(methylsulfonyl)phenyl)-2,3,4,5-tetrahydro-1H-benzo[c]azepine, L-tartrate salt (27 mg, AUC HPLC >99%) was obtained as a white solid: ¹H NMR (CD₃OD, 500 MHz) δ 8.15 (s, 1H), 7.95 (dd, J=7.5, 1.5 Hz, 2H), 7.71 (t, J=8.0 Hz, 1H), 7.61 (s, 1H), 7.53-7.44 (m, 5H), 6.74 (d, J=8.0 Hz, 1H), 5.02 (d, J=16.5 Hz, 1H), 4.63 (d, J=15.0 Hz, 1H), 4.45 (s, 2H), 4.23 (d, J=10.0 Hz, 1H), 4.04-4.02 (m, 1H), 3.66-3.58 (m, 2H), 3.16 (s, 3H), 2.84-2.82 (m, 1H), 2.72-2.68 (m, 1H); ESI MS m/z 424 [M+H]⁺.

Example 10

Preparation of (+)- and (−)-8-([1,2,4]triazolo[1,5-a]pyridin-6-yl)-5-(3,4-dichlorophenyl)-2,5-methano-2,3,4,5-tetrahydro-1H-benzo[c]azepine, L-tartrate Salts

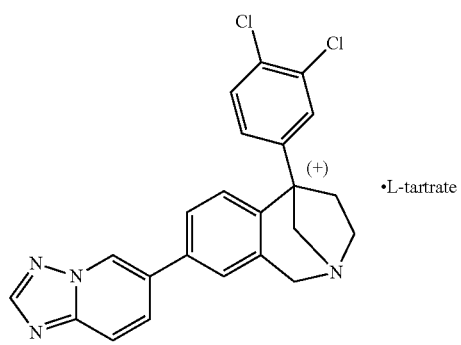

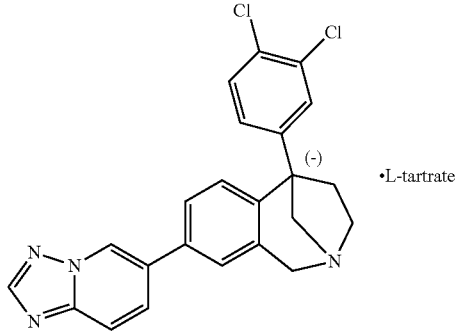

Step A: To a mixture of pyrrolidin-3-ol (3.8 g, 44 mmol) and 3-methoxybenzaldehyde (5.0 g, 37 mmol) in 1,2-dichloroethane (100 mL), was added sodium triacetoxyborohydride (15.5 g, 73 mmol) portionwise at 0° C. Acetic acid (2.8 mL, 44 mmol) was subsequently added. The reaction mixture was warmed to 45° C. and stirred overnight. A saturated solution of sodium bicarbonate was added and the resulting mixture was extracted with methylene chloride. The organic layer was dried over anhydrous sodium sulfate and concentrated in vacuo. The crude product, 1-(3-methoxybenzyl)pyrrolidin-3-ol, obtained (6.0 g, 79%) as a yellow oil, was used as such in the next reaction: ¹H NMR (CDCl₃, 400 MHz) δ 7.28-7.18 (m, 1H), 6.92-6.86 (m, 2H), 6.82-6.76 (m, 1H), 4.32 (tdd, J=2.3, 5.0, 7.3 Hz, 1H), 3.83-3.78 (m, 3H), 3.59 (s, 2H), 2.86 (dt, J=4.9, 8.6 Hz, 1H), 2.68 (d, J=9.8 Hz, 1H), 2.53 (dd, J=5.3, 10.3 Hz, 1H), 2.45 (br s, 1H), 2.30 (dt, J=6.5, 8.9 Hz, 1H), 2.24-2.13 (m, 1H), 1.78-1.68 (m, 1H); ESI MS (m/z) 208 [M+H]⁺.

Step B: To a solution of oxalyl chloride (14.6 mL, 170 mmol) in methylene chloride (100 mL) at −78° C., was added dimethyl sulfoxide (14.3 mL, 170 mmol). After 15 min, a solution of 1-(3-methoxybenzyl)pyrrolidin-3-ol (11.8 g, 56.8 mmol) from Step A above in methylene chloride (100 mL) was added dropwise. After 4 h, triethylamine (52 mL, 369 mmol) was added and the reaction mixture was warmed to ambient temperature. Water (50 mL) was added and the aqueous layer was separated and extracted with methylene chloride. The organic layer was dried over anhydrous sodium sulfate and concentrated in vacuo. The residue was purified by column chromatography (methylene chloride to 1:1 methylene chloride/ethyl acetate) to provide 1-(3-methoxybenzyl)pyrrolidin-3-one (8.0 g, 68%) as a colorless oil: ¹H NMR (CD₃OD, 400 MHz) δ 7.26 (t, J=7.9 Hz, 1H), 7.00-6.92 (m, 2H), 6.89-6.81 (m, 1H), 3.81 (s, 3H), 3.72 (s, 2H), 2.99-2.95 (m, 2H), 2.94 (s, 2H), 2.41 (t, J=7.0 Hz, 2H); ESI MS (m/z) 206 [M+H]⁺.

Step C: To a solution of 3,4-dichloro-1-iodobenzene (1.33 g, 4.90 mmol) in tetrahydrofuran (10 mL) at room temperature, was added isopropylmagnesium bromide (2.4 mL of a 2.0 M solution in THF, 4.9 mmol) dropwise. After 2 h, a solution of 1-(3-methoxybenzyl)pyrrolidin-3-one (500 mg, 2.43 mmol) from Step B above in tetrahydrofuran (3 mL) was added dropwise at 0° C. The reaction mixture was warmed to ambient temperature and stirred for 2 h. The reaction mixture was quenched with saturated ammonium chloride (5 mL). The mixture was diluted with ethyl acetate (100 mL) and washed with saturated ammonium chloride (20 mL), water (20 mL), and brine (20 mL), dried over anhydrous sodium sulfate and concentrated in vacuo. Purification by silica gel chromatography (5% ethyl acetate/methylene chloride to 80% ethyl acetate/methylene chloride) gave 3-(3,4-dichlorophenyl)-1-(3-methoxybenzyl)pyrrolidin-3-ol (500 mg, 58%) as a yellow oil: ESI MS (m/z) 352 [M+H]+.

Step D: To 3-(3,4-dichlorophenyl)-1-(3-methoxybenzyl)pyrrolidin-3-ol (6.0 g, 17.0 mmol) from Step C above in methylene chloride (60 mL) was added triflic acid (24 mL). After 3.5 h, the reaction mixture was carefully poured over ice (ca. 10 g), made strongly basic with 6N sodium hydroxide and extracted with methylene chloride. The organic layer was dried over sodium sulfate and concentrated in vacuo. The residue was purified by column chromatography (methylene chloride to 90:9:1 methylene chloride/methanol/ammonium hydroxide) to provide 5-(3,4-dichlorophenyl)-8-methoxy-2,5-methano-2,3,4,5-tetrahydro-1H-benzo[c]azepine (5.0 g, 88%): $^1$H NMR (CD$_3$OD, 400 MHz) δ 7.72 (d, J=1.8 Hz, 1H), 7.46 (d, J=2.0 Hz, 1H), 7.24 (t, J=7.9 Hz, 1H), 6.99 (s, 1H), 6.97 (s, 1H), 6.87-6.81 (m, 1H), 3.81 (s, 3H), 3.73 (s, 2H), 2.98-2.88 (m, 3H), 2.86-2.80 (m, 1H), 2.32-2.22 (m, 1H), 2.20-2.11 (m, 1H); ESI MS (m/z) 334 [M+H]+.

Step E: A solution of 5-(3,4-dichlorophenyl)-8-methoxy-2,5-methano-2,3,4,5-tetrahydro-1H-benzo[c]azepine (5.0 g, 15 mmol) from Step D above in 48% aqueous hydrobromic acid (75 mL) and acetic acid (75 mL) was heated to 135° C. After 12 h, the reaction mixture was cooled to ambient temperature, brought to ca. pH=7-8 with 1 N sodium hydroxide and saturated sodium bicarbonate and extracted with ethyl acetate (2×). The combined organics were washed with brine and concentrated in vacuo. The residue was purified by column chromatography (methylene chloride to 90:9:1 methylene chloride/methanol/ammonium hydroxide) to provide 5-(3,4-dichlorophenyl)-2,5-methano-2,3,4,5-tetrahydro-1H-benzo[c]azepin-8-ol (2.5 g, 52%) as a white solid: $^1$H NMR (CD$_3$OD, 400 MHz) δ 7.55 (d, J=7.8 Hz, 2H), 7.38-7.25 (m, 1H), 6.52 (s, 1H), 6.49-6.43 (m, 1H), 6.28 (d, J=8.5 Hz, 1H), 4.50 (s, 1H), 3.93 (s, 1H), 3.64 (s, 1H), 3.43 (br s, 1H), 3.11-3.03 (m, 1H), 2.96 (d, J=10.5 Hz, 1H), 2.51-2.32 (m, 2H); ESI MS (m/z) 320 [M+H]+.

Step F: To a suspension of 5-(3,4-dichlorophenyl)-2,5-methano-2,3,4,5-tetrahydro-1H-benzo[c]azepin-8-ol (500 mg, 1.6 mmol) from Step E above in methylene chloride (10 mL) at 0° C., was added pyridine (0.16 g, 2.0 mmol) and triflic anhydride (0.6 g, 2.0 mmol). The reaction mixture was warmed to room temperature. After 12 h, the reaction mixture was diluted with methylene chloride (50 mL) and saturated sodium bicarbonate (10 mL) was added. The organic layer was separated and washed with brine (10 mL), dried over sodium sulfate and concentrated in vacuo to provide 5-(3,4-chlorophenyl)-2,5-methano-2,3,4,5-tetrahydro-1H-benzo[c]azepin-8-yl trifluoromethanesulfonate (0.8 g of crude product, ~100%) which was used directly in the next step: ESI MS (m/z) 452 [M+H]+.

Step G: A mixture of bis(pinacolato)diboron (622 mg, 2.45 mmol), potassium acetate (611 mg, 6.22 mmol) and 5-(3,4-chlorophenyl)-2,5-methano-2,3,4,5-tetrahydro-1H-benzo[c]azepin-8-yl trifluoromethanesulfonate (800 mg, 1.9 mmol) from Step F above in DMF (16 mL) was purged with nitrogen for 5 min. Next, dichloro[1,1'-bis(diphenylphosphino)ferrocene]palladium(II) dichloromethane adduct (231 mg, 0.28 mmol) was added and the mixture was purged again with nitrogen. The reaction mixture was heated at 80° C. for 2 h. After the completion of reaction, as monitored by LC-MS, 6-bromo-[1,2,4]triazolo[1,5-a]pyridine (409 mg, 2.1 mmol), cesium carbonate (2.02 g, 6.2 mmol), and water (3 mL) were sequentially added. The reaction mixture was purged with nitrogen and then dichloro[1,1'-bis(diphenylphosphino)ferrocene]palladium(II) dichloromethane adduct (230 mg, 0.28 mmol) was added. The mixture was degassed again and heated to 90° C. for 3 h. The reaction mixture was diluted with water (25 mL) and extracted with ethyl acetate (2×25 mL). The combined organics were washed with water (2×20 mL) and brine (20 mL), dried over sodium sulfate, filtered and concentrated in vacuo. The residue was purified by column chromatography (methylene chloride to 90:9:1 methylene chloride/methanol/ammonium hydroxide) to afford 8-([1,2,4]triazolo[1,5-a]pyridin-6-yl)-5-(3,4-dichlorophenyl)-2,5-methano-2,3,4,5-tetrahydro-1H-benzo[c]azepine, (350 mg, 54%) as a brownish solid: ESI MS (m/z) 421 [M+H]+.

Step H: The benzazepine (350 mg) from Step G above was resolved by preparative chiral HPLC (Chiralcel OJ column, using 60:40:0.2 hexane/ethanol/diethylamine as the eluent) to give the (−)-enantiomer [110 mg, [α]$^{25}_D$ −33.6° (c 0.21, methanol)] and the (+)-enantiomer [115 mg, [α]$^{25}_D$ +33.6° (c 0.21, methanol)].

Step I: To a solution of the (−)-enantiomer (110 mg, 0.26 mmol) from Step H above in acetonitrile (5 mL) was added L-tartaric acid (39 mg, 0.26 mmol) followed by water (15 mL). The solution was then frozen and lyophilized for 48 h to provide (−)-8-([1,2,4]triazolo[1,5-a]pyridin-6-yl)-5-(3,4-dichlorophenyl)-2,5-methano-2,3,4,5-tetrahydro-1H-benzo[c]azepine, L-tartrate salt (140 mg, 97%, AUC HPLC >98%) as a white solid: $^1$H NMR (CD$_3$OD, 400 MHz) δ 9.10 (s, 1H), 8.47 (s, 1H), 8.05-7.99 (m, 1H), 7.91-7.85 (m, 1H), 7.74-7.63 (m, 3H), 7.60 (d, J=8.3 Hz, 1H), 7.50-7.35 (m, 1H), 6.79 (d, J=8.0 Hz, 1H), 4.70-4.58 (m, 1H), 4.48 (s, 3H), 4.25 (d, J=10.3 Hz, 1H), 4.10-3.96 (m, 1H), 3.71-3.55 (m, 2H), 2.90-2.79 (m, 1H), 2.76-2.68 (m, 1H); ESI MS (m/z) 421 [M+H]+.

Step J: To a solution of the (+)-enantiomer (115 mg, 0.27 mmol) from Step H above in methanol (5 mL) was added L-tartaric acid (41 mg, 0.27 mmol) followed by water (15 mL). The solution was then frozen and lyophilized for 48 h to provide (+)-8-([1,2,4]triazolo[1,5-a]pyridin-6-yl)-5-(3,4-dichlorophenyl)-2,5-methano-2,3,4,5-tetrahydro-1H-benzo[c]azepine, L-tartrate salt (146 mg, 97%, AUC HPLC >99%) as a white solid: $^1$H NMR (CD$_3$OD, 400 MHz) δ 9.10 (s, 1H), 8.47 (s, 1H), 8.02 (dd, J=1.8, 9.3 Hz, 1H), 7.88 (d, J=9.3 Hz, 1H), 7.76-7.65 (m, 3H), 7.60 (d, J=8.3 Hz, 1H), 7.50-7.34 (m, 1H), 6.79 (d, J=8.0 Hz, 1H), 4.70-4.59 (m, 1H), 4.48 (s, 3H), 4.29-4.20 (m, 1H), 4.12-3.96 (m, 1H), 3.71-3.55 (m, 2H), 2.90-2.80 (m, 1H), 2.78-2.67 (m, 1H); ESI MS (m/z) 421 [M+H]+.

Example 11

Preparation of (+)- and (−)-8-(2-oxo-2,3-dihydrobenzo[d]oxazol-6-yl)-5-(3,4-dichlorophenyl)-2,5-methano-2,3,4,5-tetrahydro-1H-benzo[c]azepine, L-tartrate Salts

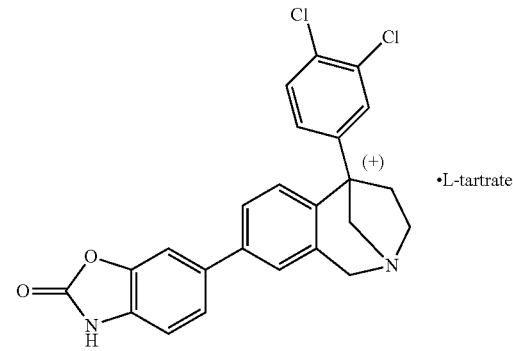

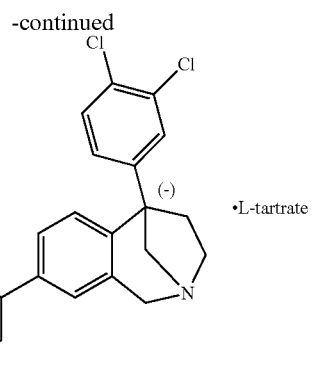

•L-tartrate

Step A: A mixture of bis(pinacolato)diboron (389 mg, 1.52 mmol), potassium acetate (379 mg, 3.87 mmol) and 5-(3,4-chlorophenyl)-2,5-methano-2,3,4,5-tetrahydro-1H-benzo[c]azepin-8-yl trifluoromethanesulfonate (529 mg, 1.17 mmol) from Step F of Example 10 in DMF (6 mL), was purged with nitrogen for 5 min. Next, 1,1'-bis(diphenylphosphino)ferrocene dichloropalladium (143 mg, 0.17 mmol) was added and the mixture was purged again with nitrogen. The reaction mixture was heated at 80° C. for 2 h. After the completion of reaction, as monitored by LC-MS, 6-bromo-3,3a-dihydrobenzo[d]oxazol-2(7aH)-one (420 mg, 1.96 mmol), cesium carbonate (1.32 g, 6.4 mmol), and water (3 mL) were sequentially added. The reaction mixture was purged with nitrogen and then dichloro[1,1'-bis(diphenylphosphino)ferrocene]palladium(II) dichloromethane adduct (143 mg, 0.17 mmol) was added. The mixture was degassed again and heated to 90° C. for 3 h. The reaction mixture was diluted with water (25 mL) and extracted with ethyl acetate (2×25 mL). The combined organics were washed with water (2×20 mL) and brine (20 mL), dried over sodium sulfate, filtered and concentrated in vacuo. The residue was purified by column chromatography (methylene chloride to 90:9:1 methylene chloride/methanol/ammonium hydroxide) to afford 8-(2-oxo-2,3-dihydrobenzo[d]oxazol-6-yl)-5-(3,4-dichlorophenyl)-2,5-methano-2,3,4,5-tetrahydro-1H-benzo[c]azepine (150 mg, 29%) as a brownish solid: ESI MS (m/z) 437 [M+H]$^+$.

Step B: The benzazepine (150 mg) from Step A above was resolved by preparative chiral HPLC (CHIRALPAK AD-H column, using 50:50:0.2 hexane/ethanol/diethylamine as the eluent) to give the (+)-enantiomer [33 mg, $[\alpha]^{25}_D$ +29.0° (c 0.17, methanol)] and the (−)-enantiomer [31 mg, $[\alpha]^{25}_D$ −31.3° (c 0.15, methanol)].

Step C: To a solution of the (+)-enantiomer (33 mg, 0.075 mmol) from Step B above in acetonitrile (5 mL) was added L-tartaric acid (11 mg, 0.075 mmol) followed by water (15 mL). The solution was then frozen and lyophilized for 48 h to provide (+)-8-(2-oxo-2,3-dihydrobenzo[d]oxazol-6-yl)-5-(3,4-dichlorophenyl)-2,5-methano-2,3,4,5-tetrahydro-1H-benzo[c]azepine, L-tartrate (41 mg, 95%, AUC HPLC 95.1%) as a white solid: $^1$H NMR (CD$_3$OD, 400 MHz) δ 7.67 (d, J=8.3 Hz, 2H), 7.52 (d, J=10.5 Hz, 2H), 7.48-7.35 (m, 3H), 7.17 (d, J=8.3 Hz, 1H), 6.70 (d, J=8.0 Hz, 1H), 4.67-4.54 (m, 1H), 4.47 (s, 3H), 4.28-4.17 (m, 1H), 4.09-3.96 (m, 1H), 3.70-3.53 (m, 2H), 2.87-2.77 (m, 1H), 2.74-2.66 (m, 1H); ESI MS (m/z) 437 [M+H]$^+$.

Step D: To a solution of the (−)-enantiomer (31 mg, 0.068 mmol) from Step B above in acetonitrile (5 mL) was added L-tartaric acid (10 mg, 0.068 mmol) followed by water (15 mL). The solution was then frozen and lyophilized for 48 h to provide (−)-8-(2-oxo-2,3-dihydrobenzo[d]oxazol-6-yl)-5-(3,4-dichlorophenyl)-2,5-methano-2,3,4,5-tetrahydro-1H-benzo[c]azepine, L-tartrate (38 mg, 97%, AUC HPLC 96.8%) as a white solid: $^1$H NMR (CD$_3$OD, 400 MHz) δ 7.66 (br s, 2H), 7.52 (d, J=9.0 Hz, 2H), 7.48-7.35 (m, 3H), 7.17 (d, J=8.0 Hz, 1H), 6.69 (d, J=8.3 Hz, 1H), 4.67-4.53 (m, 1H), 4.46 (s, 3H), 4.27-4.15 (m, 1H), 4.10-3.93 (m, 1H), 3.71-3.54 (m, 2H), 2.88-2.78 (m, 1H), 2.75-2.65 (m, 1H); ESI MS (m/z) 437 [M+H]$^+$.

Example 12

Preparation of 5-(4-chlorophenyl)-8-methoxy-2,5-ethano-2,3,4,5-tetrahydro-1H-2-benzo[c]azepine, L-tartrate Salt

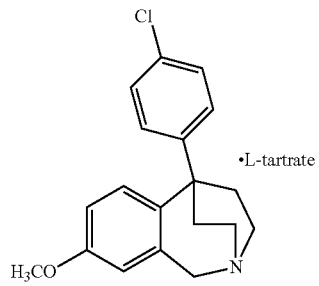 [SMILES: COc1ccc2c(c1)CN1CCC2(c2ccc(Cl)cc2)CC1]

•L-tartrate

Step A: A mixture of 3-methoxybenzaldehyde (10.0 g, 73.4 mmol), 1,4-dioxa-8-azaspiro[4.5]decane (10.5 g, 73.4 mmol), sodium triacetoxyborohydride (20.2 g, 95.3 mmol), and acetic acid (4.2 mL), in methylene chloride (400 mL), was stirred at ambient temperature. After 19 h, a 2 N aqueous sodium carbonate solution (220 mL) was added portionwise. After stirring for 15 min, the aqueous layer was separated and extracted with methylene chloride (100 mL). The combined organic layers were washed with brine (100 mL), dried over sodium sulfate and concentrated in vacuo to provide 8-(3-methoxybenzyl)-1,4-dioxa-8-azaspiro[4.5]decane (18.3 g, 95%) as a yellow oil: $^1$H NMR (CDCl$_3$, 500 MHz) δ 7.25-7.19 (m, 1H), 6.91-6.89 (m, 2H), 6.80-6.77 (m, 1H), 3.94 (s, 4H), 3.80 (s, 3H), 3.50 (s, 2H), 2.53-2.49 (m, 4H), 1.76-1.72 (m, 4H).

Step B: To 8-(3-methoxybenzyl)-1,4-dioxa-8-azaspiro[4.5]decane (2.3 g, 8.7 mmol) from Step A above was added an ice-cold solution of concentrated hydrochloric acid (40 mL). The suspension was stirred at 0° C. for 5 min and then allowed to warm to ambient temperature. After 0.5 h, the homogeneous solution was poured into a 0° C. sodium hydroxide solution (21.5 g in 200 mL of water) and then extracted with methylene chloride (2×150 mL). The combined organic layers were dried over sodium sulfate and concentrated in vacuo. Purification by silica gel chromatography (methylene chloride to 1:1 ethyl acetate/methylene chloride) gave 1-(3-methoxybenzyl)piperidin-4-one (1.4 g, 73%) as a colorless oil: $^1$H NMR (DMSO-d$_6$, 500 MHz) δ 7.25-7.19 (m, 1H), 6.92-6.91 (m, 2H), 6.85-6.83 (m, 1H), 3.75 (s, 3H), 3.58 (s, 2H), 2.69-2.65 (m, 4H), 2.37-2.32 (m, 4H).

Step C: To 1-bromo-4-chlorobenzene (397 mg, 2.07 mmol) in tetrahydrofuran (10 mL), at −78° C., was added n-butyllithium (0.91 mL of a 2.5 M solution in hexanes, 2.3 mmol) dropwise. After 0.5 h, a solution of the ketone (500 mg, 2.28 mmol) from Step B above in tetrahydrofuran (5 mL) was added dropwise. The reaction mixture was stirred at −78° C. for 1.5 h and then warmed to 0° C. After 1 h, the reaction mixture was quenched with saturated ammonium chloride (5 mL) and warmed to ambient temperature. The mixture was diluted with ethyl acetate (50 mL) and washed with saturated ammonium chloride (20 mL), water (20 mL), brine (20 mL), dried over sodium sulfate and concentrated in vacuo. Purification by silica gel chromatography (5% ethyl acetate/methylene chloride to ethyl acetate) gave 4-(4-chlorophenyl)-1-(3-methoxybenzyl)piperidin-4-ol (370 mg, 53%) as a colorless oil: $^1$H NMR (DMSO-d$_6$, 500 MHz) δ 7.50 (d, J=8.5 Hz, 2H), 7.35 (d, J=8.5 Hz, 2H), 7.24-7.21 (m, 1H), 6.90-6.89 (m, 2H), 6.81-6.79 (m, 1H), 4.87 (s, 1H), 3.74 (s, 3H), 3.47 (s, 2H), 2.61-2.59 (m, 2H), 2.43-2.38 (m, 2H), 1.94-1.87 (m, 2H), 1.57-1.54 (m, 2H).

Step D: To 4-(4-chlorophenyl)-1-(3-methoxybenzyl)piperidin-4-ol (1.35 g, 4.07 mmol) from Step C above in methylene chloride (15 mL) was added triflic acid (15 mL). After 2 h, the reaction mixture was carefully poured over ice (ca. 100 g), made strongly basic with 6 N sodium hydroxide and extracted with methylene chloride (2×). The combined organic layers were washed with brine, dried over sodium sulfate and concentrated in vacuo to provide 5-(4-chlorophenyl)-8-methoxy-2,5-ethano-2,3,4,5-tetrahydro-1H-benzo[c]azepine (1.2 g, 94%) as a yellow residue: $^1$H NMR (CDCl$_3$, 500 MHz) δ 7.35-7.32 (m, 2H), 7.22-7.19 (m, 2H), 6.65 (d, J=2.7 Hz, 1H), 6.45 (dd, J=8.2, 2.7 Hz, 1H), 6.16 (d, J=8.7 Hz, 1H), 4.36 (s, 2H), 3.76 (s, 3H), 3.21-3.15 (m, 2H), 3.08-3.02 (m, 2H), 2.54-2.48 (m, 2H), 2.11-2.05 (m, 2H).

Step E: A portion of 5-(4-chlorophenyl)-8-methoxy-2,5-ethano-2,3,4,5-tetrahydro-1H-benzo[c]azepine from Step D above was purified by column chromatography (methylene chloride to 90:9:1 methylene chloride/methanol/ammonium hydroxide). To a portion of the purified material (19 mg, 0.060 mmol) in methanol (3 mL) was added L-tartaric acid (9.1 mg, 0.060 mmol) in water (12 mL). The resultant solution was lyophilized to give 5-(4-chlorophenyl)-8-methoxy-2,5-ethano-2,3,4,5-tetrahydro-1H-benzo[c]azepine, L-tartrate salt (26 mg, 100%, AUC HPLC 97.4%) as a white solid: $^1$H NMR (CD$_3$OD, 500 MHz) δ 7.43 (d, J=8.6 Hz, 2H), 7.31 (d, J=8.6 Hz, 2H), 6.82 (d, J=2.4 Hz, 1H), 6.64 (dd, J=8.8, 2.5 Hz, 1H), 6.26 (d, J=8.8 Hz, 1H), 4.73 (s, 2H), 4.39 (s, 1.6H), 3.74 (s, 3H), 3.57-3.52 (m, 2H), 3.38-3.30 (m, 2H), 2.73-2.68 (m, 2H), 2.40-2.43 (m, 2H); ESI MS m/z 314 [M+H]$^+$.

Example 13

Preparation of 5-(4-chlorophenyl)-2,5-ethano-2,3,4,5-tetrahydro-1H-2-benzo[c]azepin-8-ol, L-tartrate Salt

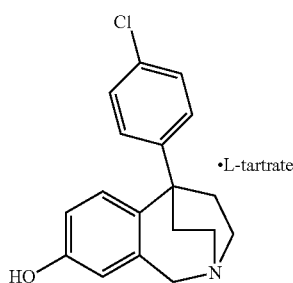 [SMILES: Oc1ccc2c(c1)CN1CCC2(c2ccc(Cl)cc2)CC1]

Step A: A mixture of 5-(4-chlorophenyl)-8-methoxy-2,5-ethano-2,3,4,5-tetrahydro-1H-benzo[c]azepine (1.1 g, 3.4 mmol) from Step D of Example 12 in 48% hydrobromic acid in water (15 mL) and acetic acid (15 mL) was heated to 135° C. After 9 h, the reaction mixture was cooled to ambient temperature, brought to ca. pH=8.5-10 with 6 N sodium hydroxide and saturated sodium bicarbonate and extracted with ethyl acetate (2×75 mL). The combined organics were concentrated in vacuo to provide 5-(4-chlorophenyl)-2,5-ethano-2,3,4,5-tetrahydro-1H-benzo[c]azepin-8-ol (860 mg, 84%): $^1$H NMR (DMSO-d$_6$, 300 MHz) δ 9.13 (s, 1H), 7.42 (d, J=8.4 Hz, 2H), 7.27 (d, J=8.4 Hz, 2H), 6.49 (d, J=2.4 Hz, 1H), 6.28 (dd, J=8.7, 2.7 Hz, 1H), 5.85 (d, J=8.7 Hz, 1H), 4.16 (s, 2H), 3.04-2.96 (m, 2H), 2.91-2.82 (m, 2H), 2.43-2.37 (m, 2H), 1.99-1.89 (m, 2H).

Step B: A portion of 5-(4-chlorophenyl)-2,5-ethano-2,3,4,5-tetrahydro-1H-benzo[c]azepin-8-ol was purified by column chromatography (methylene chloride to 90:9:1 methylene chloride/methanol/ammonium hydroxide). To a portion of the purified material (23 mg, 0.076 mmol) in methanol (1.5 mL) and acetonitrile (3 mL) was added L-tartaric acid (11.5 mg, 0.076 mmol) in water (18 mL). The resultant solution was lyophilized to give 5-(4-chlorophenyl)-2,5-ethano-2,3,4,5-tetrahydro-1H-benzo[c]azepin-8-ol, L-tartrate salt (34 mg, 96%, AUC HPLC 98.1%) as a white solid: $^1$H NMR (DMSO-d$_6$, 500 MHz) δ 9.30 (br s, 1H), 7.45 (d, J=8.5 Hz, 2H), 7.29 (d, J=8.5 Hz, 2H), 6.58 (d, J=2.0 Hz, 1H), 6.38 (dd, J=8.5, 2.5 Hz, 1H), 5.92 (d, J=8.5 Hz, 1H), 4.41 (s, 2H), 4.07 (s, 2.2H), 3.25-3.21 (m, 2H), 3.08-3.04 (m, 2H), 2.54-2.49 (m, 2H), 2.12-2.06 (m, 2H); ESI MS m/z 300 [M+H]$^+$.

Example 14

Preparation of 5-(4-chlorophenyl)-8-(6-(difluoromethoxy)pyridazin-3-yl)-2,5-ethano-2,3,4,5-tetrahydro-1H-2-benzo[c]azepine, L-tartrate Salt

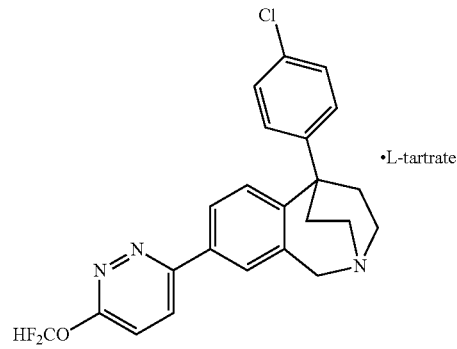

Step A: To a suspension of 5-(4-chlorophenyl)-2,5-ethano-2,3,4,5-tetrahydro-1H-benzo[c]azepin-8-ol (860 mg, 2.9 mmol) from Step A of Example 13 in methylene chloride (30 mL), at −20° C., was added pyridine (0.25 mL, 3.1 mmol) and triflic anhydride (0.53 mL, 3.1 mmol). After 1 h, additional pyridine (0.05 mL, 0.60 mmol) and triflic anhydride (0.10 mL, 0.60 mmol) was added to the golden solution. After 0.5 h, the reaction mixture was diluted with methylene chloride (25 mL) and saturated sodium bicarbonate (10 mL) was added. The organic layer was separated, washed with brine, dried over sodium sulfate, and concentrated in vacuo to provide 5-(4-chlorophenyl)-2,5-ethano-2,3,4,5-tetrahydro-1H-benzo[c]azepin-8-yl trifluoromethanesulfonate (1.2 g, quantitative crude yield): $^1$H NMR (DMSO-d$_6$, 300 MHz) δ 7.46 (d, J=8.7 Hz, 2H), 7.33-7.28 (m, 3H), 7.05 (dd, J=9.0, 2.7 Hz, 1H), 6.23 (d, J=8.7 Hz, 1H), 4.31 (s, 2H), 3.11-3.01 (m, 2H), 2.94-2.84 (m, 2H), 2.58-2.53 (m, 2H), 2.06-1.96 (m, 2H).

Step B: A mixture of bis(pinacolato)diboron (875 mg, 3.44 mmol), potassium acetate (845 mg, 8.61 mmol) and the triflate (1.2 g, 2.9 mmol) from Step A above, in DMSO (25 mL), was purged with argon for 5 min. Next, 1,1'-bis(diphenylphosphino)ferrocenedichloropalladium (210 mg, 0.29 mmol) was added and the mixture was purged again with argon. The reaction was heated at 80° C. for 1.5 h. After cooling to ambient temperature, the reaction mixture was diluted with ethyl acetate (100 mL), washed with water (2×50 mL), brine (25 mL), dried over sodium sulfate and concentrated in vacuo to provide 5-(4-chlorophenyl)-2,5-ethano-8-(4,4,5,5-tetramethyl-1,3,2-dioxaborolan-2-yl)-2,3,4,5-tetrahydro-1H-2-benzoazepine (1.9 g, quantitative crude yield) as a brown solid: ESI MS m/z 410 [M+H]$^+$.

Step C: A mixture of the boronate ester (200 mg, 0.49 mmol) from Step B above, 3-chloro-6-(difluoromethoxy)pyridazine (106 mg, 0.58 mmol) and cesium carbonate (477 mg, 1.46 mmol), in water (0.6 mL) and N,N-dimethylformamide (2.5 mL), was degassed with argon. Next, [1,1'-bis(diphenylphosphino)ferrocene]palladium(II) dichloromethane adduct (18 mg, 0.02 mmol) was added, the mixture was degassed again and heated to 90° C. After 3 h, the reaction mixture was diluted with ethyl acetate (25 mL), washed with water (2×20 mL), brine (10 mL), dried over sodium sulfate and concentrated in vacuo. The residue was purified by column chromatography (methylene chloride to 90:9:1 methylene chloride/methanol/ammonium hydroxide) and preparative TLC (90:9:1 methylene chloride/methanol/ammonium hydroxide). To the obtained material (63 mg, 0.15 mmol) in acetonitrile (2 mL) and methanol (2 mL) was added L-tartaric acid (22 mg, 0.15 mmol) in water (20 mL). The resultant solution was lyophilized to give 5-(4-chlorophenyl)-8-(6-(difluoromethoxy)pyridazin-3-yl)-2,5-ethano-2,3,4,5-tetrahydro-1H-2-benzo[c]azepine, L-tartrate salt (87 mg, 30%, AUC HPLC >99%) as an off-white solid: $^1$H NMR (CD$_3$OD, 500 MHz) δ 8.20 (d, J=9.5 Hz, 1H), 8.00 (s, 1H), 7.75 (t, J=66.0 Hz, 1H), 7.75-7.74 (m, 1H), 7.48-7.44 (m, 3H), 7.36 (d, J=8.0 Hz, 2H), 6.55 (d, J=8.5 Hz, 1H), 4.93 (s, 2H), 4.43 (s, 2.2H), 3.66-3.59 (m, 2H), 3.46-3.40 (m, 2H), 2.85-2.78 (m, 2H), 2.50-2.44 (m, 2H); ESI MS m/z 428 [M+H]$^+$. Anal. Calcd. For C$_{23}$H$_{20}$ClF$_2$N$_3$O.1.1C$_4$H$_6$O$_6$.0.75H$_2$O: C, 54.26; H, 4.67; N, 6.93.
Found: C, 54.26; H, 4.47; N, 6.86.

Example 15

Preparation of 5-(4-chlorophenyl)-8-(6-(difluoromethoxy)pyridazin-3-yl)-2,5-ethano-2,3,4,5-tetrahydro-1H-2-benzo[c]azepine, L-tartrate Salt

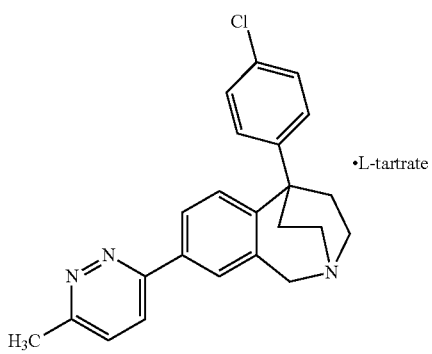 [SMILES: Cc1ccc(-c2ccc3c(c2)CN2CCC3(c3ccc(Cl)cc3)CC2)nn1]

A procedure similar to Step C of Example 14 was used to couple 5-(4-chlorophenyl)-2,5-ethano-8-(4,4,5,5-tetramethyl-1,3,2-dioxaborolan-2-yl)-2,3,4,5-tetrahydro-1H-2-benzoazepine from Step B of Example 14 with 3-chloro-6-(trifluoromethyl)pyridazine. The desired coupling product was obtained and converted to the corresponding L-tartrate salt as in Step C, except no methanol was used, to provide 5-(4-chlorophenyl)-2,5-ethano-8-(6-(trifluoromethyl)pyridazin-3-yl)-2,3,4,5-tetrahydro-1H-benzo[c]azepine, L-tartrate salt (96 mg, 32%, AUC HPLC >99%) as an off-white solid: $^1$H NMR (CD$_3$OD, 500 MHz) δ 8.34 (d, J=8.5 Hz, 1H), 8.18 (s, 1H), 8.15 (d, J=9.0 Hz, 1H), 7.90 (dd, J=8.0, 1.5 Hz, 1H), 7.48 (d, J=8.5 Hz, 2H), 7.37 (d, J=9.0 Hz, 2H), 6.60 (d, J=8.0 Hz, 1H), 4.97 (s, 2H), 4.43 (s, 2.2H), 3.69-3.62 (m, 2H), 3.48-3.42 (m, 2H), 2.85-2.80 (m, 2H), 2.51-2.46 (m, 2H); ESI MS m/z 430 [M+H]$^+$. Anal. Calcd. For C$_{24}$H$_{19}$ClF$_3$N$_3$.1.1C$_4$H$_6$O$_6$–1.25H$_2$O: C, 53.30; H, 4.59; N, 6.81. Found: C, 53.01; H, 4.23; N, 6.68.

Example 16

Preparation of 5-(4-chlorophenyl)-2,5-ethano-8-(pyrimidin-5-yl)-2,3,4,5-tetrahydro-1H-benzo[c]azepine, L-tartrate Salt

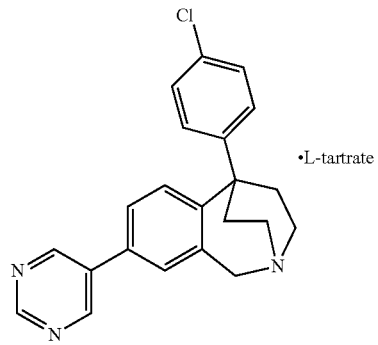 [SMILES: Clc1ccc(C23CCN(CC2)Cc2cc(-c4cncnc4)ccc23)cc1]

A procedure similar to step C of Example 14 was used to couple 5-(4-chlorophenyl)-2,5-ethano-8-(4,4,5,5-tetramethyl-1,3,2-dioxaborolan-2-yl)-2,3,4,5-tetrahydro-1H-2-benzoazepine from Step B of Example 14 with 5-bromopyrimidine. The desired coupling product was obtained and converted to the corresponding L-tartrate salt as in Step C, except no acetonitrile was used, to provide 5-(4-chlorophenyl)-2,5-ethano-8-(pyrimidin-5-yl)-2,3,4,5-tetrahydro-1H-benzo[c]azepine, L-tartrate salt (54 mg, 26%, AUC HPLC 99.0%) as an off-white solid: $^1$H NMR (CD$_3$OD, 500 MHz) δ 9.13 (s, 1H), 9.05 (s, 2H), 7.68 (s, 1H), 7.49-7.46 (m, 3H), 7.36 (d, J=8.5 Hz, 2H), 6.55 (d, J=8.0 Hz, 1H), 4.91 (s, 2H), 4.43 (s, 2.2H), 3.65-3.58 (m, 2H), 3.45-3.40 (m, 2H), 2.82-2.78 (m, 2H), 2.49-2.43 (m, 2H); ESI MS m/z 362 [M+H]$^+$. Anal. Calcd. For C$_{22}$H$_{20}$ClN$_3$.1.1C$_4$H$_6$O$_6$–1.5H$_2$O: C, 57.24; H, 5.39; N, 7.58. Found: C, 57.03; H, 5.21; N, 7.40.

Example 17

Preparation of 5-(4-chlorophenyl)-2,5-ethano-8-(pyrazin-2-yl)-2,3,4,5-tetrahydro-1H-benzo[c]azepine, L-tartrate Salt

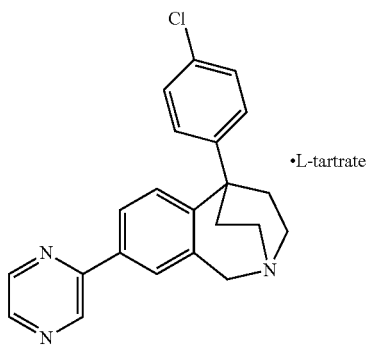 [SMILES: Clc1ccc(C23CCN(CC2)Cc2cc(-c4cnccn4)ccc23)cc1]

A procedure similar to Step C of Example 14 was used to couple 5-(4-chlorophenyl)-2,5-ethano-8-(4,4,5,5-tetramethyl-1,3,2-dioxaborolan-2-yl)-2,3,4,5-tetrahydro-1H-2-benzoazepine from Step B of Example 14 with 5-chloro-2,3-dihydropyrazine. The desired coupling product was obtained and converted to the corresponding L-tartrate salt as in Step C, except no methanol was used, to provide 5-(4-chlorophenyl)-2,5-ethano-8-(pyrazin-2-yl)-2,3,4,5-tetrahydro-1H-benzo[c]azepine, L-tartrate salt (31 mg, 24%, AUC HPLC >99%) as an off-white solid: $^1$H NMR (CD$_3$OD, 500 MHz) δ 9.08 (s, 1H), 8.66-8.65 (m, 1H), 8.53 (d, J=2.5 Hz, 1H), 8.05 (s, 1H), 7.82 (dd, J=8.5, 1.5 Hz, 1H), 7.47 (d, J=8.5 Hz, 2H), 7.37 (d, J=8.5 Hz, 2H), 6.54 (d, J=8.5 Hz, 1H), 4.94 (s, 2H), 4.43 (s, 2.2H), 3.68-3.60 (m, 2H), 3.48-3.40 (m, 2H), 2.82-2.78 (m, 2H), 2.49-2.43 (m, 2H); ESI MS m/z 362 [M+H]$^+$.

Example 18

Preparation of 5-(5-(4-chlorophenyl)-2,5-ethano-2,3,4,5-tetrahydro-1H-benzo[c]azepin-8-yl)pyrazin-2-amine, L-tartrate Salt

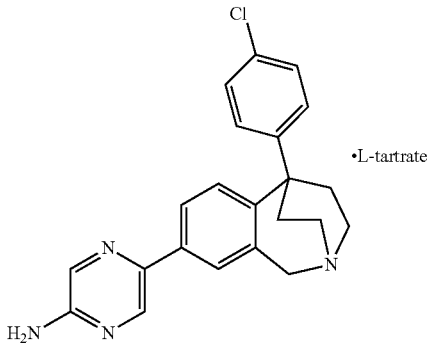 [SMILES: Nc1cnc(-c2ccc3c(c2)CN2CCC3(c3ccc(Cl)cc3)CC2)cn1]

A procedure similar to Step C of Example 14 was used to couple 5-(4-chlorophenyl)-2,5-ethano-8-(4,4,5,5-tetramethyl-1,3,2-dioxaborolan-2-yl)-2,3,4,5-tetrahydro-1H-2-benzoazepine from Step B of Example 14 with 5-bromopyrazin-2-amine. The desired coupling product was obtained and converted to the corresponding L-tartrate salt as in Step C, except no acetonitrile was used, to provide 5-(5-(4-chlorophenyl)-2,5-ethano-2,3,4,5-tetrahydro-1H-benzo[c]azepin-8-yl)pyrazin-2-amine, L-tartrate salt (46 mg, 16%, AUC HPLC 98.4%) as an off-white solid: $^1$H NMR (CD$_3$OD, 500 MHz) δ 8.35 (s, 1H), 8.00 (s, 1H), 7.81 (s, 1H), 7.60 (d, J=8.5 Hz, 1H), 7.47 (d, J=8.5 Hz, 2H), 7.35 (d, J=8.5 Hz, 2H), 6.45 (d, J=8.5 Hz, 1H), 4.93 (s, 2H), 4.46 (s, 4.6H), 3.69-3.62 (m, 2H), 3.49-3.43 (m, 2H), 2.83-2.78 (m, 2H), 2.50-2.45 (m, 2H); ESI MS m/z 377 [M+H]$^+$. Anal. Calcd. For C$_{22}$H$_{21}$ClN$_4$·2.3C$_4$H$_6$O$_6$·2H$_2$O: C, 49.43; H, 5.16; N, 7.39. Found: C, 49.21; H, 5.04; N, 7.70.

Example 19

Preparation of 8-([1,2,4]triazolo[1,5-a]pyridin-6-yl)-5-(4-chlorophenyl)-2,5-ethano-2,3,4,5-tetrahydro-1H-benzo[c]azepine, L-tartrate Salt

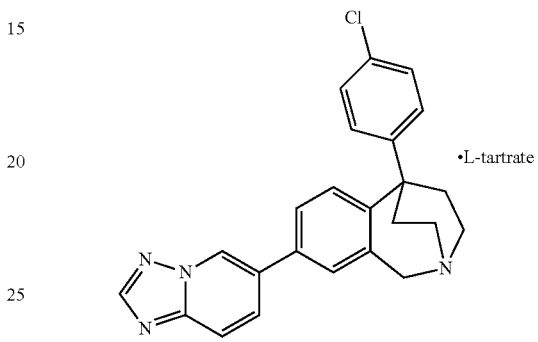

A procedure similar to Step C of Example 14 was used to couple 5-(4-chlorophenyl)-2,5-ethano-8-(4,4,5,5-tetramethyl-1,3,2-dioxaborolan-2-yl)-2,3,4,5-tetrahydro-1H-2-benzoazepine from Step B of Example 14 with 6-bromo-[1,2,4]triazolo[1,5-a]pyridine. The desired coupling product was obtained and converted to the corresponding L-tartrate salt as in Step C, except no methanol was used, to provide 8-([1,2,4]triazolo[1,5-a]pyridin-6-yl)-5-(4-chlorophenyl)-2,5-ethano-2,3,4,5-tetrahydro-1H-benzo[c]azepine, L-tartrate salt (74 mg, 25%, AUC HPLC 99.0%) as an off-white solid: $^1$H NMR (CD$_3$OD, 500 MHz) δ 9.07 (s, 1H), 8.43 (s, 1H), 8.0 (dd, J=9.5, 1.5 Hz, 1H), 7.84 (d, J=9.0 Hz, 1H), 7.69 (s, 1H), 7.50-7.46 (br s, 3H), 7.37 (d, J=8.5 Hz, 2H), 6.53 (d, J=8.5 Hz, 1H), 4.93 (s, 2H), 4.43 (s, 2.3H), 3.69-3.62 (m, 2H), 3.48-3.42 (m, 2H), 2.84-2.78 (m, 2H), 2.50-2.45 (m, 2H); ESI MS m/z 401 [M+H]$^+$. Anal. Calcd. For C$_{24}$H$_{21}$ClN$_4$·1.2C$_4$H$_6$O$_6$·0.75H$_2$O: C, 58.18; H, 5.04; N, 9.42. Found: C, 58.13; H, 4.67; N, 9.51.

Example 20

Preparation of 5-(4-chlorophenyl)-2,5-ethano-8-(3-methyl-[1,2,4]triazolo[4,3-a]pyridin-6-yl)-2,3,4,5-tetrahydro-1H-benzo[c]azepine, L-tartrate Salt

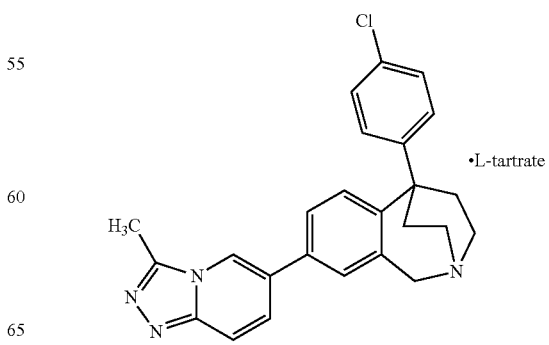

A procedure similar to Step C of Example 14 was used to couple 5-(4-chlorophenyl)-2,5-ethano-8-(4,4,5,5-tetramethyl-1,3,2-dioxaborolan-2-yl)-2,3,4,5-tetrahydro-1H-2-benzoazepine from Step B of Example 14 with 6-bromo-3-methyl-[1,2,4]triazolo[4,3-a]pyridine. The desired coupling product was obtained and converted to the corresponding L-tartrate salt as in Step C, except no methanol was used, to provide 5-(4-chlorophenyl)-2,5-ethano-8-(3-methyl-[1,2,4]triazolo[4,3-a]pyridin-6-yl)-2,3,4,5-tetrahydro-1H-benzo[c]azepine, L-tartrate salt (28 mg, 20%, AUC HPLC >99%) as an off-white solid: $^1$H NMR (CD$_3$OD, 500 MHz) δ 8.49 (s, 1H), 7.75 (s, 2H), 7.70 (s, 1H), 7.50-7.46 (m, 3H), 7.36 (d, J=8.5 Hz, 2H), 6.51 (d, J=8.5 Hz, 1H), 4.93 (s, 2H), 4.43 (s, 2.2H), 3.68-3.61 (m, 2H), 3.48-3.40 (m, 2H), 2.82-2.78 (m, 5H), 2.49-2.43 (m, 2H); ESI MS m/z 415 [M+H]$^+$.

Example 21

Preparation of 5-(4-chlorophenyl)-2,5-ethano-8-(quinoxalin-2-yl)-2,3,4,5-tetrahydro-1H-benzo[c]azepine, L-tartrate Salt

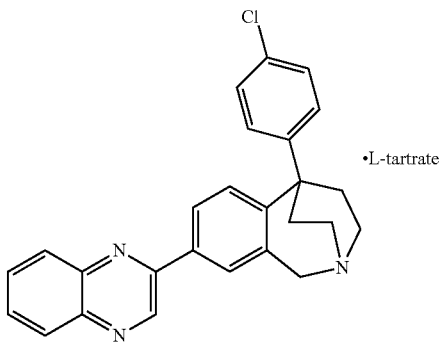 [SMILES: Clc1ccc(C23CCN(CC2)Cc2cc(-c4cnc5ccccc5n4)ccc23)cc1]

A procedure similar to Step C of Example 14 was used to couple 5-(4-chlorophenyl)-2,5-ethano-8-(4,4,5,5-tetramethyl-1,3,2-dioxaborolan-2-yl)-2,3,4,5-tetrahydro-1H-2-benzoazepine from Step B of Example 14 with 2-chloroquinoxaline. The desired coupling product was obtained and converted to the corresponding L-tartrate salt as in Step C to provide 5-(4-chlorophenyl)-2,5-ethano-8-(quinoxalin-2-yl)-2,3,4,5-tetrahydro-1H-benzo[c]azepine, L-tartrate salt (40 mg, 30%, AUC HPLC 96.8%) as an off-white solid: $^1$H NMR (CD$_3$OD, 500 MHz) δ 9.39 (s, 1H), 8.26 (s, 1H), 8.14-8.09 (m, 2H), 8.01 (d, J=8.5 Hz, 1H), 7.88-7.82 (m, 2H), 7.49 (d, J=8.5 Hz, 2H), 7.38 (d, J=8.5 Hz, 2H), 6.60 (d, J=8.5 Hz, 1H), 4.98 (s, 2H), 4.43 (s, 2H), 3.68-3.61 (m, 2H), 3.42-3.48 (m, 2H), 2.86-2.81 (m, 2H), 2.51-2.45 (m, 2H); ESI MS m/z 412 [M+H]$^+$.

Example 22

Preparation of 6-(5-(4-chlorophenyl)-2,5-ethano-2,3,4,5-tetrahydro-1H-benzo[c]azepin-8-yl)-3,3a-dihydrobenzo[d]oxazol-2(7aH)-one, L-tartrate Salt

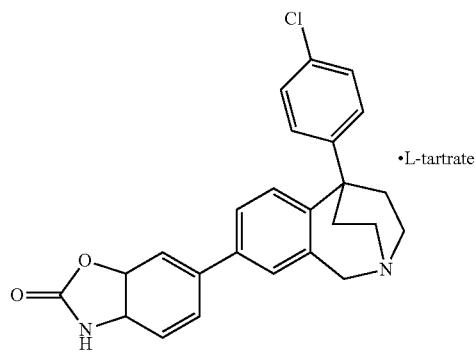 [SMILES: O=C1NC2C=CC(c3ccc4c(c3)CN3CCC4(c4ccc(Cl)cc4)CC3)=CC2O1]

A procedure similar to Step C of Example 14 was used to couple 5-(4-chlorophenyl)-2,5-ethano-8-(4,4,5,5-tetramethyl-1,3,2-dioxaborolan-2-yl)-2,3,4,5-tetrahydro-1H-2-benzoazepine from Step B of Example 14 with 6-bromo-3,3a-dihydrobenzo[d]oxazol-2(7aH)-one. The desired coupling product was obtained and converted to the corresponding L-tartrate salt as in Step C to provide 6-(5-(4-chlorophenyl)-2,5-ethano-2,3,4,5-tetrahydro-1H-benzo[c]azepin-8-yl)-3,3a-dihydrobenzo[d]oxazol-2(7aH)-one, L-tartrate salt (34 mg, 11%, AUC HPLC >99%) as an off-white solid: $^1$H NMR (CD$_3$OD, 500 MHz) δ 7.55 (s, 1H), 7.48-7.45 (m, 3H), 7.42 (dd, J=8.5, 2.0 Hz, 1H), 7.38-7.35 (m, 3H), 7.13 (d, J=8.5 Hz, 1H), 6.45 (d, J=8.5 Hz, 1H), 4.91 (s, 2H), 4.43 (s, 2H), 3.68-3.61 (m, 2H), 3.48-3.41 (m, 2H), 2.82-2.78 (m, 2H), 2.49-2.43 (m, 2H); ESI MS m/z 417 [M+H]$^+$. Anal. Calcd. For C$_{25}$H$_{21}$ClN$_2$O$_2$·C$_4$H$_6$O$_6$·3H$_2$O: C, 56.09; H, 5.36; N, 4.51. Found: C, 56.42; H, 5.09; N, 4.29.

Example 23

Preparation of 2-(5-(4-chlorophenyl)-2,5-ethano-2,3,4,5-tetrahydro-1H-benzo[c]azepin-8-yl)-[1,2,4]triazolo[4,3-a]pyridin-3(2H)-one, L-tartrate Salt

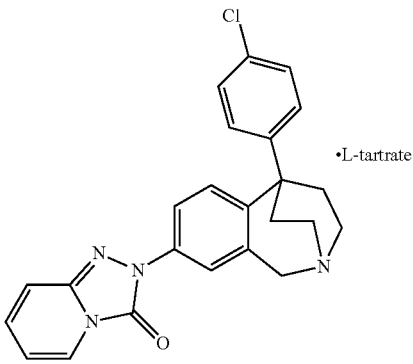 [SMILES: O=c1n(-c2ccc3c(c2)CN2CCC3(c3ccc(Cl)cc3)CC2)nc2ccccn12]

Step A: To a solution of 5-(4-chlorophenyl)-2,5-ethano-8-(4,4,5,5-tetramethyl-1,3,2-dioxaborolan-2-yl)-2,3,4,5-tetrahydro-1H-2-benzoazepine (1.1 g, 1.9 mmol, crude) from Step B of Example 14 in a mixture of methanol (25 mL) and water (25 mL) was added copper(II) bromide (1.25 g, 5.6 mmol). The reaction mixture was heated under reflux for 2 h and then it was cooled to room temperature, quenched with ethylene diamine (1.2 mL). The resultant mixture was diluted with water, extracted with dichloromethane (2×). The combined organic extract was dried over sodium sulfate and concentrated in vacuo. The residue obtained was purified by flash column chromatography (99.5:0.45:0.05 to 92:7.2:0.8 dichloromethane/methanol/concentrated ammonium hydroxide) to give 8-bromo-5-(4-chlorophenyl)-2,5-ethano-2,3,4,5-tetrahydro-1H-benzo[c]azepine (0.28 g, 41%): $^1$H NMR (CDCl$_3$, 500 MHz) δ 7.36-7.33 (m, 2H), 7.20-7.03 (m, 2H), 7.02 (dd, J=8.5, 2.5 Hz, 1H), 6.13 (d, J=8.5 Hz, 1H), 4.34 (s, 2H), 3.21-3.15 (m, 2H), 3.06-3.00 (m, 2H), 2.53-2.48 (m, 2H), 2.12-2.07 (m, 2H).

Step B: A mixture of the 8-bromo-ethanobenzazepine (0.28 g, 0.77 mmol) from Step A above, [1,2,4]triazolo[4,3-a]pyridin-3(2H)-one (0.21 g, 1.5 mmol), potassium phosphate (0.49 g, 2.3 mmol), dimethyl ethylenediamine (0.066 mL, 0.62 mmol), copper iodide (73 mg, 0.39 mmol), L-proline (71 mg, 0.62 mmol) in 1,4-dioxane (8 mL) and DMSO (8 mL) was stirred at 120° C. for 16 h. The reaction was then cooled to rt, diluted with dichloromethane and filtered through a pad of celite. The filtrate obtained was concentrated in vacuo and the resultant residue was diluted with ethyl acetate, washed with water (2×) and brine, dried over sodium sulfate and concentrated in vacuo. The crude product obtained was purified by flash column chromatography (ethyl acetate to 91:8.1:0.9 ethyl acetate/methanol/concentrated ammonium hydroxide), then preparative thin layer chromatography (93:6.3:0.7 ethyl acetate/methanol/concentrated ammonium hydroxide, followed by 93:6.3:0.7 dichloromethane/methanol/concentrated ammonium hydroxide) to give 2-(5-(4-chlorophenyl)-2,5-ethano-2,3,4,5-tetrahydro-1H-benzo[c]azepin-8-yl)-[1,2,4]triazolo[4,3-a]pyridin-3(2H)-one (60.8 mg, 19%). Following the procedure from Step C of Example 14, this free base ethanobenzazepine was converted to its L-tartrate to form 2-(5-(4-chlorophenyl)-2,5-ethano-2,3,4,5-tetrahydro-1H-benzo[c]azepin-8-yl)-[1,2,4]triazolo[4,3-a]pyridin-3(2H)-one, L-tartrate salt (74 mg, 89%, AUC HPLC 98.7%) as a white solid: $^1$H NMR (CD$_3$OD, 500 MHz) δ 8.06 (d, J=2.0 Hz, 1H), 7.86 (dd, J=7.5, 1.0 Hz, 1H), 7.80 (dd, J=8.5, 2.0 Hz, 1H), 7.48-7.46 (m, 2H), 7.37-7.34 (m, 2H), 7.29 (dd, J=6.5, 1.0 Hz, 1H), 7.21 (dd, J=9.5, 1.0 Hz, 1H), 6.68 (t, J=7.0 Hz, 1H), 6.50 (d, J=9.0 Hz, 1H), 4.88 (s, 2H), 4.42 (s, 2.2H), 3.65-3.57 (m, 2H), 3.46-3.38 (m, 2H), 2.83-2.77 (m, 2H), 2.47-2.40 (m, 2H); ESI MS m/z 417 [M+H]$^+$. Anal. Calcd. for C$_{24}$H$_{21}$ClN$_4$O.1.1C$_4$H$_6$O$_6$.2H$_2$O: C, 55.19; H, 5.15; N, 9.07. Found: C, 55.02; H, 5.09; N, 8.82.

Example 24

Preparation of 1-(5-(4-chlorophenyl)-2,5-ethano-2,3,4,5-tetrahydro-1H-benzo[c]azepin-8-yl)pyridin-2(1H)-one, L-tartrate Salt

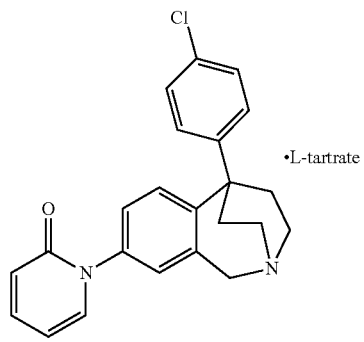 [SMILES: O=c1ccccn1-c1ccc2c(c1)CN1CCC2(c2ccc(Cl)cc2)CC1]

Step A: To a solution of 5-(4-chlorophenyl)-2,5-ethano-8-(4,4,5,5-tetramethyl-1,3,2-dioxaborolan-2-yl)-2,3,4,5-tetrahydro-1H-2-benzoazepine (1.1 g, 1.9 mmol, crude) from Step B of Example 14 in a mixture of methanol (25 mL) and water (25 mL) was added copper(II) bromide (1.25 g, 5.6 mmol). The reaction mixture was heated under reflux for 2 h and then it was cooled to room temperature, quenched with ethylene diamine (1.2 mL). The resultant mixture was diluted with water, extracted with dichloromethane (2×). The combined organic extract was dried over sodium sulfate and concentrated in vacuo. The residue obtained was purified by flash column chromatography (99.5:0.45:0.05 to 92:7.2:0.8 dichloromethane/methanol/concentrated ammonium hydroxide) to give 8-bromo-5-(4-chlorophenyl)-2,5-ethano-2,3,4,5-tetrahydro-1H-benzo[c]azepine (0.28 g, 41%): $^1$H NMR (CDCl$_3$, 500 MHz) δ 7.36-7.33 (m, 2H), 7.20-7.03 (m, 2H), 7.02 (dd, J=8.5, 2.5 Hz, 1H), 6.13 (d, J=8.5 Hz, 1H), 4.34 (s, 2H), 3.21-3.15 (m, 2H), 3.06-3.00 (m, 2H), 2.53-2.48 (m, 2H), 2.12-2.07 (m, 2H).

Step B: A mixture of the 8-bromo-ethanobenzazepine (0.12 g, 0.33 mmol) from Step A above, pyridin-2-ol (62.9 mg, 0.66 mmol), copper iodide (30.5 mg, 0.16 mmol), L-proline (37.9 mg, 0.33 mmol) and potassium phosphate (0.21 g, 1.0 mmol) in DMSO (6 mL) was stirred at 140° C. for 14 h. The reaction was then cooled to room temperature, diluted with ethyl acetate washed with aqueous ammonium chloride (2×) and brine, dried over sodium sulfate and concentrated in vacuo. The crude product obtained was purified by preparative thin layer chromatography (90:9:1 dichloromethane/methanol/concentrated ammonium hydroxide) to form 1-(5-(4-chlorophenyl)-2,5-ethano-2,3,4,5-tetrahydro-1H-benzo[c]azepin-8-yl)pyridin-2(1H)-one (25 mg, 20%). Following the procedure from Step C of Example 14, this free base ethanobenzoazepine was converted to its L-tartrate to form 1-(5-(4-chlorophenyl)-2,5-ethano-2,3,4,5-tetrahydro-1H-benzo[c]azepin-8-yl)pyridin-2(1H)-one, L-tartrate salt (33 mg, 98%, AUC HPLC 98.9%) as a white solid: $^1$H NMR (CD$_3$OD, 500 MHz) δ 7.62 (td, J=6.5, 2.0 Hz, 1H), 7.55 (dd, J=7.0, 2.0 Hz, 1H), 7.56-7.45 (m, 2H), 7.36-7.34 (m, 3H), 7.14 (dd, J=8.5, 2.0 Hz, 1H), 6.62 (d, J=9.5 Hz, 1H), 6.53 (d, J=8.5 Hz, 1H), 6.47 (td, J=6.5, 1.0 Hz, 1H), 4.89-4.61 (m, 2H), 4.42 (s, 2.4H), 3.63-3.54 (m, 2H), 3.47-3.39 (m, 2H), 2.82-2.73 (m, 2H), 2.48-2.37 (m, 2H); ESI MS m/z 377 [M+H]$^+$.

Example 25

Preparation of 2-(5-(4-chlorophenyl)-2,5-ethano-2,3,4,5-tetrahydro-1H-benzo[c]azepin-8-yl)-5-methyl-1,3,4-thiadiazole, L-tartrate Salt

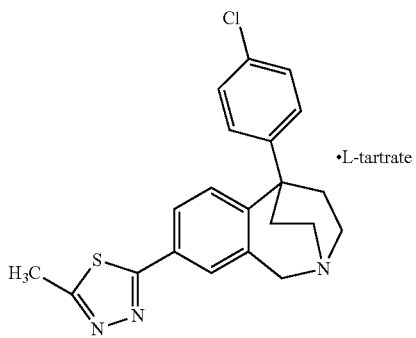 [SMILES: Cc1nnc(-c2ccc3c(c2)CN2CCC3(c3ccc(Cl)cc3)CC2)s1]

A mixture of 5-(4-chlorophenyl)-2,5-ethano-8-(4,4,5,5-tetramethyl-1,3,2-dioxaborolan-2-yl)-2,3,4,5-tetrahydro-1H-2-benzoazepine (80 mg, 0.19 mmol) from Step B of Example 14, 2-bromo-5-methyl-1,3,4-thiadiazole (35 mg, 0.19 mmol) and potassium carbonate (81 mg, 0.58 mmol), in N,N-dimethylformamide (2 mL), was degassed with argon. Next, tetrakis(triphenylphosphine)palladium(0) (33 mg, 0.028 mmol) was added, the mixture was degassed again and heated to 100° C. After stirring for 17 h, the reaction mixture was cooled to ambient temperature, diluted with ethyl acetate (25 mL), washed with water (10 mL), dried over sodium sulfate and concentrated in vacuo. The residue was purified by preparative TLC (90:9:1 methylene chloride/methanol/ammonium hydroxide). To the obtained material (6.3 mg, 0.016 mmol) in acetonitrile (1.5 mL) was added L-tartaric acid (2.5 mg, 0.016 mmol) in water (6 mL). The resultant solution was lyophilized to give 2(5(4-chlorophenyl)-2,5-ethano-2,3,4,5-tetrahydro-1H-benzo[c]azepin-8-yl)-5-methyl-1,3,4-thiadiazole, L-tartrate salt (11 mg, 11%, AUC HPLC 98.7%) as a white solid: $^1$H NMR (CD$_3$OD, 500 MHz) δ 7.90 (s, 1H), 7.64 (d, J=8.5 Hz, 1H), 7.47 (d, J=9.0 Hz, 2H), 7.35 (d, J=8.5 Hz, 2H), 6.53 (d, J=8.5 Hz, 1H), 4.90 (s, 2H), 4.43 (s, 2H), 3.65-3.61 (m, 2H), 3.46-3.39 (m, 2H), 2.83-2.78 (m, 5H), 2.48-2.43 (m, 2H); ESI MS m/z 382 [M+H]$^+$.

Example 26

Preparation of 5-(4-chlorophenyl)-2,5-ethano-8-(4-(methylsulfonyl)phenyl)-2,3,4,5-tetrahydro-1H-benzo[c]azepine, L-tartrate Salt

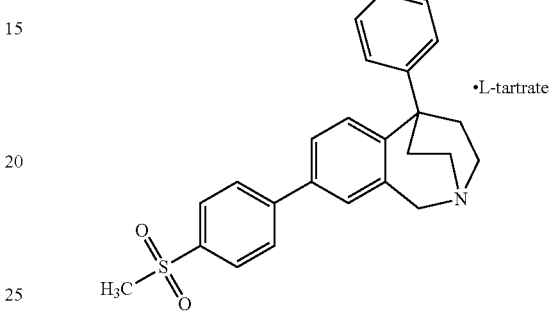

A procedure similar to Step C of Example 14 was used to couple 5-(4-chlorophenyl)-2,5-ethano-8-(4,4,5,5-tetramethyl-1,3,2-dioxaborolan-2-yl)-2,3,4,5-tetrahydro-1H-2-benzoazepine from Step B of Example 14 with 1-bromo-4-(methylsulfonyl)benzene. The desired coupling product was obtained and converted to the corresponding L-tartrate salt as in Step C to provide 5-(4-chlorophenyl)-2,5-ethano-8-(4-(methylsulfonyl)phenyl)-2,3,4,5-tetrahydro-1H-benzo[c]azepine, L-tartrate salt (69 mg, 31%, AUC HPLC >99%) as an off-white solid: $^1$H NMR (CD$_3$OD, 500 MHz) δ 8.00 (d, J=8.5 Hz, 2H), 7.86 (d, J=8.0 Hz, 2H), 7.60 (s, 1H), 7.47-7.45 (m, 3H), 7.36 (d, J=9.0 Hz, 2H), 6.51 (d, J=8.0 Hz, 1H), 4.91 (s, 2H), 4.43 (s, 2H), 3.68-3.61 (m, 2H), 3.48-3.40 (m, 2H), 3.14 (s, 3H), 2.82-2.78 (m, 2H), 2.49-2.43 (m, 2H); ESI MS m/z 438 [M+H]$^+$. Anal. Calcd. For C$_{25}$H$_{24}$ClNO$_2$S.C$_4$H$_6$O$_6$.1.75H$_2$O: C, 56.22; H, 5.45; N, 2.26. Found: C, 56.10; H, 5.22; N, 2.47.

Example 27

Preparation of 3-(5-(4-chlorophenyl)-2,5-ethano-2,3,4,5-tetrahydro-1H-benzo[c]azepin-8-yl)benzonitrile, L-tartrate Salt

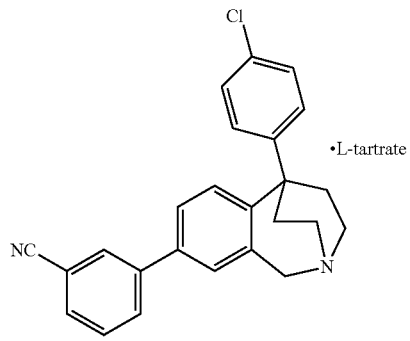 [SMILES: N#Cc1cccc(-c2ccc3c(c2)CN2CCC3(c3ccc(Cl)cc3)CC2)c1]

A procedure similar to Step C of Example 14 was used to couple 5-(4-chlorophenyl)-2,5-ethano-8-(4,4,5,5-tetramethyl-1,3,2-dioxaborolan-2-yl)-2,3,4,5-tetrahydro-1H-2-benzoazepine from Step B of Example 14 with 3-bromobenzonitrile. The desired coupling product was obtained and converted to the corresponding L-tartrate salt as in step C, except no methanol was used, to provide 34544-chlorophenyl)-2,5-ethano-2,3,4,5-tetrahydro-1H-benzo[c]azepin-8-yl)benzonitrile, L-tartrate salt (36 mg, 26%, AUC HPLC 97.8%) as an off-white solid: $^1$H NMR (CD$_3$OD, 500 MHz) δ 7.98 (s, 1H), 7.93-7.91 (m, 1H), 7.70 (d, J=7.5 Hz, 1H), 7.63-7.60 (m, 2H), 7.46 (d, J=8.0 Hz, 2H), 7.41 (d, J=8.5 Hz, 1H), 7.35 (d, J=8.5 Hz, 2H), 6.49 (d, J=8.0 Hz, 1H), 4.87 (br s, 2H), 4.41 (s, 2.2H), 3.68-3.50 (m, 2H), 3.50-3.35 (m, 2H), 2.81-2.75 (m, 2H), 2.48-2.41 (m, 2H); ESI MS m/z 385 [M+H]$^+$. Anal. Calcd. For C$_{25}$H$_{21}$ClN$_2$·1.1C$_4$H$_6$O$_6$·1.75H$_2$O: C, 60.72; H, 5.39; N, 4.82. Found: C, 60.72; H, 5.22; N, 4.96.

Examples 28 and 29

Preparation of 4-(5-(4-chlorophenyl)-2,5-ethano-2,3,4,5-tetrahydro-1H-benzo[c]azepin-8-yl)morpholine, L-tartrate salt and 4-(2,5-ethano-5-(4-morpholinophenyl)-2,3,4,5-tetrahydro-1H-benzo[c]azepin-8-yl)morpholine, L-tartrate Salt

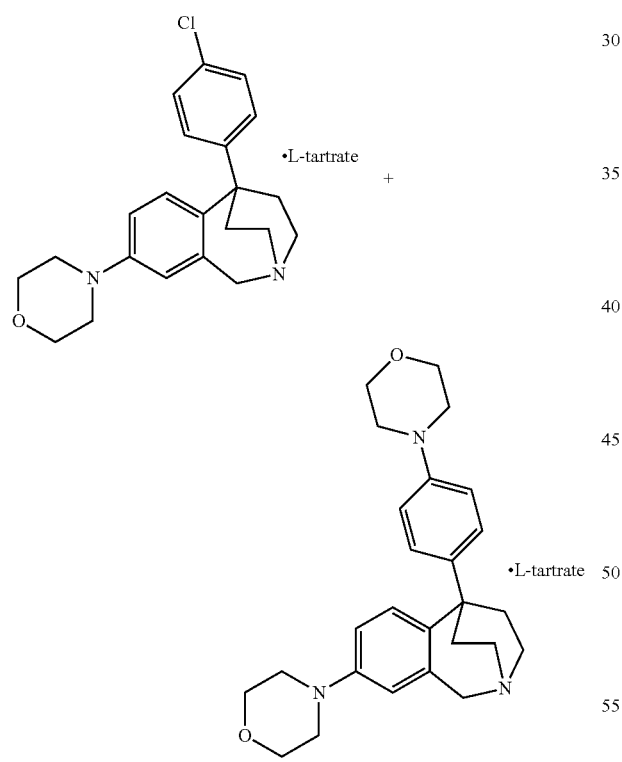

A mixture of 5-(4-chlorophenyl)-2,5-ethano-2,3,4,5-tetrahydro-1H-benzo[c]azepin-8-yl trifluoromethanesulfonate (145 mg, 0.33 mmol) from Step A of Example 14, 2-(dicyclohexylphosphino)-2',4',6'-tri-1-isopropyl-1,1'-biphenyl (16 mg, 0.033 mmol) and cesium carbonate (328 mg, 1.0 mmol) in toluene (5 mL) was degassed with argon. Next, palladium(II) acetate (8.0 mg, 0.033 mmol) and morpholine (58 mg, 0.67 mmol) were added and the mixture was degassed again and then heated to 100° C. for 12 h. After cooling to ambient temperature, the reaction mixture was diluted with ethyl acetate (50 mL), washed with water (20 mL) and brine (20 mL), dried over sodium sulfate and concentrated in vacuo. The residue was purified by column chromatography (methylene chloride to 90:9:1 methylene chloride/methanol/ammonium hydroxide) and preparative TLC (90:9:1 methylene chloride/methanol/ammonium hydroxide). Further purification by preparative HPLC gave the desired products as the trifluoroacetate salts. Each product was free-based and converted to the L-tartrate salt to provide: 4-(5-(4-chlorophenyl)-2,5-ethano-2,3,4,5-tetrahydro-1H-benzo[c]azepin-8-yl)morpholine, L-tartrate salt (5 mg, 3%, AUC HPLC 93.1%) as an off-white solid: $^1$H NMR (CD$_3$OD, 500 MHz) δ 7.43 (d, J=8.5 Hz, 2H), 7.31 (d, J=8.5 Hz, 2H), 6.84 (s, 1H), 6.69 (dd, J=8.5, 2.0 Hz, 1H), 6.24 (d, J=9.0 Hz, 1H), 4.80 (s, 2H), 4.43 (s, 1.8H), 3.80-3.78 (m, 4H), 3.63-3.57 (m, 2H), 3.44-3.35 (m, 2H), 3.11-3.09 (m, 4H), 2.74-2.68 (m, 2H), 2.42-2.37 (m, 2H); ESI MS m/z 369 [M+H]$^+$ and 4-(2,5-ethano-5-(4-morpholinophenyl)-2,3,4,5-tetrahydro-1H-benzo[c]azepin-8-yl)morpholine, L-tartrate salt (15 mg, 8%, AUC HPLC 97.6%) as an off-white solid: $^1$H NMR (CD$_3$OD, 500 MHz) δ 7.20 (d, J=8.5 Hz, 2H), 7.02 (d, J=8.5 Hz, 2H), 6.82 (d, J=2.5 Hz, 1H), 6.67 (dd, J=9.0, 2.5 Hz, 1H), 6.31 (d, J=9.0 Hz, 1H), 4.79 (s, 2H), 4.43 (s, 2H), 3.86-3.84 (m, 4H), 3.80-3.78 (m, 4H), 3.63-3.58 (m, 2H), 3.42-3.38 (m, 2H), 3.18-3.16 (m, 4H), 3.10-3.08 (m, 4H), 2.71-2.67 (m, 2H), 2.42-2.37 (m, 2H); ESI MS m/z 420 [M+H]$^+$.

Examples 30 and 31

Preparation of 5-(4-chlorophenyl)-8-(4-(ethylsulfonyl)piperazin-1-yl)-2,5-ethano-2,3,4,5-tetrahydro-1H-benzo[c]azepine, L-tartrate salt and 8-(4-(ethylsulfonyl)piperazin-1-yl)-5-(4-(4-(ethylsulfonyl)piperazin-1-yl)phenyl)-2,5-ethano-2,3,4,5-tetrahydro-1H-benzo[c]azepine, L-tartrate Salt

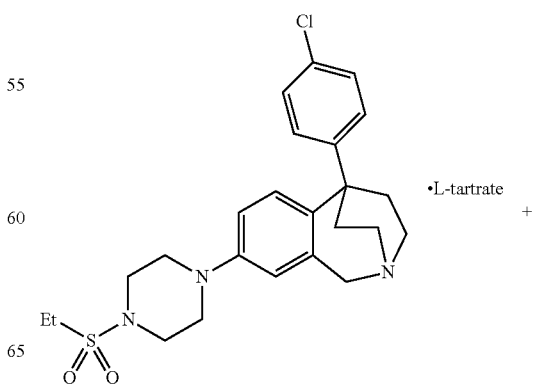

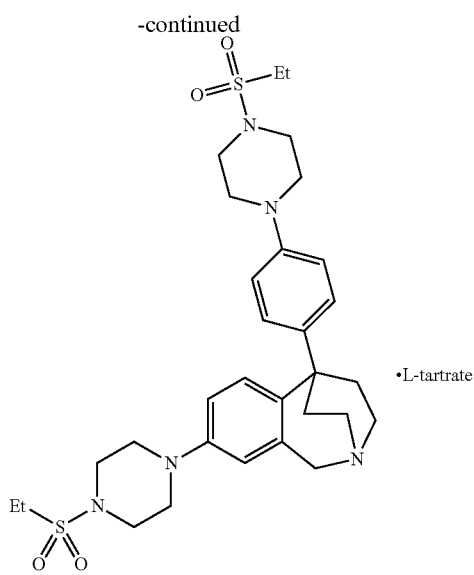

A mixture of 5-(4-chlorophenyl)-2,5-ethano-2,3,4,5-tetrahydro-1H-benzo[c]azepin-8-yl trifluoromethanesulfonate (145 mg, 0.33 mmol) from Step A of Example 14, 2-(dicyclohexylphosphino)-2',4',6'-tri-1-isopropyl-1,1'-biphenyl (16 mg, 0.033 mmol) and cesium carbonate (328 mg, 1.0 mmol) in toluene (5 mL) was degassed with argon. Next, palladium(II) acetate (8 mg, 0.033 mmol) and 1-(ethylsulfonyl)piperazine (120 mg, 0.67 mmol) were added and the mixture was degassed again and then heated to 100° C. for 12 h. After cooling to ambient temperature, the reaction mixture was diluted with ethyl acetate (50 mL), washed with water (20 mL) and brine (20 mL), dried over sodium sulfate and concentrated in vacuo. The residue was purified by column chromatography (methylene chloride to 90:9:1 methylene chloride/methanol/ammonium hydroxide) and by preparative HPLC gave the desired products as the trifluoroacetate salts. Each product was free-based and converted to the L-tartaric acid salt to provide: 5-(4-chlorophenyl)-8-(4-(ethylsulfonyl)piperazin-1-yl)-2,5-ethano-2,3,4,5-tetrahydro-1H-benzo[c]azepine, L-tartrate salt (24 mg, 11%, AUC HPLC 98.1%) as a white solid: $^1$H NMR (CD$_3$OD, 500 MHz) δ 7.43 (d, J=8.5 Hz, 2H), 7.31 (d, J=8.5 Hz, 2H), 6.88 (s, 1H), 6.71 (dd, J=9.0, 2.5 Hz, 1H), 6.25 (d, J=9.0 Hz, 1H), 4.79 (s, 2H), 4.43 (s, 2H), 3.65-3.58 (m, 2H), 3.42-3.36 (m, 6H), 3.22-3.20 (m, 4H), 3.06 (q, J=14.5, 7.5 Hz, 2H), 2.73-2.69 (m, 2H), 2.41-2.36 (m, 2H), 1.33 (t, J=7.5 Hz, 3H); ESI MS m/z 460 [M+H]$^+$ and 8-(4-(ethylsulfonyl)piperazin-1-yl)-5-(4-(4-(ethylsulfonyl)piperazin-1-yl)phenyl)-2,5-ethano-2,3,4,5-tetrahydro-1H-benzo[c]azepine, L-tartrate salt (49 mg, 18%, AUC HPLC 97.7%) as a white solid: $^1$H NMR (CD$_3$OD, 500 MHz) δ 7.20 (d, J=9.0 Hz, 2H), 7.05 (d, J=9.0 Hz, 2H), 6.86 (d, J=2.5 Hz, 1H), 6.70 (dd, J=8.5, 2.5 Hz, 1H), 6.32 (d, J=9.0 Hz, 1H), 4.79 (s, 2H), 4.43 (s, 2.6H), 3.62-3.58 (m, 2H), 3.46-3.37 (m, 10H), 3.28-3.26 (m, 4H), 3.21-3.19 (m, 4H), 3.12-3.04 (m, 4H), 2.72-2.68 (m, 2H), 2.42-2.37 (m, 2H), 1.37-1.31 (m, 6H); ESI MS m/z 602 [M+H]$^+$.

Example 32

Preparation of 5-(4-chlorophenyl)-2,5-ethano-8-(6-(trifluoromethyl)pyridazin-3-yloxy)-2,3,4,5-tetrahydro-1H-benzo[c]azepine, L-tartrate Salt

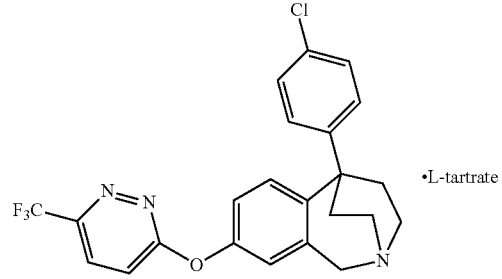 [SMILES: FC(F)(F)c1ccc(Oc2ccc3c(c2)CN2CCC3(c3ccc(Cl)cc3)CC2)nn1]

A suspension of 5-(4-chlorophenyl)-2,5-ethano-2,3,4,5-tetrahydro-1H-benzo[c]azepin-8-ol (400 mg, 1.3 mol) from Step A of Example 13, 3-chloro-6-(trifluoromethyl)pyridazine (243 mg, 1.3 mmol) and potassium carbonate (553 mg, 4.0 mmol) in dimethyl sulfoxide (4 mL) was heated to 100° C. for 1.5 h. After cooling to ambient temperature, the reaction mixture was decanted from the solids and diluted with methylene chloride (25 mL). The organics were washed with water (2×) and brine, dried over sodium sulfate and concentrated in vacuo. The residue was purified by column chromatography (methylene chloride to 90:9:1 methylene chloride/methanol/ammonium hydroxide). To the obtained material (480 mg, 1.1 mmol) in acetonitrile (5 mL) was added L-tartaric acid (162 mg, 1.1 mmol) in water (20 mL). The resultant solution was lyophilized to give 5-(4-chlorophenyl)-2,5-ethano-8-(6-(trifluoromethyl)pyridazin-3-yloxy)-2,3,4,5-tetrahydro-1H-benzo[c]azepine, L-tartrate salt (641 mg, 82%, AUC HPLC >99%) as a white solid: $^1$H NMR (DMSO-d$_6$, 500 MHz) δ 8.28 (d, J=9.5 Hz, 1H), 7.71 (d, J=9.0 Hz, 1H), 7.48 (d, J=8.5 Hz, 2H), 7.36 (d, J=9.0 Hz, 2H), 7.17 (d, J=2.5 Hz, 1H), 6.92 (dd, J=8.5, 2.0 Hz, 1H), 6.21 (d, J=8.5 Hz, 1H), 4.45 (s, 2H), 4.15 (s, 2H), 3.24-3.19 (m, 2H), 3.10-3.05 (m, 2H), 2.64-2.59 (m, 2H), 2.15-2.10 (m, 2H); ESI MS m/z 446

[M+H]+. Anal. Calcd. For C23H19ClF3N3O.C4H6O6.H2O: C, 52.82; H, 4.43; N, 6.84. Found: C, 53.00; H, 4.31; N, 6.79.

Example 33

Preparation of 5-(4-chlorophenyl)-2,5-ethano-8-(pyrazin-2-yloxy)-2,3,4,5-tetrahydro-1H-benzo[c]azepine, L-tartrate Salt

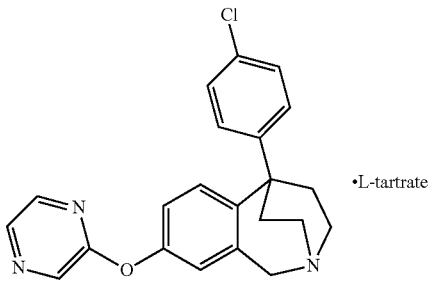 [SMILES: Clc1ccc(C23CCN(CC2)Cc2cc(Oc4cnccn4)ccc23)cc1]

A mixture of 5-(4-chlorophenyl)-2,5-ethano-2,3,4,5-tetrahydro-1H-benzo[c]azepin-8-olhydrochloride (109 mg, 0.32 mmol) from Step A of Example 13, 2-chloropyrazine (44 µL, 0.49 mmol) and cesium carbonate (316 mg, 0.97 mmol) in toluene (2 mL) was degassed with argon. Next, palladium(II) acetate (7 mg, 0.032 mmol) and racemic-2,2'-bis(diphenylphosphino)-1,1'-binaphthyl (20 mg, 0.032 mmol) were added and the mixture was degassed again and then heated to reflux. After 2.5 h, additional 2-chloropyrazine (25 µL, 0.28 mmol), palladium(II) acetate (7.3 mg, 0.032 mmol) and racemic-2,2'-bis(diphenylphosphino)-1,1'-binaphthyl (20 mg, 0.032 mmol) were added. After 2.5 h, the reaction mixture was cooled to ambient temperature and diluted with methylene chloride (30 mL). The organics were washed with water (15 mL) and brine (15 mL), dried over sodium sulfate and concentrated in vacuo. The residue was purified by column chromatography (methylene chloride to 90:9:1 methylene chloride/methanol/ammonium hydroxide) and preparative TLC (90:9:1 methylene chloride/methanol/ammonium hydroxide). To the obtained material (30 mg, 0.079 mmol) in acetonitrile (2.5 mL) and methanol (0.5 mL) was added L-tartaric acid (12 mg, 0.079 mmol) in water (5 mL). The resultant solution was lyophilized to give 5-(4-chlorophenyl)-2,5-ethano-8-(pyrazin-2-yloxy)-2,3,4,5-tetrahydro-1H-benzo[c]azepine, L-tartrate salt (44 mg, 23%, AUC HPLC 97.4%) as an off-white solid: 1H NMR (CD3OD, 500 MHz) δ 8.42 (d, J=1 Hz, 1H), 8.28 (d, J=2.5 Hz, 1H), 8.11-8.09 (m, 1H), 7.46 (d, J=8.5 Hz, 2H), 7.36 (d, J=8.5 Hz, 2H), 7.16 (d, J=2.5 Hz, 1H), 6.93 (dd, J=8.5, 2.5 Hz, 1H), 6.43 (d, J=8.5 Hz, 1H), 4.8 (s, 2H), 4.43 (s, 2.2H), 3.66-3.60 (m, 2H), 3.47-3.41 (m, 2H), 2.82-2.76 (m, 2H), 2.47-2.41 (m, 2H); ESI MS m/z 378 [M+H]+. Anal. Calcd. For C22H20ClN3O.1.1C4H6O6.2.25H2O: C, 54.34; H, 5.37; N, 7.20. Found: C, 54.10; H, 5.04; N, 6.89.

Example 34

Preparation of 5-(5-(4-chlorophenyl)-2,5-ethano-2,3,4,5-tetrahydro-1H-benzo[c]azepin-8-yloxy)pyrazin-2-amine, L-tartrate Salt

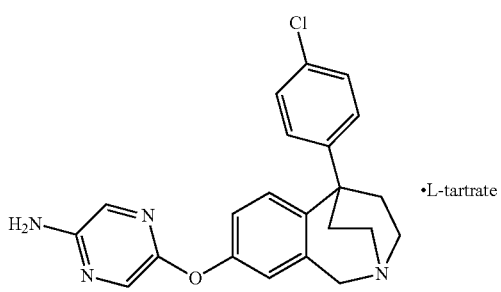 [SMILES: Nc1cnc(Oc2ccc3c(c2)CN2CCC3(c3ccc(Cl)cc3)CC2)cn1]

A mixture of 5-(4-chlorophenyl)-2,5-ethano-2,3,4,5-tetrahydro-1H-benzo[c]azepin-8-ol (200 mg, 0.66 mol) from Step A of Example 13, 5-bromopyrazin-2-amine (348 mg, 2.0 mmol), potassium carbonate (230 mg, 1.7 mmol) and copper (nanopowder, 212 mg, 3.3 mmol) in pyridine (10 mL) was degassed with argon. The mixture was heated to reflux for 21 h and then cooled to ambient temperature. The reaction mixture was diluted with diethyl ether and filtered and the filtrate was concentrated in vacuo. The residue was purified by column chromatography (methylene chloride to 90:9:1 methylene chloride/methanol/ammonium hydroxide) and preparative TLC (90:9:1 methylene chloride/methanol/ammonium hydroxide). To the obtained material (64 mg, 0.16 mmol) in acetonitrile (3 mL) was added L-tartaric acid (24 mg, 0.16 mmol) in water (6 mL). The resultant solution was lyophilized to give 5-(5-(4-chlorophenyl)-2,5-ethano-2,3,4,5-tetrahydro-1H-benzo[c]azepin-8-yloxy)pyrazin-2-amine, L-tartrate salt (63 mg, 16%, AUC HPLC >99%) as an off-white solid: 1H NMR (CD3OD, 500 MHz) δ 7.75 (s, 1H), 7.58 (s, 1H), 7.44 (d, J=8.5 Hz, 2H), 7.33 (d, J=8.5 Hz, 2H), 6.96 (d, J=2.0 Hz, 1H), 6.73 (dd, J=8.5, 2.0 Hz, 1H), 6.35 (d, J=9.0 Hz, 1H), 4.77 (s, 2H), 4.42 (s, 2.2H), 3.63-3.57 (m, 2H), 3.44-3.85 (m, 2H), 2.78-2.72 (m, 2H), 2.44-2.38 (m, 2H); ESI MS m/z 393 [M+H]+. Anal. Calcd. For C22H21ClN4O.1.1C4H6O6.1.25H2O: C, 54.62; H, 5.23; N, 9.65. Found: C, 54.43; H, 5.02; N, 6.55.

Example 35

Preparation of 5-(4-chlorophenyl)-2,5-ethano-8-(3-(pyridin-4-yl)propoxy)-2,3,4,5-tetrahydro-1H-benzo[c]azepine, L-tartrate Salt

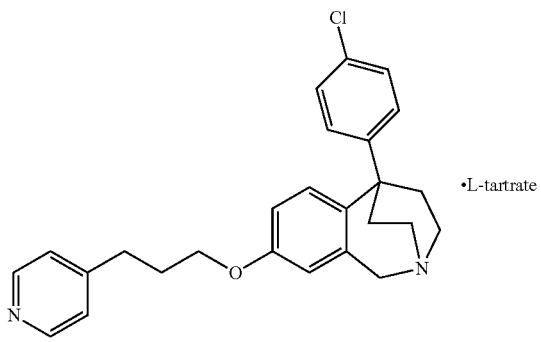 [SMILES: Clc1ccc(C23CCN(CC2)Cc2cc(OCCCc4ccncc4)ccc23)cc1]

Step A: To a solution of the 5-(4-chlorophenyl)-2,5-ethano-2,3,4,5-tetrahydro-1H-benzo[c]azepin-8-ol (0.10 g, 0.33 mmol) from Step A of Example 13 in DMF at room temperature were added cesium carbonate (0.50 g, 1.5 mmol) and 3-(pyridin-4-yl)propyl methanesulfonate (0.15 g, 0.70 mmol, prepared from corresponding alcohol). The reaction solution was stirred at 45° C. for 14 h and then it was quenched with water and extracted with dichloromethane. The organic extract was washed with brine, dried over sodium sulfate and concentrated in vacuo. The residue obtained was purified by preparative thin layer chromatography (90:9:1 dichloromethane/methanol/concentrated ammonium hydroxide) to give 5-(4-chlorophenyl)-2,5-ethano-8-(3-(pyridin-4-yl)propoxy)-2,3,4,5-tetrahydro-1H-benzo[c]azepine (27 mg, 20%) as a brown oil.

Step B: The free base of the ethanobenzoazepine from Step A above was converted to its L-tartrate salt to form 5-(4-chlorophenyl)-2,5-ethano-8-(3-(pyridin-4-yl)propoxy)-2,3,4,5-tetrahydro-1H-benzo[c]azepine, L-tartrate salt (32 mg, 90%, AUC HPLC >99.0%) as an off-white solid: $^1$H NMR (CD$_3$OD, 500 MHz) δ 8.40 (dd, J=5.5, 1.0 Hz, 2H), 7.43 (dd, J=6.4, 2.0 Hz, 2H), 7.32-7.29 (m, 4H), 6.81 (s, 1H), 6.65 (dd, J=8.5, 2.5 Hz, 1H), 6.27 (d, J=9.0 Hz, 1H), 4.77 (s, 2H), 4.42 (s, 2H), 3.95 (t, J=6.0 Hz, 2H), 3.64-3.57 (m, 2H), 3.41-3.36 (m, 2H), 2.84 (t, J=8.0 Hz, 2H), 2.73-2.67 (m, 2H), 2.42-2.37 (m, 2H), 2.13-2.07 (m, 2H); ESI MS m/z 419 [M+H]$^+$.

Example 36

Preparation of 5-(4-chlorophenyl)-2,5-ethano-8-(3-(pyridin-3-yl)propoxy)-2,3,4,5-tetrahydro-1H-benzo[c]azepine, L-tartrate Salt

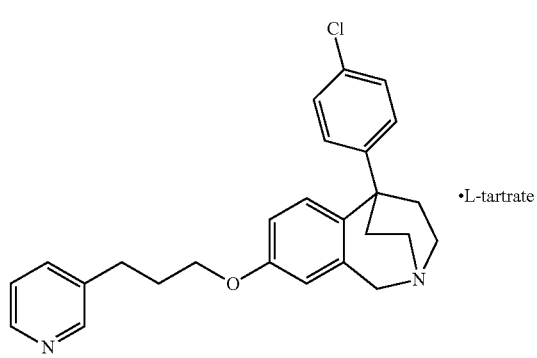 [SMILES: Clc1ccc(C23CCN(CC2)Cc2cc(OCCCc4cccnc4)ccc23)cc1]

Step A: To a suspension of 5-(4-chlorophenyl)-2,5-ethano-2,3,4,5-tetrahydro-1H-benzo[c]azepin-8-ol (0.10 g, 0.33 mmol) from Step A of Example 13 and 3-(pyridin-3-yl)propan-1-ol (0.09 mL, 0.67 mmol) in THF (4 mL) at room temperature were added diisopropyl azodicarboxylate (0.20 mL, 1.0 mmol) and triphenyl phosphine (0.26 g, 1.0 mmol). The reaction solution was stirred at room temperature for 30 min and then it was concentrated in vacuo. The residue obtained was purified by flash column chromatography (88:10.2:1.8 dichloromethane/methanol/concentrated ammonium hydroxide) to give 5-(4-chlorophenyl)-2,5-ethano-8-(3-(pyridin-3-yl)propoxy)-2,3,4,5-tetrahydro-1H-benzo[c]azepine (36 mg, 26%) as a light yellow oil.

Step B: The free base of the ethanobenzoazepine from Step A above was converted to its L-tartrate salt to form 5-(4-chlorophenyl)-2,5-ethano-8-(3-(pyridin-3-yl)propoxy)-2,3,4,5-tetrahydro-1H-benzo[c]azepine, L-tartrate salt (48 mg, 97%, AUC HPLC 97.7%) as a white solid: $^1$H NMR (CD$_3$OD, 500 MHz) δ 8.38-8.35 (m, 2H), 7.72 (d, J=8.0 Hz, 1H), 7.44 (d, J=9.0 Hz, 2H), 7.35 (dd, J=8.0, 5.0 Hz, 1H), 7.32 (d, J=8.5 Hz, 2H), 6.82 (d, J=2.0 Hz, 1H), 6.65 (dd, J=9.0, 2.5 Hz, 1H), 6.27 (d, J=8.5 Hz, 1H), 4.77 (s, 2H), 4.41 (s, 2,2H), 3.95 (t, J=6.5 Hz, 2H), 3.60-3.56 (m, 2H), 3.39-3.30 (m, 2H), 2.84 (t, J=6.5 Hz, 2H), 2.74-2.70 (m, 2H), 2.43-2.37 (m, 2H), 2.10-2.06 (m, 2H); ESI MS m/z 419 [M+H]$^+$. Anal. Calcd. for C$_{26}$H$_{27}$ClN$_2$O.1.1C$_4$H$_6$O$_6$–2.75H$_2$O: C, 57.63; H, 6.22; N, 4.42. Found: C, 57.46; H, 5.88; N, 4.37.

Example 37

Preparation of 8-([1,2,4]triazolo[1,5-a]pyridin-6-yl)-5-(3,4-dichlorophenyl)-2,5-ethano-2,3,4,5-tetrahydro-1H-benzo[c]azepine, L-tartrate Salt

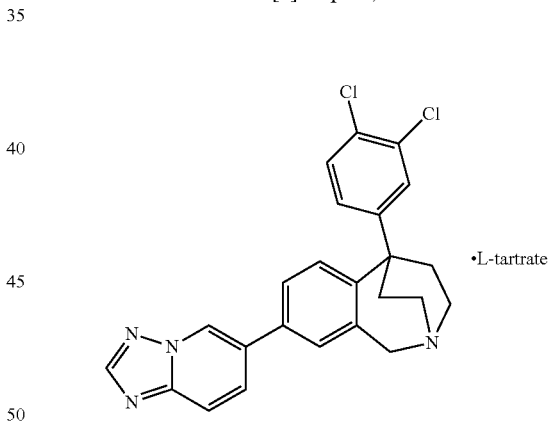

Step A: A mixture of 3-methoxybenzaldehyde (10.0 g, 73.4 mmol), 1,4-dioxa-8-azaspiro[4.5]decane (21.0 g, 146.9 mmol), sodium triacetoxyborohydride (31.1 g, 146.9 mmol), and acetic acid (4.4 mL, 73.45 mmol) in 1,2-dichloroethane (100 mL), was stirred at ambient temperature. After 19 h, a 2 N aqueous sodium carbonate solution (220 mL) was added portionwise. After stirring for 15 min, the aqueous layer was separated and extracted with methylene chloride (200 mL). The combined organic layers were washed with brine (100 mL), dried over anhydrous sodium sulfate and concentrated in vacuo to provide 8-(3-methoxybenzyl)-1,4-dioxa-8-azaspiro[4.5]decane (16.0 g, 82%) as a yellow oil: $^1$H NMR (CDCl$_3$, 400 MHz) δ 7.27-7.20 (m, 1H), 6.93-6.88 (m, 2H), 6.79 (dd, J=2.4, 8.2 Hz, 1H), 3.94 (s, 4H), 3.82-3.78 (m, 3H), 3.50 (s, 2H), 2.56-2.47 (m, 4H), 1.74 (t, J=5.6 Hz, 4H); ESI MS (m/z) 264 [M+H].

Step B: To a solution of 8-(3-methoxybenzyl)-1,4-dioxa-8-azaspiro[4.5]decane (16.0 g, 60.76 mmol) from Step A above was added an ice-cold solution of concentrated hydrochloric acid (320 mL). The suspension was stirred at 0° C. for 5 min and then allowed to warm to ambient temperature. After 1 h, the homogeneous solution was poured into a sodium hydroxide solution (21.5 g in 200 mL of water) at 0° C. and then extracted with methylene chloride (2×150 mL). The combined organic layers were dried over anhydrous sodium sulfate and concentrated in vacuo. Purification by silica gel chromatography (methylene chloride to 1:1 ethyl acetate/methylene chloride) gave 1-(3-methoxybenzyl)piperidin-4-one (11.0 g, 83%) as a colorless oil: $^1$H NMR (CDCl$_3$, 400 MHz) δ 7.28-7.22 (m, 1H), 6.97-6.90 (m, 2H), 6.82 (dd, J=2.1, 7.9 Hz, 1H), 3.82 (s, 3H), 3.60 (s, 2H), 2.75 (t, J=6.1 Hz, 4H), 2.46 (t, J=6.1 Hz, 4H); ESI MS (m/z) 220 [M+H].

Step C: To 3,4-dichloro-1-iodobenzene (9.00 g, 41.0 mmol) in tetrahydrofuran (80 mL) at room temperature, was added isopropylmagnesium bromide (40.5 mL of a 2.0 M solution in THF, 82.0 mmol) dropwise. After 2 h, a solution of 1-(3-methoxybenzyl)piperidin-4-one (9.0 g, 41.0 mmol) from Step B above in tetrahydrofuran (10 mL) was added dropwise at 0° C. The reaction mixture was warmed to ambient temperature and stirred for 2 h. After 1 h, the reaction mixture was quenched with saturated ammonium chloride (5 mL). The mixture was diluted with ethyl acetate (50 mL) and washed with saturated ammonium chloride (80 mL), water (80 mL), brine (80 mL), dried over anhydrous sodium sulfate and concentrated in vacuo. Purification by silica gel chromatography (dichloromethane to 10% ethyl acetate in dichloromethane) gave 4-(3,4-dichlorophenyl)-1-(3-methoxybenzyl)piperidin-4-ol (13.0 g, 86%) as a colorless oil: $^1$H NMR (CDCl$_3$, 400 MHz) δ 7.62 (d, J=2.0 Hz, 1H), 7.43-7.38 (m, 1H), 7.36-7.30 (m, 1H), 7.25-7.21 (m, 1H), 6.96-6.90 (m, 2H), 6.84-6.77 (m, 1H), 3.82 (s, 3H), 3.55 (s, 2H), 2.84-2.76 (m, 2H), 2.47-2.37 (m, 2H), 2.10 (dt, J=4.5, 13.1 Hz, 2H), 1.72-1.65 (m, J=11.5 Hz, 2H); ESI MS (m/z) 366 [M+H]$^+$.

Step D: To a solution of 4-(3,4-dichlorophenyl)-1-(3-methoxybenzyl)piperidin-4-ol (14.5 g, 39.58 mmol) from Step C above in methylene chloride (145 mL) was added triflic acid (58 mL) at 0° C. The reaction mixture was warmed to ambient temperature. After 2 h, the reaction mixture was carefully poured over ice (ca. 100 g), made strongly basic with 6N sodium hydroxide and extracted with methylene chloride (2×). The combined organic layers were washed with brine, dried over anhydrous sodium sulfate and concentrated in vacuo to provide 5-(3,4-dichlorophenyl)-8-methoxy-2,5-ethano-2,3,4,5-tetrahydro-1H-benzo[c]azepine (8.5 g, 62%) as a yellow residue: $^1$H NMR (DMSO-d$_6$, 400 MHz) δ 7.65 (d, J=8.5 Hz, 1H), 7.47 (s, 1H), 7.32-7.21 (m, 1H), 6.72 (s, 1H), 6.60-6.46 (m, 1H), 6.02 (d, J=8.8 Hz, 1H), 4.24 (s, 2H), 3.68 (s, 3H), 3.13-2.98 (m, 2H), 2.95-2.81 (m, 2H), 2.48-2.38 (m, 2H), 2.07-1.88 (m, 2H); ESI MS (m/z) 348 [M+H]$^+$.

Step E: A solution of 5-(3,4-dichlorophenyl)-8-methoxy-2,5-ethano-2,3,4,5-tetrahydro-1H-benzo[c]azepine (7.0 g, 20 mmol) from Step D above in aqueous 48% hydrobromic acid (105 mL) and acetic acid (105 mL) was heated to 135° C. After 9 h, the reaction mixture was cooled to ambient temperature, brought to ca. pH=8.5-10 with 6 N sodium hydroxide and saturated sodium bicarbonate and extracted with ethyl acetate (2×75 mL). The combined organics were concentrated in vacuo to provide 5-(3,4-dichlorophenyl)-2,5-ethano-2,3,4,5-tetrahydro-1H-benzo[c]azepin-8-ol (4.0 g, 60%): $^1$H NMR (DMSO-d$_6$, 400 MHz) δ 9.64 (s, 1H), 7.69 (d, J=8.5 Hz, 1H), 7.53 (d, J=2.3 Hz, 1H), 7.29 (dd, J=2.0, 8.5 Hz, 1H), 6.71 (d, J=2.3 Hz, 1H), 6.52 (dd, J=2.4, 8.7 Hz, 1H), 6.02 (d, J=8.5 Hz, 1H), 4.65 (br s, 2H), 3.52-3.40 (m, 2H), 3.30-3.18 (m, 2H), 2.62 (td, J=6.8, 13.4 Hz, 2H), 2.26 (br s, 2H); ESI MS (m/z) 334 [M+H]$^+$.

Step F: To a suspension of 5-(3,4-dichlorophenyl)-2,5-ethano-2,3,4,5-tetrahydro-1H-benzo[c]azepin-8-ol (500 mg, 1.49 mmol) from Step E above in methylene chloride (15 mL) at 0° C., were added pyridine (0.15 g, 1.86 mmol) and triflic anhydride (0.52 g, 1.86 mmol). After 12 h (reaction monitoring by TLC), the reaction mixture was diluted with methylene chloride (10 mL) and saturated sodium bicarbonate (10 mL) was added. The organic layer was separated, washed with brine, dried over sodium sulfate and concentrated in vacuo to provide 5-(3,4-dichlorophenyl)-2,5-ethano-2,3,4,5-tetrahydro-1H-benzo[c]azepin-8-yl trifluoromethanesulfonate (700 mg, crude product, ~100%) as a yellowish oil.

Step G: A mixture of bis(pinacolato)diboron (690 mg, 1.49 mmol), potassium acetate (482 mg, 4.91 mmol) and 5-(3,4-dichlorophenyl)-2,5-ethano-2,3,4,5-tetrahydro-1H-benzo[c]azepin-8-yl trifluoromethanesulfonate (690 mg, 1.49 mmol) from Step F above in DMF (6 mL) was purged with nitrogen for 5 min. Next, dichloro[1,1'-bis(diphenylphosphino)ferrocene]palladium(II) dichloromethane adduct (182 mg, 0.22 mmol) was added and the mixture was purged again with nitrogen. The reaction mixture was heated at 80° C. for 2 h. After the completion of reaction, as monitored by LC-MS, 6-bromo-[1,2,4]triazolo[1,5-a]pyridine (318 mg, 1.61 mmol), cesium carbonate (1.56 g, 4.81 mmol), and water (2 mL) were sequentially added. The reaction mixture was purged with nitrogen and then dichloro[1,1'-bis(diphenylphosphino)ferrocene]palladium(II) dichloromethane adduct (178 mg, 0.21 mmol) was added. The mixture was degassed again and heated to 90° C. for 3 h. The reaction mixture was diluted with water (25 mL) and extracted with ethyl acetate (2×25 mL). The combined organics were washed with water (2×20 mL), brine (20 mL), dried over sodium sulfate, filtered and concentrated in vacuo. The residue was purified by column chromatography (methylene chloride to 90:9:1 methylene chloride/methanol/ammonium hydroxide) to afford 8-([1,2,4]triazolo[1,5-a]pyridin-6-yl)-5-(3,4-dichlorophenyl)-2,5-ethano-2,3,4,5-tetrahydro-1H-benzo[c]azepine, (60 mg, 10%) as a brownish solid (AUC HPLC >95%).

Step H: To a solution of 8-([1,2,4]triazolo[1,5-a]pyridin-6-yl)-5-(3,4-dichlorophenyl)-2,5-ethano-2,3,4,5-tetrahydro-1H-benzo[c]azepine (60 mg, 0.14 mmol) from Step G above in acetonitrile (2 mL) was added L-tartaric acid (20 mg, 0.14 mmol) in water (10 mL). The resultant solution was lyophilized for 48 h to give 8-([1,2,4]triazolo[1,5-a]pyridin-6-yl)-5-(3,4-dichlorophenyl)-2,5-ethano-2,3,4,5-tetrahydro-1H-benzo[c]azepine, L-tartrate salt (78 mg, 98%, AUC HPLC 98.9%) as an off-white solid: $^1$H NMR (CD$_3$OD, 400 MHz) δ 9.11 (s, 1H), 8.47 (d, J=1.3 Hz, 1H), 8.03 (d, J=9.3 Hz, 1H), 7.88 (d, J=9.3 Hz, 1H), 7.73 (s, 1H), 7.66 (d, J=8.5 Hz, 1H), 7.63-7.50 (m, 2H), 7.35 (d, J=8.5 Hz, 1H), 6.58 (d, J=8.3 Hz, 1H), 5.05-4.93 (m, 2H), 4.53-4.43 (m, 2H), 3.77-3.59 (m, 2H), 3.57-3.40 (m, 2H), 2.91-2.74 (m, 2H), 2.57-2.41 (m, 2H); ESI MS (m/z) 435 [M+H]$^+$.

Example 38

Preparation of 6-(5-(3,4-dichlorophenyl)-2,5-ethano-2,3,4,5-tetrahydro-1H-benzo[c]azepin-8-yl)-3,3a-dihydrobenzo[d]oxazol-2(7aH)-one, L-tartrate Salt

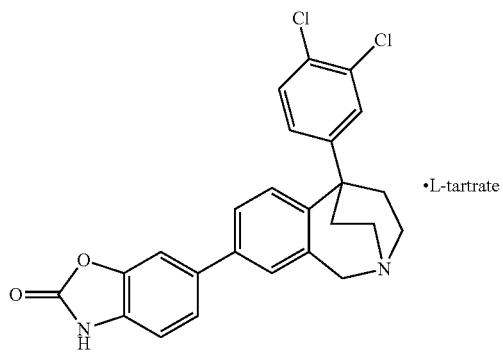 [SMILES: O=c1[nH]c2ccc(-c3ccc4c(c3)CN3CCC4(c4ccc(Cl)c(Cl)c4)CC3)cc2o1]

Step A: A mixture of bis(pinacolato)diboron (493 mg, 1.94 mmol), potassium acetate (482 mg, 4.91 mmol) and 5-(3,4-dichlorophenyl)-2,5-ethano-2,3,4,5-tetrahydro-1H-benzo[c]azepin-8-yl trifluoromethanesulfonate (690 mg, 1.49 mmol) from Step F of Example 37 in DMF (6 mL) was purged with nitrogen for 5 min. Next, dichloro[1,1'-bis(diphenylphosphino)ferrocene]palladium(II) dichloromethane adduct (182 mg, 0.22 mmol) was added and the mixture was purged again with nitrogen. The reaction mixture was heated at 80° C. for 2 h. After the completion of reaction, as monitored by LC-MS, 6-bromo-3,3a-dihydrobenzo[d]oxazol-2(7aH)-one (345 mg, 1.61 mmol), cesium carbonate (1.56 g, 4.81 mmol), and water (2 mL) were sequentially added. The reaction mixture was purged with nitrogen and then [1,1'-bis(diphenylphosphino)ferrocene]palladium(II) dichloromethane adduct (178 mg, 0.21 mmol) was added. The mixture was degassed again and heated to 90° C. for 3 h. The reaction mixture was diluted with water (25 mL) and extracted with ethyl acetate (2×25 mL). The combined organics were washed with water (2×20 mL), brine (20 mL), dried over sodium sulfate, filtered and concentrated in vacuo. The residue was purified by column chromatography (methylene chloride to 90:9:1 methylene chloride/methanol/ammonium hydroxide) to afford 6-(5-(3,4-dichlorophenyl)-2,5-ethano-2,3,4,5-tetrahydro-1H-benzo[c]azepin-8-yl)-3,3a-dihydrobenzo[d]oxazol-2(7aH)-one, (60 mg, 10%) as a brown solid.

Step B: To a solution of 6-(5-(3,4-dichlorophenyl)-2,5-ethano-2,3,4,5-tetrahydro-1H-benzo[c]azepin-8-yl)-3,3a-dihydrobenzo[d]oxazol-2(7aH)-one (60 mg, 0.13 mmol) from Step A above in acetonitrile (2 mL) was added L-tartaric acid (19 mg, 0.13 mmol) in water (10 mL). The resultant solution was lyophilized for 48 h to give 6-(5-(3,4-dichlorophenyl)-2,5-ethano-2,3,4,5-tetrahydro-1H-benzo[c]azepin-8-yl)-3,3a-dihydrobenzo[d]oxazol-2(7aH)-one, L-tartrate salt (78 mg, 98%, AUC HPLC 98.1%) as an off-white solid: $^1$H NMR (CD$_3$OD, 400 MHz) δ 7.65 (d, J=8.5 Hz, 1H), 7.61-7.56 (m, 2H), 7.52 (s, 1H), 7.49-7.41 (m, 2H), 7.37-7.32 (m, 1H), 7.17 (d, J=8.3 Hz, 1H), 6.51 (d, J=8.0 Hz, 1H), 5.06-4.93 (m, 2H), 4.48 (s, 3H), 3.77-3.61 (m, 2H), 3.57-3.42 (m, 2H), 2.93-2.74 (m, 2H), 2.57-2.40 (m, 2H); ESI MS (m/z) 451 [M+H]$^+$.

Example 39

Preparation of 5-(3,4-dichlorophenyl)-8-(6-(difluoromethoxy)pyridazin-3-yl)-2,5-ethano-2,3,4,5-tetrahydro-1H-benzo[c]azepine, L-tartrate Salt

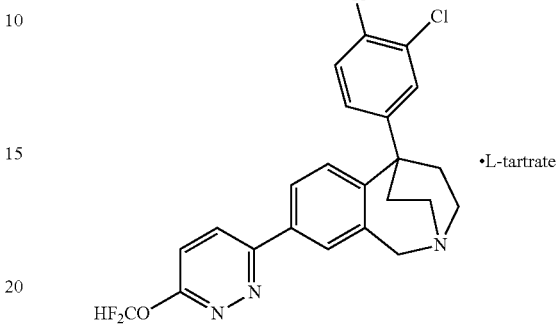

5-(4-chlorophenyl)-2,5-ethano-8-(4,4,5,5-tetramethyl-1,3,2-dioxaborolan-2-yl)-2,3,4,5-tetrahydro-1H-2-benzoazepine was prepared following the procedures in Examples 12-14, except that 4-bromo-1,2-dichlorobenzene was used in the procedure described in Step C of Example 12. A procedure similar to Step C of Example 14 was then used to convert 5-(4-chlorophenyl)-2,5-ethano-8-(4,4,5,5-tetramethyl-1,3,2-dioxaborolan-2-yl)-2,3,4,5-tetrahydro-1H-2-benzoazepine and 3-chloro-6-(difluoromethoxy)pyridazine to 5-(3,4-dichlorophenyl)-8-(6-(difluoromethoxy)pyridazin-3-yl)-2,5-ethano-2,3,4,5-tetrahydro-1H-benzo[c]azepine, L-tartrate salt (53 mg, 13%, AUC HPLC >99%) as an off-white solid: $^1$H NMR (DMSO-d$_6$, 500 MHz) δ 8.30 (d, J=9.5 Hz, 1H), 7.93 (t, J=72.0 Hz, 1H), 7.96 (br s, 1H), 7.73-7.68 (m, 2H), 7.62 (d, J=9.5 Hz, 1H), 7.54 (br s, 1H), 7.33-7.31 (m, 1H), 6.32 (d, J=8.0 Hz, 1H), 4.52 (s, 2H), 4.14 (s, 1.5H), 3.22-3.12 (m, 2H), 3.09-3.01 (m, 2H), 2.67-2.59 (m, 2H), 2.19-2.08 (m, 2H); ESI MS m/z 462 [M+H]$^+$. Anal. Calcd. For $C_{23}H_{19}Cl_2F_2N_3O \cdot 0.75C_4H_6O_6 \cdot H_2O$: C, 52.67; H, 4.33; N, 7.09. Found: C, 52.54; H, 4.17; N, 6.98.

Example 40

Preparation of 5-(3,4-dichlorophenyl)-8-(6-methoxypyridazin-3-yl)-2,5-ethano-2,3,4,5-tetrahydro-1H-benzo[c]azepine, L-tartrate Salt

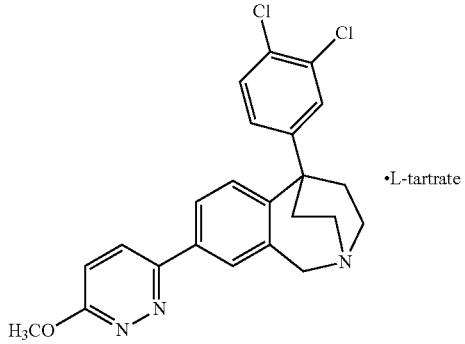 [SMILES: COc1ccc(-c2ccc3c(c2)CN2CCC3(c3ccc(Cl)c(Cl)c3)CC2)nn1]

5-(4-chlorophenyl)-2,5-ethano-8-(4,4,5,5-tetramethyl-1,3,2-dioxaborolan-2-yl)-2,3,4,5-tetrahydro-1H-2-benzoazepine was prepared following the procedures in Examples 12-14, except that 4-bromo-1,2-dichlorobenzene was used in the procedure described in Step C of Example 12. A procedure similar to Step C of Example 14 was then used to convert 5-(4-chlorophenyl)-2,5-ethano-8-(4,4,5,5-tetramethyl-1,3,2-dioxaborolan-2-yl)-2,3,4,5-tetrahydro-1H-2-benzoazepine and 3-chloro-6-methoxypyridazine to 5-(3,4-dichlorophenyl)-8-(6-methoxypyridazin-3-yl)-2,5-ethano-2,3,4,5-tetrahydro-1H-benzo[c]azepine, L-tartrate salt (27 mg, 7%, AUC HPLC >99%) as a white solid: $^1$H NMR (DMSO-$d_6$, 500 MHz) δ 8.07 (d, J=9.5 Hz, 1H), 7.92 (s, 1H), 7.70-7.67 (m, 2H), 7.54 (dd, J=1.5 Hz, 1H), 7.34-7.29 (m, 2H), 6.30 (d, J=8.0 Hz, 1H), 4.53 (s, 2H), 4.15 (s, 2H), 4.06 (s, 3H), 3.26-3.20 (m, 2H), 3.10-3.02 (m, 2H), 2.65-2.58 (m, 2H), 2.18-2.08 (m, 2H); ESI MS m/z 426 [M+H]$^+$.

Example 41

Preparation of 6-(5-(3,4-dichlorophenyl)-2,5-ethano-2,3,4,5-tetrahydro-1H-benzo[c]azepin-8-yl)pyridazin-3-ol, L-tartrate Salt

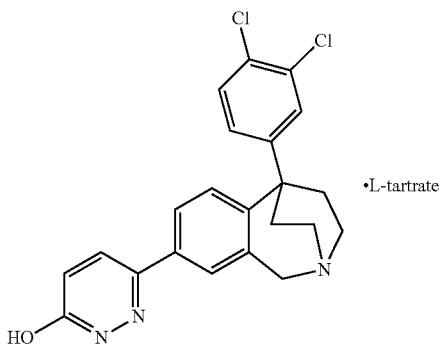 [SMILES: Oc1ccc(-c2ccc3c(c2)CN2CCC3(c3ccc(Cl)c(Cl)c3)CC2)nn1]

A mixture of 5-(3,4-dichlorophenyl)-8-(6-methoxypyridazin-3-yl)-2,5-ethano-2,3,4,5-tetrahydro-1H-benzo[c]azepine (44 mg, 0.10 mmol) from Example 40 and 6 N hydrochloric acid was heated to reflux. After 2 h the mixture was cooled to ambient temperature, brought to pH=10 with 6 N sodium hydroxide, and extracted with ethyl acetate. The organic layer was washed with brine, dried over sodium sulfate, and concentrated in vacuo. To the obtained material (31 mg, 0.073 mmol) in acetonitrile (2 mL) was added L-tartaric acid (11 mg, 0.073 mmol) in water (6 mL). The resultant solution was lyophilized to give 6-(5-(3,4-dichlorophenyl)-2,5-ethano-2,3,4,5-tetrahydro-1H-benzo[c]azepin-8-yl)pyridazin-3-ol, L-tartrate salt (41 mg, 65%, AUC HPLC >99%) as a white solid: $^1$H NMR (DMSO-$d_6$, 500 MHz) δ 13.16 (s, 1H), 7.94 (d, J=10.0 Hz, 1H), 7.71-7.68 (m, 2H), 7.53 (s, 1H), 7.50-7.48 (m, 1H), 7.31-7.29 (m, 1H), 6.98 (d, J=10.0 Hz, 1H), 6.27 (d, J=8.0 Hz, 1H), 4.52 (s, 2H), 4.16 (s, 2.6H), 3.25-3.18 (m, 2H), 3.10-3.02 (m, 2H), 2.63-2.56 (m, 2H), 2.18-2.08 (m, 2H); ESI MS m/z 412 [M+H]$^+$. Anal. Calcd. For $C_{22}H_{19}Cl_2N_3O \cdot 1.3C_4H_6O_6 - 1.5H_2O$: C, 51.49; H, 4.73; N, 6.62. Found: C, 51.53; H, 4.57; N, 6.60.

Example 42

Preparation of 5-(5-(3,4-dichlorophenyl)-2,5-ethano-2,3,4,5-tetrahydro-1H-benzo[c]azepin-8-yl)pyrazin-2-amine, L-tartrate Salt

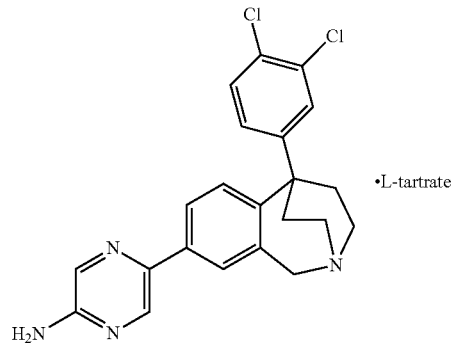 [SMILES: Nc1cnc(-c2ccc3c(c2)CN2CCC3(c3ccc(Cl)c(Cl)c3)CC2)cn1]

5-(4-chlorophenyl)-2,5-ethano-8-(4,4,5,5-tetramethyl-1,3,2-dioxaborolan-2-yl)-2,3,4,5-tetrahydro-1H-2-benzoazepine was prepared following the procedures in Examples 12-14, except that 4-bromo-1,2-dichlorobenzene was used in the procedure described in Step C of Example 12. A procedure similar to Step C of Example 14 was then used to convert 5-(4-chlorophenyl)-2,5-ethano-8-(4,4,5,5-tetramethyl-1,3,2-dioxaborolan-2-yl)-2,3,4,5-tetrahydro-1H-2-benzoazepine and 5-bromopyrazin-2-amine to 5-(5-(3,4-dichlorophenyl)-2,5-ethano-2,3,4,5-tetrahydro-1H-benzo[c]azepin-8-yl)pyrazin-2-amine, L-tartrate salt (64 mg, 16%, AUC HPLC 97.9%) as an off-white solid: $^1$H NMR (DMSO-$d_6$, 500 MHz) δ 8.42 (s, 1H), 7.92 (d, J=1.5 Hz, 1H), 7.77 (s, 1H), 7.68 (d, J=8.5 Hz, 1H), 7.54-7.52 (m, 2H), 7.31 (dd, J=8.5, 2.0 Hz, 1H), 6.54 (br s, 2H), 6.20 (d, J=8.0 Hz, 1H), 4.52 (s, 2H), 4.13 (s, 2.2H), 3.25-3.20 (m, 2H), 3.11-3.04 (m, 2H), 2.63-2.55 (m, 2H), 2.17-2.09 (m, 2H); ESI MS m/z 411 [M+H]$^+$. Anal. Calcd. For $C_{22}H_{20}Cl_2N_4 \cdot 1.1C_4H_6O_6 \cdot 1.25H_2O$: C, 52.94; H, 4.90; N, 9.35. Found: C, 52.92; H, 4.75; N, 9.20.

Example 43

Preparation of 5-(3,4-dichlorophenyl)-2,5-ethano-8-(7-methyl-[1,2,4]triazolo[1,5-a]pyridin-6-yl)-2,3,4,5-tetrahydro-1H-benzo[c]azepine, L-tartrate Salt

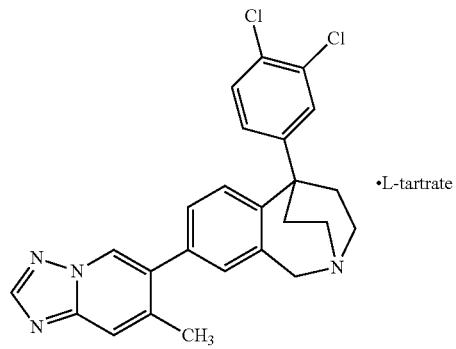 [SMILES: Cc1cc2ncnn2cc1-c1ccc2c(c1)CN1CCC2(c2ccc(Cl)c(Cl)c2)CC1]

5-(4-chlorophenyl)-2,5-ethano-8-(4,4,5,5-tetramethyl-1,3,2-dioxaborolan-2-yl)-2,3,4,5-tetrahydro-1H-2-benzoazepine was prepared following the procedures in Examples 12-14, except that 4-bromo-1,2-dichlorobenzene was used in the procedure described in Step C of Example 12. A procedure similar to Step C of Example 14 was then used to convert 5-(4-chlorophenyl)-2,5-ethano-8-(4,4,5,5-tetramethyl-1,3,2-dioxaborolan-2-yl)-2,3,4,5-tetrahydro-1H-2-benzoazepine and 6-bromo-7-methyl-[1,2,4]triazolo[1,5-a]pyridine to 5-(3,4-dichlorophenyl)-2,5-ethano-8-(7-methyl-[1,2,4]triazolo[1,5-a]pyridin-6-yl)-2,3,4,5-tetrahydro-1H-benzo[c]azepine, L-tartrate salt (115 mg, 27%, AUC HPLC >99%) as an off-white solid: $^1$H NMR (DMSO-$d_6$, 500 MHz) δ 8.74 (s, 1H), 8.44 (s, 1H), 7.77 (s, 1H), 7.71 (d, J=8.4 Hz, 1H), 7.58 (d, J=2.1 Hz, 1H), 7.37-7.33 (m, 2H), 7.15 (dd, J=8.1, 1.5 Hz, 1H), 6.26 (d, J=8.1 Hz, 1H), 4.52 (s, 2H), 4.16 (s, 2H), 3.30-3.20 (m, 2H), 3.14-3.03 (m, 2H), 2.71-2.60 (m, 2H), 2.31 (s, 3H), 2.21-2.10 (m, 2H); ESI MS m/z 449 [M+H]$^+$. Anal. Calcd. For $C_{25}H_{22}Cl_2N_4 \cdot 1.1C_4H_6O_6 \cdot 0.75H_2O$: C, 56.23; H, 4.83; N, 8.92. Found: C, 56.11; H, 4.82; N, 9.09.

Example 44

Preparation of 5-(3,4-dichlorophenyl)-2,5-ethano-8-(pyrazin-2-yloxy)-2,3,4,5-tetrahydro-1H-benzo[c]azepine, L-tartrate Salt

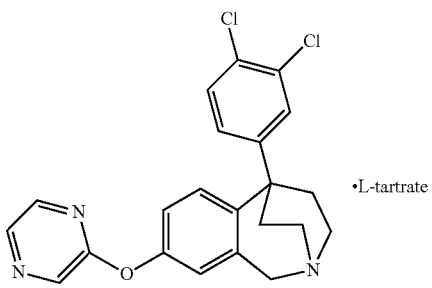 [SMILES: Clc1ccc(C23CCN(CC2)Cc2cc(Oc4cnccn4)ccc23)cc1Cl]

Step A: A suspension of 5-(3,4-dichlorophenyl)-2,5-ethano-2,3,4,5-tetrahydro-1H-benzo[c]azepin-8-ol (300 mg, 0.89 mmol) from Step E of Example 37, 2-chloropyrazine (143 mg, 1.25 mmol) and cesium carbonate (585 mg, 1.79 mmol) in dimethyl formamide (4.5 mL) was heated to 75° C. for 12 h. After cooling to ambient temperature, the reaction mixture was diluted with water and then extracted with ethyl acetate (25 mL). The organics were washed with water (2×), brine, dried over anhydrous sodium sulfate and concentrated in vacuo. The residue was purified by column chromatography (methylene chloride to 90:9:1 methylene chloride/methanol/ammonium hydroxide) to provide 5-(3,4-dichlorophenyl)-2,5-ethano-8-(pyrazin-2-yloxy)-2,3,4,5-tetrahydro-1H-benzo[c]azepine (60 mg, 17%) as a colourless solid.

Step B: To a solution of 5-(3,4-dichlorophenyl)-2,5-ethano-8-(pyrazin-2-yloxy)-2,3,4,5-tetrahydro-1H-benzo[c]azepine (60 mg, 0.15 mmol) from Step A above in acetonitrile (5 mL) was added L-tartaric acid (22 mg, 0.15 mmol) in water (15 mL). The resultant solution was lyophilized to give 5-(3,4-dichlorophenyl)-2,5-ethano-8-(pyrazin-2-yloxy)-2,3,4,5-tetrahydro-1H-benzo[c]azepine, L-tartrate salt (80 mg, 97%, AUC HPLC 98.7%) as a white solid: $^1$H NMR (CD$_3$OD, 400 MHz) δ 8.46 (s, 1H), 8.31 (d, J=2.8 Hz, 1H), 8.16-8.10 (m, 1H), 7.63 (d, J=8.5 Hz, 1H), 7.57 (d, J=2.0 Hz, 1H), 7.34 (dd, J=2.0, 8.5 Hz, 1H), 7.20 (d, J=2.0 Hz, 1H), 6.99 (dd, J=2.3, 8.8 Hz, 1H), 6.47 (d, J=8.5 Hz, 1H), 4.87-4.78 (m, 2H), 4.45 (s, 2H), 3.73-3.57 (m, 2H), 3.53-3.40 (m, 2H), 2.90-2.73 (m, 2H), 2.52-2.39 (m, 2H); ESI MS (m/z) 412 [M+H]$^+$.

Example 45

Preparation of 5-(3,4-dichlorophenyl)-2,5-ethano-8-(6-(trifluoromethyl)pyridazin-3-yloxy)-2,3,4,5-tetrahydro-1H-benzo[c]azepine, L-tartrate Salt

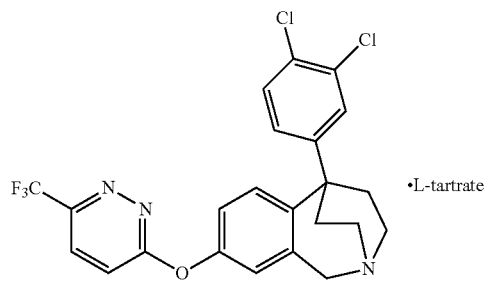 [SMILES: FC(F)(F)c1ccc(Oc2ccc3c(c2)CN2CCC3(c3ccc(Cl)c(Cl)c3)CC2)nn1]

The procedures described in Steps A and B of Example 44 were used to convert 5-(3,4-dichlorophenyl)-2,5-ethano-2,3,4,5-tetrahydro-1H-benzo[c]azepin-8-ol from Step E of Example 37 and 3-chloro-6-(trifluoromethyl)pyridazine to 5-(3,4-dichlorophenyl)-2,5-ethano-8-(6-(trifluoromethyl)pyridazin-3-yloxy)-2,3,4,5-tetrahydro-1H-benzo[c]azepine, L-tartrate salt (167 mg, 42%, AUC HPLC 98.8%) as an off-white solid: $^1$H NMR (DMSO-$d_6$, 300 MHz) δ 8.28 (d, J=9.3 Hz, 1H), 7.73-7.67 (m, 2H), 7.55 (d, J=2.1 Hz, 1H), 7.33 (dd, J=8.7, 2.1 Hz, 1H), 7.16 (d, J=2.4 Hz, 1H), 6.94 (d, J=8.4, 2.7 Hz, 1H), 6.24 (d, J=8.7 Hz, 1H), 4.42 (s, 2H), 3.25-3.12 (m, 2H), 3.08-3.00 (m, 2H), 2.68-2.55 (m, 2H), 2.17-2.05 m, 2H); ESI MS m/z 480 [M+H]$^+$. Anal. Calcd. For $C_{23}H_{18}Cl_2F_3N_3O \cdot 1.1C_4H_6O_6 \cdot 0.75H_2O$: C, 49.95; H, 3.99; N, 6.38. Found: C, 50.11; H, 3.93; N, 6.30.

Example 46

Preparation of 5-(3,4-dichlorophenyl)-2,5-ethano-8-(difluoromethoxy)-2,3,4,5-tetrahydro-1H-benzo[c]azepine, L-tartrate Salt

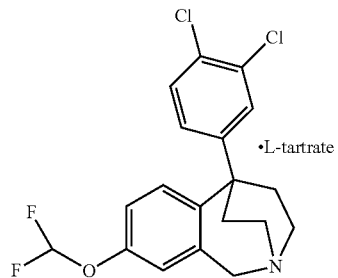 [SMILES: FC(F)Oc1ccc2c(c1)CN1CCC2(c2ccc(Cl)c(Cl)c2)CC1]

Step A: A suspension of 5-(3,4-dichlorophenyl)-2,5-ethano-2,3,4,5-tetrahydro-1H-benzo[c]azepin-8-ol (300 mg, 0.89 mmol) from Step E of Example 37, sodium difluorochloroacetate (192 mg, 1.25 mmol) and cesium carbonate (585 mg, 1.79 mmol) in DMF (5 mL) was heated to 75° C. for 12 h. After cooling to ambient temperature, the reaction mixture was diluted with water and then extracted with ethyl acetate (25 mL). The organics were washed with water (2×)

and brine, dried over anhydrous sodium sulfate, filtered, and concentrated in vacuo. The residue was purified by column chromatography (methylene chloride to 90:9:1 methylene chloride/methanol/ammonium hydroxide) to provide 5-(3,4-dichlorophenyl)-2,5-ethano-8-(difluoromethoxy)-2,3,4,5-tetrahydro-1H-benzo[c]azepine (70 mg, 21%) as a colorless solid.

Step B: To a solution of 5-(3,4-dichlorophenyl)-2,5-ethano-8-(difluoromethoxy)-2,3,4,5-tetrahydro-1H-benzo[c]azepine (70 mg, 0.18 mmol) from Step A above in acetonitrile (5 mL) was added L-tartaric acid (27 mg, 0.18 mmol) in water (15 mL). The resultant solution was lyophilized to give 5-(3,4-dichlorophenyl)-2,5-ethano-8-(difluoromethoxy)-2,3,4,5-tetrahydro-1H-benzo[c]azepine, L-tartrate salt (97 mg, 98%, AUC HPLC 95.1%) as a white solid: $^1$H NMR (CD$_3$OD, 400 MHz) δ 7.62 (d, J=8.5 Hz, 1H), 7.53 (d, J=2.3 Hz, 1H), 7.30 (dd, J=2.1, 8.4 Hz, 1H), 7.13 (s, 1H), 6.94 (dd, J=2.3, 8.8 Hz, 1H), 6.84 (t, J=72.0 Hz, 1H), 6.43 (d, J=8.8 Hz, 1H), 4.84 (s, 2H), 4.46 (s, 2H), 3.69-3.58 (m, 2H), 3.46-3.36 (m, 2H), 2.83-2.70 (m, 2H), 2.49-2.37 (m, 2H); ESI MS (m/z) 384 [M+H]$^+$.

Example 47

Preparation of 5-(3-chloro-4-fluorophenyl)-2,5-ethano-8-(6-(trifluoromethyl)pyridazin-3-yloxy)-2,3,4,5-tetrahydro-1H-benzo[c]azepine, L-tartrate Salt

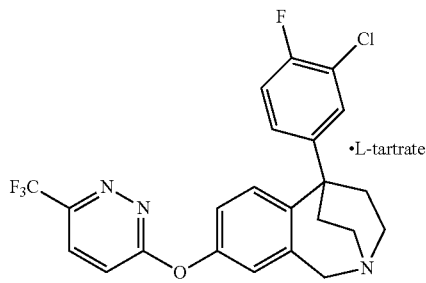 [SMILES: Fc1ccc(C23CCN(CC2)Cc2cc(Oc4ccc(C(F)(F)F)nn4)ccc23)cc1Cl]

Step A: To (3-chloro-4-fluorophenyl)magnesium bromide (6.8 ml of a 0.5 M solution in tetrahydrofuran, 3.4 mmol) was added a solution of 1-(3-methoxybenzyl)piperidin-4-one (500 mg, 2.28 mmol) from Step B of Example 12 in tetrahydrofuran (10 mL). The reaction mixture was stirred at ambient temperature for 3 h and then was quenched with saturated ammonium chloride. The mixture was extracted with ethyl acetate (2×) and the combined organics were washed with brine, dried over sodium sulfate and concentrated in vacuo. Purification by silica gel chromatography (10% ethyl acetate/methylene chloride to ethyl acetate) gave 4-(3-chloro-4-fluorophenyl)-1-(3-methoxybenzyl)piperidin-4-ol (209 mg, 26%): $^1$H NMR (CDCl$_3$, 500 MHz) δ 7.59-7.55 (m, 1H), 7.39-7.33 (m, 1H), 7.27-7.22 (m, 1H), 7.13-7.07 (m, 1H), 6.95-6.93 (m, 2H), 6.83-6.80 (m, 1H), 3.84 (s, 3H), 3.60-3.55 (m, 2H), 2.82-2.73 (m, 2H), 2.48-2.40 (m, 2H), 2.18-2.02 (m, 2H), 1.72-1.68 (m, 2H), 1.59-1.56 (m, 1H).

Step B: A procedure similar to Step D of Example 12 was used to convert 4-(3-chloro-4-fluorophenyl)-1-(3-methoxybenzyl)piperidin-4-ol from Step A above to 5-(3-chloro-4-fluorophenyl)-8-methoxy-2,5-ethano-2,3,4,5-tetrahydro-1H-benzo[c]azepine (185 mg, 95% crude) as a yellow foam: $^1$H NMR (CDCl$_3$, 300 MHz) δ 7.31-7.29 (m, 1H), 7.14-7.12 (m, 2H), 6.66-6.59 (m, 1H), 6.48 (dd, J=8.5, 3 Hz, 1H), 6.16 (d, J=8.5 Hz, 1H), 4.35 (s, 2H), 3.79 (s, 3H), 3.21-3.15 (m, 2H), 3.07-3.02 (m, 2H), 2.55-2.45 (m, 2H), 2.13-2.04 (m, 2H).

Step C: A procedure similar to Step A of Example 13 was used to convert 5-(3-chloro-4-fluorophenyl)-8-methoxy-2,5-ethano-2,3,4,5-tetrahydro-1H-benzo[c]azepine from Step B above to 5-(3-chloro-4-fluorophenyl)-2,5-ethano-2,3,4,5-tetrahydro-1H-benzo[c]azepin-8-ol (140 mg, 79% crude) as an off-white solid: $^1$H NMR (DMSO-d$_6$, 500 MHz) δ 9.13 (s, 1H), 7.42-7.37 (m, 2H), 7.27-7.23 (m, 1H), 6.50 (d, J=2.5 Hz, 1H), 6.30 (dd, J=9.0, 2.5 Hz, 1H), 5.86 (d, J=8.5 Hz, 1H).

Step D: The procedure described in Example 32 was used to convert 5-(3-chloro-4-fluorophenyl)-2,5-ethano-2,3,4,5-tetrahydro-1H-benzo[c]azepin-8-ol from Step C above and 3-chloro-6-(trifluoromethyl)pyridazine to 5-(3-chloro-4-fluorophenyl)-2,5-ethano-8-(6-(trifluoromethyl)pyridazin-3-yloxy)-2,3,4,5-tetrahydro-1H-benzo[c]azepine, L-tartrate salt (184 mg, 66%, AUC HPLC 99.0%) as an off-white solid: $^1$H NMR (DMSO-d$_6$, 300 MHz) δ 8.11 (d, J=9.0 Hz, 1H), 7.60 (d, J=9.0 Hz, 1H), 7.51-7.49 (m 1H), 7.35-7.33 (m, 2H), 7.25 (d, J=2.0 Hz, 1H), 7.03 (dd, J=9.0, 2.5 Hz, 1H), 6.49 (d, J=9.0 Hz, 1H), 4.84 (s, 2H), 4.43 (s, 2H), 3.65-3.60 (m, 2H), 3.44-3.42 (m, 2H), 2.85-2.77 (m, 2H), 2.46-2.41 (m, 2H); ESI MS m/z 464 [M+H]$^+$. Anal. Calcd. For C$_{23}$H$_{18}$ClF$_4$N$_3$O.C$_4$H$_6$O$_6$.H$_2$O: C, 51.32; H, 4.15; N, 6.65. Found: C, 51.30; H, 3.99; N, 6.70.

Example 48

Preparation of 5-(4-chloro-3-fluorophenyl)-2,5-ethano-8-(6-(trifluoromethyl)pyridazin-3-yloxy)-2,3,4,5-tetrahydro-1H-benzo[c]azepine, L-tartrate Salt

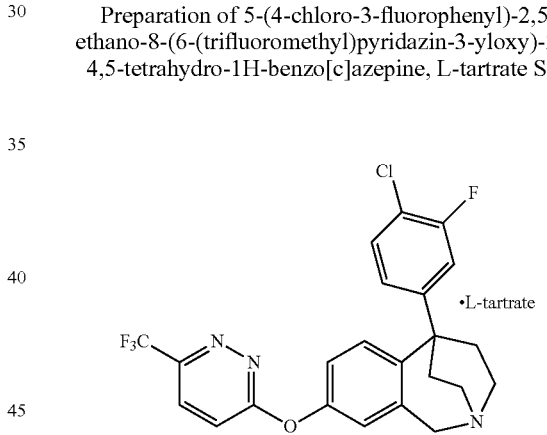

Step A: A procedure similar to Step A of Example 47 was used, except that (4-chloro-3-fluorophenyl)magnesium bromide was added instead and the reaction mixture was heated to reflux, resulting in the formation of 4-(4-chloro-3-fluorophenyl)-1-(3-methoxybenzyl)piperidin-4-ol (110 mg, 14%) as a yellow oil: $^1$H NMR (CDCl$_3$, 500 MHz) δ 7.37-7.31 (m, 2H), 7.26-7.20 (m, 2H), 6.94-6.92 (m, 2H), 6.82-6.80 (m, 1H), 3.82 (s, 3H), 3.57-3.55 (m, 2H), 2.82-2.74 (m, 2H), 2.48-2.39 (m, 2H), 2.15-2.06 (m, 2H), 1.70-1.67 (m, 2H), 1.60 (br s, 1H).

Step B: A procedure similar to Step D of Example 12 was used to convert 4-(4-chloro-3-fluorophenyl)-1-(3-methoxybenzyl)piperidin-4-ol from Step A above to 5-(4-chloro-3-fluorophenyl)-8-methoxy-2,5-ethano-2,3,4,5-tetrahydro-1H-benzo[c]azepine (196 mg, 100% crude) as a yellow foam: $^1$H NMR (CDCl$_3$, 500 MHz) δ 7.40-7.37 (m, 1H), 7.07 (dd, J=11.5, 2.5 Hz, 1H), 7.0 (dd, J=8.5, 2.0 Hz, 1H), 6.66 (d, J=2.0 Hz, 1H), 6.48 (dd, J=8.5, 3.0 Hz, 1H), 6.17 (d, J=9.0 Hz, 1H), 4.37 (s, 2H), 3.75 (s, 3H), 3.21-3.17 (m, 2H), 3.09-3.03 (m, 2H), 2.55-2.45 (m, 2H), 2.11-1.98 (m, 2H).

Step C: A procedure similar to Step A of Example 13 was used to convert 5-(4-chloro-3-fluorophenyl)-8-methoxy-2,5-ethano-2,3,4,5-tetrahydro-1H-benzo[c]azepine from Step B above to 5-(4-chloro-3-fluorophenyl)-2,5-ethano-2,3,4,5-tetrahydro-1H-benzo[c]azepin-8-ol (150 mg, 80% crude) as a yellow oil: $^1$H NMR (DMSO-$d_6$, 500 MHz) δ 9.14 (s, 1H), 7.57 (dd, J=8.0, 8.0 Hz, 1H), 7.26 (d, J=11.5 Hz, 1H), 7.12 (d, J=8.0 Hz, 1H), 6.50 (d, J=2.0 Hz, 1H), 6.31 (dd, J=8.5, 2.0 Hz, 1H), 5.87 (d, J=8.5 Hz, 1H), 4.15 (s, 2H), 3.01-2.98 (m, 2H), 2.87-2.85 (m, 2H), 2.42-2.39 (m, 2H), 1.99-1.91 (m, 2H).

Step D: The procedure described in Example 32 was used to convert 5-(4-chloro-3-fluorophenyl)-2,5-ethano-2,3,4,5-tetrahydro-1H-benzo[c]azepin-8-ol from Step C above and 3-chloro-6-(trifluoromethyl)pyridazine to 5-(4-chloro-3-fluorophenyl)-2,5-ethano-8-(6-(trifluoromethyl)pyridazin-3-yloxy)-2,3,4,5-tetrahydro-1H-benzo[c]azepine, L-tartrate salt (139 mg, 46%, AUC HPLC 97.8%) as an off-white solid: $^1$H NMR (DMSO-$d_6$, 300 MHz) δ 8.29 (d, J=9.3 Hz, 1H), 7.32-7.61 (m, 2H), 7.39 (dd, J=11.7, 2.1 Hz, 1H), 7.23-7.16 (m, 2H), 6.93 (dd, J=8.4, 2.4 Hz, 1H), 6.24 (d, J=8.7 Hz, 1H), 4.43 (s, 2H), 4.15 (s, 2.2H), 3.24-3.18 (m, 2H), 3.09-3.04 (m, 2H), 2.65-2.59 (m, 2H), 2.16-2.07 (m, 2H); ESI MS m/z 464 [M+H]$^+$. Anal. Calcd. For $C_{23}H_{18}ClF_4N_3O·1.1C_4H_6O_6·0.75H_2O$: C, 51.22; H, 4.09; N, 6.54. Found: C, 51.39; H, 4.01; N, 6.56.

Example 49

Preparation of 5-(3-chlorophenyl)-2,5-ethano-8-(6-(trifluoromethyl)pyridazin-3-yloxy)-2,3,4,5-tetrahydro-1H-benzo[c]azepine, L-tartrate Salt

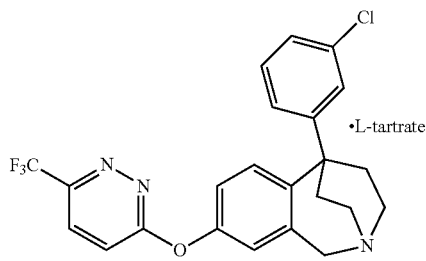 [SMILES: FC(F)(F)c1ccc(Oc2ccc3c(c2)CN2CCC3(c3cccc(Cl)c3)CC2)nn1]

Step A: To 1-bromo-3-chlorobenzene (480 mg, 2.51 mmol) in diethyl ether (10 mL), at −78° C., was added t-butyllithium (3.0 mL of a 1.7 M solution in hexanes, 5.0 mmol) dropwise. After 1 h, a solution of 1-(3-methoxybenzyl)piperidin-4-one (500 mg, 2.28 mmol) in diethyl ether (5 mL) was added dropwise. The reaction mixture was stirred at −78° C. for 0.5 h, warmed to ambient temperature and quenched with saturated ammonium chloride. The organic layer was separated, washed with brine, dried over sodium sulfate and concentrated in vacuo. Purification by silica gel chromatography (10% ethyl acetate/methylene chloride to ethyl acetate) gave 4-(3-chlorophenyl)-1-(3-methoxybenzyl)piperidin-4-ol (668 mg, 80%) as an oil: $^1$H NMR (CDCl$_3$, 300 MHz) δ 7.53-7.52 (m, 1H), 7.40-7.36 (m, 1H), 7.30-7.20 (m, 3H), 6.96-6.93 (m, 2H), 6.82-6.79 (m, 1H), 3.82 (s, 3H), 3.58 (s, 2H), 2.82-2.70 (m, 2H), 2.49-2.41 (m, 2H), 2.18-2.08 (m, 2H), 1.73-1.67 (m, 2H), 1.60 (s, 1H).

Step B: A procedure similar to Step D of Example 12 was used to convert 4-(3-chlorophenyl)-1-(3-methoxybenzyl)piperidin-4-ol from Step A above to 5-(3-chlorophenyl)-8-methoxy-2,5-ethano-2,3,4,5-tetrahydro-1H-benzo[c]azepine (575 mg, 91% crude) as an off-white solid: $^1$H NMR (CDCl$_3$, 500 MHz) δ 7.32-7.24 (m, 3H), 7.17-7.15 (m, 1H), 6.66 (d, J=2.5 Hz, 1H), 6.48 (dd, J=8.5, 3.0 Hz, 1H), 6.19 (d, J=9.0 Hz, 1H), 4.37 (s, 2H), 3.74 (s, 3H), 3.25-3.18 (m, 2H), 3.09-3.06 (m, 2H), 2.58-2.48 (m, 2H), 2.16-2.09 (m, 2H).

Step C: A procedure similar to Step A of Example 13 was used, except the reaction mixture was brought to pH=6-7, resulting in the conversion of 5-(3-chlorophenyl)-8-methoxy-2,5-ethano-2,3,4,5-tetrahydro-1H-benzo[c]azepine from Step B above to 5-(3-chlorophenyl)-2,5-ethano-2,3,4,5-tetrahydro-1H-benzo[c]azepin-8-ol (610 mg, 79% crude). This material was used directly in the next step without further purification.

Step D: The procedure described in Example 32 was used to couple 5-(3-chlorophenyl)-2,5-ethano-2,3,4,5-tetrahydro-1H-benzo[c]azepin-8-ol from Step C above and 3-chloro-6-(trifluoromethyl)pyridazine, except that after silica gel chromatography, potassium carbonate (30 mg) and methanol (10 mL) were added and the mixture was stirred for 1 h and concentrated in vacuo. The obtained material was then purified by preparative thin layer chromatography (90:9:1 dichloromethane/methanol/concentrated ammonium hydroxide) to provide 5-(3-chlorophenyl)-2,5-ethano-8-(6-(trifluoromethyl)pyridazin-3-yloxy)-2,3,4,5-tetrahydro-1H-benzo[c]azepine. A similar procedure was then continued as in Example 32 for conversion of the free base to the corresponding L-tartrate salt to give 5-(3-chlorophenyl)-2,5-ethano-8-(6-(trifluoromethyl)pyridazin-3-yloxy)-2,3,4,5-tetrahydro-1H-benzo[c]azepine, L-tartrate salt (16 mg, 5.6%, AUC HPLC 98.8%) as a white solid: $^1$H NMR (DMSO-$d_6$, 500 MHz) δ 8.28 (d, J=9.5 Hz, 1H), 7.71 (d, J=9.5 Hz, 1H), 7.48-7.30 (m, 4H), 7.17 (br s, 1H), 6.95-6.92 (m, 1H), 6.23 (d, J=8.5 Hz, 1H), 4.45 (s, 2H), 4.17 (s, 1.6H), 3.25-3.22 (m, 2H), 3.08-3.02 (m, 2H), 2.67-2.61 (m, 2H), 2.15-2.10 (m, 2H); ESI MS m/z 446 [M+H]$^+$.

Example 50

Preparation of 2,5-ethano-5-(4-(trifluoromethyl)phenyl)-8-(6-(trifluoromethyl)pyridazin-3-yloxy)-2,3,4,5-tetrahydro-1H-benzo[c]azepine, L-tartrate Salt

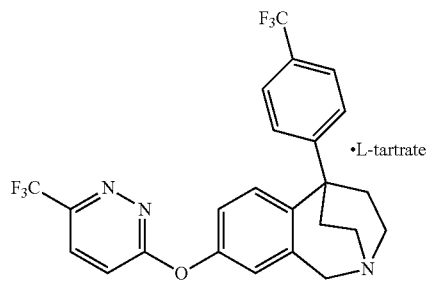 [SMILES: FC(F)(F)c1ccc(C23CCN(CC2)Cc2cc(Oc4ccc(C(F)(F)F)nn4)ccc23)cc1]

Step A: A procedure similar to Step A of Example 49 was used, except that 1-bromo-4-(trifluoromethyl)benzene was added instead, resulting in the formation of 1-(3-methoxybenzyl)-4-(4-(trifluoromethyl)phenyl)piperidin-4-ol (679 mg, 54%) as an off-white solid: $^1$H NMR (CDCl$_3$, 500 MHz) δ 7.65-7.59 (m, 4H), 7.26-7.23 (m, 1H), 6.98-6.92 (m, 2H), 6.85-6.80 (m, 1H), 3.76 (s, 3H), 3.61-3.52 (m, 2H), 2.89-2.77 (m, 2H), 2.52-2.62 (m, 2H), 2.22-2.12 (m, 2H), 1.74-1.70 (m, 2H), 1.65 (s, 1H).

Step B: A procedure similar to Step D of Example 12 was used, except the material was purified by column chromatography (methylene chloride to 90:9:1 methylene chloride/ methanol/ammonium hydroxide) to convert 1-(3-methoxybenzyl)-4-(4-(trifluoromethyl)phenyl)piperidin-4-ol from Step A above to 8-methoxy-2,5-ethano-5-(4-(trifluoromethyl)phenyl)-2,3,4,5-tetrahydro-1H-benzo[c]azepine (184 mg, 29%): $^1$H NMR (CDCl$_3$, 500 MHz) δ 7.64 (d, J=8.0 Hz, 2H), 7.39 (d, J=8.0 Hz, 2H), 6.681 (br s, 1H), 6.49-6.48 (m, 1H), 6.12 (d, J=9.0 Hz, 1H), 4.41 (s, 2H), 3.74 (s, 3H), 3.27-3.22 (m, 2H), 3.13-3.07 (m, 2H), 2.61-2.55 (m, 2H), 2.17-2.12 (m, 2H).

Step C: A procedure similar to Step A of Example 13 was used to convert 8-methoxy-2,5-ethano-5-(4-(trifluoromethyl)phenyl)-2,3,4,5-tetrahydro-1H-benzo[c]azepine from Step B above to 2,5-ethano-5-(4-(trifluoromethyl)phenyl)-2,3,4,5-tetrahydro-1H-benzo[c]azepin-8-ol (137 mg, 79% crude) as an off-white solid: $^1$H NMR (DMSO-d$_6$, 300 MHz) δ 9.45 (br s, 1H), 7.72 (d, J=8.4 Hz, 2H), 7.48 (d, J=8.1 Hz, 2H), 6.52 (d, J=2.4 Hz, 1H), 6.29 (dd, J=8.7, 2.7 Hz, 1H), 5.79 (d, J=8.4 Hz, 1H), 4.24 (s, 2H), 3.19-2.98 (m, 2H), 2.92-2.83 (m, 2H), 2.55-2.51 (m, 2H), 2.02-1.92 (m, 2H).

Step D: The procedure described in Example 32 was used to convert 2,5-ethano-5-(4-(trifluoromethyl)phenyl)-2,3,4,5-tetrahydro-1H-benzo[c]azepin-8-ol from Step C above and 3-chloro-6-(trifluoromethyl)pyridazine to 2,5-ethano-5-(4-(trifluoromethyl)phenyl)-8-(6-(trifluoromethyl)pyridazin-3-yloxy)-2,3,4,5-tetrahydro-1H-benzo[c]azepine, L-tartrate salt (132 mg, 50%, AUC HPLC >99%) as a white solid: $^1$H NMR (DMSO-d$_6$, 300 MHz) δ 8.28 (d, J=9.0 Hz, 1H), 7.79 (d, J=8.4 Hz, 2H), 7.72 (d, J=9.0 Hz, 1H), 7.57 (d, J=8.4 Hz, 2H), 7.18 (br s, 1H), 6.94-6.91 (m, 1H), 6.16 (d, J=9.0 Hz, 1H), 4.45 (s, 2H), 4.16 (s, 2H), 3.26-3.17 (m, 2H), 3.10-3.04 (m, 2H), 2.73-2.60 (m, 2H), 2.19-2.12 (m, 2H); ESI MS m/z 480 [M+H]$^+$. Anal. Calcd. For C$_{24}$H$_{19}$F$_6$N$_3$O.C$_4$H$_6$O$_6$.0.75H$_2$O: C, 52.30; H, 4.15; N, 6.53. Found: C, 52.13; H, 4.02; N, 6.46.

Example 51

Preparation of 5-(3,4-difluorophenyl)-2,5-ethano-8-(6-(trifluoromethyl)pyridazin-3-yloxy)-2,3,4,5-tetrahydro-1H-benzo[c]azepine, L-tartrate Salt

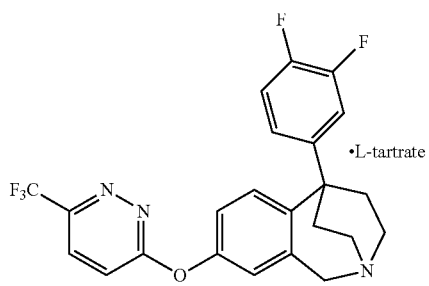 [SMILES: Fc1ccc(C23CCN(CC2)Cc2cc(Oc4ccc(C(F)(F)F)nn4)ccc23)cc1F]

Step A: A procedure similar to Step A of Example 47 was used, except that (3,4-difluorophenyl)magnesium bromide was added instead and the reaction mixture was heated to reflux, resulting in the formation of 4-(3,4-difluorophenyl)-1-(3-methoxybenzyl)piperidin-4-ol (590 mg, 77%) as a colorless oil: $^1$H NMR (CDCl$_3$, 500 MHz) δ 7.37-7.32 (m, 1H), 7.26-7.19 (m, 2H), 7.14-7.08 (m, 1H), 6.94-6.92 (m, 2H), 6.82-6.80 (m, 1H), 3.83 (s, 3H), 3.55 (s, 2H), 2.82-2.79 (m, 2H), 2.46-2.41 (m, 2H), 2.12-2.04 (m, 2H), 1.71-1.68 (m, 2H), 1.58 (s, 1H).

Step B: A procedure similar to Step D of Example 12 was used to convert 4-(3,4-difluorophenyl)-1-(3-methoxybenzyl) piperidin-4-ol from Step A above to 5-(3,4-difluorophenyl)-8-methoxy-2,5-ethano-2,3,4,5-tetrahydro-1H-benzo[c] azepine (530 mg, 91% crude) as an off-white solid: $^1$H NMR (CDCl$_3$, 300 MHz) δ 7.20-7.05 (m, 2H), 7.02-6.96 (m, 1H), 6.66 (d, J=2.7 Hz, 1H), 6.47 (dd, J=8.7, 2.7 Hz, 1H), 6.16 (d, J=8.7 Hz, 1H), 4.35 (s, 2H), 3.74 (s, 3H), 3.23-3.13 (m, 2H), 3.09-3.01 (m, 2H), 2.54-2.40 (m, 2H), 2.12-2.02 (m, 2H).

Step C: A procedure similar to Step A of Example 13 was used to convert 5-(3,4-difluorophenyl)-8-methoxy-2,5-ethano-2,3,4,5-tetrahydro-1H-benzo[c]azepine from Step B above to 5-(3,4-difluorophenyl)-2,5-ethano-2,3,4,5-tetrahydro-1H-benzo[c]azepin-8-ol (508 mg, 99% crude) as an off-white solid: $^1$H NMR (DMSO-d$_6$, 500 MHz) δ 9.21 (s, 1H), 7.44-7.38 (m, 1H), 7.29-7.24 (m, 1H), 7.10-7.07 (m, 1H), 6.63 (br s, 1H), 6.31-6.29 (m, 1H), 5.86 (d, J=8.5 Hz, 1H), 4.15 (s, 2H), 3.03-2.97 (m, 2H), 2.89-2.83 (m, 2H), 2.45-2.40 (m, 2H), 1.96-1.90 (m, 2H).

Step D: The procedure described in Example 32 was used to convert 5-(3,4-difluorophenyl)-2,5-ethano-2,3,4,5-tetrahydro-1H-benzo[c]azepin-8-ol from Step C above and 3-chloro-6-(trifluoromethyl)pyridazine to 5-(3,4-difluorophenyl)-2,5-ethano-8-(6-(trifluoromethyl)pyridazin-3-yloxy)-2,3,4,5-tetrahydro-1H-benzo[c]azepine, L-tartrate salt (115 mg, 55%, AUC HPLC 98.5%) as an off-white solid: $^1$H NMR (DMSO-d$_6$, 500 MHz) δ 8.28 (d, J=9.0 Hz, 1H), 7.71 (d, J=9.5 Hz, 1H), 7.51-7.45 (m, 1H), 7.42-7.38 (m, 1H), 7.19-7.16 (m, 2H), 6.92-6.91 (m, 1H), 6.23 (d, J=8.5 Hz, 1H), 4.43 (s, 2H), 4.16 (s, 2.2H), 3.23-3.17 (m, 2H), 3.07-3.03 (m, 2H), 2.63-2.60 (m, 2H), 2.14-2.07 (m, 2H); ESI MS m/z 448 [M+H]$^+$. Anal. Calcd. For C$_{23}$H$_{18}$F$_5$N$_3$O.1.1C$_4$H$_6$O$_6$.0.75H$_2$O: C, 52.57; H, 4.20; N, 6.71. Found: C, 52.66; H, 4.16; N, 6.48.

Example 52

Preparation of 5-(4-fluorophenyl)-2,5-ethano-8-(6-(trifluoromethyl)pyridazin-3-yloxy)-2,3,4,5-tetrahydro-1H-benzo[c]azepine, L-tartrate Salt

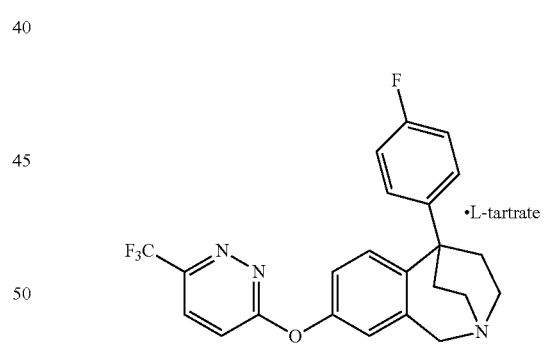

Step A: A procedure similar to Step A of Example 47 was used, except that (4-fluorophenyl)magnesium bromide was added instead and the reaction mixture was heated to reflux, resulting in the formation of 4-(4-fluorophenyl)-1-(3-methoxybenzyl)piperidin-4-ol (560 mg, 78%) as a colorless oil: $^1$H NMR (CDCl$_3$, 300 MHz) δ 7.50-7.45 (m, 2H), 7.27-7.21 (m, 1H), 7.05-6.92 (m, 4H), 6.82-6.79 (m, 1H), 3.82 (s, 3H), 3.49 (s, 2H), 2.81-2.77 (m, 2H), 2.50-2.40 (m, 2H), 2.18-2.08 (m, 2H), 1.74-1.69 (m, 2H), 1.57 (br s, 1H).

Step B: A procedure similar to Step D of Example 12 was used to convert 4-(4-fluorophenyl)-1-(3-methoxybenzyl)piperidin-4-ol from Step A above to 5-(4-fluorophenyl)-8-methoxy-2,5-ethano-2,3,4,5-tetrahydro-1H-benzo[c]azepine (465 mg, 88% crude) as an off-white solid: $^1$H NMR (CDCl$_3$, 500 MHz) δ 7.26-7.22 (m, 2H), 7.03-7.03 (m, 2H), 6.66 (d, J=2.5 Hz, 1H), 6.46 (dd, J=8.5, 2.5 Hz, 1H), 6.15 (d, J=8.5 Hz, 1H), 4.36 (s, 2H), 3.75 (s, 3H), 3.21-3.15 (m, 2H), 3.02-3.02 (m, 2H), 2.55-2.49 (m, 2H), 2.12-2.07 (m, 2H).

Step C: A procedure similar to Step A of Example 13 was used to convert 5-(4-fluorophenyl)-8-methoxy-2,5-ethano-2,3,4,5-tetrahydro-1H-benzo[c]azepine from Step B above to 5-(4-fluorophenyl)-2,5-ethano-2,3,4,5-tetrahydro-1H-benzo[c]azepin-8-ol (359 mg, 81% crude) as an off-white solid: $^1$H NMR (DMSO-$d_6$, 500 MHz) δ 9.10 (s, 1H), 7.29-7.26 (m, 2H), 7.20-7.26 (m, 2H), 6.49 (br s, 1H), 6.27 (dd, J=8.5, 2.0 Hz, 1H), 5.85 (d, J=8.5 Hz, 1H), 4.16 (s, 2H), 3.02-2.98 (m, 2H), 2.87-2.83 (m, 2H), 2.45-2.42 (m, 2H), 1.97-1.93 (m, 2H).

Step D: The procedure described in Example 32 was used to convert 5-(4-fluorophenyl)-2,5-ethano-2,3,4,5-tetrahydro-1H-benzo[c]azepin-8-ol from Step C above and 3-chloro-6-(trifluoromethyl)pyridazine to 5-(4-fluorophenyl)-2,5-ethano-8-(6-(trifluoromethyl)pyridazin-3-yloxy)-2,3,4,5-tetrahydro-1H-benzo[c]azepine, L-tartrate salt (164 mg, 79%, AUC HPLC 98.4%) as an off-white solid: $^1$H NMR (DMSO-$d_6$, 500 MHz) δ 8.28 (d, J=9.0 Hz, 1H), 7.71 (d, J=9.5 Hz, 1H), 7.39-7.35 (m, 2H), 7.27-7.23 (m, 2H), 7.16 (d, J=2.5 Hz, 1H), 6.92 (dd, J=8.5, 2.5 Hz, 1H), 6.21 (d, J=9.0 Hz, 1H), 4.46 (s, 2H), 4.14 (s, 2H), 3.26-3.20 (m, 2H), 3.10-3.04 (m, 2H), 2.66-2.60 (m, 2H), 2.17-2.07 (m, 2H); ESI MS m/z 430 [M+H]$^+$. Anal. Calcd. For $C_{23}H_{19}F_4N_3O \cdot C_4H_6O_6 \cdot 0.75H_2O$: C, 54.69; H, 4.50; N, 7.09. Found: C, 54.82; H, 4.45; N, 6.97.

Example 53

Preparation of 5-(3-chloro-4-fluorophenyl)-2,5-ethano-8-(6-(trifluoromethyl)pyridazin-3-yl)-2,3,4,5-tetrahydro-1H-benzo[c]azepine, L-Tartrate Salt

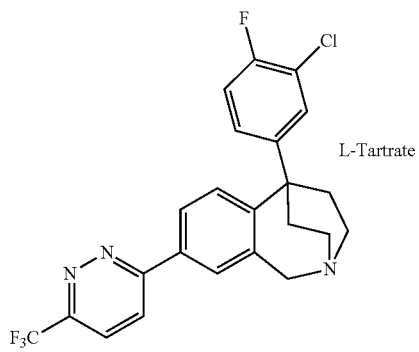 [SMILES: Fc1ccc(C23CCN(CC2)Cc2cc(-c4ccc(C(F)(F)F)nn4)ccc23)cc1Cl]

Step A: A mixture of bis(pinacolato)diboron (388 mg, 1.592 mmol), potassium acetate (346 mg, 3.53 mmol) and 5-(3-chloro-4-fluorophenyl)-2,5-ethano-2,3,4,5-tetrahydro-1H-benzo[c]azepin-8-yl trifluoromethanesulfonate (529 mg, 1.176 mmol), which was prepared using a similar procedure described in step A of Example 14, in DMF (5.5 mL) was purged with nitrogen for 5 minutes. 1,1'-bis(diphenylphosphino)ferrocene dichloropalladium (96 mg, 0.118 mmol) was added and the mixture was purged again with nitrogen and was heated at 80° C. for 2 hours. After the completion of reaction, as monitored by LC-MS, 3-chloro-6-(trifluoromethyl)pyridazine (231 mg, 1.268 mmol), cesium carbonate (1.127 g, 3.46 mmol), and water (2 mL) were sequentially added. The reaction mixture was purged with nitrogen and then [1,1'-bis(diphenylphosphino)ferrocene]palladium(II) dichloromethane adduct (94 mg, 0.115 mmol) was added. The mixture was degassed again and heated to 90° C. for 3 hours. The reaction mixture was diluted with water (25 mL) and extracted with ethyl acetate (2×25 mL). The combined organics were washed with water (2×20 mL), brine (20 mL), dried over sodium sulfate, filtered, and concentrated in vacuo. The residue was purified by column chromatography (methylene chloride to 90:9:1 methylene chloride/methanol/ammonium hydroxide) to afford 5-(3-chloro-4-fluorophenyl)-2,5-ethano-8-(6-(trifluoromethyl)pyridazin-3-yl)-2,3,4,5-tetrahydro-1H-benzo[c]azepine (129 mg, 25%) as a brownish solid (AUC HPLC >95%).

Step B: The product from Step A (129 mg, 0.288 mmol) acetonitrile (2 mL) was added L-tartaric acid (43 mg, 0.288 mmol) in water (10 mL). The resultant solution was lyophilized for 48 hours to give 5-(3-chloro-4-fluorophenyl)-2,5-ethano-8-(6-(trifluoromethyl)pyridazin-3-yl)-2,3,4,5-tetrahydro-1H-benzo[c]azepine, L-tartrate salt (169 mg, 98%, AUC HPLC: 95.7%) as an off-white solid: $^1$H NMR (400 MHz, CD$_3$OD) δ=8.39 (d, J=8.8 Hz, 1H), 8.21-8.17 (m, 2H), 7.97-7.94 (m, 1H), 7.54 (d, J=7.2 Hz, 1H), 7.39-7.37 (m, 2H), 6.63 (d, J=8.4 Hz, 1H), 5.03 (s, 2H), 4.47 (s, 2H), 3.72 (m, 2H), 3.50-3.49 (m, 2H), 2.85 (m, 2H), 2.53-2.49 (m, 2H); ESI MS (m/z): 448 [M$^+$+1].

Example 54

Preparation of 8-([1,2,4]triazolo[1,5-a]pyridin-6-yl)-5-(3-chloro-4-fluorophenyl)-2,5-ethano-2,3,4,5-tetrahydro-1H-benzo[c]azepine, L-Tartrate Salt

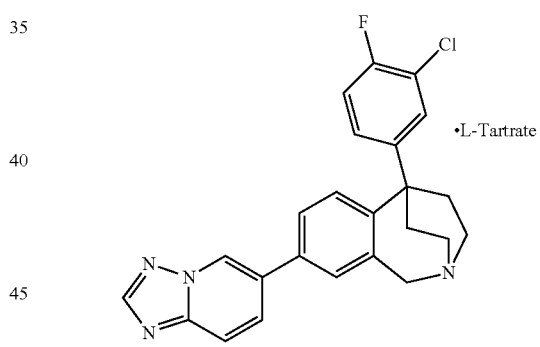

Step A: A mixture of bis(pinacolato)diboron (388 mg, 1.592 mmol), potassium acetate (346 mg, 3.53 mmol) and 5-(3-chloro-4-fluorophenyl)-2,5-ethano-2,3,4,5-tetrahydro-1H-benzo[c]azepin-8-yl trifluoromethanesulfonate from Step A of Example 53 (529 mg, 1.176 mmol) in DMF (5.5 mL) was purged with nitrogen for 5 minutes. 1,1'-bis(diphenylphosphino)ferrocene dichloropalladium (96 mg, 0.118 mmol) was added and the mixture was purged again with nitrogen. The reaction mixture was heated at 80° C. for 2 hours. After the completion of reaction, as monitored by LC-MS, 6-bromo-[1,2,4]triazolo[1,5-a]pyridine (251 mg, 1.268 mmol), cesium carbonate (1.127 g, 3.46 mmol), and water (2 mL) were sequentially added. The reaction mixture was purged with nitrogen and then [1,1'-bis(diphenylphosphino)ferrocene]palladium(II) dichloromethane adduct (94 mg, 0.115 mmol) was added. The mixture was degassed again and heated to 90° C. for 3 hours. The reaction mixture was diluted with water (25 mL) and extracted with ethyl acetate (2×25 mL). The combined organics were washed with water (2×20 mL), brine (20 mL), dried over sodium sulfate, filtered, and concentrated in vacuo. The residue was purified by column chromatography (methylene chloride to 90:9:1 methylene chloride/methanol/ammonium hydroxide) to afford 8-([1,2,4]triazolo[1,5-a]pyridin-6-yl)-5-(3-chloro-4-fluorophenyl)-2,5-ethano-2,3,4,5-tetrahydro-1H-benzo[c]azepine (100 mg, 21%) as a brownish solid (AUC HPLC >95%).

Step B: The product from Step A (100 mg, 0.239 mmol) in acetonitrile (2 mL) was added L-tartaric acid (36 mg, 0.239 mmol) in water (10 mL). The resultant solution was lyophilized for 48 hours to give 8-([1,2,4]triazolo[1,5-a]pyridin-6-yl)-5-(3-chloro-4-fluorophenyl)-2,5-ethano-2,3,4,5-tetrahydro-1H-benzo[c]azepine, L-tartrate salt (133 mg, 98%, AUC HPLC: 95.7%) as an off-white solid: $^1$H NMR (400 MHz, CD$_3$OD) δ=9.12 (s, 1H), 8.46 (d, J=5.2 1H), 8.03 (d, J=8 1H), 7.87 (d, J=8 Hz, 1H), 7.80 (m, 3H), 7.38 (d, J=6.8 Hz, 2H), 6.63-6.56 (m, 1H), 5.54-4.85 (m, 2H), 4.49 (s, 2H), 3.94-3.77 (m, 2H), 3.72-3.32 (m, 2H), 2.84 (m, 2H) 1.65-1.31 (m, 2H); ESI MS (m/z): 419 [M$^+$+1].

Example 55

Preparation of (+)- and (−)-8-([1,2,4]triazolo[1,5-a]pyridin-6-yl)-5-(3-chloro-4-fluorophenyl)-2,5-methano-2,3,4,5-tetrahydro-1H-benzo[c]azepine, L-Tartrate Salts

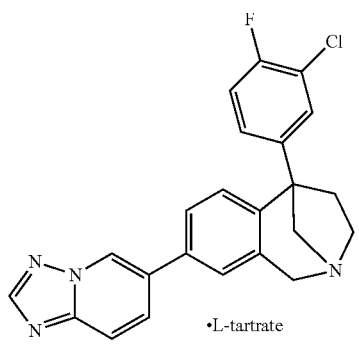 [SMILES: Fc1ccc(C23CCN(Cc4cc(-c5ccc6ncnn6c5)ccc42)C3)cc1Cl]

Step A: A mixture of bis(pinacolato)diboron (606 mg, 2.386 mmol), potassium acetate (540 mg, 5.51 mmol), and 5-(3-chloro-4-fluorophenyl)-2,5-methano-2,3,4,5-tetrahydro-1H-benzo[c]azepin-8-yl trifluoromethanesulfonate (800 mg, 1.836 mmol), which was prepared using a similar procedure described in Step A of Example 3, in DMF (16 mL), was purged with nitrogen for 5 minutes. 1,1'-bis(diphenylphosphino)ferrocene dichloropalladium (150 mg, 0.184 mmol) was added and the mixture was purged again with nitrogen. The reaction mixture was heated at 80° C. for 2 hours. After the completion of reaction, as monitored by LC-MS, 6-bromo-[1,2,4]triazolo[1,5-a]pyridine (388 mg, 1.96 mmol), cesium carbonate (1.74 g, 5.34 mmol), and water (3 mL) were sequentially added. The reaction mixture was purged with nitrogen and then [1,1'-bis(diphenylphosphino)ferrocene]palladium(II) dichloromethane adduct (145 mg, 0.178 mmol) was added. The mixture was degassed again and heated to 90° C. for 3 hours. The reaction mixture was diluted with water (25 mL) and extracted with ethyl acetate (2×25 mL). The combined organics were washed with water (2×20 mL), brine (20 mL), dried over sodium sulfate, filtered, and concentrated in vacuo. The residue was purified by column chromatography (methylene chloride to 90:9:1 methylene chloride/methanol/ammonium hydroxide) to afford the racemic mixture of 8-([1,2,4]triazolo[1,5-a]pyridin-6-yl)-5-(3-chloro-4-fluorophenyl)-2,5-methano-2,3,4,5-tetrahydro-1H-benzo[c]azepine (216 mg, 30%) as a brownish solid: ESI MS (m/z): 405 [M+H]$^+$.

Step B: The above product (216 mg) was resolved by preparative chiral HPLC (Chiralpak AD-H column, using 50:50:0.2 hexane/ethanol/diethylamine as the eluent) to give the (+)-enantiomer [90 mg, [α]$^{25}_D$+22.7° (c 0.11, methanol)] and the (−)-enantiomer [90 mg, [α]$^{25}_D$-27.7° (c 0.094, methanol)].

Step C: To a solution of the above (+)-enantiomer (90 mg, 0.22 mmol) in acetonitrile (5 mL), was added L-tartaric acid (33 mg, 0.22 mmol) followed by water (15 mL). The solution was then frozen and lyophilized for 48 hours to provide (+)-8-([1,2,4]triazolo[1,5-a]pyridin-6-yl)-5-(3-chloro-4-fluorophenyl)-2,5-methano-2,3,4,5-tetrahydro-1H-benzo[c]azepine, L-tartrate salt (120 mg, 97%, AUC HPLC >98.43%) as a white solid: $^1$H NMR (400 MHz, CD$_3$OD) δ=9.10 (s, 1H), 8.47 (s, 1H), 8.03-8.00 (m, 1H), 7.89-7.87 (d, J=9.2 1H), 7.68-7.39 (m, 4H), 6.81-6.79 (d, J=8.0 Hz, 1H), 5.05 (m, 1H), 4.68 (m, 1H), 4.49 (s, 2H), 4.30 (m, 1H), 4.08 (m, 1H), 3.72-3.62 (m, 2H), 2.87 (m, 1H), 2.74 (m, 1H); ESI MS (m/z): 405 [M+H]$^+$.

Step D: To a solution of the above (−)-enantiomer (90 mg, 0.22 mmol) in acetonitrile (5.0 mL) was added L-tartaric acid (33 mg, 0.22 mmol) followed by water (15.0 mL). The solution was then frozen and lyophilized for 48 hours to provide 8-([1,2,4]triazolo[1,5-a]pyridin-6-yl)-5-(3-chloro-4-fluorophenyl)-2,5-methano-2,3,4,5-tetrahydro-1H-benzo[c]azepine, L-tartrate salt (120 mg, 97%, AUC HPLC >95%) as a white solid: $^1$H NMR (400 MHz, CD$_3$OD) δ=9.09 (s, 1H), 8.47 (s, 1H), 8.03-8.00 (m, 1H), 7.88-7.87 (d, J=9.2 1H), 7.68-7.38 (m, 5H), 6.79-6.78 (d, J=8.0 Hz, 1H), 5.04 (m, 1H), 4.69 (m, 1H), 4.49 (s, 2H), 4.27 (m, 1H), 4.09 (m, 1H), 3.69-3.63 (m, 2H), 2.86-2.75 (m, 2H); ESI MS (m/z); ESI MS (m/z): 405 [M+H]$^+$.

Example 56

Preparation of (+)- and (−)-5-(3-chloro-4-fluorophenyl)-2,5-methano-8-(6-(trifluoromethyl)pyridazin-3-yl)-2,3,4,5-tetrahydro-1H-benzo[c]azepine, L-Tartrate Salt

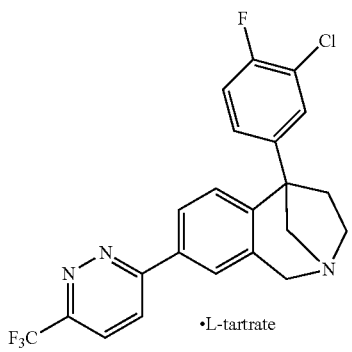 [SMILES: Fc1ccc(C23CCN(Cc4cc(-c5ccc(C(F)(F)F)nn5)ccc42)C3)cc1Cl]

Step A: A mixture of bis(pinacolato)diboron (606 mg, 2.386 mmol), potassium acetate (540 mg, 5.51 mmol) and 5-(3-chloro-4-fluorophenyl)-2,5-methano-2,3,4,5-tetrahydro-1H-benzo[c]azepin-8-yl trifluoromethanesulfonate (800 mg, 1.836 mmol) from Step A of Example 55 in DMF (16 mL), was purged with nitrogen for 5 minutes. 1,1'-bis(diphenylphosphino)ferrocene dichloropalladium (150 mg, 0.184 mmol) was added and the mixture was purged again with nitrogen. The reaction mixture was heated at 80° C. for 2 hours. After the completion of reaction, as monitored by LC-MS, 3-chloro-6-(trifluoromethyl)pyridazine (358 mg, 1.96 mmol), cesium carbonate (1.74 g, 5.34 mmol), and water (3 mL) were sequentially added. The reaction mixture was purged with nitrogen and then [1,1'-bis(diphenylphosphino)ferrocene]palladium(II) dichloromethane adduct (145 mg, 0.178 mmol) was added. The mixture was degassed again and heated to 90° C. for 3 hours. The reaction mixture was diluted with water (25 mL) and extracted with ethyl acetate (2×25 mL). The combined organics were washed with water (2×20 mL), brine (20 mL), dried over sodium sulfate, filtered, and concentrated in vacuo. The residue was purified by column chromatography (methylene chloride to 90:9:1 methylene chloride/methanol/ammonium hydroxide) to afford the racemic 5-(3-chloro-4-fluorophenyl)-2,5-methano-8-(6-(trifluoromethyl)pyridazin-3-yl)-2,3,4,5-tetrahydro-1H-benzo[c]azepine (270 mg, 35%) as a brownish solid: ESI MS (m/z): 434 [M+H]$^+$.

Step B: The above racemic mixture (216 mg) was resolved by preparative chiral HPLC (Chiralpak AD-H column, using 50:50:0.2 hexane/ethanol/diethylamine as the eluent) to give the (+)-enantiomer [90 mg, $[\alpha]^{25}_D$+36.71° (c 0.128, methanol)] and the (–)-enantiomer [90 mg, $[\alpha]^{25}_D$−39.00° (c 0.10, methanol)].

Step C: To a solution of the above (+)-enantiomer (120 mg, 0.277 mmol) in acetonitrile (5 mL), was added L-tartaric acid (42 mg, 0.277 mmol) followed by water (15 mL). The solution was then frozen and lyophilized for 48 hours to provide (+)-5-(3-chloro-4-fluorophenyl)-2,5-methano-8-(6-(trifluoromethyl)pyridazin-3-yl)-2,3,4,5-tetrahydro-1H-benzo[c]azepine, L-tartrate salt (158 mg, 98%, AUC HPLC >97%) as a white solid: $^1$H NMR (400 MHz, CD$_3$OD) δ=8.34 (d, J=8.8, 1H), 8.19-8.14 (m, 2H), 7.99-7.97 (m, 1H), 7.63-7.37 (m, 3H), 6.84 (d, J=8, 1H), 5.00 (d, J=14.4.0 Hz, 1H), 4.61 (d, J=16.8 1H), 4.47 (s, 2H), 4.21 (d, J=10.8, 2 H), 3.98 (m, 1H), 3.61-3.43 (m, 2H), 2.83-2.69 (m, 2H); ESI MS (m/z): 434 [M+H]$^+$.

Step D: To a solution of the above (–)-enantiomer (120 mg, 0.277 mmol) in acetonitrile (5.0 mL) was added L-tartaric acid (42 mg, 0.277 mmol) followed by water (15.0 mL). The solution was then frozen and lyophilized for 48 hours to provide (–)-5-(3-chloro-4-fluorophenyl)-2,5-methano-8-(6-(trifluoromethyl)pyridazin-3-yl)-2,3,4,5-tetrahydro-1H-benzo[c]azepine, L-tartrate salt (120 mg, 74%, AUC HPLC >95%) as a white solid: $^1$H NMR (400 MHz, CD$_3$OD) δ=8.38 (d, J=9.2, 1H), 8.19-8.14 (m, 2H), 7.99-7.97 (m, 1H), 7.63-7.39 (m, 3H), 6.84 (d, J=8.4, 1H), 5.00 (d, J=16.40 Hz, 1H), 4.612 (d J=16 Hz, 1H), 4.46 (s, 2H), 4.23-4.20 (m, 1H), 4.02-3.97 (m, 1H) 3.59-3.49 (m, 2H), 2.86-2.71 (m, 2H); ESI MS (m/z): 434 [M+H]$^+$.

Example 57

Preparation of 2-(5-(3-chloro-4-fluorophenyl)-1,3,4,5-tetrahydro-2,5-ethanobenzo[c]azepin-8-yl)-N-methylpyrimidine-5-carboxamide

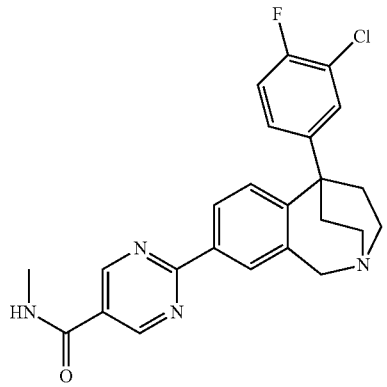 [SMILES: CNC(=O)c1cnc(-c2ccc3c(c2)CN2CCC3(c3ccc(F)c(Cl)c3)CC2)nc1]

Step A: A mixture of bis(pinacolato)diboron (388 mg, 1.592 mmol), potassium acetate (346 mg, 3.53 mmol), and 5-(3-chloro-4-fluorophenyl)-2,5-ethano-2,3,4,5-tetrahydro-1H-benzo[c]azepin-8-yl trifluoromethanesulfonate from Step A of Example 53 (529 mg, 1.176 mmol) in DMF (5.5 mL) was purged with nitrogen for 5 minutes. 1,1'-bis(diphenylphosphino)ferrocene dichloropalladium (96 mg, 0.118 mmol) was added and the mixture was purged again with nitrogen and was heated at 80° C. for 2 hours. The crude reaction mixture was diluted with water (25 mL) and extracted with ethyl acetate (2×25 mL). The combined organics were washed with water (2×20 mL), brine (20 mL), dried over sodium sulfate, filtered, and concentrated in vacuo. The crude boronate ester (90% purity) was taken for the next step.

Step B: A mixture of 2-chloro-N-methylpyrimidine-5-carboxamide (93 mg, 0.54 mmol), boronate ester step-A (220 mg, 0.514 mmol), cesium carbonate (503 mg, 1.54 mmol), DMF (2 ml), and water (0.2 mL) was purged with nitrogen and then [1,1'-bis(diphenylphosphino)ferrocene]palladium (II) dichloromethane adduct (34 mg, 0.054 mmol) was added. The mixture was degassed again and heated to 90° C. for 3 hours. The reaction mixture was diluted with water (10 mL) and extracted with ethyl acetate (2×10 mL). The combined organics were washed with water (2×10 mL), brine (10 mL), dried over sodium sulfate, filtered, and concentrated in vacuo. The residue was ISCO purified (methylene chloride to 90:9:1 methylene chloride/methanol/ammonium hydroxide) to afford 2-(5-(3-chloro-4-fluorophenyl)-1,3,4,5-tetrahydro-2,5-ethanobenzo[c]azepin-8-yl)-N-methylpyrimidine-5carboxamide (45 mg, 50% HPLC purity) as a brownish solid. This compound was further purified by prep-HPLC to give a white solid (HPLC purity is 94.5%). $^1$H NMR (400 MHz, CD$_3$OD): δ 9.18 (s, 2H), 8.34 (s, 1H), 8.10 (q, J=8.4 Hz, 1H), 7.46 (m, 1H), 7.33 (m, 2H), 6.44 (d, J=8.0 Hz, 1H), 4.56 (s, 2H), 3.28-3.10 (m, 4H), 2.98 (s, 3H), 2.68 (m, 2H), 2.25 (m, 2H). ESI MS (m/z): 437 [M$^+$+1].

Example 58

Preparation of 6-(5-(3-chloro-4-fluorophenyl)-1,3,4, 5-tetrahydro-2,5-ethanobenzo[c]azepin-8-yl)-N-methylpyridazine-3-carboxamide, L-Tartrate

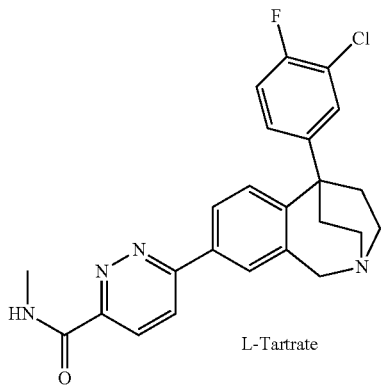 [SMILES: CNC(=O)c1ccc(-c2ccc3c(c2)CN2CCC3(c3ccc(F)c(Cl)c3)CC2)nn1]

L-Tartrate

Step A: A mixture of bis(pinacolato)diboron (388 mg, 1.592 mmol), potassium acetate (346 mg, 3.53 mmol), and 5-(3-chloro-4-fluorophenyl)-2,5-ethano-2,3,4,5-tetrahydro-1H-benzo[c]azepin-8-yl trifluoromethanesulfonate from Step A of Example 53 (529 mg, 1.176 mmol) in DMF (5.5 mL) was purged with nitrogen for 5 minutes. 1,1'-bis(diphenylphosphino)ferrocene dichloropalladium (96 mg, 0.118 mmol) was added and the mixture was purged again with nitrogen and was heated at 80° C. for 2 hours. The crude reaction mixture was diluted with water (25 mL) and extracted with ethyl acetate (2×25 mL). The combined organics were washed with water (2×20 mL), brine (20 mL), dried over sodium sulfate, filtered, and concentrated in vacuo. The crude boronate ester (90% purity) was taken for the next step.

Step B: A mixture of 6-chloro-N-methylpyridazine-3-carboxamide (93 mg, 0.54 mmol), boronate ester step-1 (220 mg, 0.514 mmol), cesium carbonate (503 mg, 1.54 mmol), DMF (2 ml), and water (0.2 mL) was purged with nitrogen and then [1,1'-bis(diphenylphosphino)ferrocene]palladium (II) dichloromethane adduct (34 mg, 0.054 mmol) was added. The mixture was degassed again and heated to 90° C. for 3 hours. The reaction mixture was diluted with water (10 mL) and extracted with ethyl acetate (2×10 mL). The combined organics were washed with water (2×10 mL), brine (10 mL), dried over sodium sulfate, filtered, and concentrated in vacuo. The residue was ISCO purified (methylene chloride to 90:9:1 methylene chloride/methanol/ammonium hydroxide) to afford BBRC-17178 (50 mg, HPLC purity is 65%) as a brownish solid. This material was further purified by preparative HPLC to afford 6-(5-(3-chloro-4-fluorophenyl)-1,3,4,5-tetrahydro-2,5-ethanobenzo[c]azepin-8-yl)-N-methylpyridazine-3-carboxamide (19 mg).

Step C: To the product from Step B (19 mg, 43 mmol) acetonitrile (0.5 mL) was added L-tartaric acid (6.5 mg, 43 mmol) in water (2 mL). The resultant solution was lyophilized for 48 hours to give 6-(5-(3-chloro-4-fluorophenyl)-1,3,4,5-tetrahydro-2,5-ethanobenzo[c]azepin-8-yl)-N-methylpyridazine-3-carboxamide, L-tartrate salt (22 mg, 98%, HPLC: 98.8%) as an off-white solid: $^1$H NMR (400 MHz, CD$_3$OD): δ 8.32 (m, 2H), 8.16 (s, 1H), 7.91 (d, J=8.0 Hz, 1H), 7.53 (d, J=7.2 Hz, 1H), 7.37 (m, 2H), 6.62 (d, J=8.4 Hz, 1H), 4.95 (m, 2H), 4.46 (s, 2H), 3.65-3.34 (m, 4H), 3.06 (s, 3H), 2.84 (m, 2H), 2.50 (m, 2H). ESI MS (m/z): 437 [M'+1].

Example 59

Primary Binding Assay

Preparation of Membranes

Recombinant HEK-293 cells expressing either the hSERT, hDAT, or hNET proteins were harvested from T-175 flasks as follows. The medium was removed from the flasks and the cells rinsed with HBSS without Ca and without Mg. The cells were then incubated for 5-10 minutes in 10 mM Tris-Cl, pH 7.5, 5 mM EDTA before the cells were lifted with a combination of pipetting and scraping, as needed. The cell suspension was collected into centrifuge bottles and homogenized for 30 seconds with a Polytron homogenizer. The suspension was centrifuged for 30 minutes at 32,000×g, 4° C. The supernatant was decanted and the pellet resuspended and homogenized in 50 mM Tris-Cl, pH 7.5, 1 mM EDTA for 10 seconds. The suspension was then centrifuged again for 30 minutes at 32,000×g, 4° C. The supernatant was decanted and the pellet resuspended in 50 mM Tris-Cl, pH 7.5, 1 mM EDTA and briefly homogenized. A Bradford assay (Bio-rad) was performed and the membrane preparation diluted to 2 mg/ml with 50 mM Tris-Cl, pH 7.5, 1 mM EDTA. Aliquots were prepared, and then frozen and stored at −80° C.

SERT Radioligand Binding Assay

Compounds were dissolved in 100% DMSO at a concentration 100 times the desired highest assay concentration, serially diluted 1:3 in 100% DMSO, and 0.4 μl/well of each solution was dispensed to a Nunc polypropylene, round bottom, 384-well plate. 100% inhibition is defined with 0.4 μl/well of 1 mM fluoxetine dissolved in DMSO. 20 μl/well of a 2× membrane preparation (15 μg/ml in 50 mM Tris-Cl, pH 7.5, 120 mM NaCl, 5 mM KCl) and 20 μl/well of a 2× radioligand solution (520 pM [$^{125}$I]RTI-55 in 50 mM Tris-Cl, pH 7.5, 120 mM NaCl, 5 mM KCl) were added to each well and the reaction incubated for 1 hour at room temperature. The contents of the assay plate were then transferred to a Millipore Multiscreen$_{HTS}$ GF/B filter plate which was pretreated with 0.5% PEI for at least one hour. The plate was vacuum filtered and washed with 7 washes of 100 μA/well 50 mM Tris-Cl, pH 7.5, 120 mM NaCl, 5 mM KCl chilled to 4° C. The filtration and washing were completed in less than 90 seconds. The plates were air-dried overnight, 12 μl/well of MicroScint scintillation fluid added, and the plates counted in a Trilux.

DAT Radioligand Binding Assay

Compounds were dissolved in 100% DMSO at a concentration 100 times the desired highest assay concentration, serially diluted 1:3 in 100% DMSO, and 0.4 μl/well of each solution was dispensed to a Nunc polypropylene, round bottom, 384-well plate. 100% inhibition is defined with 0.4 μl/well of 1 mM GBR-12935 dissolved in DMSO. 20 ul/well of a 2× membrane preparation (12.5 μg/ml in 30 mM sodium phosphate buffer, pH 7.9 at 4° C.) and 20 μl/well of a 2× radioligand solution (250 pM [$^{125}$I]RTI-55 in 30 mM sodium phosphate buffer, pH 7.9 at 4° C.) were added to the well and the reaction incubated for 1 hour at room temperature. The contents of the assay plate were then transferred to a Millipore Multiscreen$_{HTS}$ GF/B filter plate which was pretreated with 0.5% PEI for at least one hour. The plate was vacuum-filtered and washed with 7 washes of 100 μl/well 50 mM Tris-Cl, pH 7.5, 120 mM NaCl, 5 mM KCl chilled to 4° C. The filtration and washing were completed in less than 90 seconds. The plates were air-dried overnight, 12 μl/well of MicroScint scintillation fluid added, and the plates counted in a Trilux.
NET Radioligand Binding Assay Compounds were dissolved in 100% DMSO at a concentration 100 times the desired highest assay concentration, serially diluted 1:3 in 100% DMSO, and 1.0 μl/well of each solution was dispensed to a Nunc polypropylene, round bottom, 384-well plate. 100% inhibition is defined with 1.0 μl/well of 10 mM desipramine dissolved in DMSO. 50 μl/well of a 2× membrane preparation (0.4 mg/ml in 50 mM Tris-Cl, pH 7.5, 120 mM NaCl, 5 mM KCl) and 50 μl/well of a 2× radioligand solution (4 nM [$^3$H]nisoxetine in 50 mM Tris-Cl, pH 7.5, 120 mM NaCl, 5 mM KCl) were added to the well and the reaction incubated for 1 hour at room temperature. The contents of the assay plate were then transferred to a Millipore Multiscreen$_{HTS}$ GF/B filter plate which was pretreated with 0.5% PEI for at least one hour. The plate was vacuum filtered and washed with 7 washes of 100 μl/well 50 mM Tris-Cl, pH 7.5, 120 mM NaCl, 5 mM KCl chilled to 4° C. The filtration and washing were completed in less than 90 seconds. The plates were air-dried overnight, 12 μl/well of MicroScint scintillation fluid added, and the plates counted in a Trilux.
Data Analysis The raw data was normalized to percent inhibition using control wells defining 0% (DMSO only) and 100% (selective inhibitor) inhibition which were run on each plate. Each plate was run in triplicate, and the concentration response curve thus generated was fit using the four-parameter dose response equation, Y=Bottom+(Top-Bottom)/(1+10^((Log IC$_{50}$-X) *HillSlope)) in order to determine the IC$_{50}$ value for each compound. The radioligand concentration chosen for each assay corresponds to the K$_d$ concentration determined through saturation binding analysis for each assay.

Example 60

Occupancy Assay

The general procedure for brain tissue collection and transporter occupancy assessment is briefly described as follows. Mice were sacrificed by asphyxiation in CO$_2$, rats by decapitation and dogs by IV injection of euthanasia solution. For mice and rats, after the brains were removed from the skull, the forebrain tissue (removal of the brainstem and cerebellum) was used for SERT, NET, and DAT occupancy assessment. In dogs, the striatum was dissected for DAT occupancy and the remaining forebrain tissue (without the striatum, brainstem, and cerebellum) was used for SERT and NET occupancy assessment. The brain tissues were frozen in chilled isopentane and stored at −80° C. until homogenization.

The brain tissues were thawed and then homogenized using a polytron homogenizer (Kinematica). Sample aliquots were frozen immediately and stored at −80° C. Protein content was measured for each sample using a Coomassie protein assay kit (Pierce).

On the day of ex vivo binding for occupancy assessment, frozen sample aliquots were thawed and needle homogenized, and 100 μg of the tissue was incubated for SERT, NET, and DAT binding under assay conditions summarized in Table 1. After incubation, the reactions were terminated by the addition of ice-cold assay buffer and rapid filtration through a Brandel Cell Harvester using FPXLR-196 filters. The filters were washed twice with ice-cold incubation buffer, punched into a clear plate prior to the addition of 200 ul scintillation fluid per well. Radioligand was measured using a Wallac Microbeta liquid scintillation counter.

TABLE 1

Ex Vivo Binding Assay Conditions for Serotonin, Norepinephrine and Dopamine Transporter Occupancy.

| Transporter | Radioligand | Non-Specific Drug (μM) | Buffer (nM) | Incubation Time and Temperature |
|---|---|---|---|---|
| SERT | 2 nM [$^3$H]Citalopram | Fluoxetine, 10 | Tris, 50 NaCl, 120 KCl, 5 | 10 minutes at 4° C. |
| DAT | 0.1 nM [$^{125}$I]RTI-55 (+0.5 μM) citalopram) | GBR-12935, 10 | Sodium phosphate buffer, 30 | 10 minutes at 4° C. |
| NET | 5 nM [$^3$H]-Nisoxetine | Reboxetine, 10 | Tris, 50 NaCl, 300 KCl, 5 | 20 minutes at 4° C. |

The specific binding was calculated by subtracting the value of the non-specific binding from that of the total binding in each sample. The percent occupancy was calculated as (1−specific binding in drug treated/specific binding in vehicle treated)×100%. For estimation of in vivo occupancy EC$_{50}$ (total plasma concentration of compound producing 50% occupancy), plots of occupancy values versus plasma concentrations were fitted to a one-site binding model using nonlinear regression according to the following equation: % Occupancy=Emax*C/(EC$_{50}$+C) where Emax is the maximal specific binding, C is the drug concentration, and EC$_{50}$ is the total plasma concentration required for 50% binding site occupancy. Nonlinear regression was performed using GraphPad Prism version 3.00 (GraphPad Software, San Diego, Calif.).

The results are shown in Table 2, below:

TABLE 2

IC$_{50}$ and Occupancy Values

| Example* | Binding Affinity (IC$_{50}$, nM) | | | % Occupancy | | | Dose (mg/kg) | Time Point (h)[†] |
|---|---|---|---|---|---|---|---|---|
| | SERT | DAT | NET | SERT | DAT | NET | | |
| 1 | 74.2 | 93.7 | 675.1 | | | | | |
| 2 | 125.6 | 53.9 | 384.6 | | | | | |
| 3(+) | 9.4 | 339.6 | 816.6 | | | | | |
| 3(−) | 5.2 | 141.2 | 443.0 | | | | | |
| 4 | 11.3 | 603.3 | 70.5 | | | | | |
| 5 | 10.1 | 74.2 | 273.5 | | | | | |
| 6(+) | 19.3 | 1,057 | 1,166 | | | | | |
| 6(−) | 5.9 | 87.2 | 274.8 | 59 | 12 | 0 | 3 | 3 |
| 7(+) | 62.5 | 148.3 | 674.4 | | | | | |
| 7(−) | 6.4 | 16.6 | 102.8 | 70 | 1 | 46 | 1 | 3 |
| 8 | 16.6 | 449.6 | 1209 | | | | | |
| 9 | 23.5 | 434.8 | 302.5 | | | | | |
| 10(+) | 4.6 | 49.5 | 242.3 | | | | | |
| 10(−) | 5.6 | 37.5 | 73.7 | | | | | |
| 11(+) | 3.5 | 50.0 | 368.6 | | | | | |
| 11(−) | 3.9 | 19.6 | 92.4 | | | | | |
| 12 | 7.8 | 52.0 | 881.4 | | | | | |
| 13 | 16.3 | 21.1 | 691.0 | | | | | |
| 14 | 1.1 | 57.3 | 264.5 | 79 | 12 | 0 | 3 | 3 |
| 15 | 2.6 | 121.4 | 383.8 | | | | | |
| 16 | 7.3 | 156.3 | 2,929 | | | | | |
| 17 | 5.3 | 83.8 | 2,305 | 77 | 0 | 12 | 1 | 3 |
| 18 | 3.5 | 47.6 | 925.2 | 89 | 15 | 6 | 3 | 3 |
| 20 | 12.1 | 219.5 | 1,020 | | | | | |
| 21 | 5.2 | 353.4 | 1,545 | | | | | |
| 22 | 3.4 | 58.6 | 805.9 | 60 | 5 | 0 | 3 | 3 |
| 23 | 1.5 | 37.5 | 175.5 | | | | | |
| 24 | 7.3 | 856.5 | 5,332 | | | | | |
| 25 | 6.4 | 168.9 | 392.4 | | | | | |
| 26 | 7.2 | 63.0 | 432.0 | 14 | 3 | 0 | 1 | 3 |

TABLE 2-continued

IC$_{50}$ and Occupancy Values

| Example* | Binding Affinity (IC$_{50}$, nM) | | | % Occupancy | | | Dose (mg/kg) | Time Point (h)† |
|---|---|---|---|---|---|---|---|---|
| | SERT | DAT | NET | SERT | DAT | NET | | |
| 27 | 3.4 | 134.9 | 355.5 | | | | | |
| 28 | 8.0 | 58.9 | 438.2 | | | | | |
| 29 | 327.9 | 5,263 | 5,461 | | | | | |
| 30 | 10.0 | 13.6 | 55.8 | | | | | |
| 31 | 2,316 | 4,017 | 8,295 | | | | | |
| 32 | 4.3 | 36.5 | 123.6 | 74 | 42 | 0 | 3 | 3 |
| 33 | 6.1 | 116.2 | 910.4 | | | | | |
| 34 | 2.3 | 103.5 | 429.5 | | | | | |
| 35 | 4.2 | 205.3 | 54.8 | | | | | |
| 36 | 1.2 | 65.7 | 62.3 | | | | | |
| 37 | 8.6 | 18.5 | 119.0 | | | | | |
| 38 | 9.3 | 25.5 | 451.1 | | | | | |
| 39 | 3.8 | 26.1 | 53.5 | 59 | | 41 | 3 | 3 |
| 40 | 9.8 | 5.9 | 147.9 | | | | | |
| 41 | 5.0 | 5.1 | 79.2 | | | | | |
| 42 | 5.9 | 9.2 | 155.1 | 82 | 54 | 39 | 3 | 3 |
| 43 | 18.9 | 43.8 | 373.0 | | | | | |
| 44 | 4.7 | 33.9 | 160.7 | | | | | |
| 45 | 4.8 | 0.7 | 35.1 | 46 | 17 | 0 | 1 | 3 |
| 46 | 3.0 | 55.2 | 140.3 | | | | | |
| 47 | 6.4 | 9.0 | 112.4 | 34 | 17 | 0 | 1 | 3 |
| 48 | 7.2 | 10.1 | 133.5 | 21 | 12 | 0 | 1 | 3 |
| 49 | 24.2 | 55.9 | 450.7 | | | | | |
| 50 | 10.9 | 613.9 | 1,049 | | | | | |
| 51 | 20.2 | 63.2 | 231.3 | | | | | |
| 52 | 8.9 | 42.8 | 206.1 | | | | | |
| 53 | 2.1 | 120.4 | 344.6 | | | | | |
| 54 | 4.4 | 78.0 | 540.9 | | | | | |
| 55(+) | 18.6 | 120.8 | 955.6 | | | | | |
| 55(−) | 2.2 | 35.3 | 175.2 | | | | | |
| 56(+) | 2.4 | 11.4 | 78.6 | | | | | |
| 56(−) | 57.8 | 243.0 | 798.5 | | | | | |

*All compounds were dosed orally.
†Time point equals time until sacrifice.

Example 61

In Vivo Behavioral Assays

For All Tests

All animals were maintained in accordance with the guidelines of the Committee on Animals of the Bristol-Myers Squibb Company and *Guide for Care and Use of Laboratory Animals*, Institute of Animal Laboratory Resources, 1996, which are hereby incorporated by reference in their entirety. Research protocols were approved by the Bristol-Myers Squibb Company Institutional Animal Care and Use Committee.

Mouse Tail Suspension Assay

Male Swiss Webster mice were housed 3-4 per cage in rooms maintained at a constant temperature (21-23° C.) and humidity (50±10%) on a 12-hour light/dark cycle. Animals had ad libitum access to water and food throughout studies. On the day of testing, they were brought into the testing room and allowed to acclimate for 1 hour. To begin testing, the tail was attached to a piece of tape which was then attached to a hook on the ceiling of a sound-attenuated chamber Immobility was automatically recorded using the Med Associates software. Compounds were administered acutely at a fixed pretreatment interval before session.

Rat Forced Swim Assay

Male Sprague Dawley rats are housed in pairs in rooms maintained at a constant temperature (21-23° C.) and humidity (50±10%) on a 12-hour light/dark cycle. Animals have ad libitum access to water and food throughout studies. Animals are handled for two minutes each on the two days prior to the start of the experiment. On the first day of testing, rats are placed in the swim tank (a Pyrex cylinder 46 cm tall×21 cm in diameter, filled with 30 cm of water ranging between 24-26° C.) for 15 minutes (the pre-swim session). At the end of the 15-minute session, rats are dried and replaced in their home cage. Compounds are administered at three time points in the next 24 hour (23.5, 5, and 1 hour), prior to a second test swim. This swim test is 5 minutes in duration and the animals' behavior is videotaped and active behaviors (immobility, swimming, climbing) are scored. At the end of each 5-second period during the 5-minute test session the rat's behavior is scored as one of the following: immobility (the rat remained floating in the water without struggling and made only those movements necessary to keep its head above water), swimming (the rat made active swimming motions, more than necessary to merely maintain its head above water, e.g., moving around in the cylinder), or climbing (the rat made active movements with its forepaws in and out of the water, usually directed against the cylinder wall). Compounds are only identified by a predesignated code and the experimenter remains blinded throughout the experiment (including while scoring videotapes).

Rat and Mouse Locomotor Activity

Animals are housed according to conditions described above for the two species. The testing apparatus consists of Plexiglas chambers equipped with Digiscan activity monitors (Omnitech Electronics, Columbus, Ohio) that detect interruptions of eight photobeams. Horizontal activity is recorded in 5-minute bins for a total of 60 minutes and expressed as total distance covered (in cm). Compounds are administered acutely at a fixed pretreatment interval prior to testing.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A compound of formula (I) having the following structure:

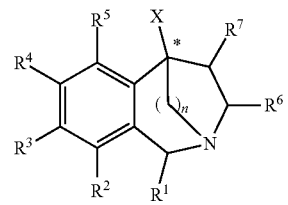

wherein:

n is 2;

X is phenyl, naphthyl, benzofuranyl, benzothiophenyl, indolyl, or indazolyl, each optionally substituted from 1-4 times with substituents as defined below in $R^{13}$;

$R^1$ is H;

$R^2$, $R^4$, and $R^5$ are each independently H, halogen, methyl, ethyl, isopropyl, hydroxy, methoxy, trifluoromethoxy, difluoromethoxy, —CN, —NH$_2$, —NHMe, or —NMe$_2$;

$R^3$ is H, halogen, —NR$^8$R$^9$, OR$^{10}$, S(O)$_p$R$^{11}$, —CN, —C(O)R$^{11}$, C$_1$-C$_6$ alkyl, C$_2$-C$_6$ alkenyl, C$_2$-C$_6$ alkynyl, C$_3$-C$_6$ cycloalkyl, or C$_4$-C$_7$ cycloalkylalkyl, where each of the C$_1$-C$_6$ alkyl, C$_2$-C$_6$ alkenyl, C$_2$-C$_6$ alkynyl, C$_3$-C$_6$ cycloalkyl, and $C_4$-$C_7$ cycloalkylalkyl is optionally substituted from 1 to 3 times with substituents as defined below in $R^{12}$; or $R^3$ is a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substituents selected from the group consisting of $C_1$-$C_3$ alkyl, —C(O)$R^{11}$, and —S(O)$_p R^{11}$; or $R^3$ is a monocyclic or bicyclic aryl or heteroaryl selected from the group consisting of phenyl, pyridyl, 2-oxopyridin-1(2H)-yl, pyrimidinyl, pyridazinyl, 6-oxopyridazin-1(6H)-yl, pyrazinyl, triazinyl, pyranyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indanyl, indenyl, indolyl, isoindolyl, benzofuranyl, benzothiophenyl, indolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, naphthyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, 3-thio-[1,2,4]triazolo[4,3-a]pyridin-2(3H)-yl, and other 5- or 6-membered aromatic or non-aromatic monocyclic carbocycles or heterocycles, or [5,5]-, [6,5]-, [6,6]-, or [6,7]-fused bicyclic carbocycles or heterocycles containing 1-5 heteroatoms selected from the group consisting of oxygen, nitrogen, and sulfur, each optionally substituted from 1 to 4 times with substituents as defined below in $R^{13}$; or $R^3$ is —OR$^{14}$;

$R^6$ and $R^7$ are each independently H, methyl, ethyl, gem-dimethyl, or gem-diethyl, $R^8$ and $R^9$ are each independently selected from the group consisting of H, —C(O)$R^{11}$, $C_1$-$C_4$ alkyl, $C_3$-$C_6$ cycloalkyl, and $C_4$-$C_7$ cycloalkylalkyl, where each of $C_1$-$C_4$ alkyl, $C_3$-$C_6$ cycloalkyl, and $C_4$-$C_7$ cycloalkylalkyl is optionally substituted from 1 to 3 times with substituents as defined below in $R^{10}$; or $R^8$ and $R^9$ are each independently selected from the group consisting of phenyl, benzyl, and other 5- or 6-membered monocyclic heterocycles, where each of the phenyl, benzyl, and 5- or 6-membered monocyclic heterocycle is optionally substituted from 1 to 3 times with substituents as defined below in $R^{13}$; or $R^8$ and $R^9$ are taken together with the nitrogen to which they are attached to form a saturated or partially saturated monocyclic or fused bicyclic heterocycle selected from the group consisting of piperidine, pyrrolidine, morpholine, thiomorpholine, [1,2]oxazinane, isoxazolidine, 2-oxopiperidinyl, 2-oxopyrrolidinyl, 3-oxomorpholino, 3-oxothiomorpholino, 5,6,7,8-tetrahydroimidazo[1,2-a]pyrazine, 5,6,7,8-tetrahydro-[1,2,4]triazolo[4,3-a]pyrazine, and other monocyclic or fused bicyclic heterocycles containing 1-4 heteroatoms selected from oxygen, nitrogen and sulfur, wherein the heterocycle is attached to the benzazepine core via the nitrogen atom, and is optionally substituted from 1 to 3 times with a substituent selected independently at each occurrence thereof from the group consisting of halogen, cyano, —OR$^{10}$, —NR$^{10}$R$^{11}$, —S(O)$_p$R$^{11}$, C(O)R$^{11}$, oxo, and $C_1$-$C_4$ alkyl, where each $C_1$-$C_4$ alkyl is optionally substituted from 1 to 3 times with substituents as defined below in $R^{12}$; or $R^8$ and $R^9$ are taken together with the nitrogen to which they are attached to form a heterocycle selected from the group consisting of piperazine, 2-oxopiperazinyl, 2-oxo-1,4-diazepanyl, 5-oxo-1,4-diazepanyl, 1,4-diazepane, and other heterocycles containing at least two nitrogens in the ring, where the heterocycle is optionally substituted on a ring carbon from 1 to 3 times with a substituent selected independently at each occurrence thereof from the group consisting of halogen, cyano, —OR$^{10}$, —NR$^{10}$R$^{11}$, —S(O)$_p$R$^{11}$, —C(O)R$^{11}$, oxo, and $C_1$-$C_4$ alkyl, or on one or more of the at least two nitrogens in the ring from 1 to 3 times with a substituent selected independently at each occurrence thereof from the group consisting of S(O)$_p$R$^{11}$, —C(O)R$^{11}$, $C_1$-$C_4$ alkyl, aryl, and heteroaryl, wherein each $C_1$-$C_4$ alkyl is optionally substituted from 1 to 3 times with substituents as defined below in $R^{12}$ and wherein each of the aryl or heteroaryl groups is optionally substituted from 1 to 4 times with substituents as defined below in $R^{13}$; or $R^8$ and $R^9$ are taken together with the nitrogen to which they are attached to form a heterocycle selected from the group consisting of piperazine, 2-oxopiperazinyl, 2-oxo-1,4-diazepanyl, 5-oxo-1,4-diazepanyl, 1,4-diazepane, and other heterocycles containing one additional nitrogen atom in the ring, where the heterocycle is optionally substituted on the additional nitrogen atom with a substituent selected independently at each occurrence thereof from the group consisting of phenyl, benzyl, and 5- or 6-membered aromatic heterocycles containing 1-3 heteroatoms selected from the group consisting of oxygen, nitrogen, and sulfur, where each of the phenyl, benzyl, and 5- and 6-membered heterocycle is optionally substituted from 1 to 3 times with substituents as defined below in $R^{13}$; or when $R^3$ is —NR$^8$R$^9$ or —C(O)NR$^8$R$^9$, either $R^8$ or $R^9$ is a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substituents selected from the group consisting of $C_1$-$C_3$ alkyl, —C(O)R$^{11}$, and —S(O)$_p$R$^{11}$, or either $R^8$ or $R^9$ is a $C_1$-$C_3$ alkyl substituted with a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substituents selected from the group consisting of $C_1$-$C_3$ alkyl, —C(O)R$^{11}$, and —S(O)$_p$R$^{11}$;

$R^{10}$ is selected from the group consisting of H, OH, alkoxy, $C_1$-$C_4$ alkyl, $C_3$-$C_6$ cycloalkyl, $C_4$-$C_7$ cycloalkylalkyl, and —C(O)R$^{11}$, where each of C$_1$-C$_4$ alkyl, C$_3$-C$_6$ cycloalkyl, and C$_4$-C$_7$ cycloalkylalkyl is optionally substituted from 1 to 3 times with substituents as defined below in R$^{12}$;

R$^{11}$ is selected from the group consisting of —NR$^8$R$^9$, C$_1$-C$_4$ alkyl, C$_3$-C$_6$ cycloalkyl, and C$_4$-C$_7$ cycloalkylalkyl, where each of C$_1$-C$_4$ alkyl, C$_3$-C$_6$ cycloalkyl, and C$_4$-C$_7$ cycloalkylalkyl is optionally substituted from 1 to 3 times with substituents as defined below in R$^{12}$; or R$^{10}$ and R$^{11}$ are each independently selected from the group consisting of phenyl, benzyl, pyridazinyl, pyrimidinyl, pyrazinyl, 5- or 6-membered aromatic monocyclic heterocycles, and [5,5]-, [6,5]-, [6,6]-, or [6,7]-fused bicyclic carbocycles or heterocycles, the heterocycles containing 1-5 heteroatoms selected from the group consisting of oxygen, nitrogen, and sulfur, optionally substituted from 1 to 4 times with substituents as defined below in R$^{13}$; or when R$^{10}$ and R$^{11}$ are together attached to a nitrogen, R$^{10}$ and R$^{11}$ are taken together with the nitrogen to which they are attached to form a heterocycle selected from the group consisting of piperidine, pyrrolidine, piperazine, 1,4-diazepane, morpholine, thiomorpholine, and other heterocycles containing 1-4 heteroatoms selected from the group consisting of oxygen, nitrogen, and sulfur, where the heterocycle is optionally substituted from 1 to 3 times with a substituent selected independently at each occurrence thereof from the group consisting of halogen, cyano, —OR$^8$, —S(O)$_p$R$^8$, —C(O)R$^8$, —C(O)NR$^8$R$^9$ and C$_1$-C$_4$ alkyl, where each of C$_1$-C$_4$ alkyl is optionally substituted from 1 to 3 times with substituents as defined below in R$^{12}$;

p is 0, 1, or 2;

R$^{12}$ is independently selected at each occurrence from a substituent in the group consisting of —CN, halogen, C(O)R", C$_1$-C$_3$ alkyl, —OR$^{10}$, —NR$^8$R$^9$, —S(O)$_p$R$^{11}$, aryl, and heteroaryl, where each of the aryl or heteroaryl groups is optionally substituted from 1 to 4 times with substituents as defined below in R$^{13}$;

R$^{13}$ is independently selected at each occurrence from a substituent in the group consisting of halogen, —NO$_2$, —OR$^{10}$, —NR$^8$R$^9$, —NR$^{10}$C(O)$_2$R$^{11}$, —NR$^{10}$C(O) NR$^{10}$R$^{11}$, —S(O)$_p$R$^{11}$, —CN, —C(O)R$^{11}$, C$_1$-C$_6$ alkyl, C$_2$-C$_6$ alkenyl, C$_2$-C$_6$ alkynyl, C$_3$-C$_6$ cycloalkyl, and C$_4$-C$_7$ cycloalkylalkyl, where each of C$_1$-C$_6$ alkyl, C$_2$-C$_6$ alkenyl, C$_2$-C$_6$ alkynyl, C$_3$-C$_6$ cycloalkyl, and C$_4$-C$_7$ cycloalkylalkyl is optionally substituted from 1 to 3 times with substituents as defined above in R$^{12}$; and R$^{14}$ is a 5- or 6-membered aromatic or non-aromatic monocyclic carbocycle or heterocycle, or [5,5]-, [6,5]-, [6,6]-, or [6,7]-fused bicyclic carbocycle or heterocycle containing 1-5 heteroatoms selected from the group consisting of oxygen, nitrogen, and sulfur, optionally substituted from 1 to 4 times with substituents as defined above in R$^{13}$;

with the proviso that when R$^1$, R$^2$, R$^3$, R$^4$, R$^5$, R$^6$, and R$^7$ are all hydrogen, X cannot be phenyl;

or an oxide thereof, or a pharmaceutically acceptable salt thereof.

2. The compound according to claim 1, wherein X is phenyl optionally substituted from 1-4 times with substituents as defined in R$^{13}$, and R$^3$ is substituted monocyclic or bicyclic aryl or heteroaryl.

3. The compound according to claim 2, wherein:
X is phenyl, optionally substituted from 1 to 3 times with chloro or fluoro;
R$^1$, R$^2$, R$^4$, R$^5$, R$^6$, and R$^7$ are all H;
R$^3$ is substituted monocyclic or bicyclic aryl or heteroaryl.

4. The compound according to claim 1, wherein X is phenyl optionally substituted from 1-4 times with substituents as defined in R$^{13}$, and R$^3$ is H, —NR$^8$R$^9$, —OR$^{10}$, —OR$^{14}$, —S(O)$_p$R$^{11}$, C(O)R$^{11}$, —CN, halogen, and C$_1$-C$_6$ alkyl, where each of the C$_1$-C$_6$ alkyl is optionally substituted from 1 to 3 times with substituents as defined below in R$^{12}$.

5. The compound according to claim 4, wherein:
X is phenyl, optionally substituted from 1 to 3 times with chloro or fluoro;
R$^1$, R$^2$, R$^4$, R$^5$, R$^6$, and R$^7$ are all H; and
R$^3$ is H, —NR$^8$R$^9$, —OR$^{10}$, —OR$^{14}$, —S(O)$_p$R$^{11}$, C(O)R$^{11}$, —CN, halogen, or C$_1$-C$_6$ alkyl, where each of the C$_1$-C$_6$ alkyl is optionally substituted from 1 to 3 times with substituents as defined above in R$^{12}$.

6. The compound according to claim 1, wherein
X is phenyl, optionally substituted from 1 to 3 times with chloro or fluoro;
R$^1$, R$^2$, R$^4$, R$^5$, R$^6$, and R$^7$ are all H; and
R$^3$ is hydroxy, methoxy, difluoromethoxy, [1,2,4]triazolo[1,5-a]pyridin-6-yl, 7-methyl-[1,2,4]triazolo[1,5-a]pyridin-6-yl, [1,2,4]triazolo[4,3-a]pyridin-6-yl, 3-methyl-[1,2,4]triazolo[4,3-a]pyridin-6-yl, 3-(trifluoromethyl)[1,2,4]triazolo[4,3-a]pyridin-6-yl, 3-oxo-[1,2,4]triazolo[4,3-a]pyridin-2(3H)-yl, 2-oxo-pyridin-1-yl, 6-(methoxy)pyridazin-3-yl, 6-(hydroxy)pyridazin-3-yl, 6-(trifluoromethyl)pyridazin-3-yl, 6-(difluoromethoxy)pyridazin-3-yl, 6-(hydroxy)pyridazin-3-yl, 4-cyanophenyl, 3-cyanophenyl, 4-(methylsulfonyl)phenyl, 2-oxo-2,3-dihydrobenzo[d]oxazol-6-yl, pyrimidin-5-yl, pyrazinyl, 5-aminopyrazinyl, quinoxalin-2-yl, 5-methyl-1,3,4-thiadiazol-2-yl, morpholinyl, 4-(ethylsulfonyl)piperazin-1-yl, 6-(trifluoromethyl)pyridazin-3-yloxy, pyrazin-2-yloxy, 5-amino-pyrazin-2-yloxy, 3-(pyridin-4-yl)propoxy, 3-(pyridin-3-yl)propoxy, 5-(methylsulfonyl)pyrimidin-2-yl, 6-(methylcarbamoyl)pyridazin-3-yl, 6-carbamoylpyridazin-3-yl, 5-(methylcarbamoyl)pyrimidin-2-yl, or 5-carbamoylpyrimidin-2-yl.

7. The compound according to claim 1, wherein:
X is phenyl, optionally substituted from 1 to 3 times with chloro or fluoro;
R$^1$, R$^2$, R$^4$, R$^5$, R$^6$, and R$^7$ are all H; and
R$^3$ is 6-(1-hydroxyethyl)pyridazin-3-yl, 6-(2-hydroxypropan-2-yl)pyridazin-3-yl, 6-(2,2,2-trifluoro-1-hydroxyethyl)pyridazin-3-yl, 6-(2,2-difluoro-1-hydroxyethyl)pyridazin-3-yl, 2-(1-hydroxyethyl)pyrimidin-5-yl, 2-(2-hydroxypropan-2-yl)pyrimidin-5-yl, 2-(2,2,2-trifluoro-1-hydroxyethyl)pyrimidin-5-yl, or 2-(2,2-difluoro-1-hydroxyethyl)pyrimidin-5-yl.

8. The compound according to claim 1, wherein the compound is selected from the following group consisting of:
5-(4-chlorophenyl)-8-methoxy-2,5-ethano-2,3,4,5-tetrahydro-1H-2-benzo[c]azepine;
5-(4-chlorophenyl)-2,5-ethano-2,3,4,5-tetrahydro-1H-2-benzo[c]azepin-8-ol;
5-(4-chlorophenyl)-8-(6-(difluoromethoxy)pyridazin-3-yl)-2,5-ethano-2,3,4,5-tetrahydro-1H-2-benzo[c]azepine;
5-(4-chlorophenyl)-2,5-ethano-8-(pyrimidin-5-yl)-2,3,4,5-tetrahydro-1H-benzo[c]azepine;
5-(4-chlorophenyl)-2,5-ethano-8-(pyrazin-2-yl)-2,3,4,5-tetrahydro-1H-benzo[c]azepine;
5-(5-(4-chlorophenyl)-2,5-ethano-2,3,4,5-tetrahydro-1H-benzo[c]azepin-8-yl)pyrazin-2-amine;
8-([1,2,4]triazolo[1,5-a]pyridin-6-yl)-5-(4-chlorophenyl)-2,5-ethano-2,3,4,5-tetrahydro-1H-benzo[c]azepine;

5-(4-chlorophenyl)-2,5-ethano-8-(3-methyl-[1,2,4]triazolo[4,3-a]pyridin-6-yl)-2,3,4,5-tetrahydro-1H-benzo[c]azepine;

5-(4-chlorophenyl)-2,5-ethano-8-(quinoxalin-2-yl)-2,3,4,5-tetrahydro-1H-benzo[c]azepine;

6-(5-(4-chlorophenyl)-2,5-ethano-2,3,4,5-tetrahydro-1H-benzo[c]azepin-8-yl)-3,3a-dihydrobenzo[d]oxazol-2(7aH)-one;

2-(5-(4-chlorophenyl)-2,5-ethano-2,3,4,5-tetrahydro-1H-benzo[c]azepin-8-yl)-[1,2,4]triazolo[4,3-a]pyridin-3(2H)-one;

1-(5-(4-chlorophenyl)-2,5-ethano-2,3,4,5-tetrahydro-1H-benzo[c]azepin-8-yl)pyridin-2(1H)-one;

2-(5-(4-chlorophenyl)-2,5-ethano-2,3,4,5-tetrahydro-1H-benzo[c]azepin-8-yl)-5-methyl-1,3,4-thiadiazole;

5-(4-chlorophenyl)-2,5-ethano-8-(4-(methylsulfonyl)phenyl)-2,3,4,5-tetrahydro-1H-benzo[c]azepine;

3-(5-(4-chlorophenyl)-2,5-ethano-2,3,4,5-tetrahydro-1H-benzo[c]azepin-8-yl)benzonitrile;

4-(5-(4-chlorophenyl)-2,5-ethano-2,3,4,5-tetrahydro-1H-benzo[c]azepin-8-yl)morpholine;

5-(4-chlorophenyl)-8-(4-(ethylsulfonyl)piperazin-1-yl)-2,5-ethano-2,3,4,5-tetrahydro-1H-benzo[c]azepine;

5-(4-chlorophenyl)-2,5-ethano-8-(6-(trifluoromethyl)pyridazin-3-yloxy)-2,3,4,5-tetrahydro-1H-benzo[c]azepine;

5-(4-chlorophenyl)-2,5-ethano-8-(pyrazin-2-yloxy)-2,3,4,5-tetrahydro-1H-benzo[c]azepine;

5-(5-(4-chlorophenyl)-2,5-ethano-2,3,4,5-tetrahydro-1H-benzo[c]azepin-8-yloxy)pyrazin-2-amine;

5-(4-chlorophenyl)-2,5-ethano-8-(3-(pyridin-4-yl)propoxy)-2,3,4,5-tetrahydro-1H-benzo[c]azepine;

5-(4-chlorophenyl)-2,5-ethano-8-(3-(pyridin-3-yl)propoxy)-2,3,4,5-tetrahydro-1H-benzo[c]azepine;

8-([1,2,4]triazolo[1,5-a]pyridin-6-yl)-5-(3,4-dichlorophenyl)-2,5-ethano-2,3,4,5-tetrahydro-1H-benzo[c]azepine;

6-(5-(3,4-dichlorophenyl)-2,5-ethano-2,3,4,5-tetrahydro-1H-benzo[c]azepin-8-yl)-3,3a-dihydrobenzo[d]oxazol-2(7aH)-one;

5-(3,4-dichlorophenyl)-8-(6-(difluoromethoxy)pyridazin-3-yl)-2,5-ethano-2,3,4,5-tetrahydro-1H-benzo[c]azepine;

5-(3,4-dichlorophenyl)-8-(6-methoxypyridazin-3-yl)-2,5-ethano-2,3,4,5-tetrahydro-1H-benzo[c]azepine;

6-(5-(3,4-dichlorophenyl)-2,5-ethano-2,3,4,5-tetrahydro-1H-benzo[c]azepin-8-yl)pyridazin-3-ol;

5-(5-(3,4-dichlorophenyl)-2,5-ethano-2,3,4,5-tetrahydro-1H-benzo[c]azepin-8-yl)pyrazin-2-amine;

5-(3,4-dichlorophenyl)-2,5-ethano-8-(7-methyl-[1,2,4]triazolo[1,5-a]pyridin-6-yl)-2,3,4,5-tetrahydro-1H-benzo[c]azepine;

5-(3,4-dichlorophenyl)-2,5-ethano-8-(pyrazin-2-yloxy)-2,3,4,5-tetrahydro-1H-benzo[c]azepine;

5-(3,4-dichlorophenyl)-2,5-ethano-8-(6-(trifluoromethyl)pyridazin-3-yloxy)-2,3,4,5-tetrahydro-1H-benzo[c]azepine;

5-(3,4-dichlorophenyl)-2,5-ethano-8-(difluoromethoxy)-2,3,4,5-tetrahydro-1H-benzo[c]azepine;

5-(3-chloro-4-fluorophenyl)-2,5-ethano-8-(6-(trifluoromethyl)pyridazin-3-yloxy)-2,3,4,5-tetrahydro-1H-benzo[c]azepine;

5-(4-chloro-3-fluorophenyl)-2,5-ethano-8-(6-(trifluoromethyl)pyridazin-3-yloxy)-2,3,4,5-tetrahydro-1H-benzo[c]azepine;

5-(3-chlorophenyl)-2,5-ethano-8-(6-(trifluoromethyl)pyridazin-3-yloxy)-2,3,4,5-tetrahydro-1H-benzo[c]azepine;

2,5-ethano-5-(4-(trifluoromethyl)phenyl)-8-(6-(trifluoromethyl)pyridazin-3-yloxy)-2,3,4,5-tetrahydro-1H-benzo[c]azepine;

5-(3,4-difluorophenyl)-2,5-ethano-8-(6-(trifluoromethyl)pyridazin-3-yloxy)-2,3,4,5-tetrahydro-1H-benzo[c]azepine;

5-(4-fluorophenyl)-2,5-ethano-8-(6-(trifluoromethyl)pyridazin-3-yloxy)-2,3,4,5-tetrahydro-1H-benzo[c]azepine;

5-(3-chloro-4-fluorophenyl)-2,5-ethano-8-(6-(trifluoromethyl)pyridazin-3-yl)-2,3,4,5-tetrahydro-1H-benzo[c]azepine;

8-([1,2,4]triazolo[1,5-a]pyridin-6-yl)-5-(3-chloro-4-fluorophenyl)-2,5-ethano-2,3,4,5-tetrahydro-1H-benzo[c]azepine;

5-(4-chlorophenyl)-2,5-ethano-8-(5-(methylsulfonyl)pyrimidin-2-yl)-1,3,4,5-tetrahydro-1H-benzo[c]azepine;

5-(4-fluorophenyl)-2,5-ethano-8-(5-(methylsulfonyl)pyrimidin-2-yl)-1,3,4,5-tetrahydro-1H-benzo[c]azepine;

5-(3,4-difluorophenyl)-2,5-ethano-8-(5-(methylsulfonyl)pyrimidin-2-yl)-1,3,4,5-tetrahydro-1H-benzo[c]azepine;

5-(3,4-dichlorophenyl)-2,5-ethano-8-(5-(methylsulfonyl)pyrimidin-2-yl)-1,3,4,5-tetrahydro-1H-benzo[c]azepine;

5-(3-chloro-4-fluorophenyl)-2,5-ethano-8-(5-(methylsulfonyl)pyrimidin-2-yl)-1,3,4,5-tetrahydro-1H-benzo[c]azepine;

5-(4-chloro-3-fluorophenyl)-2,5-ethano-8-(5-(methylsulfonyl)pyrimidin-2-yl)-1,3,4,5-tetrahydro-1H-benzo[c]azepine;

6-(5-(4-chlorophenyl)-1,3,4,5-tetrahydro-2,5-ethanobenzo[c]azepin-8-yl)-N-methylpyridazine-3-carboxamide;

6-(5-(4-fluorophenyl)-1,3,4,5-tetrahydro-2,5-ethanobenzo[c]azepin-8-yl)-N-methylpyridazine-3-carboxamide;

6-(5-(3,4-difluorophenyl)-1,3,4,5-tetrahydro-2,5-ethanobenzo[c]azepin-8-yl)-N-methylpyridazine-3-carboxamide;

6-(5-(3,4-dichlorophenyl)-1,3,4,5-tetrahydro-2,5-ethanobenzo[c]azepin-8-yl)-N-methylpyridazine-3-carboxamide;

6-(5-(4-chloro-3-fluorophenyl)-1,3,4,5-tetrahydro-2,5-ethanobenzo[c]azepin-8-yl)-N-methylpyridazine-3-carboxamide;

6-(5-(3-chloro-4-fluorophenyl)-1,3,4,5-tetrahydro-2,5-ethanobenzo[c]azepin-8-yl)-N-methylpyridazine-3-carboxamide;

6-(5-(4-chlorophenyl)-1,3,4,5-tetrahydro-2,5-ethanobenzo[c]azepin-8-yl)-pyridazine-3-carboxamide;

6-(5-(4-fluorophenyl)-1,3,4,5-tetrahydro-2,5-ethanobenzo[c]azepin-8-yl)-pyridazine-3-carboxamide;

6-(5-(3,4-difluorophenyl)-1,3,4,5-tetrahydro-2,5-ethanobenzo[c]azepin-8-yl)-pyridazine-3-carboxamide;

6-(5-(3,4-dichlorophenyl)-1,3,4,5-tetrahydro-2,5-ethanobenzo[c]azepin-8-yl)-pyridazine-3-carboxamide;

6-(5-(4-chloro-3-fluorophenyl)-1,3,4,5-tetrahydro-2,5-ethanobenzo[c]azepin-8-yl)-pyridazine-3-carboxamide;

6-(5-(3-chloro-4-fluorophenyl)-1,3,4,5-tetrahydro-2,5-ethanobenzo[c]azepin-8-yl)-pyridazine-3-carboxamide;

2-(5-(4-chlorophenyl)-1,3,4,5-tetrahydro-2,5-ethanobenzo[c]azepin-8-yl)-N-methylpyrimidine-5-carboxamide;
2-(5-(4-fluorophenyl)-1,3,4,5-tetrahydro-2,5-ethanobenzo[c]azepin-8-yl)-N-methylpyrimidine-5-carboxamide;
2-(5-(3,4-dichlorophenyl)-1,3,4,5-tetrahydro-2,5-ethanobenzo[c]azepin-8-yl)-N-methylpyrimidine-5-carboxamide;
2-(5-(3,4-difluorophenyl)-1,3,4,5-tetrahydro-2,5-ethanobenzo[c]azepin-8-yl)-N-methylpyrimidine-5-carboxamide;
2-(5-(3-chloro-4-fluorophenyl)-1,3,4,5-tetrahydro-2,5-ethanobenzo[c]azepin-8-yl)-N-methylpyrimidine-5-carboxamide;
2-(5-(4-chloro-3-fluorophenyl)-1,3,4,5-tetrahydro-2,5-ethanobenzo[c]azepin-8-yl)-N-methylpyrimidine-5-carboxamide;
2-(5-(4-chlorophenyl)-1,3,4,5-tetrahydro-2,5-ethanobenzo[c]azepin-8-yl)-pyrimidine-5-carboxamide;
2-(5-(4-fluorophenyl)-1,3,4,5-tetrahydro-2,5-ethanobenzo[c]azepin-8-yl)-pyrimidine-5-carboxamide;
2-(5-(3,4-dichlorophenyl)-1,3,4,5-tetrahydro-2,5-ethanobenzo[c]azepin-8-yl)-pyrimidine-5-carboxamide;
2-(5-(3,4-difluorophenyl)-1,3,4,5-tetrahydro-2,5-ethanobenzo[c]azepin-8-yl)-pyrimidine-5-carboxamide;
2-(5-(3-chloro-4-fluorophenyl)-1,3,4,5-tetrahydro-2,5-ethanobenzo[c]azepin-8-yl)-pyrimidine-5-carboxamide; and
2-(5-(4-chloro-3-fluorophenyl)-1,3,4,5-tetrahydro-2,5-ethanobenzo[c]azepin-8-yl)-pyrimidine-5-carboxamide.

9. A pharmaceutical composition comprising a pharmaceutically acceptable carrier and a therapeutically effective amount of the compound of claim 1.

10. A compound of formula (I) having the following structure:

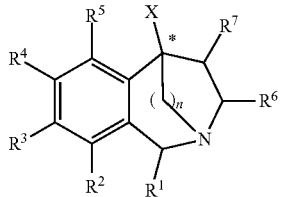

wherein:
n is 2;
X is phenyl, optionally substituted from 1-4 times with substituents as defined below in $R^{13}$;
$R^1$ is H;
$R^2$, $R^4$, and $R^5$ are each independently H, halogen, methyl, ethyl, isopropyl, hydroxy, methoxy, trifluoromethoxy, difluoromethoxy, —CN, —NH$_2$, —NHMe, or —NMe$_2$;
$R^3$ is H, halogen, —NR$^8$R$^9$, OR$^{10}$, S(O)$_p$R$^{11}$, CN, —C(O)R$^{11}$, $C_1$-$C_6$ alkyl, $C_2$-$C_6$ alkenyl, $C_2$-$C_6$ alkynyl, $C_3$-$C_6$ cycloalkyl, or $C_4$-$C_7$ cycloalkylalkyl, where each of the $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted from 1 to 3 times with substituents as defined below in $R^{12}$;
$R^3$ is a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substitutents selected from the group consisting of $C_1$-$C_3$ alkyl, —C(O)R$^{11}$, and —S(O)$_p$R$^{11}$; or
$R^3$ is a monocyclic or bicyclic aryl or heteroaryl selected from the group consisting of phenyl, pyridyl, 2-oxopyridin-1(2H)-yl, pyrimidinyl, pyridazinyl, 6-oxopyridazin-1(6H)-yl, pyrazinyl, triazinyl, pyranyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indanyl, indenyl, indolyl, isoindolyl, benzofuranyl, benzothiophenyl, indolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, naphthyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, 3-thio-[1,2,4]triazolo[4,3-a]pyridin-2(3H)-yl, and other 5- or 6-membered aromatic or non-aromatic monocyclic carbocycles or heterocycles, or [5,5]-, [6,5]-, [6,6]-, or [6,7]-fused bicyclic carbocycles or heterocycles containing 1-5 heteroatoms selected from the group consisting of oxygen, nitrogen, and sulfur, each optionally substituted from 1 to 4 times with substituents as defined below in $R^{13}$; or
$R^3$ is —OR$^{14}$;
$R^6$ and $R^7$ are each independently H, methyl, ethyl, gem-dimethyl, or gem-diethyl;
$R^8$ and $R^9$ are each independently selected from the group consisting of H, —C(O)R$^{11}$, $C_1$-$C_4$ alkyl, $C_3$-$C_6$ cycloalkyl, and $C_4$-$C_7$ cycloalkylalkyl, where each of $C_1$-$C_4$ alkyl, $C_3$-$C_6$ cycloalkyl, and $C_4$-$C_7$ cycloalkylalkyl is optionally substituted from 1 to 3 times with substituents as defined below in $R^{10}$; or
$R^8$ and $R^9$ are each independently selected from the group consisting of phenyl, benzyl, and other 5- or 6-membered monocyclic heterocycles, where each of the phenyl, benzyl, and 5- or 6-membered monocyclic heterocycle is optionally substituted from 1 to 3 times with substituents as defined below in $R^{13}$; or
$R^8$ and $R^9$ are taken together with the nitrogen to which they are attached to form a saturated or partially saturated monocyclic or fused bicyclic heterocycle selected from the group consisting of piperidine, pyrrolidine, morpholine, thiomorpholine, [1,2]oxazinane, isoxazolidine, 2-oxopiperidinyl, 2-oxopyrrolidinyl, 3-oxomorpholino, 3-oxothiomorpholino, 5,6,7,8-tetrahydroimidazo[1,2-a]pyrazine, 5,6,7,8-tetrahydro-[1,2,4]triazolo[4,3-a]pyrazine, and other monocyclic or fused bicyclic heterocycles containing 1-4 heteroatoms selected from oxygen, nitrogen and sulfur, wherein the heterocycle is attached to the benzazepine core via the nitrogen atom, and is optionally substituted from 1 to 3 times with a substituent selected independently at each occurrence thereof from the group consisting of halogen, cyano, —OR$^{10}$, —NR$^{10}$R$^{11}$, —S(O)$_p$R$^{11}$, C(O)R$^{11}$, oxo, and C$_1$-C$_4$ alkyl, where each C$_1$-C$_4$ alkyl is optionally substituted from 1 to 3 times with substituents as defined below in R$^{12}$; or R$^8$ and R$^9$ are taken together with the nitrogen to which they are attached to form a heterocycle selected from the group consisting of piperazine, 2-oxopiperazinyl, 2-oxo-1,4-diazepanyl, 5-oxo-1,4-diazepanyl, 1,4-diazepane, and other heterocycles containing at least two nitrogens in the ring, where the heterocycle is optionally substituted on a ring carbon from 1 to 3 times with a substituent selected independently at each occurrence thereof from the group consisting of halogen, cyano, —OR$^{10}$, —NR$^{10}$R$^{11}$, —S(O)$_p$R$^{11}$, —C(O)R$^{11}$, oxo, and C$_1$-C$_4$ alkyl, or on one or more of the at least two nitrogens in the ring from 1 to 3 times with a substituent selected independently at each occurrence thereof from the group consisting of S(O)$_p$R$^{11}$, —C(O)R$^{11}$, C$_1$-C$_4$ alkyl, aryl, and heteroaryl, wherein each C$_1$-C$_4$ alkyl is optionally substituted from 1 to 3 times with substituents as defined below in R$^{12}$ and wherein each of the aryl or heteroaryl groups is optionally substituted from 1 to 4 times with substituents as defined below in R$^{13}$; or R$^8$ and R$^9$ are taken together with the nitrogen to which they are attached to form a heterocycle selected from the group consisting of piperazine, 2-oxopiperazinyl, 2-oxo-1,4-diazepanyl, 5-oxo-1,4-diazepanyl, 1,4-diazepane, and other heterocycles containing one additional nitrogen atom in the ring, where the heterocycle is optionally substituted on the additional nitrogen atom with a substituent selected independently at each occurrence thereof from the group consisting of phenyl, benzyl, and 5- or 6-membered aromatic heterocycles containing 1-3 heteroatoms selected from the group consisting of oxygen, nitrogen, and sulfur, where each of the phenyl, benzyl, and 5- and 6-membered heterocycle is optionally substituted from 1 to 3 times with substituents as defined in R$^{13}$; or when R$^3$ is —NR$^8$R$^9$ or —C(O)NR$^8$R$^9$, either R$^8$ or R$^9$ is a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substituents selected from the group consisting of C$_1$-C$_3$ alkyl, —C(O)R$^{11}$, and —S(O)$_p$R$^{11}$, or either R$^8$ or R$^9$ is a C$_1$-C$_3$ alkyl substituted with a bridged bicyclic ring containing 6-12 carbon atoms and optionally containing one or more heteroatoms selected from the group consisting of oxygen, nitrogen, and sulfur, where the bridged bicyclic ring is optionally substituted from 1 to 3 times with substitutents selected from the group consisting of C$_1$-C$_3$ alkyl, —C(O)R$^{11}$, and —S(O)$_p$R$^{11}$;

R$^{10}$ is selected from the group consisting of H, OH, alkoxy, C$_1$-C$_4$ alkyl, C$_3$-C$_6$ cycloalkyl, C$_4$-C$_7$ cycloalkylalkyl, and —C(O)R$^{11}$, where each of C$_1$-C$_4$ alkyl, C$_3$-C$_6$ cycloalkyl, and C$_4$-C$_7$ cycloalkylalkyl is optionally substituted from 1 to 3 times with substituents as defined below in R$^{12}$;

R$^{11}$ is selected from the group consisting of —NR$^8$R$^9$, C$_1$-C$_4$ alkyl, C$_3$-C$_6$ cycloalkyl, and C$_4$-C$_7$ cycloalkylalkyl, where each of C$_1$-C$_4$ alkyl, C$_3$-C$_6$ cycloalkyl, and C$_4$-C$_7$ cycloalkylalkyl is optionally substituted from 1 to 3 times with substituents as defined below in R$^{12}$; or R$^{10}$ and R$^{11}$ are each independently selected from the group consisting of phenyl, benzyl, pyridazinyl, pyrimidinyl, pyrazinyl, 5- or 6-membered aromatic monocyclic heterocycles, and [5,5]-, [6,5]-, [6,6]-, or [6,7]-fused bicyclic carbocycles or heterocycles, the heterocycles containing 1-5 heteroatoms selected from the group consisting of oxygen, nitrogen, and sulfur, optionally substituted from 1 to 4 times with substituents as defined below in R$^{13}$; or when R$^{10}$ and R$^{11}$ are together attached to a nitrogen, R$^{10}$ and R$^{11}$ are taken together with the nitrogen to which they are attached to form a heterocycle selected from the group consisting of piperidine, pyrrolidine, piperazine, 1,4-diazepane, morpholine, thiomorpholine, and other heterocycles containing 1-4 heteroatoms selected from the group consisting of oxygen, nitrogen, and sulfur, where the heterocycle is optionally substituted from 1 to 3 times with a substituent selected independently at each occurrence thereof from the group consisting of halogen, cyano, —OR$^8$, —S(O)$_p$R$^8$, —C(O)R$^8$, —C(O)NR$^8$R$^9$ and C$_1$-C$_4$ alkyl, where each of C$_1$-C$_4$ alkyl is optionally substituted from 1 to 3 times with substituents as defined below in R$^{12}$;

p is 0, 1, or 2;

R$^{12}$ is independently selected at each occurrence from a substituent in the group consisting of —CN, halogen, C(O)R$^{11}$, C$_1$-C$_3$ alkyl, —OR$^{10}$, —NR$^8$R$^9$, —S(O)$_p$R$^{11}$, aryl, and heteroaryl, where each of the aryl or heteroaryl groups is optionally substituted from 1 to 4 times with substituents as defined above in R$^{13}$;

R$^{13}$ is independently selected at each occurrence from a substituent in the group consisting of halogen, —NO$_2$, —OR$^{10}$, —NR$^8$R$^9$, —NR$^{10}$C(O)$_2$R$^{11}$, —NR$^{10}$C(O)NR$^{10}$R$^{11}$, S(O)$_p$R$^{11}$, —CN, —C(O)R$^{11}$, C$_1$-C$_6$ alkyl, C$_2$-C$_6$ alkenyl, C$_2$-C$_6$ alkynyl, C$_3$-C$_6$ cycloalkyl, and C$_4$-C$_7$ cycloalkylalkyl, where each of C$_1$-C$_6$ alkyl, C$_2$-C$_6$ alkenyl, C$_2$-C$_6$ alkynyl, C$_3$-C$_6$ cycloalkyl, and C$_4$-C$_7$ cycloalkylalkyl is optionally substituted from 1 to 3 times with substituents as defined above in R$^{12}$; and R$^{14}$ is a 5- or 6-membered aromatic or non-aromatic monocyclic carbocycle or heterocycle, or [5,5]-, [6,5]-, [6,6]-, or [6,7]-fused bicyclic carbocycle or heterocycle containing 1-5 heteroatoms selected from the group consisting of oxygen, nitrogen, and sulfur, optionally substituted from 1 to 4 times with substituents as defined below in R$^{13}$;

with the proviso that when R$^1$, R$^2$, R$^3$, R$^4$, R$^5$, R$^6$, and R$^7$ are all hydrogen, X cannot be phenyl;

or an oxide thereof, or a pharmaceutically acceptable salt thereof.

\* \* \* \* \*

UNITED STATES PATENT AND TRADEMARK OFFICE
CERTIFICATE OF CORRECTION

| | | |
|---|---|---|
| PATENT NO. | : 9,045,468 B2 | Page 1 of 1 |
| APPLICATION NO. | : 13/211678 | |
| DATED | : June 2, 2015 | |
| INVENTOR(S) | : Peter R. Guzzo et al. | |

It is certified that error appears in the above-identified patent and that said Letters Patent is hereby corrected as shown below:

In the claims,

In claim 1, col. 100, line 64, delete "$OR^{10}$, $S(O)_pR^{11}$" and insert in its place -- —$OR^{10}$, —$S(O)_pR^{11}$ --.

In claim 1, col. 102, line 13, delete "$C(O)R^{11}$" and insert in its place -- —$C(O)R^{11}$ --.

In claim 1, col. 103, line 31, delete "R'$^2$" and insert in its place -- $R^{12}$ --.

In claim 1, col. 103, line 35, delete "C(O)R'" and insert in its place -- —$C(O)R^{11}$ --.

In claim 4, col. 104, line 6, delete "as defined below in $R^{12}$" and insert in its place -- as defined in $R^{12}$ --.

In claim 8, col. 105, lines 32-33, delete "5-(4-chlorophenyl)-2,5-ethano-8-(3-(pyridin-4-yl)propoxy)-2,3,4,5-tetrahydro-1*H*-benzo[c] azepine" and insert in its place -- 5-(4-chlorophenyl)-2,5-ethano-8-(3-(pyridin-4-yl)propoxy)-2,3,4,5-tetrahydro-1*H*-benzo[c]azepine --.

In claim 10, col. 107, line 57, delete "$OR^{10}$, $S(O)_pR^{11}$, CN" and insert in its place -- —$OR^{10}$, —$S(O)_pR^{11}$, —CN --.

In claim 10, col. 108, lines 31-32, delete "3,4-dihydro-2H-benzo [b][1,4]oxazinyl" and insert in its place -- 3,4-dihydro-2H-benzo[b][1,4]oxazinyl --.

In claim 10, col. 109, line 6, delete "$C(O)R^{11}$" and insert in its place -- —$C(O)R^{11}$ --.

In claim 10, col. 110, line 39, delete "as defined above in $R^{13}$" and insert in its place -- as defined below in $R^{13}$ --.

In claim 10, col. 110, line 43, delete "$S(O)_pR^{11}$" and insert in its place -- —$S(O)_pR^{11}$ --.

In claim 10, col. 110, lines 54-55, delete "as defined below in $R^{13}$" and insert in its place -- as defined above in $R^{13}$ --.

Signed and Sealed this
Fifth Day of January, 2016

Michelle K. Lee
*Director of the United States Patent and Trademark Office*